United States Patent
Chokhawala et al.

(10) Patent No.: US 11,692,208 B2
(45) Date of Patent: *Jul. 4, 2023

(54) PRODUCTION OF CHEMICALS FROM RENEWABLE SOURCES

(71) Applicant: ZYMOCHEM, INC., San Leandro, CA (US)

(72) Inventors: Harshal Akshay Chokhawala, Castro Valley, CA (US); Jonathan Kuchenreuther, Fremont, CA (US); Jorge Alonso-Gutiérrez, San Francisco, CA (US); Yi-Shu Tai, Alameda, CA (US)

(73) Assignee: ZYMOCHEM, INC., San Leandro, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,048

(22) Filed: Sep. 16, 2022

(65) Prior Publication Data

US 2023/0109883 A1    Apr. 13, 2023

Related U.S. Application Data

(63) Continuation of application No. 17/605,389, filed as application No. PCT/US2020/029981 on Apr. 25, 2020.

(60) Provisional application No. 62/868,824, filed on Jun. 28, 2019, provisional application No. 62/838,793, filed on Apr. 25, 2019.

(51) Int. Cl.
| | |
|---|---|
| *C12N 1/20* | (2006.01) |
| *C12N 15/52* | (2006.01) |
| *C12N 15/70* | (2006.01) |
| *C12P 7/40* | (2006.01) |
| *C12P 7/625* | (2022.01) |
| *C12P 7/62* | (2022.01) |

(52) U.S. Cl.
CPC ............. *C12P 7/625* (2013.01); *C12N 1/20* (2013.01); *C12N 15/52* (2013.01); *C12N 15/70* (2013.01); *C12P 7/40* (2013.01); *C12P 7/62* (2013.01); *C12Y 106/05005* (2013.01); *C12Y 401/01004* (2013.01); *C12Y 401/02045* (2013.01); *C12Y 402/0103* (2013.01); *C12Y 402/01034* (2013.01); *C12N 2800/101* (2013.01)

(58) Field of Classification Search
CPC .... C12P 7/625; C12P 7/40; C12P 7/62; C12N 1/20; C12N 15/52; C12N 15/70; C12N 2800/101; C12Y 106/05005; C12Y 401/01004; C12Y 401/02045; C12Y 402/0103; C12Y 402/01034

See application file for complete search history.

(56) References Cited

U.S. PATENT DOCUMENTS

| | | |
|---|---|---|
| 9,523,105 B2 | 12/2016 | Zanghellini |
| 2006/0252135 A1 | 11/2006 | Brazeau et al. |
| 2008/0020435 A1 | 1/2008 | Burke et al. |
| 2011/0177571 A1 | 7/2011 | Lee |
| 2011/0195466 A1 | 8/2011 | Burgard et al. |
| 2011/0236938 A1 | 9/2011 | Yoshikuni et al. |
| 2012/0282661 A1 | 11/2012 | Burk et al. |
| 2015/0147793 A1 | 5/2015 | Walther et al. |
| 2017/0044551 A1 | 2/2017 | Chokhawala |
| 2020/0255840 A1 | 8/2020 | Chokhawala |
| 2022/0372528 A1 | 11/2022 | Chokhawala et al. |

FOREIGN PATENT DOCUMENTS

| | | |
|---|---|---|
| CN | 102066551 A | 5/2011 |
| WO | WO-2009/151728 A2 | 12/2009 |
| WO | WO-2013/090837 A2 | 6/2013 |
| WO | WO-2015/042201 A2 | 3/2015 |

OTHER PUBLICATIONS

Crits-Christoph et al., GenBank accession No. PYN48855 Jun. 12, 2018.*
U.S. Appl. No. 17/307,850, filed May 4, 2021, Chokhawala.
U.S. Appl. No. 17/605,389, filed Oct. 21, 2021, Chokhawala.
Andrews, F. H. and McLeish, M. J., Substrate specificity in thiamin diphosphate-dependent decarboxylases, Bioorganic Chemistry, 43:26-36, (2012).
Baker, P. and Seah, S.Y.K., Rational design of stereoselectivity in the Class II Pyruvate Aldolase Bphl, Journal of the American Chemical Society, 134(1):507-513, (2012).
Baker, P., et. al., Probing the molecular basis of substrate specificity, stereospecificity, and catalysis in the class II pyruvate aldolase, Bphl, Biochemistry including biophysical chemistry and molecular biology,50(17):3559-3569, (2011).
Branden et al., Introduction to Protein Structure, Garland Publishing Inc., 247 (1991).
Breitkreuz, K. E. et al., A Novel γ-Hydroxybutyrate Dehydrogenase, Identification and Expression of an *Arabidopsis* cDNA and Potential Role Under Oxygen Deficiency, The Journal of Biological Chemistry, 278(42):41552-41556, (2003).
Cheng, G., 1,6-Hexanediol Process Study, Thesis, 84 pages (Mar. 1, 2006). English Abstract on p. 3.
Cheriyan et al., Directed evolution of a pyruvate aldolase to recognize a long chain acyl substrate, Bioorganic & Medicinal Chemistry, 19:6447-6453 (2011).
De la Plaza, M. et al., Biochemical and molecular characterization of a-ketoisovalerate decarboxylase, an enzyme involved in the formation of aldehydes from amino acids by *Lactococcus lactis*, FEMS Microbiology Letters 238:367-374, (2004).
Eaton, R. W. and Chapman, P. J., Bacterial Metabolism of Naphthalene: Construction and Use of Recombinant Bacteria to Study Ring Cleavage of 1,2-Dihydroxynaphthalene and Subsequent Reactions, Journal of Bacteriology, 174(23):7542-7554, (1992).

(Continued)

*Primary Examiner* — Delia M Ramirez

(74) *Attorney, Agent, or Firm* — Choate, Hall & Stewart LLP; Xiaodong Li; Brennan A. Murphy

(57) ABSTRACT

Among other things, the present disclosure provides biosynthesis polypeptides, methods, and non-naturally occurring microbial organisms for preparing various compounds such as 1,5-pentanediol, adipic acid, 1,6-hexanediol, 6-hydroxy hexanoic acid, and 2-keto carboxylic acids.

14 Claims, 3 Drawing Sheets

Specification includes a Sequence Listing.

(56) References Cited

OTHER PUBLICATIONS

Eaton, R. W., trans-o-Hydroxybenzylidenepyruvate Hydratase-Aldolase as a Biocatalyst, Applied and Environmental Microbiology, 66(6):2668-2672, (2000).
Ehrlich, K.C. et al, An Acid Phosphatase from *Aspergillus ficuum* Has Homology to *Penicillium chrysogenum* PhoA, Biochem. Biophys. Res. Commun., 204(1):63-68 (1994).
Ferrara, S. et al., Characterization of the aldol condensation activity of the trans-o-hydroxybenzylidenepyruvate hydratase-aldolase (tHBP-HA) cloned from Pseudomonas fluorescens N3, Biochimica et Biophysica Acta (BBA)—Proteins and Proteomics, 1814(5):622-629, (2011).
Gocke, D. et al., Comparative characterisation of thiamin diphosphate-dependent decarboxylases, Journal of Molecular Catalysis B: Enzymatic: 61(1-2):30-35, (2009).
Hara et al., Characterization of the 4-Carboxy-4-Hydroxy-2-Oxoadipate Aldolase Gene and Operon Structure of the Proctocatechuate 4,5-Cleavage Pathway Genes in Sphingomonas paucimobilis SYK-6, Journal of Bacteriology, 41-50 (2003).
International Search Report for PCT/US2014/056175, 4 pages (dated Mar. 24, 2015).
International Search Report for PCT/US2020/029981 filed Apr. 25, 2020, 4 pages, (dated Sep. 24, 2020).
Iwabuchi, T. and Harayama, S., Biochemical and Genetic Characterization of trans-2'-Carboxybenzalpyruvate Hydratase-Aldolase from a Phenanthrene-Degrading *Nocardioides* Strain, American Society for Microbiology, Journal of Bacteriology, 180(4):945-949, (1998).
Liu, X. et al., Two novel metal-independent long-chain alkyl alcohol dehydrogenases from *Geobacillus thermodenitrificans* NG80-2, Microbiology, 155(6):2078-2085, (2009).
Locus AAA62393.1, Aspergillus niger acid phosphatase protein, Accession L20566-1, 1 page (Feb. 23, 1995).
Mueller, L. S. et al., Sbi00515, a Protein of Unknown Function from *Streptomyces bingchenggensis*, Highlights the Functional Versatility of the Acetoacetate Decarboxylase Scaffold, Biochemistry, 54(25):3978-3988, (2015).
Petersen, D. J., et al., Molecular Cloning of an Alcohol (Butanol) Dehydrogenase Gene Cluster from *Clostridium acetobutylicum* ATCC 824, Journal of Bacteriology, 173(5):1831-1834, (1991).
Rea, et. al., Crystal Structure and Functional Assignement of YfaU, a metal Ion Dependent class II Aldolase from *Escherichia coli* K12, American Chemical Society, 47(38):9955-9965, (2008).
Rodriguez, G. M. and Atsumi, S., Isobutyraldehyde production from *Escherichia coli* by removing aldehyde reductase activity, Microbial Cell Factories, 11:90:1-11, (2012), [http://www.microbialcellfactories.com/content/11/1/90].
Sadowski., M.I., and Jones, J.T., The sequence-structure relationship and protein function prediction, Current Opinion in Structural Biology, 19:357-362 (2009).
Saito, N. et al., Metabolite Profiling Reveals YihU as a Novel Hydroxybutyrate Dehydrogenase for Alternative Succinic Semialdehyde Metabolism in *Escherichia coli*, The Journal of Biological Chemistry, 284(24):16442-16451, (2009).
Seffernick et al., Melamine Deaminase and Atrazine Chlorohydrolase: 98 Percent Identical but Functionally Different, J. Bacteriol. 183(8):2405-2410 (2001).
Sello, G. and Gennaro, P. D., Aldol Reactions of the trans-o-Hydroxybenzylidenepyruvate Hydratase-Aldolase (tHBP-HA) from *Pseudomonas fluorescens* N3, Applied Biochemistry and Biotechnology, 170:1702-1712, (2013).
Siegert, P. et al., Exchanging the substrate specificities of pyruvate decarboxylase from *Zymomonas mobilis* and benzoylformate decarboxylase from Pseudomonas putida, Protein Engineering, Design & Selection, 18(7):345-357, (2005).
Sousa, S.,et. al., The ARO4 gene of Candida albicans encodes a tyrosine-sensitive DAHP synthase: evolution, functional conservation and phenotype of Aro3p-, Aro4p-deficient mutants, Microbiology148(Pt5):1291-1303 (2002).
Tani, A. et al., Thermostable NADP1-Dependent Medium-Chain Alcohol Dehydrogenase from *Acinetobacter* sp. Strain M-1: Purification and Characterization and Gene Expression in *Escherichia coli*, Applied and Environmental Microbiology, 66(12):5231-5235, (2000).
Wang, W. et. al., Comparison of two metal-dependant pyruvate alsolases related by convergent evolution:Substrate specificity, Kinetic mechanism, and substrate channeling, Biochemistry including biophysical chemistry abd molecular biology, 49(17):3774-3782, (2010).
Witkowski et al., Conversion of a B-Ketoacyl Synthase to a Malonyl Decaboxylase by Replacement of the Active-Site Cysteine with Glutamine, Biochemistry, 38:11643-11650 (1999).
Wolff, R. A. and Kenealy, W. R., Purification and Characterization of the Oxygen-Sensitive 4-Hydroxybutanoate Dehydrogenase from *Clostridium kluyveri*, Protein Expression and Purification, 6(2):206-212, (1995).
Wolterink-Van Loo, S. et al., "Improving low-temperature activity of Sulfolobus acidocaldarius 2-keto-3-deoxygluconate aldolase," Archaea 2, 233-239 (2009).
Written Opinion for PCT/US2014/056175, 7 pages (dated Mar. 24, 2015).
Written Opinion for PCT/US2020/029981 filed Apr. 25, 2020, 9 pages, (dated Sep. 24, 2020).

\* cited by examiner

PRODUCTION OF CHEMICALS FROM RENEWABLE SOURCES

CROSS-REFERENCE TO RELATED APPLICATIONS

This application is a Continuation of U.S. application Ser. No. 17/605,389, which is a National Stage Entry of PCT/US2020/029981, filed Apr. 25, 2020, which claims priority to U.S. Provisional Application Nos. 62/838,793, filed Apr. 25, 2019, and 62/868,824, filed Jun. 28, 2019, the entirety of each of which is incorporated herein by reference.

SEQUENCE LISTING

The present application contains a Sequence Listing, which has been submitted electronically in XML format and is hereby incorporated by reference in its entirety. Said XML file, created on Sep. 27, 2022, is named Sequence-Listing.xml and is 130,687 bytes in size.

TECHNICAL FIELD

This disclosure relates generally to compositions and methods of preparation of industrially useful chemicals.

BACKGROUND

Adipic acid (AA) is a widely used chemical with an estimated 2.3 million metric tons demand in 2012 (IHS Chemical, Process Economics Program Report: Bio-Based Adipic Acid (December 2012)). Along with hexamethylenediamine (HMDA), it is used in the production of nylon6,6, polyester resins, plasticizers, foods, and other materials. Thus, methods of preparing adipic acid in high yield using renewable sources are highly desirable.

1,5-Pentanediol is a major component of polyurethanes and polyesters (PDL). 1,6-Hexanediol (HDO), is a linear diol with terminal hydroxyl groups. It is used in polyesters for industrial coating applications, two-component polyurethane coatings for automotive applications. It is also used for production of macrodiols for example adipate esters and polycarbonate diols used in elastomers and polyurethane dispersions for parquet flooring and leather coatings.

6-Hydroxy hexanoic acid (6HH) can be cyclized to make ε-caprolactone which can then be aminated to make ε-caprolactam. ε-Caprolactam is used for the production of Nylon6, a widely used polymer in many different industries. ε-Caprolactone is polymerized to make polycaprolactone (PCL) a biodegradable polyester with applications for the production of specialty polyurethanes.

2-Keto carboxylic acids are useful intermediates for the preparation of a number of industrially relevant chemicals and pharmaceutical drugs. They are precursors for production of amino acids, as well as industrially useful α-hydroxy carboxylic acids.

SUMMARY

Among other things, the present disclosure encompasses the recognition that certain biosynthesis peptides, e.g., various enzymes, can be utilized to efficiently prepare various compounds, in many embodiments, from substrates that are structurally different from their natural and/or characterized substrates. In some embodiments, the present disclosure provides technologies (e.g., enzymes, nucleic acids, organisms, cultures, etc.) for preparing various compounds utilizing one or more such enzymes.

For example, in some embodiments, the present disclosure provides that aldol-dehydration product biosynthesis polypeptides, such as various hydratase-aldolases, can be effectively utilized to prepare a number of compounds from aliphatic aldehydes other than their typical aromatic aldehyde substrates. In some embodiments, the present disclosure provides a method comprising: contacting pyruvate and an aliphatic aldehyde with an aldol-dehydration product biosynthesis polypeptide so that an aldol-dehydration product is produced, wherein:

the carbonyl group of the aliphatic aldehyde is not conjugated to a alkenyl, alkynyl, or aromatic group; and the aldol-dehydration product is a compound comprising an aldehyde or ketone group and a double bond conjugated with the aldehyde or ketone group.

In some embodiments, an aldehyde, e.g., an aliphatic aldehyde has the structure of formula A-1:

$$R^a\text{-}L^2\text{-}L^1\text{-}C(O)H, \qquad \text{A-1}$$

or a salt thereof, wherein:

$R^a$ is R" or —OR", each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R$^1$, —C(O)R$^1$, —CO$_2$R$^1$, or —SO$_2$R$^1$;

R$^1$ is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or: two or more R$^1$ groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, $L^1$ is optionally substituted —CH$_2$—. In some embodiments, $L^1$ is optionally monosubstituted —CH$_2$—. In some embodiments, $L^1$ is —CH$_2$—.

In some embodiments, an aldol-dehydration product has the structure of formula P-2:

$$R^a\text{-}L^2\text{-}L^1\text{-}CH\!=\!CH\text{-}C(O)\text{-}C(O)OH, \qquad \text{P-2}$$

or a salt thereof, wherein each variable is independently as described herein.

As described herein, an aldol-dehydration product, e.g., a compound of formula P-2 or a salt thereof, can be further processed, in some embodiments, through one or more biosynthetic processes to provide various products, such as 1,5-pentanediol, HDO, 6HH, adipic acid, etc. (e.g., see FIGS. 2-5) and various products made therefrom, including various polymeric products made therefrom.

In some embodiments, as shown herein, an aldol-dehydration product, e.g., a compound of formula P-2 or a salt thereof may also be prepared from an aldol product, e.g., a compound of formula P-1:

$$R^a\text{-}L^2\text{-}L^1\text{-}CH(OH)\text{---}CH_2\text{---}C(O)\text{---}C(O)OH, \quad\quad \text{P-1}$$

or a salt thereof, wherein each variable is independently as described herein.

In some embodiments, an aldol-dehydration product is manufactured by contacting an aldol product with a dehydration product biosynthesis polypeptide.

In some embodiments, an aldol product is manufactured by contacting suitable substrates with an aldol product biosynthesis polypeptide.

In some embodiments, the present disclosure demonstrates that various alkene reduction product biosynthesis polypeptides can be utilized to manufacture various compounds from their natural or non-natural substrates. In some embodiments, the present disclosure provides a method comprising:

contacting an alkene with an alkene reduction product biosynthesis polypeptide so that an alkene reduction product is produced, wherein:

the alkene comprises a double bond conjugated to a carbonyl group; and a double bond conjugated to a carbonyl group in the alkene is reduced to a single bond to provide an alkene reduction product.

In some embodiments, an alkene is an aldol-dehydration product, e.g. one of formula P-2 or a salt thereof. In some embodiments, an alkene reduction product has the structure of formula P-3:

$$R^a\text{-}L^2\text{-}L^1\text{-}CH_2\text{---}CH_2\text{---}C(O)\text{---}C(O)OH, \quad\quad \text{P-3}$$

or a salt thereof, wherein each variable is independently as described herein.

Among other things, disclosed herein are enzymes, methods, and recombinant microorganisms for preparing 2-keto carboxylic acids, 1,5-pentanediol, adipic acid, 1,6-hexanediol, and 6-hydroxy hexanoic acid using renewable sources.

In one aspect, provided herein is a method for producing a 2-keto carboxylic acid of formula:

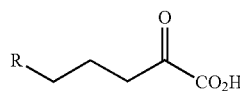

wherein R is H, CH₃, or CH₂OH;
the method comprising or consisting essentially of contacting pyruvate and

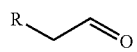

with a hydratase-aldolase and a quinone oxidoreductase in a culture or organisms comprising one or more non-naturally occurring microorganisms to produce the 2-keto carboxylic acid; wherein the hydratase-aldolase and the quinone oxidoreductase are expressed by the one or more non-naturally occurring microorganisms.

In another aspect, provided herein is a method for producing a 2-keto carboxylic acid of formula:

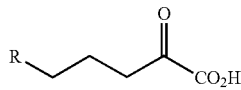

wherein R is H, CH₃, or CH₂OH;
the method comprising or consisting essentially of contacting pyruvate and

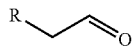

with a hydratase-aldolase and a quinone oxidoreductase in a culture or organisms comprising two or more non-naturally occurring microorganisms to produce the 2-keto carboxylic acid; wherein the hydratase-aldolase and the quinone oxidoreductase are expressed by the two or more non-naturally occurring microorganisms.

In another aspect, provided herein is a method for producing 1,5-pentanediol, the method comprising or consisting essentially of, contacting pyruvate and 3-hydroxy-propanal with a hydratase-aldolase and a quinone oxidoreductase to produce a 2-keto carboxylic acid of formula:

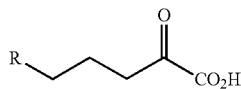

wherein R is CH₂OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol,
wherein the method is performed in a culture comprising one or more non-naturally occurring microbial organisms.

In another aspect, provided herein is a method for producing 1,5-pentanediol, the method comprising or consisting essentially of, contacting pyruvate and 3-hydroxy-propanal with a hydratase-aldolase and a quinone oxidoreductase to produce a 2-keto carboxylic acid of formula:

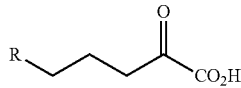

wherein R is CH₂OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol,
wherein the method is performed in a culture comprising two or more non-naturally occurring microbial organisms.

In another aspect, provided herein is a method for producing 1,6-hexanediol, the method comprising contacting pyruvate and 3-hydroxy-propanal with a hydratase-aldolase and a quinone oxidoreductase to produce a 2-keto carboxylic acid of formula:

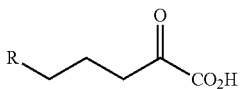

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxy-hexanoyl-CoA transferase to produce 6-hydroxy-hexanoate;
contacting the 6-hydroxy-hexanoate with a 6-hydroxy-hexanoate 1-reductase to produce 6-hydroxy-hexanal; and
contacting the 6-hydroxy-hexanal with a 6-hydroxyhexanal 1-reductase to produce the 1,6-hexanediol,
wherein the method is performed in a culture comprising one or more non-naturally occurring microbial organisms.

In another aspect, provided herein is a method for producing 1,6-hexanediol, the method comprising
contacting pyruvate and 3-hydroxy-propanal with a hydratase-aldolase and a quinone oxidoreductase to produce a 2-keto carboxylic acid of formula:

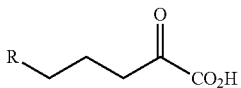

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxy-hexanoyl-CoA transferase to produce 6-hydroxy-hexanoate;
contacting the 6-hydroxy-hexanoate with a 6-hydroxy-hexanoate 1-reductase to produce 6-hydroxy-hexanal; and
contacting the 6-hydroxy-hexanal with a 6-hydroxyhexanal 1-reductase to produce the 1,6-hexanediol,
wherein the method is performed in a culture comprising two or more non-naturally occurring microbial organisms.

In another aspect, provided herein is a method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

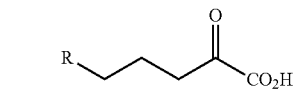

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA; and
contacting the 6-hydroxy-hexanoyl-CoA with a 6-hydroxy-hexanoyl-CoA transferase to produce the 6-hydroxy-hexanoate;
wherein the method is performed in a culture comprising one or more non-naturally occurring microbial organisms.

In another aspect, provided herein is a method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

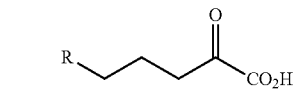

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA; and
contacting the 6-hydroxy-hexanoyl-CoA with a 6-hydroxy-hexanoyl-CoA transferase to produce the 6-hydroxy-hexanoate;
wherein the method is performed in a culture comprising two or more non-naturally occurring microbial organisms.

In another aspect, provided herein is a method for producing adipic acid, the method comprising
contacting pyruvate and 3-hydroxy-propanal with a hydratase-aldolase and a quinone oxidoreductase to produce a 2-keto carboxylic acid of formula:

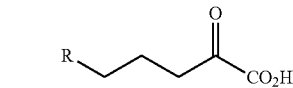

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxy-hexanoyl-CoA transferase to produce 6-hydroxy-hexanoate;

contacting the 6-hydroxy-hexanoate with a 6-hydroxy-hexanoate dehydrogenase to produce 6-oxo-hexanoate; and contacting the 6-oxo-hexanoate with a 6-oxo-hexanoate oxidase to produce the adipic acid, wherein the method is performed in a culture comprising one or more non-naturally occurring microbial organisms.

In another aspect, provided herein is a method for producing adipic acid, the method comprising contacting pyruvate and 3-hydroxy-propanal with a hydratase-aldolase and a quinone oxidoreductase to produce a 2-keto carboxylic acid of formula:

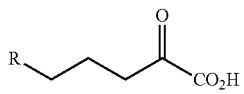

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxy-hexanoyl-CoA transferase to produce 6-hydroxy-hexanoate;

contacting the 6-hydroxy-hexanoate with a 6-hydroxy-hexanoate dehydrogenase to produce 6-oxo-hexanoate; and contacting the 6-oxo-hexanoate with a 6-oxo-hexanoate oxidase to produce the adipic acid, wherein the method is performed in a culture comprising two or more non-naturally occurring microbial organisms.

In some embodiments, the hydratase-aldolase is an enzyme having an EC number 4.1.2.45, EC number 4.1.2.34 or EC number 4.1.1.4. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

In some embodiments, the hydratase-aldolase is an enzyme having an EC number 4.1.2.45, EC number 4.1.2.34 or EC number 4.1.1.4. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1, or a portion (e.g., a domain, a set of amino acid residues (can be continuous or separated), etc.) thereof that promotes the formation of a aldol-dehydration product. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase is an enzyme selected from Tables 1 and 5-8. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from Tables 1 and 5-8.

In some embodiments, the quinone oxidoreductase is an enzyme having an EC number 1.6.5. In some embodiments, the quinone oxidoreductase is an enzyme having an EC number 1.6.5.5. In some embodiments, the quinone oxidoreductase is an enzyme selected from the group of enzymes identified under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP 026197277.1, Q5NKZ3, WP_012333034.1, or WP_136898000.1. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under GenBank, RefSeq, or Uniprot ID Nos. P28304, P40783, Q0K2I0, A0A1Z1SRY9, P43903, 17G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the hydratase-aldolase and the quinone oxidoreductase are expressed by the one or more non-naturally occurring microbial organisms. In some embodiments, at least one of the hydratase-aldolase and the quinone oxidoreductase enzymes are expressed by one or more exogenous genes expressed by the one or more non-naturally occurring microorganisms. In some embodiments, the hydratase-aldolase is exogenously expressed by the one or more non-naturally occurring microorganisms. In some embodiments, the quinone oxidoreductase is exogenously expressed by the one or more non-naturally occurring microbial organisms. In some embodiments, the quinone oxidoreductase is overexpressed by the one or more non-naturally occurring microbial organisms. In some embodiments, the hydratase-aldolase is exogenously expressed by the one or more non-naturally occurring microbial organisms and the quinone oxidoreductase is overexpressed by the one or more non-naturally occurring microbial organisms.

In some embodiments, the hydratase-aldolase and the quinone oxidoreductase are expressed by the two or more non-naturally occurring microbial organisms. In some embodiments, at least one of the hydratase-aldolase and the quinone oxidoreductase enzymes are expressed by one or more exogenous genes expressed by the two or more non-naturally occurring microorganisms. In some embodiments, the hydratase-aldolase is exogenously expressed by the two or more non-naturally occurring microorganisms. In some embodiments, the quinone oxidoreductase is exogenously expressed by the two or more non-naturally occurring microbial organisms. In some embodiments, the quinone oxidoreductase is overexpressed by the one or more non-naturally occurring microbial organisms. In some embodiments, the hydratase-aldolase is exogenously expressed by the two or more non-naturally occurring microbial organisms and the quinone oxidoreductase is overexpressed by the two or more non-naturally occurring microbial organisms.

In some embodiments, one or more of the hydratase-aldolase and quinone oxidoreductase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a 2-keto carboxylic acid further comprises or consists essentially of separating the 2-keto carboxylic acid from the one or more non-naturally occurring microbial organisms or a culture comprising the one or more non-naturally occurring microbial organisms. In some embodiments, the method further comprises or consists essentially of separating the 2-keto carboxylic acid from the two or more non-naturally occurring microbial organisms or a culture comprising the two or more non-naturally occurring microbial organisms.

In some embodiments, the 2-keto-acid-decarboxylase is an enzyme selected from the group of enzymes identified under an EC number 4.1.1.1; EC number 4.1.1.2; EC number 4.1.1.3; EC number 4.1.1.4; EC number 4.1.1.5; EC number 4.1.1.6; EC number 4.1.1.7; EC number 4.1.1.11; EC number 4.1.1.12; EC number 4.1.1.15; EC number 4.1.1.16; EC number 4.1.1.17; EC number 4.1.1.18; EC number 4.1.1.19; EC number 4.1.1.20; EC number 4.1.1.34; EC number 4.1.1.35; EC number 4.1.1.40; EC number 4.1.1.54; EC number 4.1.1.56; EC number 4.1.1.71; EC number 4.1.1.72; EC number 4.1.1.73; EC number 4.1.1.74; EC number 4.1.1.75; or EC number 4.1.1.77. In some embodiments, the 2-keto-acid-decarboxylase is an enzyme selected from the group of enzymes identified under Uniprot ID No. Q6QBS4, A7M7D6, or P20906. In some embodiments, the 2-keto-acid-decarboxylase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot ID No. Q6QBS4, A7M7D6, or P20906.

In some embodiments, the primary alcohol dehydrogenase is an enzyme having an EC number 1.1.1.61. In some embodiments, the primary alcohol dehydrogenase is an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP 001210625.1, AB067118, AB068223, BAE77068.1, or CAA47743.1. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot or GenBank ID Nos. NP_417279.1, NP_349892.1, NP 349891.1, BAB12273.1, L21902.1, Q94B07, AAB03015.1, NP_014032.1, NP_013892.1, NP_015019.1, NP 010996.2, ABX39192.1, XP_001210625.1, AB067118, AB068223, BAE77068.1, or CAA47743.1. In some embodiments, the primary alcohol dehydrogenase is an enzyme comprising a sequence of SEQ ID NO:70, SEQ ID NO:71, SEQ ID NO:72, SEQ ID NO:73, or SEQ ID NO:74. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70, SEQ ID NO:71, SEQ ID NO:72, SEQ ID NO:73, or SEQ ID NO:74.

In some embodiments, the hydratase-aldolase is an enzyme identified under Uniprot ID No. A0A286PH18; the quinone oxidoreductase is an enzyme identified under Uniprot ID No. P28304; the 2-keto-acid-decarboxylase is an enzyme identified under Uniprot ID No. Q6QBS4; and the primary alcohol dehydrogenase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694. In some embodiments, the hydratase-aldolase is an enzyme comprising a sequence of SEQ ID NO:8; the quinone oxidoreductase is an enzyme comprising a sequence of SEQ ID NO:45; the 2-keto-acid-decarboxylase is an enzyme comprising a sequence of SEQ ID NO:83; and the primary alcohol dehydrogenase is an enzyme comprising a sequence of SEQ ID NO:70.

In some embodiments, the 2-keto-acid-decarboxylase and the primary alcohol dehydrogenase are expressed by the one or more non-naturally occurring microbial organisms. In some embodiments, the 2-keto-acid-decarboxylase and the primary alcohol dehydrogenase are exogenously expressed by the one or more non-naturally occurring microbial organisms.

In some embodiments, the 2-keto-acid-decarboxylase and the primary alcohol dehydrogenase are expressed by the two or more non-naturally occurring microbial organisms. In some embodiments, the 2-keto-acid-decarboxylase and the primary alcohol dehydrogenase are exogenously expressed by the two or more non-naturally occurring microbial organisms.

In some embodiments, one or more of the hydratase-aldolase, quinone oxidoreductase, 2-keto-acid-decarboxylase, and primary alcohol dehydrogenase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a 1,5-pentanediol further comprises or consists essentially of separating the 1,5-pentanediol from the one or more non-naturally occurring microbial organisms or a culture comprising the one or more non-naturally occurring microbial organisms. In some embodiments, the method further comprises or consists essentially of separating the 1,5-pentanediol from the two or more non-naturally occurring microbial organisms or a culture comprising the two or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the one or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the one or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the two or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the two or more non-naturally occurring microbial organisms.

In some embodiments, the 6-hydroxy-2-oxohexanoate-2-reductase is an enzyme selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme selected from the group of enzymes identified under an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxyhexanoate 1-reductase is an enzyme having an EC number 1.2.99.6; and the 6-hydroxyhexanal 1-reductase is an enzyme having an EC number 1.1.1.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme selected from the group of enzymes identified under Uniprot ID No. T4VW93; the 2,6-dihydroxy-hexanoyl-CoA 2-dehydratase is an enzyme selected from the group of enzymes identified under Uniprot ID Nos. Q5U924, Q5U925, and Q5U923; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93; the 6-hydroxyhexanoate 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55, SEQ ID NO:56, SEQ ID NO:57, or SEQ ID NO:58; the 6-hydroxyhexanoate 1-reductase is an enzyme comprising a sequence of SEQ ID NO:66, SEQ ID NO:67, or SEQ ID NO:68; and the 6-hydroxyhexanal 1-reductase is an enzyme comprising a sequence of SEQ ID NO:70.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:66, SEQ ID NO:67, or SEQ ID NO:68; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70.

In some embodiments, the 6-hydroxy-2-oxohexanoate-2-reductase is an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme identified under Uniprot ID Nos. T4VW93, A0A0C7GD16, A0A175L1W4, or A0A2X3BTQ9; the 2,6-dihydroxy-hexanoyl-CoA 2-dehydratase is an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93, A0A0C7GD16, A0A175L1W4, or A0A2X3BTQ9; the 6-hydroxyhexanoate 1-reductase is an enzyme identified under Uniprot or GenBank ID Nos D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A0C7GD16, A0A175L1W4, or A0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. T4VW93, A0A0C7GD16, A0A175L1W4, or A0A2X3BTQ9; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing 1,6-hexanediol further comprises or consists essentially of separating the 1,6-hexanediol from the one or more non-naturally occurring microbial organisms or a culture comprising the one or more non-naturally occurring microbial organisms. In some embodiments, the method further comprises or consists essentially of separating the 1,6-hexanediol from the two or more non-naturally occurring microbial organisms or a culture comprising the two or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxy-hexanoyl-CoA transferase are expressed by the one or more non-naturally occurring microbial organisms. In some embodiments, 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the one or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxy-hexanoyl-CoA transferase are expressed by the two or more non-naturally occurring microbial organisms. In some embodiments, 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the two or more non-naturally occurring microbial organisms.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; and the 6-hydroxyhexanoyl-CoA transferase is an enzyme having an EC number 2.8.3, EC number 2.8.3.1, or EC number 2.8.3.12.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme identified under Uniprot ID Nos. T4VW93, A0A2X3BTQ9, A0A0C7GD16, or A0A175L1W4; the 2,6-dihydroxy-hexanoyl-CoA 2-dehydratase is an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase is an enzyme identified under Uniprot ID No. Q73Q47; and the 6-hydroxyhexanoyl-CoA transferase is an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase is an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; and the 6-hydroxyhexanoyl-CoA transferase is an enzyme comprising a sequence of SEQ ID NO:55, SEQ ID NO:56, SEQ ID NO:57, or SEQ ID NO:58.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:5, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a 6-hydroxy-hexanoate further comprises or consists essentially of separating the 6-hydroxy-hexanoate from the one or more non-naturally occurring microbial organisms or a culture comprising the one or more non-naturally occurring microbial organisms. In some embodiments, the method further comprises or consists essentially of separating the 6-hydroxy-hexanoate from the two or more non-naturally occurring microbial organisms or a culture comprising the two or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate dehydrogenase, and the 6-oxo-hexanoate oxidase are expressed by the one or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate dehydrogenase, and the 6-oxo-hexanoate oxidase are exogenously expressed by the one or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate dehydrogenase, and the 6-oxo-hexanoate oxidase are expressed by the two or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate dehydrogenase, and the 6-oxo-hexanoate oxidase are exogenously expressed by the two or more non-naturally occurring microbial organisms.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxy-hexanoate dehydrogenase is an enzyme having an EC number 1.1.1.258; and the 6-oxo-hexanoate oxidase is an enzyme having an EC number 1.2.1.63.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC6409; the 2,6-dihydroxy-hexanoate CoA-transferase is an enzyme identified under Uniprot ID Nos. T4VW93 or A0A2X3BTQ9; the 2,6-dihydroxy-hexanoyl-CoA 2-dehydratase is an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID Nos. T4VW93 or A0A2X3BTQ9; the 6-hydroxyhexanoate dehydrogenase is an enzyme identified under Uniprot ID Nos. Q7WVD0 or Q84H78; and the 6-oxo-hexanoate oxidase is an enzyme identified under Uniprot ID No. Q9R2F4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q7WVD0 or Q84H78; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q9R2F4.

In some embodiments, the 6-hydroxy-2-oxohexanoate-2-reductase is an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55 or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55 or SEQ ID NO:58; the 6-hydroxyhexanoate dehydrogenase is an enzyme identified comprising a sequence of SEQ ID NO:71 or SEQ ID NO:72; and the 6-oxo-hexanoate oxidase is an enzyme comprising a sequence of SEQ ID NO:75.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified comprising a sequence of SEQ ID NO:71 and SEQ ID NO:72; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:75.

In some embodiments, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, 6-hydroxyhexanoate dehydrogenase, and the 6-oxo-hexanoate oxidase are further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a adipic acid further comprises or consists essentially of separating the adipic acid from the one or more non-naturally occurring microbial organisms or a culture comprising the one or more non-naturally occurring microbial organisms. In some embodiments, the method further comprises or consists essentially of separating the adipic acid from the two or more non-naturally occurring microbial organisms or a culture comprising the two or more non-naturally occurring microbial organisms.

In some embodiments, the pyruvate is produced from carbon sources is selected from glycerol, glucose, xylose, arabinose, galactose, mannose, fructose, sucrose, and starch, or a combination thereof. In some embodiments,

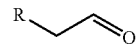

is 3-hydroxy-propanal. In some embodiments, the 3-hydroxy-propanal is produced by dehydration of glycerol by a glycerol dehydratase enzyme exogenously expressed by the one or more non-naturally occurring microbial organisms.

In another aspect, provided herein is a recombinant microbial organism comprising a first exogenous nucleic acid encoding an aldolase hydratase enzyme, wherein the recombinant microbial organism is further modified to express an increased amount of quinone oxidoreductase as compared to wild-type or the same microbial organism that is not modified, and optionally wherein the microbial organism is Corynebacterium glutamicum, a clostridium species, or E. coli. In some embodiments, the organism comprises a second exogenous nucleic acid encoding quinone oxidoreductase. In some embodiments, the first and/or second exogenous nucleic acid further comprises a regulatory element that drives expression of the second exogenous nucleic acid. Alternatively, the first and second nucleic are under the control of the same promoter regulatory element. In some embodiments, the regulatory element is selected from a promoter or an enhancer. In some embodiments, the aldolase hydratase enzyme has an EC number 4.1.2.45 or EC number 4.1.2.34 or EC number 4.1.1.4. In some embodiments, the aldolase hydratase enzyme is an enzyme selected from the group of enzymes identified under Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1. In some embodiments, the aldolase hydratase enzyme is an enzyme selected from the group of enzymes identified under Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the aldolase hydratase enzyme is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the first exogenous nucleic acid and the second exogenous nucleic acid are each contained in a vector, e.g., a plasmid or viral vector. In some embodiments, the first exogenous nucleic acid and the second exogenous nucleic acid are each contained in the same vector. In some embodiments, the first exogenous nucleic acid and the second exogenous nucleic acid are each contained in their own separate vectors. In some embodiments, the vector is a plasmid. In some embodiments, a quinone oxidoreductase is an enzyme having an EC number 1.6.5. In some embodiments, a quinone oxidoreductase is an enzyme having an EC number 1.6.5.5. In some embodiments, the quinone oxidoreductase is an enzyme selected from the group of enzymes identified under GenBank, RefSeq, or Uniprot ID Nos. P28304, P40783, Q0K2I0, A0A1Z1SRY9, P43903, 17G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97. In some embodiments, the recombinant microbial organism is capable of producing a 2-keto carboxylic acid of formula:

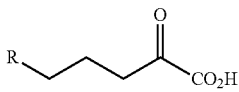

wherein R is H, CH$_3$, or CH$_2$OH. In some embodiments, the recombinant microbial organism is capable of producing 1,5-pentanediol, 1,6-hexanediol, adipic acid, or 6-hydroxy hexanoate. In some embodiments, the recombinant microbial organism is genetically modified to improve production of pyruvate from a carbon source. In some embodiments, the carbon source is selected from glycerol, glucose, xylose, arabinose, galactose, mannose, fructose, sucrose, and starch, or a combination thereof.

In another aspect, provided herein is a culture comprising the recombinant microbial organisms disclosed herein.

In another aspect, provided herein is a population of recombinant microbial organisms as disclosed herein. In some embodiments, the population is substantially homogenous.

In another aspect, provided herein is a culture comprising the populations disclosed herein.

In another aspect, provided herein is a method of producing 1,5-pentanediol, 1,6-hexanediol, adipic acid, or 6-hydroxy hexanoate, comprising culturing the population or recombinant microorganisms as disclosed herein under suitable conditions that promote expression of the exogenous nucleic acids as disclosed herein. In one aspect, the exogenous nucleic acids are overexpressed as compared to a wild-type or unmodified counterpart microbial organism. In some embodiments, the method further comprises isolating the 1,5-pentanediol, 1,6-hexanediol, adipic acid, or 6-hydroxy hexanoate from the culture or the microbial organisms.

DETAILED DESCRIPTION

Definitions

Figure 1:
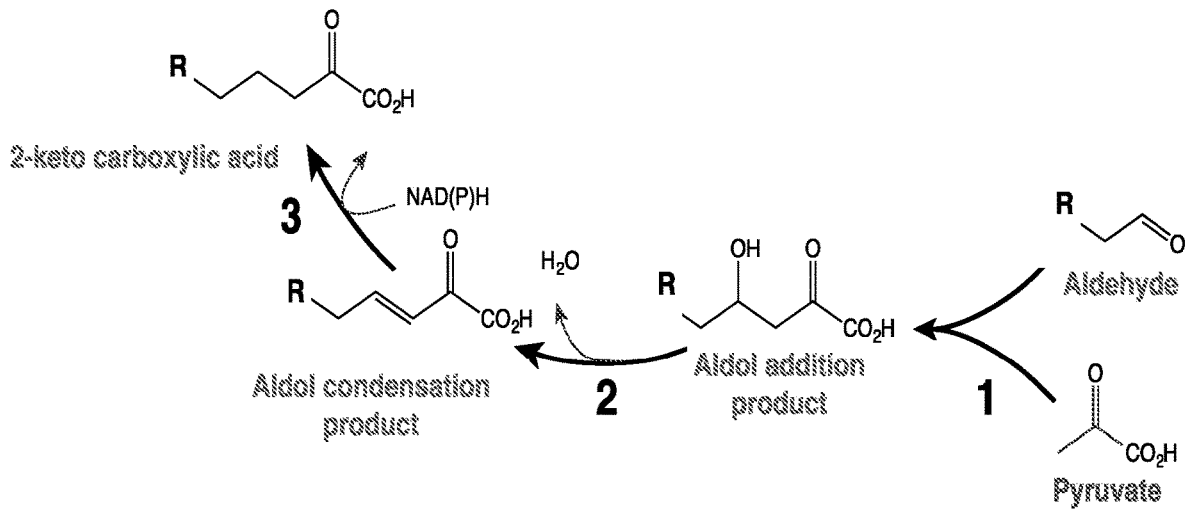
FIG. 1 shows a two-enzyme biosynthetic pathway for production of 2-keto carboxylic acids from pyruvate and aldehydes as an example. An aldol-dehydration product (e.g., an aldol condensation product described herein) can be generated from a process catalyzed by a single enzyme (e.g., an aldol-dehydration product biosynthesis polypeptide such as a hydratase-aldolase (in some embodiments, referred as Ads-Hyd) through, without the intention to be limited by theory, step 1 and 2 as depicted. As those skilled in the art will appreciate, the double bond in the illustrated aldol condensation product may exist as E or Z. In many embodiments, step 3 as illustrated can catalyzed by an oxidoreductase, e.g., one belonging to EC 1.6.5 (e.g., EC 1.6.5.5) that utilizes NADH and/or NADPH for reduction of quinones. As described herein, various aldehydes may be utilized. For example, in the illustrated aldehydes in some embodiments, R is H, CH$_3$, CH$_2$CH$_3$, OH, CH$_2$OH, or CH$_2$CH$_2$OH.

As used herein, certain terms may have the following defined meanings. As used herein, the singular form "a," "an" and "the" include singular and plural references unless the context clearly indicates otherwise.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Aspects defined by each of these transition terms are within the scope of the present disclosure. Accordingly, it is intended that the methods and compositions can include additional steps and components (comprising) or alternatively including steps and compositions of no significance (consisting essentially of) or alternatively, intending only the stated method steps or compositions (consisting of).

As used therein, the term "aldol-dehydration product biosynthesis polypeptide" refers to a polypeptide that is involved in the synthesis of an aldol-dehydration product as described herein. In some embodiments, an aldol-dehydration product biosynthesis polypeptide may be or comprise an aldolase polypeptide, a hydratase, a hydratase-aldolase polypeptide (e.g., a hydratase-aldolase) as described herein. In some embodiments, an aldol-dehydration product biosynthesis polypeptide may be or comprise a hydratase-aldolase polypeptide (e.g., a hydratase-aldolase) as described herein. In some embodiments, an aldol-dehydration product biosynthesis polypeptide has an amino acid sequence that is found in nature, for example in a microbe (e.g., in a reference aldol-dehydration biosynthesis polypeptide found in nature). Alternatively or additionally, in some embodiments, an aldol-dehydration biosynthesis polypeptide shares a characteristic sequence element and/or an overall percent identity with an appropriate reference aldol-dehydration biosynthesis polypeptide (e.g., as is found in nature and/or is presented herein (e.g., in one or more of relevant Tables (e.g., Tables 1 and 5-8))) or a portion thereof (e.g., a portion (e.g., a domain (e.g., a relevant catalytic domain) and/or a set of amino acid residues (which can be continuous or separated)) that promotes a relevant reaction).

As used herein, an "aldol-dehydration product" refers to a compound comprising an aldehyde or ketone group and a double bond conjugated with the aldehyde or ketone group. In some embodiments, an aldol-dehydration product is a compound of formula P-2 or a salt thereof.

As used herein, the term "aldol product" refers to a compound which comprises an aldehyde or ketone group and a hydroxyl group attached to a beta-carbon of an aldehyde or ketone carbonyl group. In some embodiments, an aldol product is a product of an aldol reaction. In some embodiments, an aldol product has a structure formula P-1 or a salt thereof.

As used herein, the term "aldol product biosynthesis polypeptide" refers to a polypeptide that is involved in the synthesis of an aldol product as described herein. In some embodiments, an aldol product biosynthesis polypeptide may be or comprise an aldolase polypeptide, a hydratase-aldolase polypeptide (e.g., a hydratase-aldolase) as described herein. In some embodiments, an aldol product biosynthesis polypeptide is or comprises a aldolase polypeptide as described herein. In some embodiments, an aldol product biosynthesis polypeptide has an amino acid sequence that is found in nature, for example in a microbe (e.g., in a reference aldol biosynthesis polypeptide found in nature). Alternatively or additionally, in some embodiments, an aldol biosynthesis polypeptide shares a characteristic sequence element and/or an overall percent identity with an appropriate reference aldol biosynthesis polypeptide (e.g., as is found in nature and/or is presented herein (e.g., in one or more of relevant Tables)) or a portion thereof (e.g., a portion (e.g., a domain (e.g., a relevant catalytic domain) and/or a set of amino acid residues (which can be continuous or separated)) that promotes a relevant reaction).

As used herein, the term "alkene reduction product biosynthesis polypeptide" refers to a polypeptide that is involved in the conversion of a double bond into a single bond as described herein (and forming an alkene reduction product). In some embodiments, an alkene reduction product biosynthesis polypeptide may be or comprise quinone oxidoreductase as described herein. In some embodiments, an alkene reduction product biosynthesis polypeptide has an amino acid sequence that is found in nature, for example in a microbe (e.g., in a reference alkene reduction biosynthesis polypeptide found in nature). Alternatively or additionally, in some embodiments, an aldol biosynthesis polypeptide shares a characteristic sequence element and/or an overall percent identity with an appropriate reference aldol biosynthesis polypeptide (e.g., as is found in nature and/or is presented herein (e.g., in one or more of relevant Tables)) or a portion thereof (e.g., a portion (e.g., a domain (e.g., a relevant catalytic domain) and/or a set of amino acid residues (which can be continuous or separated)) that promotes a relevant reaction).

As used herein, the term "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "aryl", used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but is not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

As used herein, the term "cycloaliphatic," "carbocycle," "carbocyclyl," "carbocyclic radical," and "carbocyclic ring," are used interchangeably, and refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

As used herein, the term "heteroaliphatic" is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted forms thereof). In some embodiments, a heteroaliphatic group is heteroalkyl. In some embodiments, a heteroaliphatic group is heteroalkenyl.

As used herein, the term "heteroalkyl" is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

As used herein, the terms "heteroaryl" and "heteroar-", used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

As used herein, the term "heteroatom" refers to an atom that is not carbon or hydrogen. In some embodiments, a heteroatom is boron, oxygen, sulfur, nitrogen, phosphorus, or silicon (including oxidized forms of nitrogen, sulfur, phosphorus, or silicon; charged forms of nitrogen (e.g., quaternized forms, forms as in iminium groups, etc.), phosphorus, sulfur, oxygen; etc.). In some embodiments, a heteroatom is oxygen, sulfur or nitrogen.

As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Optionally Substituted: As described herein, chemical entities, e.g., various compounds, of the disclosure may contain optionally substituted and/or substituted moieties. In general, the term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is substituted. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Certain substituents are described below.

Suitable monovalent substituents on a substitutable atom, e.g., a suitable carbon atom, are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —Si(R°)$_3$; —OSi(R°)$_3$; —B(R°)$_2$; —OB(R°)$_2$; —OB(OR°)$_2$; —P(R°)$_2$; —P(OR°)$_2$; —P(R°)(OR°); —OP(R°)$_2$; —OP(OR°)$_2$; —OP(R°)(OR°); —P(O)(R°)$_2$; —P(O)(OR°)$_2$; —OP(O)(R°)$_2$; —OP(O)(OR°)$_2$; —OP(O)(OR°)(SR°); —SP(O)(R°)$_2$; —SP(O)(OR°)$_2$; —N(R°)P(O)(R°)$_2$; —N(R°)P(O)(OR°)$_2$; —P(R°)$_2$[B(R°)$_3$]; —P(OR°)$_2$[B(R°)$_3$]; —OP(R°)$_2$[B(R°)$_3$]; —OP(OR°)$_2$[B(R°)$_3$]; —(C$_{1-4}$ straight or branched alkylene)O—N(R°)$_2$; or —(C$_{1-4}$ straight or branched alkylene)C(O)O—N(R°)$_2$, wherein each R° may be substituted as defined herein and is independently hydrogen, C$_{1-20}$ aliphatic, C$_{1-20}$ heteroaliphatic having 1-5 heteroatoms independently selected from nitrogen, oxygen, sulfur, silicon and phosphorus, —CH$_2$—(C$_{6-14}$ aryl), —O(CH$_2$)$_{0-1}$(C$_{6-14}$ aryl), —CH$_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R°, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•$$_2$, —NO$_2$, —SiR$^•$$_3$, —OSiR$^•$$_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, and a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents, e.g., on a suitable carbon atom, are independently the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, and an unsubstituted 5-6-membered saturated, partially unsaturated, and aryl ring having 0-4 heteroatoms independently selected from nitrogen, oxygen, and sulfur.

Suitable substituents on the aliphatic group of R* are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$$_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

In some embodiments, suitable substituents on a substitutable nitrogen are independently —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C1-6 aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$2, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

"Wild-type" defines the cell, composition, tissue or other biological material as it exists in nature.

In some embodiments, the 3-hydroxy-propanal and pyruvate are prepared from one or more of glycerol, C5 sugars, C6 sugars, phosphor-glycerates, other carbon sources, intermediates of the glycolysis pathway, and combinations thereof. In some embodiments, the C5 sugars comprise or alternatively consists essentially of, or yet further consists of, one or more of xylose, xylulose, ribulose, arabinose, lyxose, and ribose, and the C6 sugars comprise or alternatively consist essentially of, or yet further consist of, allose, altrose, glucose, mannose, gulose, idose, talose, fructose, psicose, sorbose, and tagatose. In some embodiments, the other carbon source is a feedstock suitable as a carbon source for a microorganism wherein the feedstock comprises or alternatively consists essentially of, or yet further consists of, one or more of amino acids, lipids, corn stover, *miscanthus*, municipal waste, energy cane, sugar cane, bagasse, starch stream, dextrose stream, formate, methanol, and combinations thereof.

As used herein, the term "C5 sugar" refers to a sugar molecule containing 5 carbons.

As used herein, the term "C6 sugar" refers to a sugar molecule containing 6 carbons.

In some embodiments, the term "aldol addition" refers to a chemical reaction in which a pyruvate molecule forms a corresponding enol or an enolate ion or a Schiff's base or an enamine that reacts with the aldehyde functional group of the C$_N$ aldehyde to produce a C$_{N+3}$ 4-hydroxy-2-carboxylic acid intermediate. In some embodiments, the C$_N$ aldehyde is 3-hydroxy-propanal and the C$_{N+3}$ 4-hydroxy-2-keto-carboxylic acid intermediate is 4,6-dihydroxy-2-keto-hexanoic acid.

In some embodiments, the term "aldol condensation" refers to a chemical reaction in which a pyruvate molecule forms a corresponding enol or an enolate ion or a Schiff's base or an enamine that reacts with the aldehyde functional group of the C$_N$ aldehyde to produce a C$_{N+3}$ 3,4-dehydro-2-keto-carboxylic acid. In some embodiments, the C$_N$ aldehyde is 3-hydroxy-propanal and the C$_{N+3}$ 3,4-dehydro-2-keto-carboxylic acid is 6-hydroxy-3,4-dehydro-2-keto-hexanoic acid.

As used herein, the term "solution" refers to a liquid composition that contains a solvent and a solute, such as a starting material used in the methods described herein. In some embodiments, the solvent is water. In some embodiments, the solvent is an organic solvent.

As used herein, the term "enzymatic step" or "enzymatic reaction" refers to a molecular reaction catalyzed by an enzyme that is selected to facilitate the desired enzymatic reaction. Enzymes are large biological molecules and highly selective catalysts. Most enzymes are proteins, but some catalytic RNA molecules have been identified.

Throughout the application, enzymatic steps may be denoted as "step 1", "step 2" and so on so forth and the enzyme specifically catalyzing these steps is denoted as "1", "2" and so on so forth, respectively. Such an enzyme is also referred to as a "reaction specific enzyme".

As used herein, the term "CoA" or "coenzyme A" is intended to mean an organic cofactor or prosthetic group (nonprotein portion of an enzyme) whose presence is required for the activity of many enzymes to form an active enzyme system.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "non-naturally occurring" or "non-natural" when used in reference to a microbial organism or microorganism of the present disclosure is intended to mean that the microbial organism has at least one genetic alteration not normally found in a naturally occurring strain of the referenced species, including wild-type strains of the referenced species. Genetic alterations include, for example, but are not limited to, modifications introducing expressible nucleic acids encoding polypeptides, other nucleic acid additions, nucleic acid deletions and/or other functional disruption of the microbial organism's genetic material. Such modifications include, for example, but are not limited to, coding regions and functional fragments thereof, for heterologous, homologous or both heterologous and homologous polypeptides for the referenced species. Additional modifications include, for example, but are not limited to, non-coding regulatory regions in which the modifications alter expression of a gene or operon.

As is used herein "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to an enzymatic activity, the term refers to an activity that is introduced into the host reference organism.

The source can be, for example, a homologous or heterologous encoding nucleic acid that expresses the referenced activity following introduction into the host microbial organism. Therefore, the term "endogenous" refers to a referenced molecule or activity that is originally or naturally present in the wild-type host. Similarly, the term when used in reference to expression of an encoding nucleic acid refers to expression of an encoding nucleic acid contained within the wild-type microorganism.

The term "heterologous" refers to a molecule or activity derived from a source other than the referenced species whereas "homologous" when used in this context refers to a molecule or activity derived from the host microbial organism. Accordingly, exogenous expression of an encoding nucleic acid can utilize either or both a heterologous or homologous encoding nucleic acid.

It is understood that when more than one exogenous nucleic acid is included in a microbial organism, that the more than one exogenous nucleic acids refers to the referenced encoding nucleic acid or enzymatic activity, as discussed above. It is further understood, as disclosed herein, that more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein, a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or enzymatic activities refers to the number of encoding nucleic acids or the number of enzymatic activities, not the number of separate nucleic acids introduced into the host organism.

In some embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

Those skilled in the art will understand that the genetic alterations are described with reference to a suitable host organism such as *E. coli* and their corresponding metabolic reactions or a suitable source organism for desired genetic material such as genes for a desired biosynthetic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

Sources of encoding nucleic acids the pathway enzymes can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Pseudomonas knackmussii, Pseudomonas putida, Pseudomonas fluorescens, Klebsiella pneumoniae, Serratia proteamaculans, Streptomyces* sp. 2065, *Pseudomonas aeruginosa, Ralstonia eutropha, Clostridium acetobutylicum, Euglena gracilis, Treponema denticola, Clostridium kluyveri, Homo sapiens, Rattus norvegicus, Acinetobacter* sp. ADP1, *Streptomyces coelicolor, Eubacterium barkeri, Peptostreptococcus asaccharolyticus, Clostridium botulinum, Clostridium tyrobutyricum, Clostridium thermoaceticum (Moorella thermoaceticum), Acinetobacter calcoaceticus, Mus musculus, Sus scrofa, Flavobacterium* sp, *Arthrobacter aurescens, Penicillium chrysogenum, Aspergillus niger, Aspergillus nidulans, Bacillus subtilis, Saccharomyces cerevisiae, Zymomonas mobilis, Mannheimia succiniciproducens, Clostridium ljungdahlii, Clostridium carboxydivorans, Geobacillus stearothermophilus, Agrobacterium tumefaciens, Achromobacter denitrificans, Arabidopsis thaliana, Haemophilus influenzae, Acidaminococcus fermentans, Clostridium* sp. M62/1, *Fusobacterium nucleatum*, as well as other exemplary species disclosed herein or available as source organisms for corresponding genes (see Examples). However, with the complete genome sequence available for now more than 400 microorganism genomes and a variety of yeast, fungi, plant, and mammalian genomes, the identification of genes encoding the requisite pathway enzymes, for one or more genes in related or distant species, including for example, homologues, orthologs, paralogs and nonorthologous gene displacements of known genes, and the interchange of genetic alterations between organisms is routine and well known in the art.

Ortholog refers to genes in different species that evolved from a common ancestral gene by speciation. Normally, orthologs retain the same function in the course of evolution. Identification of orthologs is critical for reliable prediction of gene function in newly sequenced genomes.

Paralog refers to genes related by duplication within a genome. While orthologs generally retain the same function in the course of evolution, paralogs can evolve new functions, even if these are related to the original one.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

As used herein, the terms "microorganism" or "microbial organism" or "microbes" are used interchangeably and refer to a living biological and isolated prokaryotic or eukaryotic cell that can be transformed or transfected via insertion of an exogenous or recombinant nucleic acid, such as DNA or RNA. Any suitable prokaryotic or eukaryotic microorganism may be used in the present disclosure so long as it remains viable after being transformed with a sequence of nucleic acids. A suitable microorganism of the present disclosure is one capable of expressing one or more nucleic acid constructs encoding one or more recombinant proteins that can catalyze at least one step in the methods. Microorganism can be selected from group of bacteria, yeast, fungi, mold, and archaea. These are commercially available.

As used herein, "fungal" refers to any eukaryotic organism categorized within the kingdom of Fungi. Phyla within the kingdom of Fungi include Ascomycota, Basidiomycota, Blastocladiomycota, Chytridiomycota, Glomeromycota, Microsporidia, and Neocallimastigomycota. As used herein, "yeast" refers to fungi growing in single-celled forms (for example, by budding), whereas "mold" refers to fungi growing in filaments made of multicellular hyphae or mycelia (McGinnis, M. R. and Tyring, S. K. "Introduction to Mycology." Medical Microbiology. 4$^{th}$ ed. Galveston: Univ. of TX Medical Branch at Galveston, 1996).

In some embodiments, the microorganisms are yeast cells. In some embodiments, the yeast cell is from a *Candida, Hansenula, Issatchenkia, Kluyveromyces, Pichia, Saccharomyces, Schizosaccharomyces*, or *Yarrowia* species.

In some embodiments, the microorganisms are mold cells. In some embodiments, the mold host cell is from a *Neurospora, Trichoderma, Aspergillus, Fusarium*, or *Chrysosporium* species.

In some embodiments, the microorganism is an archaea. In some embodiments, a suitable archaea is from an *Archaeoglobus, Aeropyrum, Halobacterium, Pyrobaculum, Pyrococcus, Sulfolobus, Methanococcus, Methanosphaera, Methanopyrus, Methanobrevibacter, Methanocaldococcus*, or *Methanosarcina* species.

The term "bacteria" refers to any microorganism within the domain or kingdom of prokaryotic organisms. Phyla within the domain or kingdom of bacteria include *Acidobacteria, Actinobacteria, Actinobacillus, Agrobacterium, Anaerobiospirrulum, Aquificae, Armatimonadetes, Bacteroidetes, Burkholderia, Caldiserica, Chlamydiae, Chlorobi, Chlorella, Chloroflexi, Chrysiogenetes, Citrobacter, Clostridium, Cyanobacteria, Deferribacteres, Deinococcusthermus, Dictyoglomi, Enterobacter, Elusimicrobia, Fibrobacteres, Firmicutes, Fusobacteria, Geobacillus, Gemmatimonadetes, Gluconobacter, Halanaerobium, Klebsiella, Kluyvera, Lactobacillus, Lentisphaerae, Methylobacterium, Nitrospira, Pasteurellaceae, Paenibacillus, Planctomycetes, Propionibacterium, Pseudomonas, Proteobacteria, Ralstonia, Schizochytrium, Spirochaetes, Streptomyces, Synergistetes, Tenericutes, Thermoanaerobacterium, Thermodesulfobacteria, Thermotogae, Verrucomicrobia, Zobellella*, and *Zymomonas*. In some embodiments, the bacterial microorganisms are *E. coli* cells. In some embodiments, the bacterial microorganisms are *Bacillus* sp. cells. Examples of *Bacillus* species include without limitation *Bacillus subtilis, Bacillus megaterium, Bacillus cereus, Bacillus thuringiensis, Bacillus mycoides*, and *Bacillus licheniformis*.

A carboxylic acid compound prepared by the methods of the present disclosure can form a salt with a counter ion including, but not limited to, a metal ion, e.g., an alkali metal ion, such as sodium, potassium, an alkaline earth ion, such as calcium, magnesium, or an aluminum ion; or coordinates with an organic base such as tetraalkylammonium, ethanolamine, diethanolamine, triethanolamine, trimethylamine, N-methylglucamine, and the like. The acid can form a salt with a counter ion or organic base present in the reaction conditions or can be converted to a salt by reacting with an inorganic or organic base.

Any carboxylic acid containing compound herein is referred to as either an acid or a salt, which has been used interchangeably throughout to refer to the compound in any of its neutral or ionized forms, including any salt forms thereof. It is understood by those skilled understand that the specific form will depend on the pH.

A solvate of a compound is a solid-form of the compound that crystallizes with less than one, one or more than one molecules of solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

When referring to a compound for which several isomers exist (e.g., cis and trans isomer, and R and S isomer, or a combination thereof), the compound in principle includes all possible enantiomers, diastereomers and cis/trans isomers of that compound that may be used in the method of the present disclosure.

For each species, any cell belonging to that species is considered a suitable microorganism of the present disclosure. A host cell of any species may exist as it was isolated from nature, or it may contain any number of genetic modifications (e.g., genetic mutations, deletions, or recombinant polynucleotides).

The term "recombinant nucleic acid" or "recombinant polynucleotide" as used herein refers to a polymer of nucleic acids where at least one of the following is true: (a) the sequence of nucleic acids is foreign to (i.e., not naturally found in) a given microorganism; (b) the sequence may be naturally found in a given microorganism, but in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid.

In some embodiments, recombinant polypeptides or proteins or enzymes of the present disclosure may be encoded by genetic material as part of one or more expression vectors. An expression vector contains one or more polypeptide-encoding nucleic acids, and it may further contain any desired elements that control the expression of the nucleic acid(s), as well as any elements that enable the replication and maintenance of the expression vector inside a given host cell. All of the recombinant nucleic acids may be present on a single expression vector, or they may be encoded by multiple expression vectors.

An expression vector or vectors can be constructed to include one or more pathway-encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Exogenous nucleic acid sequences involved in a pathway for synthesis of desired compounds described herein can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., J. Biol. Chem. 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. It is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". As used herein, "about" will mean up to plus or minus 10%. It also is to be understood, although not always explicitly stated, that the reagents described herein are merely exemplary and that equivalents of such are known in the art.

"Operatively linked" refers to a juxtaposition wherein the elements are in an arrangement allowing them to function.

The term "culturing" refers to the in vitro propagation of cells or organisms on or in media (culture) of various kinds. It is understood that the descendants of a cell grown in culture may not be completely identical (i.e., morphologically, genetically, or phenotypically) to the parent cell.

A "gene" refers to a polynucleotide containing at least one open reading frame (ORF) that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art.

The term "express" refers to the production of a gene product. The term overexpression refers to the production of the mRNA transcribed from the gene or the protein product encoded by the gene that is more than that of a normal or control cell, for example 0.5 times, 1.0 times, 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher than the expression level detected in a control sample or wild-type cell.

As used herein, "homology" refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

Methods of alignment of sequences for comparison are well-known in the art. For example, the determination of percent sequence identity between any two sequences can be accomplished using a mathematical algorithm. Non-limiting examples of such mathematical algorithms are the algorithm of Myers and Miller, CABIOS 4:11 17 (1988); the local homology algorithm of Smith et al., Adv. Appl. Math. 2:482 (1981); the homology alignment algorithm of Needleman and Wunsch, J. Mol. Biol. 48:443 453 (1970); the search-for-similarity-method of Pearson and Lipman, Proc. Natl. Acad. Sci. 85:2444 2448 (1988); the algorithm Karlin and Altschul Proc. Natl. Acad. Sci. USA 90:5873 5877 (1993).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch, J Mol Biol 48(3):443-453 (1970), by the search for similarity method of Pearson and Lipman, Proc Natl Acad Sci USA 85(8):2444-2448 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al., Nucleic Acids Res 25(17):3389-3402 (1997) and Altschul et al., J. Mol Biol 215(3)-403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix (see Henikoff and Henikoff, Proc Natl Acad Sci USA 89(22):10915-10919 (1992)) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc Natl Acad Sci USA 90(12):5873-5877 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross-reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

The phrase "functionally equivalent protein" refers to protein or polynucleotide which hybridizes to the exemplified polynucleotide under stringent conditions and which exhibit similar or enhanced biological activity in vivo, e.g., over 120%, or alternatively over 110%, or alternatively over 100%, or alternatively, over 90% or alternatively over 85% or alternatively over 80%, as compared to the standard or control biological activity. Additional embodiments within the scope of the present disclosure are identified by having more than 80%, or alternatively, more than 85%, or alternatively, more than 90%, or alternatively, more than 95%, or alternatively more than 97%, or alternatively, more than 98 or 99% sequence homology. Percentage homology can be determined by sequence comparison programs such as BLAST run under appropriate conditions. In some embodiments, the program is run under default parameters. In some embodiments, reference to a certain enzyme or protein includes its functionally equivalent enzyme or protein.

A population of cells intends a collection of more than one cell that is identical (clonal) or non-identical in phenotype and/or genotype. A substantially homogenous population of cells is a population having at least 70%, or alternatively at least 75%, or alternatively at least 80%, or alternatively at least 85%, or alternatively at least 90%, or alternatively at least 95%, or alternatively at least 98% identical phenotype, as measured by pre-selected markers.

When an enzyme is mentioned with reference to an enzyme class (EC), the enzyme class is a class wherein the enzyme is classified or may be on classified on the basis of the enzyme nomenclature provided by the Nomenclature Committee of the International Union of Biochemistry and Molecular Biology. Other suitable enzymes that have not yet been classified in a specific class but may be classified as such are also included.

Non-Naturally Occurring Microbial Organisms

The non-naturally occurring microbial organisms provided herein are constructed using methods well known in the art as exemplified herein to exogenously express at least one nucleic acid encoding an enzyme or protein used in a biosynthetic pathway described herein in sufficient amounts to produce compounds such as 2-keto pentanoic acid, 2-keto hexanoic acid, 6-hydroxy-2-keto-hexanoic acid, 1,5-pentanediol, adipic acid, 1,6-hexanediol, or 6-hydroxy hexanoic acid.

Successful engineering of a microbial host capable of producing the desired product described herein involves identifying the appropriate set of enzymes with sufficient activity and specificity for catalyzing various steps in the pathway, for example those described in the Examples herein and in literature. The individual enzyme or protein activities from the exogenous DNA sequences can also be assayed using methods well known in the art. In addition, these enzymes can be engineered using modern protein engineering approaches (Protein Engineering Handbook; Lutz S., & Bornscheuer U. T. Wiley-VCH Verlag GmbH & Co. KGaA: 2008; Vol. 1 & 2) such as directed evolution, rational mutagenesis, computational design (Zanghellini, A et al, 2008) or a combination thereof, for achieving the desired substrate specificity, controlling the stereoselectivity to synthesize enantiopure or racemic products, stabilizing the enzyme to withstand harsh industrial process conditions by improving half-life, thermostability, inhibitor/product tolerance and improving enzyme expression and solubility in the desired microbial production host of choice. Once the desired enzymes that can catalyze each step of the pathway are characterized, the genes encoding these enzymes will be cloned in the microorganism of choice, fermentation conditions will be optimized and product formation will be monitored following fermentation. After the enzymes are identified, the genes corresponding to one or more of the enzymes are cloned into a microbial host. In some embodiments, the genes encoding each enzyme of a particular pathway described herein are cloned into a microbial host.

Methods to introduce recombinant/exogenous nucleic acids/proteins into a microorganism, and vectors suitable for this purpose, are well known in the art. For example, various techniques are illustrated in Current Protocols in Molecular Biology, Ausubel et al., eds. (Wiley & Sons, New York, 1988, and quarterly updates). Methods for transferring expression vectors into microbial host cells are well known in the art. Specific methods and vectors may differ depending upon the species of the desired microbial host. For example, bacterial host cells may be transformed by heat shock, calcium chloride treatment, electroporation, liposomes, or phage infection. Yeast host cells may be transformed by lithium acetate treatment (may further include carrier DNA and PEG treatment) or electroporation. These methods are included for illustrative purposes and are in no way intended to be limiting or comprehensive. Routine experimentation through means well known in the art may be used to determine whether a particular expression vector or transformation method is suited for a given microbial host. Furthermore, reagents and vectors suitable for many different microbial hosts are commercially available and well known in the art.

Methods for construction, expression or overexpression of enzymes and testing the expression levels in non-naturally occurring microbial hosts are well known in art (Protein Expression Technologies: Current Status and Future Trends, Baneyx F. eds. Horizon Bioscience, 2004, Norfolk, UK; and Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999)).

Methods for carrying out fermentation of microorganisms are well known in art. For example, various techniques are illustrated in Biochemical Engineering, Clark et al., eds. (CRC press, 1997, $2^{nd}$ edition). Specific methods for fermenting may differ depending upon the species of the desired microbial host. Typically, the microorganism is grown in appropriate media along with the carbon source in a batch or a continuous fermentation mode. The use of agents known to modulate catabolite repression or enzyme activity can be used to enhance adipic acid or glutaric acid production. Suitable pH for fermentation is between 3-10. Fermentation can be performed under aerobic, anaerobic, or anoxic conditions based on the requirements of the microorganism. Fermentations can be performed in a batch, fed-batch or continuous manner. Fermentations can also be conducted in two phases, if desired. For example, the first phase can be aerobic to allow for high growth and therefore high productivity, followed by an anaerobic phase of high caprolactone yields.

The carbon source can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the present disclosure include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the present disclosure for the production of desired compound.

The reactions described herein can be monitored and the starting materials, the products or intermediates in the fermentation media can be identified by analyzing the media using high pressure liquid chromatography (HPLC) analysis, GC-MS (Gas Chromatography-Mass Spectroscopy) and LC-MS (Liquid Chromatography-Mass Spectroscopy) or other suitable analytical methods using routine procedures well known in the art.

Any of the non-naturally occurring microbial organisms described herein can be cultured to produce and/or secrete the products of the present disclosure.

Compounds prepared by the methods described herein can be isolated by methods generally known in the art for isolation of an organic compound prepared by biosynthesis or fermentation. For example, the compounds can be isolated from solution by crystallization, salt formation, pervaporation, reactive extraction, extraction (liquid-liquid and two-phase), adsorption, ion exchange, dialysis, distillation, gas stripping, and membrane based separations (Roffler et al., Trends Biotechnolgy.2: 129-136 (1984)). 1,5-Pentanediol can be isolated from solution using distillation, extraction (liquid-liquid and two-phase), pervaporation, and membrane based separations (Roffler et al., Trends Biotechnolgy.2: 129-136 (1984)).

As described herein, one exemplary growth condition for achieving biosynthesis of desired product includes anaerobic culture or fermentation conditions. In certain embodiments, the non-naturally occurring microbial organisms of the present disclosure can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also include growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of products. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production in commercial quantities.

The term "pathway enzyme expressed in a sufficient amount" implies that the enzyme is expressed in an amount that is sufficient to allow detection of the desired pathway product.

In another aspect, provided herein is a recombinant microbial organism comprising a first exogenous nucleic acid encoding an aldolase hydratase enzyme, wherein the recombinant microbial organism is further modified to express an increased amount of quinone oxidoreductase as compared to wild-type or the same microbial organism that is not modified, and optionally wherein the microbial organism is *Corynebacterium glutamicum*, a *clostridium* species, or *E. coli*.

In some embodiments, the organism comprises a second exogenous nucleic acid encoding quinone oxidoreductase. In some embodiments, the first exogenous nucleic acid and/or the second exogenous nucleic acid further comprises a regulatory element that drives expression of the second exogenous nucleic acid. In some embodiments, the first exogenous nucleic acid and the second exogenous nucleic acid further comprises a regulatory element that drives expression of the second exogenous nucleic acid. In some embodiments, the first exogenous nucleic acid or the second exogenous nucleic acid further comprises a regulatory element that drives expression of the second exogenous nucleic acid. In some embodiments, the first exogenous nucleic acid further comprises a regulatory element that drives expression of the second exogenous nucleic acid. In some embodiments, the second exogenous nucleic acid further comprises a regulatory element that drives expression of the second exogenous nucleic acid. In some embodiments, the regulatory element is selected from a promoter or an enhancer. In some embodiments, the regulatory element is a promoter. In some embodiments, the regulatory element is an enhancer.

In some embodiments, the aldolase hydratase enzyme has an EC number 4.1.2.45, EC number 4.1.2.34 or EC number 4.1.1.4. In some embodiments, the aldolase hydratase enzyme is an enzyme selected from the group of enzymes identified under Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP 107818191, A0A023WZF9, PYN48855, A0A421PAQ6, WP_028217297, WP_034507049, KMK64081.1, WP_070028041.1, or KZL92449.1. In some embodiments, the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1, or a portion (e.g., a domain, a set of amino acid residues (can be continuous or separated), etc.) thereof that promotes the formation of a aldol-dehydration product. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase is an enzyme selected from Tables 1, 5, 6, 7, and 8. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from Tables 1, 5, 6, 7, and 8.

In some embodiments, the hydratase-aldolase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the first exogenous nucleic acid and the second exogenous nucleic acid are each contained in a vector. In some embodiments, the first exogenous nucleic acid and the second exogenous nucleic acid are each contained in the same vector. In some embodiments, the first exogenous nucleic acid and the second exogenous nucleic acid are each contained in their own separate vectors. In some embodiments, the vector is a plasmid. In some embodiments, the vector is a viral vector.

In some embodiments, the quinone oxidoreductase is an enzyme having an EC number 1.6.5. In some embodiments, the quinone oxidoreductase is an enzyme having an EC number 1.6.5.5. In some embodiments, the quinone oxidoreductase is an enzyme selected from the group of enzymes identified under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP 012333034.1, or WP_136898000.1. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the recombinant microbial organism is capable of producing a 2-keto carboxylic acid of formula:

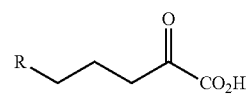

wherein R is H, $CH_3$, or $CH_2OH$.

In some embodiments, the recombinant microbial organism is capable of producing 1,5-pentanediol, 1,6-hexanediol, adipic acid, or 6-hydroxy hexanoate.

In some embodiments, the recombinant microbial organism is genetically modified to improve production of pyruvate from a carbon source. In some embodiments, the carbon source is selected from glycerol, glucose, xylose, arabinose, galactose, mannose, fructose, sucrose, and starch, or a combination thereof.

In another aspect, provided herein is a population of recombinant microbial organisms disclosed herein. In some embodiments, the population is substantially homogenous. In some embodiments, substantially homogenous refers to at least 90%, 91%, 92%, 93%, 94%, 95%, 96%, 97%, 98%, or 99%, or more, homogenous.

In another aspect, provided herein is a method of producing 1,5-pentanediol, 1,6-hexanediol, adipic acid, or 6-hydroxy hexanoate, comprising culturing the population disclosed herein under suitable conditions. In some embodiments, the method further comprises isolating the 1,5-pentanediol, 1,6-hexanediol, adipic acid, or 6-hydroxy hexanoate from the culture or the microbial organisms.

Detailed Description of Certain Embodiments

Among other things, the present disclosure encompasses the recognition that certain polypeptides, e.g., various aldol-dehydration product biosynthesis polypeptides which are or comprise hydratase-aldolase polypeptides, can be utilized to effectively produce various compounds. In some embodiments, the present disclosure demonstrates that various aldehydes, e.g., various aliphatic aldehydes described herein, which are structurally different from natural and/or known aldehyde substrates of such polypeptides, can be utilized for effective manufacturing of many products using aldol-dehydration product biosynthesis polypeptide described herein. Among other things, the present disclosure demonstrates that production of various aldol-dehydration products can be catalyzed by a single aldol-dehydration product biosynthesis polypeptide (e.g., various hydratase-aldolase polypeptides as described herein).

In some embodiments, the present disclosure provides a method comprising:

contacting pyruvate and an aldehyde with an aldol-dehydration product biosynthesis polypeptide so that an aldol-dehydration product is produced, wherein:

the aldol-dehydration product is a compound comprising an aldehyde or ketone group and a double bond conjugated with the aldehyde or ketone group.

In some embodiments, an aldehyde is an aliphatic aldehyde. In some embodiments, a —CHO group of an aldehyde is not conjugated, e.g., to a double bond, a triple bond or an aromatic group.

In some embodiments, the present disclosure provides a method comprising:

contacting pyruvate and an aliphatic aldehyde with an aldol-dehydration product biosynthesis polypeptide so that an aldol-dehydration product is produced, wherein:

the carbonyl group of the aliphatic aldehyde is not conjugated to a alkenyl, alkynyl, or aromatic group; and the aldol-dehydration product is a compound comprising an aldehyde or ketone group and a double bond conjugated with the aldehyde or ketone group.

In some embodiments, an aldol-dehydration product biosynthesis polypeptide is or comprises a hydratase-aldolase polypeptide, e.g., those exemplified herein. In some embodiments, provided methods comprise contacting pyruvate and an aliphatic aldehyde with a hydratase-aldolase to produce an aldol-dehydration product.

In some embodiments, an aldol-dehydration product biosynthesis polypeptide comprises an aldolase polypeptide. In some embodiments, an aldol-dehydration product biosynthesis polypeptide comprises a hydratase polypeptide. In some embodiments, an aldol-dehydration product biosynthesis polypeptide comprises a hydratase-aldolase polypeptide. In some embodiments, an aldol-dehydration product biosynthesis polypeptide is a hydratase-aldolase polypeptide. In some embodiments, a hydratase-aldolase polypeptide is or comprises a hydratase-aldolase as described herein, e.g., an enzyme having an EC number 4.1.2.45 or EC number 4.1.2.34, or EC 4.1.1.4, or is selected from Tables 1 and 5-8.

In some embodiments, an aldol-dehydration product biosynthesis polypeptide is within an organism, e.g., a microbe. In some embodiments, an organism expresses an engineered aldol-dehydration product biosynthesis polypeptide. In some embodiments, an organism expresses an increased level and/or activity of aldol-dehydration product biosynthesis polypeptide. In some embodiments, an organism provides an increased rate and/or yield for producing an aldol-dehydration product. In some embodiments, an organism provides an increased substrate utilization for producing an aldol-dehydration product.

In some embodiments, conversion of pyruvate and an aliphatic aldehyde into an aldol-dehydration product is catalyzed by an aldol-dehydration product biosynthesis polypeptide.

In some embodiments, an aldol-dehydration product can be provided through alternative pathways. In some embodiments, an aldol-dehydration product is produced from an aldol product.

In some embodiments, the present disclosure provides a method comprising:

contacting pyruvate and an aldehyde with an aldol product biosynthesis polypeptide so that an aldol product is produced, wherein:

the aldol-dehydration product is a compound comprising an aldehyde or ketone group and a double bond conjugated with the aldehyde or ketone group.

In some embodiments, an aldehyde is an aliphatic aldehyde. In some embodiments, a —CHO group of an aldehyde is not conjugated to a double bond, triple bond or an aromatic group.

In some embodiments, the present disclosure provides a method comprising:

contacting pyruvate and an aliphatic aldehyde with an aldol product biosynthesis polypeptide so that an aldol product is produced, wherein:

the carbonyl group of the aliphatic aldehyde is not conjugated to a alkenyl, alkynyl, or aromatic group; and the aldol product is a compound comprising an aldehyde or ketone group and a hydroxyl group attached to a beta-carbon of an aldehyde or ketone carbonyl group.

Various methods of the present disclosure comprise utilization of biosynthesis polypeptides. In some embodiments, a biosynthesis polypeptide, when used together with a particular product, e.g., an aldol product biosynthesis polypeptide, a reduction product biosynthesis polypeptide, etc., refers to a polypeptide that is involved in the synthesis of the particular product. In some embodiments, a biosynthesis polypeptide when used together with a particular product is or comprises an enzyme that catalyzes formation of the particular product. In some embodiments, a biosynthesis polypeptide has an amino acid sequence that is found in nature, for example in a microbe (e.g., in a reference biosynthesis polypeptide for a particular product found in nature). Alternatively or additionally, in some embodiments, a biosynthesis polypeptide shares a characteristic sequence element and/or an overall percent identity with an appropriate reference biosynthesis polypeptide (e.g., as is found in nature and/or is presented herein (e.g., in one or more of relevant Tables) or a portion thereof (e.g., a portion (e.g., a domain (e.g., a relevant catalytic domain) and/or a set of amino acid residues (which can be continuous or separated)) that promotes a relevant reaction).

In some embodiments, an aldol product biosynthesis polypeptide is or comprises an aldolase polypeptide. Those skilled in the art reading the present disclosure appreciate that various aldolase polypeptides can be utilized in accordance with the present disclosure. In some embodiments, an aldolase polypeptide is or comprises an aldolase described in US20170044551, the aldolases of which are incorporated herein by reference.

In some embodiments, an aldol product biosynthesis polypeptide is or comprises an aldolase-hydratase as described herein.

In some embodiments, an aldol product biosynthesis polypeptide is in an organism such as a microbe. In some embodiments, organisms are engineered to express an engineered or exogenous aldol product biosynthesis polypeptides, often at higher protein levels and/or activity levels. In some embodiments, conversion of pyruvate and an aliphatic aldehyde into an aldol product is catalyzed by an aldol product biosynthesis polypeptide. In some embodiments, a method is performed in a culture, e.g., a bacteria culture. As for other biosynthesis polypeptides, aldol product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldol product is converted into an aldol-dehydration product, either catalyzed by an enzyme, through biosynthesis, or through traditional organic synthesis without enzymatic catalysis. In some embodiments, a conversion comprises contacting an aldol product with a dehydration product biosynthesis polypeptide so that an aldol-dehydration product is produced. In some embodiments, a dehydration product biosynthesis polypeptide is or comprises a hydratase. In some embodiments, a dehydration product biosynthesis polypeptide is or comprises a dehydratase. In some embodiments, a hydratase or dehydratase is described in US20170044551, the hydratases and dehydratases of which are incorporated herein by reference. As for other biosynthesis polypeptides, dehydration product biosynthesis polypeptides may be in organisms such as bacteria, may be engineered, and/or may be expressed at increased at increased protein and/or activity levels, and their products may be generated at increased rates and/or yields and/or substrates utilization.

As appreciated by those skilled in the art, aldol-dehydration products can be utilized to manufacture various products, e.g., 1,5-pentanediol, 1,6-hexanediol, 6HH, adipic acid, etc. which can be utilized to manufacture a wide range of products, such as polymers, resins, coating products, etc. In some embodiments, utilization of aldol-dehydration products comprises one or more chemical conversions, each of which may be independently catalyzed by a polypeptide (e.g., an enzyme described herein), optionally in an organism, or performed through traditional chemical processes without utilization of enzymes. As appreciated by those skilled in the art, one or more or all steps can be performed in one or more organisms, each of which may independently perform one or more reactions using substrate(s) generated within itself or from outside of the organism, and/or one or more cultures which independently comprises one or more types of organisms (each of which may independently perform one or more reactions using substrate(s) generated within itself or from a culture (e.g., a feed compound, a compound generated by another organism, etc.)). In some embodiments, one or more or all biosynthesis polypeptides are independently in one organism, e.g., an bacterium optionally engineered. In some embodiments, one or more of a set of biosynthesis polypeptides for producing a product is expressed in one organism, e.g., an bacterium optionally engineered, and one or more of the other biosynthesis polypeptides in the set is expressed in one or more other organisms, e.g., bacteria optionally engineered. In some embodiments, an organism, e.g., a bacterium is engineered to contain one or more exogenous nucleic acids that encode one or more or all of the biosynthesis polypeptides. In some embodiments, manufacturing of a product comprises multiple steps of reactions which are performed in a single culture comprising one or more bacteria each independently comprises one or more or all, and together comprise all, required biosynthesis polypeptides. In some embodiments, manufacturing of a product comprises multiple steps of reactions which are performed in two or more cultures each independently comprising one or more bacteria each independently comprises one or more or all, and together comprise all, required biosynthesis polypeptides.

For example, in some embodiments, double bonds in aldol-dehydration products are converted to single bonds.

In some embodiments, the present disclosure provides a method comprising:

contacting an alkene with an alkene reduction product biosynthesis polypeptide so that an alkene reduction product is produced, wherein:

the alkene comprises a double bond conjugated to a carbonyl group; and a double bond conjugated to a carbonyl group in the alkene is reduced to a single bond to provide an alkene reduction product.

In some embodiments, an alkene is an aldol-dehydration product.

In some embodiments, an alkene reduction product biosynthesis polypeptide is or comprises an enzyme that catalyze reduction of aldol-dehydration product, e.g., 2-oxo-3-enoic acids, as described herein. In some embodiments, such an enzyme is a quinone oxidoreductase as described herein. In some embodiments, such an enzyme belongs to EC 1.6.5. In some embodiments, such an enzyme belongs to EC 1.6.5.5. In some embodiments, such an enzyme is selected from Table 9.

In some embodiments, alkene reduction product biosynthesis polypeptide is within an organism, e.g., a microbe. In some embodiments, an organism expresses an engineered alkene reduction product biosynthesis polypeptide. In some embodiments, an organism expresses an increased level and/or activity of alkene reduction product biosynthesis polypeptide. In some embodiments, an organism provides an increased rate and/or yield for producing an alkene reduction product. In some embodiments, an organism provides an increased substrate utilization for producing an alkene reduction product.

In some embodiments, an alkene reduction product biosynthesis polypeptide is or comprises an enzyme that encoded and/or expressed by an organism endogenously without engineering.

Those skilled in the art reading the present disclosure appreciate that various aldehydes may be utilized in accordance with the present disclosure. In some embodiments, an aldehyde is a natural or known substrate of a biosynthesis polypeptide, e.g., aldol-dehydration product biosynthesis polypeptide which is or comprises a hydratase-aldolase. In some embodiments, an aldehyde is not a natural or known substrate. For example, among other things, the present disclosure demonstrates that aliphatic aldehydes can be utilized for product manufacturing using hydratase-aldolases whose natural or known substrates are aromatic or conjugated aldehydes.

In some embodiments, an aldehyde is an aliphatic aldehyde. In some embodiments, an aldehyde has one or two alpha-hydrogen. In some embodiments, an aldehyde has the structure of formula A-1:

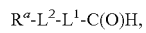

$$R^a\text{-}L^2\text{-}L^1\text{-}C(O)H, \qquad\qquad \text{A-1}$$

or a salt thereof, wherein:

$R^a$ is R" or —OR", each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO$_2$R', or —SO$_2$R$^1$;

R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more $R^1$ groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, an aldol product has the structure of formula P-1:

$$R^a\text{-}L^2\text{-}L^1\text{-}CH(OH)\text{---}CH_2\text{---}C(O)\text{---}C(O)OH, \quad \text{P-1}$$

or a salt thereof, wherein:
$R^a$ is R" or —OR",
each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
each R" is independently —R$^1$, —C(O)R$^1$, —CO$_2$R$^1$, or —SO$_2$R$^1$;
R$^1$ is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
two or more R$^1$ groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, an aldol-dehydration product has the structure of formula P-2:

$$R^a\text{-}L^2\text{-}L^1\text{-}CH\text{=}CH\text{---}C(O)\text{---}C(O)OH, \quad \text{P-2}$$

or a salt thereof, wherein:
$R^a$ is R" or —OR",
each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
each R" is independently —R', —C(O)R', —CO$_2$R', or —SO$_2$R';
R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
two or more R$^1$ groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, —CH=CH— in formula P-2 is in E configuration. In some embodiments, —CH=CH— in formula P-2 is in Z configuration.

In some embodiments, an alkene reduction product has the structure of formula P-3:

$$R^a\text{-}L^2\text{-}L^1\text{-}CH_2\text{---}CH_2\text{---}C(O)\text{---}C(O)OH, \quad \text{P-3}$$

or a salt thereof, wherein:
$R^a$ is R" or —OR",
each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
each R" is independently —R', —C(O)R', —CO$_2$R', or —SO$_2$R';
R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, $R^a$ is R". In some embodiments, $R^a$ is —OR".

In some embodiments, R" is R'. In some embodiments, R" is —C(O)R'. In some embodiments, R" is —CO$_2$R'. In some embodiments, R" is —SO$_2$R'.

In some embodiments, R' is hydrogen. In some embodiments, R' is not hydrogen.

In some embodiments, $R^a$ is R'. In some embodiments, $R^a$ is —OR'. In some embodiments, $R^a$ is —H. In some embodiments, $R^a$ is —OH.

In some embodiments, $L^1$ is a covalent bond. In some embodiments, $L^1$ is not a covalent bond.

In some embodiments, $L^1$ is optionally substituted $C_{1-6}$ alkylene. In some embodiments, $L^1$ is optionally substituted linear $C_{1-6}$ alkylene. In some embodiments, $L^1$ is optionally substituted —CH$_2$—. In some embodiments, $L^1$ is optionally substituted —CH$_2$CH$_2$—. In some embodiments, $L^1$ is optionally substituted —CH$_2$CH$_2$CH$_2$—. In some embodiments, $L^1$ is optionally substituted —CH$_2$CH$_2$CH$_2$CH$_2$—. In some embodiments, $L^1$ is optionally substituted —CH$_2$CH$_2$CH$_2$CH$_2$CH$_2$—. In some embodiments, $L^1$ is optionally substituted —CH$_2$CH$_2$CH$_2$CH$_2$CH$_2$CH$_2$—. In some embodiments, —CH$_2$— bonded to —C(O)H is unsubstituted. In some embodiments, —CH$_2$— bonded to —C(O)H is mono-substituted. In some embodiments, $L^1$ is substituted. In some embodiments, $L^1$ is unsubstituted. In some embodiments, $L^1$ is —$CH_2$—. In some embodiments, $L^1$ is —$CH_2CH_2$—. In some embodiments, $L^1$ is —$CH_2CH_2CH_2$—. In some embodiments, $L^1$ is —$CH_2CH_2CH_2CH_2$—. In some embodiments, $L^1$ is —$CH_2CH_2CH_2CH_2CH_2$—. In some embodiments, $L^1$ is —$CH_2CH_2CH_2CH_2CH_2CH_2$—.

In some embodiments, $L^2$ is a covalent bond. In some embodiments, $L^2$ is not a covalent bond.

In some embodiments, $L^2$ is optionally substituted $C_{1-6}$ alkylene. In some embodiments, $L^2$ is optionally substituted linear $C_{1-6}$ alkylene. In some embodiments, $L^2$ is optionally substituted —$CH_2$—. In some embodiments, $L^2$ is optionally substituted —$CH_2CH_2$—. In some embodiments, $L^2$ is optionally substituted —$CH_2CH_2CH_2$—. In some embodiments, $L^2$ is optionally substituted —$CH_2CH_2CH_2CH_2$—. In some embodiments, $L^2$ is optionally substituted —$CH_2CH_2CH_2CH_2CH_2$—. In some embodiments, $L^2$ is optionally substituted —$CH_2CH_2CH_2CH_2CH_2CH_2$—. In some embodiments, —$CH_2$— bonded to —C(O)H is unsubstituted. In some embodiments, —$CH_2$— bonded to —C(O)H is mono-substituted. In some embodiments, $L^2$ is substituted. In some embodiments, $L^2$ is unsubstituted. In some embodiments, $L^2$ is —$CH_2$—. In some embodiments, $L^2$ is —$CH_2CH_2$—. In some embodiments, $L^2$ is —$CH_2CH_2CH_2$—. In some embodiments, $L^2$ is —$CH_2CH_2CH_2CH_2$—. In some embodiments, $L^2$ is —$CH_2CH_2CH_2CH_2CH_2$—. In some embodiments, $L^2$ is —$CH_2CH_2CH_2CH_2CH_2CH_2$—.

In some embodiments, at least one of $L^1$ and $L^2$ is not a covalent bond.

In some embodiments, an aldehyde is $CH_3CHO$. In some embodiments, an aldehyde is $CH_3CH_2CHO$. In some embodiments, an aldehyde is $CH_3CH_2CH_2CHO$. In some embodiments, an aldehyde is $CH_2OHCHO$. In some embodiments, an aldehyde is $CH_2OHCH_2CHO$. In some embodiments, an aldehyde is $CH_2OHCH_2CH_2CHO$.

In some embodiments, an aldol product is $CH_3CH(OH)CH_2C(O)COOH$. In some embodiments, an aldol product is $CH_3CH_2CH(OH)CH_2C(O)COOH$. In some embodiments, an aldol product is $CH_3CH_2CH_2CH(OH)CH_2C(O)COOH$. In some embodiments, an aldol product is $CH_2OHCH(OH)CH_2C(O)COOH$. In some embodiments, an aldol product is $CH_2OHCH_2CH(OH)CH_2C(O)COOH$. In some embodiments, an aldol product is $CH_2OHCH_2CH_2CH(OH)CH_2C(O)COOH$.

In some embodiments, an aldol-dehydration product is $CH_3CH=CHC(O)COOH$. In some embodiments, an aldol-dehydration product is $CH_3CH_2CH=CHC(O)COOH$. In some embodiments, an aldol-dehydration product is $CH_3CH_2CH_2CH=CHC(O)COOH$. In some embodiments, an aldol-dehydration product is $CH_2OHCH=CHC(O)COOH$. In some embodiments, an aldol-dehydration product is $CH_2OHCH_2CH=CHC(O)COOH$. In some embodiments, an aldol-dehydration product is $CH_2OH\ CH_2CH_2CH=CHC(O)COOH$.

In some embodiments, an alkene reduction product is $CH_3CH_2CH_2C(O)COOH$. In some embodiments, an alkene reduction product is $CH_3CH_2CH_2CH_2C(O)COOH$. In some embodiments, an alkene reduction product is $CH_3CH_2CH_2CH_2CH_2C(O)COOH$. In some embodiments, an alkene reduction product is $CH_2OHCH_2CH_2C(O)COOH$. In some embodiments, an alkene reduction product is $CH_2OHCH_2CH_2CH_2C(O)COOH$. In some embodiments, an alkene reduction product is $CH_2OHCH_2CH_2CH_2CH_2C(O)COOH$.

In some embodiments, an alkene reduction product is converted into a carbonyl reduction product, either catalyzed by an enzyme, through biosynthesis, or through traditional organic synthesis without enzymatic catalysis. In some embodiments, an alkene reduction product comprises a carbonyl group, and the carbonyl group is converted to —CH(OH)—. In some embodiments, a method comprises contacting an alkene reduction product with a carbonyl reduction product biosynthesis polypeptide so that a carbonyl reduction product is produced, wherein:

the alkene reduction product comprises a carbonyl group; and a carbonyl group of the alkene reduction product is converted to —CH(OH)—.

In some embodiments, a carbonyl reduction product biosynthesis polypeptide is or comprises a reductase. In some embodiments, a carbonyl reduction product biosynthesis polypeptide is or comprises a keto reductase as described herein. In some embodiments, a carbonyl reduction product biosynthesis polypeptide is or comprises a 2-keto acid-2-reductase as described herein. In some embodiments, such an enzyme is a 6-hydroxy-2-oxohexanoate-2-reductase as described herein. In some embodiments, such an enzyme is described in US20170044551, the enzymes of which are incorporated herein by reference.

In some embodiments, conversion of an alkene reduction product into a carbonyl reduction product is catalyzed by a carbonyl reduction product biosynthesis polypeptide.

As for many other biosynthesis polypeptides, carbonyl reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a carbonyl reduction product has the structure of formula P-4:

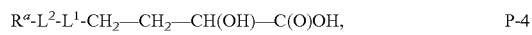

$$R^a\text{-}L^2\text{-}L^1\text{-}CH_2\text{—}CH_2\text{—}CH(OH)\text{—}C(O)OH, \quad \text{P-4}$$

or a salt thereof, wherein each variable is independently as described herein.

In some embodiments, a carbonyl reduction product is $CH_3CH_2CH_2CH(OH)COOH$. In some embodiments, a carbonyl reduction product is $CH_3CH_2CH_2CH_2CH(OH)COOH$. In some embodiments, a carbonyl reduction product is $CH_3CH_2CH_2CH_2CH_2CH(OH)COOH$. In some embodiments, a carbonyl reduction product is $CH_2OHCH_2CH_2CH(OH)COOH$. In some embodiments, a carbonyl reduction product is $CH_2OHCH_2CH_2CH_2CH(OH)COOH$. In some embodiments, a carbonyl reduction product is $CH_2OHCH_2CH_2CH_2CH_2CH(OH)COOH$.

In some embodiments, a carbonyl reduction product is converted into a CoA transfer product, either catalyzed by an enzyme, through biosynthesis, or through traditional organic synthesis without enzymatic catalysis. In some embodiments, a CoA transfer product is a compound of formula P-5:

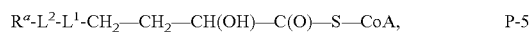

$$R^a\text{-}L^2\text{-}L^1\text{-}CH_2\text{—}CH_2\text{—}CH(OH)\text{—}C(O)\text{—}S\text{—}CoA, \quad \text{P-5}$$

or a salt thereof, wherein each variable is independently as described herein.

In some embodiments, such a conversion is catalyzed by a CoA (CoA=Coenzyme A) transfer product biosynthesis polypeptide. In some embodiments, a CoA transfer product biosynthesis polypeptide is or comprises a CoA transferase as described herein, e.g., 2,6-dihydroxy-hexanoate CoA-transferase. In some embodiments, a CoA transferase is one described in US20170044551, the CoA transferases of which are incorporated herein by reference. In some embodiments, such a conversion is catalyzed by a CoA transfer product biosynthesis polypeptide.

As for many other biosynthesis polypeptides, CoA transfer product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a CoA transfer product is $CH_3CH_2CH_2CH(OH)C(O)S$—CoA. In some embodiments, a CoA transfer product is $CH_3CH_2CH_2CH_2CH(OH)C(O)S$—COA. In some embodiments, a CoA transfer product is $CH_3CH_2CH_2CH_2CH_2CH(OH)C(O)S$—COA. In some embodiments, a CoA transfer product is $CH_2OHCH_2CH_2CH(OH)C(O)S$—COA. In some embodiments, a CoA transfer product is $CH_2OHCH_2CH_2CH_2CH(OH)C(O)S$—COA. In some embodiments, a CoA transfer product is $CH_2OHCH_2CH_2CH_2CH_2CH(OH)C(O)S$—COA.

In some embodiments, a CoA transfer product is converted into a dehydration product, either catalyzed by an enzyme, through biosynthesis, or through traditional organic synthesis without enzymatic catalysis. In some embodiments, a dehydration product is a compound of formula P-6:

$$R^a\text{-}L^2\text{-}L^1\text{-}CH_2\text{—}CH\text{=}CH\text{—}C(O)\text{—}S\text{—}CoA, \qquad \text{P-6}$$

or a salt thereof, wherein each variable is independently as described herein.

In some embodiments, such a conversion is catalyzed by a dehydration product biosynthesis polypeptide. In some embodiments, a dehydration product biosynthesis polypeptide is or comprises a dehydratase as described herein. In some embodiments, a dehydratase is or comprises a 2,6-dihydroxy-hexanoyl-CoA 2-dehydratase as described herein. In some embodiments, a dehydratase is described in US20170044551, the dehydratases of which is incorporated by reference.

In some embodiments, such a conversion is catalyzed by a dehydration product biosynthesis polypeptide.

As for many other biosynthesis polypeptides, dehydration product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a dehydration product is $CH_3CH_2CH$=$CHC(O)S$—CoA. In some embodiments, a dehydration product is $CH_3CH_2CH_2CH$=$CHC(O)S$—COA. In some embodiments, a dehydration product is $CH_3CH_2CH_2CH_2CH$=$CHC(O)S$—COA. In some embodiments, a dehydration product is $CH_2OHCH_2CH$=$CHC(O)S$—COA. In some embodiments, a dehydration product is $CH_2OHCH_2CH_2CH$=$CHC(O)S$—COA. In some embodiments, a dehydration product is $CH_2OHCH_2CH_2CH_2CH$=$CHC(O)S$—COA.

In some embodiments, a dehydration product, e.g. a compound of formula P-6 or a salt thereof, is converted into a reduction product, either catalyzed by an enzyme, through biosynthesis, or through traditional organic synthesis without enzymatic catalysis. In some embodiments, a reduction product is a compound of formula P-7:

$$R^a\text{-}L^2\text{-}L^1\text{-}CH_2\text{—}CH_2\text{—}CH_2\text{—}C(O)\text{—}S\text{—}CoA, \qquad \text{P-7}$$

or a salt thereof, wherein each variable is independently as described herein.

In some embodiments, such a conversion is catalyzed by a reduction product biosynthesis polypeptide. In some embodiments, a reduction product biosynthesis polypeptide is or comprises a 2,3-enoyl-CoA reductase, 2,3-dehydrocarboxyl CoA 2'3-reductase, e.g., 2,3-dehydro-hexanoyl-CoA 2,3-reductase as described herein. In some embodiments, a suitable reductase is described in US20170044551, the reductases of which are incorporated herein by reference. In some embodiments, such a conversion is catalyzed by a reduction product biosynthesis polypeptide.

As for many other biosynthesis polypeptides, reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a reduction product is $CH_3CH_2CH_2CH_2C(O)S$—CoA. In some embodiments, a reduction product is $CH_3CH_2CH_2CH_2CH_2C(O)S$—COA. In some embodiments, a reduction product is $CH_3CH_2CH_2CH_2CH_2CH_2C(O)S$—COA. In some embodiments, a reduction product is $CH_2OHCH_2CH_2CH_2C(O)S$—COA. In some embodiments, a reduction product is $CH_2OHCH_2CH_2CH_2CH_2C(O)S$—COA. In some embodiments, a reduction product is $CH_2OHCH_2CH_2CH_2CH_2CH_2C(O)S$—COA.

In some embodiments, a reduction product, e.g. a compound of formula P-7 or a salt thereof, is converted into a CoA transfer product, either catalyzed by an enzyme, through biosynthesis, or through traditional organic synthesis without enzymatic catalysis. In some embodiments, a CoA transfer product is a compound of formula P-8:

$$R^a\text{-}L^2\text{-}L^1\text{-}CH_2\text{—}CH_2\text{—}CH_2\text{—}C(O)\text{—}OH, \qquad \text{P-8}$$

or a salt thereof, wherein each variable is independently as described herein.

In some embodiments, such a conversion is catalyzed by a CoA transfer product biosynthesis polypeptide. In some embodiments, a CoA transfer product biosynthesis polypeptide is or comprises a CoA transferase as described herein, e.g., a 6-hydroxyhexanoyl-CoA transferase as described herein. In some embodiments, a CoA transferase is described in US20170044551, the CoA transferases of which are incorporated herein by reference. In some embodiments, such a conversion is catalyzed by a CoA transfer product biosynthesis polypeptide.

As for many other biosynthesis polypeptides, CoA transfer product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a CoA transfer product is $CH_3CH_2CH_2CH_2C(O)OH$. In some embodiments, a CoA transfer product is $CH_3CH_2CH_2CH_2CH_2C(O)OH$. In some embodiments, a CoA transfer product is $CH_3CH_2CH_2CH_2CH_2CH_2C(O)OH$. In some embodiments, a CoA transfer product is $CH_2OHCH_2CH_2CH_2C(O)OH$. In some embodiments, a CoA transfer product is $CH_2OHCH_2CH_2CH_2CH_2C(O)OH$. In some embodiments, a CoA transfer product is $CH_2OHCH_2CH_2CH_2CH_2CH_2C(O)OH$.

In some embodiments, a CoA transfer product, e.g. a compound of formula P-8 or a salt thereof wherein $R^a$ is —OH, is converted into an oxidation product, either catalyzed by an enzyme, through biosynthesis, or through traditional organic synthesis without enzymatic catalysis. In some embodiments, an oxidation product is a compound of formula P-9:

$$H\text{—}C(O)\text{-}L^2\text{-}L^1\text{-}CH_2\text{—}CH_2\text{—}CH_2\text{—}C(O)\text{—}OH, \qquad \text{P-9}$$

or a salt thereof, wherein $L^{2'}$ is a covalent bond, or a bivalent, optionally substituted, linear or branched $C_{1-19}$ aliphatic or $C_{1-19}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—, and each other variable is independently as described herein.

In some embodiments, $L^{2'}$ is a covalent bond. In some embodiments, $L^{2'}$ is not a covalent bond. In some embodiments, at least one of $L^1$ and $L^{2'}$ is not a covalent bond.

In some embodiments, $L^{2'}$ is optionally substituted $C_{1-6}$ alkylene. In some embodiments, $L^{2'}$ is optionally substituted linear $C_{1-6}$ alkylene. In some embodiments, $L^{2'}$ is optionally substituted —CH$_2$—. In some embodiments, $L^{2'}$ is optionally substituted —CH$_2$CH$_2$—. In some embodiments, $L^{2'}$ is optionally substituted —CH$_2$CH$_2$CH$_2$—. In some embodiments, $L^{2'}$ is optionally substituted —CH$_2$CH$_2$CH$_2$CH$_2$—. In some embodiments, $L^{2'}$ is optionally substituted —CH$_2$CH$_2$CH$_2$CH$_2$CH$_2$—. In some embodiments, $L^{2'}$ is optionally substituted —CH$_2$CH$_2$CH$_2$CH$_2$CH$_2$CH$_2$—. In some embodiments, —CH$_2$— bonded to —C(O)H is unsubstituted. In some embodiments, —CH$_2$— bonded to —C(O)H is mono-substituted. In some embodiments, $L^{2'}$ is substituted. In some embodiments, $L^{2'}$ is unsubstituted. In some embodiments, $L^{2'}$ is —CH$_2$—. In some embodiments, $L^{2'}$ is —CH$_2$CH$_2$—. In some embodiments, $L^{2'}$ is —CH$_2$CH$_2$CH$_2$—. In some embodiments, $L^{2'}$ is —CH$_2$CH$_2$CH$_2$CH$_2$—. In some embodiments, $L^{2'}$ is —CH$_2$CH$_2$CH$_2$CH$_2$CH$_2$—. In some embodiments, $L^{2'}$ is —CH$_2$CH$_2$CH$_2$CH$_2$CH$_2$CH$_2$—.

In some embodiments, such a conversion is catalyzed by an oxidation product biosynthesis polypeptide. In some embodiments, an oxidation product biosynthesis polypeptide is or comprises an alcohol dehydrogenase, e.g., a primary alcohol dehydrogenase such as 6-hydroxyhexanoate dehydrogenase, as described herein. In some embodiments, an alcohol dehydrogenase is described in US20170044551, the alcohol dehydrogenases of which are incorporated herein by reference. In some embodiments, such a conversion is catalyzed by an oxidation product biosynthesis polypeptide.

As for many other biosynthesis polypeptides, oxidation product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an oxidation product is HC(O)CH$_2$CH$_2$CH$_2$C(O)OH. In some embodiments, an oxidation product is HC(O)CH$_2$CH$_2$CH$_2$CH$_2$C(O)OH. In some embodiments, an oxidation product is HC(O)CH$_2$CH$_2$CH$_2$CH$_2$CH$_2$C(O)OH.

In some embodiments, an oxidation product, e.g. a compound of formula P-9 or a salt thereof, is converted into an aldehyde oxidation product, either catalyzed by an enzyme, through biosynthesis, or through traditional organic synthesis without enzymatic catalysis. In some embodiments, an oxidation product is a compound of formula P-10:

HO—C(O)-L$^{2'}$-L$^1$-CH$_2$—CH$_2$—CH$_2$—C(O)—OH,      P-10 or a salt thereof, wherein each other variable is independently as described herein.

In some embodiments, such a conversion is catalyzed by an aldehyde oxidation product biosynthesis polypeptide. In some embodiments, an aldehyde oxidation product biosynthesis polypeptide is or comprises an aldehyde dehydrogenase, e.g., a 6-hydroxyhexanoate dehydrogenase, as described herein. In some embodiments, an aldehyde dehydrogenase is described in US20170044551, the aldehyde dehydrogenases of which are incorporated herein by reference. In some embodiments, such a conversion is catalyzed by an aldehyde oxidation product biosynthesis polypeptide.

As for many other biosynthesis polypeptides, aldehyde oxidation product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldehyde oxidation product is HOC(O)CH$_2$CH$_2$CH$_2$C(O)OH. In some embodiments, an oxidation product is HOC(O)CH$_2$CH$_2$CH$_2$CH$_2$C(O)OH. In some embodiments, an oxidation product is HOC(O)CH$_2$CH$_2$CH$_2$CH$_2$CH$_2$C(O)OH.

In some embodiments, a CoA transfer product, e.g. a compound of formula P-8 or a salt thereof, is converted into a carboxyl reduction product, either catalyzed by an enzyme, through biosynthesis, or through traditional organic synthesis without enzymatic catalysis. In some embodiments, a carboxyl reduction product is a compound of formula P-9':

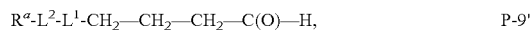
R$^a$-L$^2$-L$^1$-CH$_2$—CH$_2$—CH$_2$—C(O)—H,      P-9' or a salt thereof, wherein each variable is independently as described herein.

In some embodiments, such a conversion is catalyzed by a carboxyl reduction product biosynthesis polypeptide. In some embodiments, a carboxyl reduction product biosynthesis polypeptide is or comprises a carboxylic acid reductase or aldehyde dehydrogenase as described herein. In some embodiments, a carboxyl reduction product biosynthesis polypeptide is or comprises a 6-hydroxyhexanoate 1-reductase. In some embodiments, a carboxyl reduction product biosynthesis polypeptide is or comprises a carboxylic acid reductase or aldehyde dehydrogenase described in US20170044551, the carboxylic acid reductases or aldehyde dehydrogenases of which are incorporated herein by reference. In some embodiments, such a conversion is catalyzed by a carboxyl reduction product biosynthesis polypeptide.

As for many other biosynthesis polypeptides, carboxyl reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a carboxyl reduction product is CH$_3$CH$_2$CH$_2$CH$_2$C(O)H. In some embodiments, a carboxyl reduction product is CH$_3$CH$_2$CH$_2$CH$_2$CH$_2$C(O)H. In some embodiments, a carboxyl reduction product is CH$_3$CH$_2$CH$_2$CH$_2$CH$_2$CH$_2$C(O)H. In some embodiments, a carboxyl reduction product is CH$_2$OHCH$_2$CH$_2$CH$_2$C(O)H. In some embodiments, a carboxyl reduction product is CH$_2$OHCH$_2$CH$_2$CH$_2$CH$_2$C(O)H. In some embodiments, a carboxyl reduction product is CH$_2$OHCH$_2$CH$_2$CH$_2$CH$_2$CH$_2$C(O)H.

In some embodiments, a carboxyl reduction product, e.g. a compound of formula P-9' or a salt thereof, is converted into an aldehyde reduction product, either catalyzed by an enzyme, through biosynthesis, or through traditional organic synthesis without enzymatic catalysis. In some embodiments, an aldehyde reduction product is a compound of formula P-10':

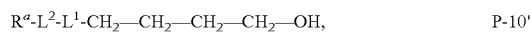
R$^a$-L$^2$-L$^1$-CH$_2$—CH$_2$—CH$_2$—CH$_2$—OH,      P-10' or a salt thereof, wherein each variable is independently as described herein.

In some embodiments, such a conversion is catalyzed by an aldehyde reduction product biosynthesis polypeptide. In some embodiments, an aldehyde reduction product biosynthesis polypeptide is or comprises an aldehyde reductase or an alcohol (e.g., primary alcohol) dehydrogenase as described herein. In some embodiments, an aldehyde reductase or an alcohol (e.g., primary alcohol) dehydrogenase is described in US20170044551, the reductases and dehydrogenases of which are incorporated herein by reference. In some embodiments, such a conversion is catalyzed by an aldehyde reduction product biosynthesis polypeptide.

As for many other biosynthesis polypeptides, aldehyde reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldehyde reduction product is $CH_3CH_2CH_2CH_2CH_2OH$. In some embodiments, an aldehyde reduction product is $CH_3CH_2CH_2CH_2CH_2CH_2OH$. In some embodiments, an aldehyde reduction product is $CH_3CH_2CH_2CH_2CH_2CH_2CH_2OH$. In some embodiments, an aldehyde reduction product is $CH_2OHCH_2CH_2CH_2CH_2OH$. In some embodiments, an aldehyde reduction product is $CH_2OHCH_2CH_2CH_2CH_2CH_2OH$. In some embodiments, an aldehyde reduction product is $CH_2OHCH_2CH_2CH_2CH_2CH_2CH_2OH$.

In some embodiments, an alkene reduction product, e.g. a compound of formula P-3 or a salt thereof, is converted into a decarboxylation product, either catalyzed by an enzyme, through biosynthesis, or through traditional organic synthesis without enzymatic catalysis. In some embodiments, a decarboxylation product is a compound of formula P-4':

$$R^a\text{-}L^2\text{-}L^1\text{-}CH_2\text{—}CH_2\text{—}C(O)\text{—}H, \quad\quad P\text{-}4'$$

or a salt thereof, wherein each variable is independently as described herein.

In some embodiments, such a conversion is catalyzed by a decarboxylation product biosynthesis polypeptide. In some embodiments, a decarboxylation product biosynthesis polypeptide is or comprises a decarboxylase as described herein. In some embodiments, a decarboxylase is a 2-keto-acid decarboxylase as described herein. In some embodiments, a decarboxylase is described in US20170044551, the decarboxylases of which are incorporated herein by reference. In some embodiments, such a conversion is catalyzed by a decarboxylation product biosynthesis polypeptide.

As for many other biosynthesis polypeptides, decarboxylation product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a decarboxylation product is $CH_3CH_2CH_2CHO$. In some embodiments, a decarboxylation product is $CH_3CH_2CH_2CH_2CHO$. In some embodiments, a decarboxylation product is $CH_3CH_2CH_2CH_2CH_2CHO$. In some embodiments, a decarboxylation product is $CH_2OHCH_2CH_2CHO$. In some embodiments, a decarboxylation product is $CH_2OHCH_2CH_2CH_2CHO$. In some embodiments, a decarboxylation product is $CH_2OHCH_2CH_2CH_2CH_2CHO$.

In some embodiments, a decarboxylation product, e.g. a compound of formula P-4' or a salt thereof, is converted into an aldehyde reduction product, either catalyzed by an enzyme, through biosynthesis, or through traditional organic synthesis without enzymatic catalysis. In some embodiments, an aldehyde reduction product is a compound of formula P-5':

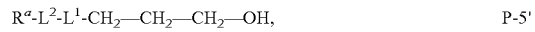

$$R^a\text{-}L^2\text{-}L^1\text{-}CH_2\text{—}CH_2\text{—}CH_2\text{—}OH, \quad\quad P\text{-}5'$$

or a salt thereof, wherein each variable is independently as described herein.

In some embodiments, such a conversion is catalyzed by an aldehyde reduction product biosynthesis polypeptide. In some embodiments, an aldehyde reduction product biosynthesis polypeptide is or comprises a primary alcohol dehydrogenase as described herein. In some embodiments, a primary alcohol dehydrogenase is described in US20170044551, the primary alcohol dehydrogenase of which are incorporated herein by reference. In some embodiments, such a conversion is catalyzed by an aldehyde reduction product biosynthesis polypeptide.

As for many other biosynthesis polypeptides, aldehyde reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldehyde reduction product is $CH_3CH_2CH_2CH_2OH$. In some embodiments, an aldehyde reduction product is $CH_3CH_2CH_2CH_2CH_2OH$. In some embodiments, an aldehyde reduction product is $CH_3CH_2CH_2CH_2CH_2CH_2OH$. In some embodiments, an aldehyde reduction product is $CH_2OHCH_2CH_2CH_2OH$. In some embodiments, an aldehyde reduction product is $CH_2OHCH_2CH_2CH_2CH_2OH$. In some embodiments, an aldehyde reduction product is $CH_2OHCH_2CH_2CH_2CH_2CH_2OH$.

In some embodiments, the present disclosure provides nucleic acids encoding one or more biosynthesis polypeptides. In some embodiments, such nucleic acids comprise unnatural sequences. In some embodiments, such nucleic acids are optimized for expression in production organisms, e.g., bacteria.

As demonstrated herein, various technologies are available for assess activities of polypeptides for biosynthesis activities. For example, various technologies for assessing activities of aldol-dehydration product biosynthesis polypeptides (e.g., hydratase-aldolases) or alkene reduction product biosynthesis polypeptides (e.g., enzymes for reducing aldol-dehydration products) are described in the Examples.

In some embodiments, various biosynthesis polypeptides, e.g., an aldol-dehydration product biosynthesis polypeptide, are in organisms, in many embodiments, microorganisms such as bacteria, fungi, etc. In some embodiments, they are expressed from one or more recombinant nucleic acids. In some embodiments, various transformations are performed biosynthetically, e.g., in organisms such as bacteria. In some embodiments, organisms (e.g., microbes such as bacteria) are engineered to contain exogenous nucleic acids that encode biosynthetic polypeptides, e.g., aldol-dehydration product biosynthesis polypeptides such as hydratase-aldolases.

In some embodiments, organism, e.g., those engineered for producing aldol-dehydration products, express modulated levels, typically increased levels and/or activities of aldol-dehydration product biosynthesis polypeptides such as hydratase-aldolase polypeptides.

In some embodiments, organisms comprise engineered nucleic acids and/or express engineered biosynthesis polypeptides, e.g., aldol-dehydration product biosynthesis polypeptides (e.g., various hydratase-aldolases). In some embodiments, an engineered nucleic acid comprises one or more sequence difference compared to a reference nucleic acid. In some embodiments, a reference nucleic acid is a corresponding nucleic acid in an organism to which an engineered nucleic acid is introduced. In some embodiments, a reference nucleic acid is a natural nucleic acid. In some embodiments, an engineered nucleic acid encodes the same polypeptide or a characteristic element thereof as a reference nucleic acid, e.g., a natural nucleic acid. In some embodiments, an engineered nucleic acid encodes a polypeptide or a characteristic element thereof which is different than that encoded by as a reference nucleic acid. In some embodiments, an engineered polypeptide comprises one or more differences compared to a reference polypeptide (e.g., encoded by a reference nucleic acid, found in nature, etc.). In some embodiments, an engineered polypeptide comprises one or more different amino acid residues compared to a reference polypeptide. In some embodiments, an engineered polypeptide is a polypeptide which is absent from an organism to which it is introduced. In some embodiments, an engineered polypeptide is homologous to a reference polypeptide, e.g., sharing 10%, 15%, 20%, 25%, 30%, 35%, 40%, 45%, 50%, 55%, 60%, 65%, 70%, 75%, 80%, 85%, 90%, 95%, 96%, 97%, 95%, 99% or more homology with a reference polypeptide or a characteristic element thereof. In some embodiments, a characteristic element is a domain which catalyzes a relevant reaction. In some embodiments, a characteristic element is a set of amino acid residues. In some embodiments, a characteristic element is a set of amino acid residues that form contact with substrates, products, co-factors, etc. and/or promotes a relevant reaction. As appreciated by those skilled in the art, residues in a set of amino acid residues can be next to each other in sequence, or can be separated. In some embodiments, two or more amino acid residues in a set may be spatially close to each other, e.g., in a catalytic pocket.

In some embodiments, for biosynthetic productions, organisms may express high levels and/or activities of one or more biosynthetic polypeptides. In some embodiments, an organism provides an increased rate and/or yield for producing a desired product.

As described herein, in some embodiments, the present disclosure provides high product yields. In some embodiments, a yield, e.g., of a one or multiple step process involving one or more biosynthesis polypeptides, is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. In some embodiments, provided technologies provide high utilization of a substrate, e.g., pyruvate, for a desired product. In some embodiments, the utilization percentage for a desired product is at least about 5%, 10%, 15%, 20%, 25%, 30%, 35%, 40%, 45%, 50%, 55%, 60%, 65%, 70%, 75%, 80%, 85%, 90%, or 95%.

Those skilled in the art appreciate that various compounds of the present disclosure, e.g., compounds of formula P-1, P-2, P-3, P-4, P-4', P-5, P-5', P-6, P-7, P-8, P-9, P-9', P-10, or P-10', or salts thereof, are useful as materials for production of various compounds, materials and products. For example, adipic acid can be used to produce nylon 6,6, polyester polyols, polyester resins, plasticizers, foods, and other materials. 1,5-Pentanediol can be used to manufacture various polyurethanes, polyester polyols, and polyesters. 1,6-Hexanediol (HDO) can be used to manufacture various polyesters, some of which are useful for industrial coating applications. HDO can also be utilized to produce polyurethane, which among other things can be used as coatings for automotive applications. In some embodiments, HDO is used for production of macrodiols, for example, adipate esters and polycarbonate diols used in, e.g., elastomers and polyurethane dispersions (e.g., for parquet flooring and leather coatings). Through traditional chemical or through biosynthesis processes or combinations thereof, 6-hydroxy hexanoic acid can be cyclized to make ε-caprolactone which can then be aminated to make ε-caprolactam. Through traditional chemical or through biosynthesis processes or combinations thereof, 6-hydroxy hexanoic acid can be aminated to make 6-amino hexanoic acid which can then be cyclized to make ε-caprolactam. ε-Caprolactam, among other things, can be used for the production of Nylon6, a widely used polymer in many different industries. ε-Caprolactone can be polymerized to make polycaprolactone (PCL) a biodegradable polyester with various applications including for the production of specialty polyurethanes. Various 2-ketocarboxylic acids are useful for various industrial relevant chemicals and pharmaceuticals. In some embodiments, such chemicals and pharmaceuticals, or intermediates thereof, are amino acids or α-hydroxy carboxylic acids. In some embodiments, compounds of the present disclosure are utilized to manufacture polyesters, polyester polyols, polyurethane, nylon (e.g., from adipic acid), polycarbonate diols (e.g., from HDO or 1,5-pentanediol, etc.), diacrylate esters (e.g., from HDO or 1,5-pentanediol, etc.), diglycidyl ethers (e.g., from HDO or 1,5-pentanediol, etc.), etc.

In some embodiments, the present disclosure provides preparations of provided processes, e.g., preparations of compounds of formula P-1, P-2, P-3, P-4, P-4', P-5, P-5', P-6, P-7, P-8, P-9, P-9', P-10, or P-10', or salts thereof, and various compounds, materials, products, etc., prepared from such compounds.

Provided technologies provide a number of advantages. Among other things, provided processes utilize one or more biosynthesis polypeptides and/or materials from renewable sources, which can improve efficiency and/or reduce pollution. In some embodiments, preparations of the present disclosure (e.g., of compounds of formula P-1, P-2, P-3, P-4, P-4', P-5, P-5', P-6, P-7, P-8, P-9, P-9', P-10, or P-10', or salts thereof, and various compounds, materials, products, etc., prepared from such compounds) comprise enriched levels of one or more isotopes, e.g., $^{14}C$, compared to those prepared from fossil carbon sources. In some embodiments, preparations using fossil carbon sources have a $^{14}C$ level of 0 or virtually 0. Technologies for assessing isotopic ratios and/or levels of various atoms in compounds, compositions, preparations products, etc., are well known to those skilled in the art and can be utilized in accordance with the present disclosure. For example, in some embodiments, isotopic enrichment can be readily assessed by mass spectrometry using techniques such as accelerated mass spectrometry (AMS) and/or Stable Isotope Ratio Mass Spectrometry (SIRMS), and/or by Site-Specific Natural Isotopic Fractionation by Nuclear Magnetic Resonance (SNIF-NMR).

As appreciated by those skilled in the art, provided methods can be performed in vitro in a system comprising one or more biosynthesis polypeptides. In many embodiments, provided technologies are performed using organisms, e.g., microorganisms such as bacteria, that express one or more biosynthesis polypeptides. In some embodiments, the present disclosure provides organisms, e.g., bacteria, that express one or more biosynthesis polypeptides as described herein. In some embodiments, such organisms are engineered. In some embodiments, such organisms are engineered and/or cultured to express increased levels of proteins and/or activities of one or more biosynthesis polypeptides. In some embodiments, such organisms are engineered and/or cultured to utilize carbon sources to more efficiently produce desired products.

In some embodiments, the present disclosure provides an organism that produces an aldol product of an aliphatic aldehyde, the microbe comprising increased expression or activity of an aldol product biosynthesis polypeptide. In some embodiments, an organism is engineered. In some embodiments, an organism is a bacterium.

In some embodiments, the present disclosure provides an organism that produces an aldol-dehydration product of an aldehyde, the microbe comprising increased expression or activity of an aldol product biosynthesis polypeptide, an aldol-dehydration product biosynthesis polypeptide, a dehydration product biosynthesis polypeptide, and combinations thereof. In some embodiments, the present disclosure provides an organism that produces an aldol-dehydration product of an aldehyde, the microbe comprises increased expression or activity of an aldol-dehydration product biosynthesis polypeptide. In some embodiments, an organism is engineered. In some embodiments, an organism is a bacterium. In some embodiments, an aldehyde is an aliphatic aldehyde.

In some embodiments, the present disclosure provides an organism that produces an alkene reduction product, the microbe comprising increased expression or activity of an alkene reduction product biosynthesis polypeptide. In some embodiments, the present disclosure provides an organism that produces an alkene reduction product from pyruvate and an aldehyde, the microbe comprising increased expression or activity of an alkene reduction product biosynthesis polypeptide. In some embodiments, an organism is engineered. In some embodiments, an organism is a bacterium.

In some embodiments, the present disclosure provides cultures of organisms as described herein. In some embodiments, the present disclosure provides cultures of bacteria. In some embodiments, a culture comprises one or more products of one or more biosynthesis polypeptides, e.g., one or more compounds of formula P-1, P-2, P-3, P-4, P-4', P-5, P-5', P-6, P-7, P-8, P-9, P-9', P-10, or P-10', or salts thereof.

As appreciated by those skilled in the art, pyruvate may be provided as pyruvic acid or a salt thereof.

In one aspect, provided herein is a method for preparing a compound of Formula I:

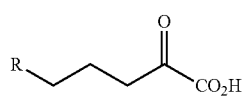

wherein R is CH$_2$OH, CH$_3$ or H,
or a salt thereof, or a solvate of the compound or the salt, wherein the method comprises enzymatic steps.

In some embodiments, the method comprises, or alternatively consists essentially of, or yet further consists of, combining or incubating a C$_N$ aldehyde of formula

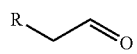

wherein R is CH$_2$OH, CH$_3$ or H, and a pyruvate in a solution under conditions that (a) convert the C$_N$ aldehyde and the pyruvate to a C$_{N+3}$ 3,4-dehydro-2-keto-carboxylic acid intermediate through an aldol condensation reaction catalyzed by a hydratase-aldolase having an EC number 4.1.2.45 or EC number 4.1.2.34 or EC number 4.1.1.4 (referred herein as Ads-Hyd); and then (b) convert the C$_{N+3}$ 3,4-dehydro-2-keto-carboxylic acid to C$_{N+3}$ 2-keto-carboxylic acid (i.e., the compound of Formula I), or salt thereof, or a solvate of the compound or the salt, using a oxidoreductase having an EC number 1.6.5. (e.g., EC number 1.6.5.5.).

In some embodiments, the method comprises, or alternatively consists essentially of, or yet further consists of, combining or incubating a C$_N$ aldehyde of formula

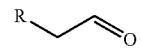

wherein R is CH$_2$OH, CH$_3$ or H, and a pyruvate in a solution under conditions that (a) convert the C$_N$ aldehyde and the pyruvate first to a C$_{N+3}$ 4-hydroxy-2-keto-carboxylic acid intermediate through an aldol addition reaction catalyzed by a hydratase-aldolase having an EC number 4.1.2.45 or EC number 4.1.2.34 or EC number 4.1.1.4 (referred herein as Ads-Hyd); then (b) convert 4-hydroxy-2-keto-carboxylic acid to C$_{N+3}$ 3,4-dehydro-2-keto-carboxylic acid using the hydratase-aldolase; and then (c) convert the C$_{N+3}$ 3,4-dehydro-2-keto-carboxylic acid to C$_{N+3}$ 2-keto-carboxylic acid (i.e., the compound of Formula I), or salt thereof, or a solvate of the compound or the salt, using a oxidoreductase having an EC number 1.6.5. (e.g., EC number 1.6.5.5.)

In another aspect, provided herein is a method for preparing a compound selected from 1,5-pentanediol, adipic acid, 1,6-hexanediol, and 6-hydroxy hexanoic acid, said method comprising, or alternatively consisting essentially of, or yet further consisting of: a) converting a 3-hydroxypropanal and a pyruvate to a 6-hydroxy-2-keto carboxylic acid intermediate using a combination of a hydratase-aldolase having an EC number 4.1.2.45 or EC number 4.1.2.34 or EC number 4.1.1.4 and a oxidoreductase having an EC number 1.6.5 (e.g., EC number 1.6.5.5); and b) converting the 6-hydroxy-2-keto carboxylic acid intermediate to the compound through enzymatic steps.

In some embodiments, the hydratase-aldolase is a trans-o-hydroxybenzylidenepyruvate hydratase-aldolase having an EC number 4.1.2.45. In some embodiments, the hydratase-aldolase is a trans-2'-carboxybenzalpyruvate hydratase-aldolase having an EC number 4.1.2.34. In some embodiments, the hydratase-aldolase is a Acetoacetate decarboxylase having an EC number 4.1.1.4.

In some embodiments, a microorganism is used as a host for the preparation of a compound of Formula I, or a compound selected from 1,5-pentanediol, adipic acid, 1,6-hexanediol, and 6-hydroxy hexanoic acid, or a salt thereof, or a solvate of the compound or the salt. As used herein, a "host" refers to a cell or microorganism that can produce one or more enzymes capable of catalyzing a reaction either inside (by, e.g., uptaking the starting material(s) and optionally secreting the product(s)) or outside (by, e.g., secreting the enzyme) the cell or microorganism.

In some embodiments, the method further comprises or alternatively consists essentially of, or yet further consists of, isolating the compound selected from 1,5-pentanediol, adipic acid, 1,6-hexanediol, and 6-hydroxy hexanoic acid or a salt thereof, or a solvate of the compound or the salt from the solution, culture, and/or the host cell.

In some embodiments, the conditions of the methods disclosed herein comprise or alternatively consist essentially of, or yet further consist of, incubating or contacting the components at a temperature from about 10 to about 200° C., or alternatively at least (all temperatures provided in degrees Celsius) 10, 15, 20, 25, 28, 29, 30, 31, 32, 33, 34, 35, 37, 37, 38, 39, 40, 45, 50, 60, 70, 80, 90, 100, 110, 120, 130, 140, 150, 160, 170, 180 or 190° C., or not higher than 190, 180, 170, 160, 150, 140, 130, 120, 110, 100, 90, 80, 70, 60, 50, 40, 39, 38, 37, 36, 35, 34, 33, 32, 31, 30, 29, 28, or 25° C. with the lower temperature limit being 10° C. In some embodiments, the conditions or alternatively consists essentially of, or yet further consists of, the pH of the incubation solution is from about 2 to about 12. In some embodiments, the pH is at least 2, or 3, 4, 5, 5.5, 6, 6.5, 7, 7.5, 8, or 9 up to about 12. In some embodiments, the pH is not higher than 12, 11, 10, 9, 8, 7.5, 7, 6.5, 6, 5.5, or 4 with the lower pH limit being no lower than 2.

In some embodiments, the conditions comprise or alternatively consist essentially of, or yet further consist of, a molar concentration of pyruvate and $C_N$ aldehyde are present at a concentration from about 0.1 μM to about 5 M. In some embodiments, the concentration is at least about 0.1, 0.5, 1, 10, 100, 500 μM or 1 M. In some embodiments, the concentration is not higher than about 4 M, 3 M, 2 M, 1 M, 500 μM, 200 μM, 100 μM, or 10 μM. The concentration of pyruvate and $C_N$ can be independently the same or different and will vary with the other conditions of the incubation.

In some embodiments, the conditions comprise the presence of a non-natural microorganism that produces one or more enzymes selected from the group consisting of a class I/II pyruvate dependent aldolase, hydratase-aldolase, dehydratase, quinone oxidoreductase, enoyl-CoA reductase, primary alcohol dehydrogenase, keto-acid decarboxylase, coenzyme A transferase, and carboxylic acid reductase. Each of these enzymes is a reaction specific enzyme.

In some embodiments, the microorganism or host is genetically engineered to overexpress the enzymes or to express enzymes in an amount greater than the wild-type counterpart. Methods to determine the expression level of an enzyme or expression product are known in the art, e.g., by PCR.

In some embodiments, the $C_N$ aldehyde is 3-hydroxy-propanal.

In some embodiments, the method further comprises or alternatively consists essentially of, or yet further consists of, preparing the 3-hydroxy-propanal and pyruvate from glycerol, C5 sugars, C6 sugars, phospho-glycerates, other carbon sources, intermediates of the glycolysis pathway, intermediates of propanoate metabolism, or combinations thereof.

In some embodiments, the 3-hydroxy-propanal is obtained through dehydration of glycerol.

In some embodiments, the C5 sugar comprises or alternatively consists essentially of, or yet further consists of, one or more of xylose, xylulose, ribulose, arabinose, lyxose, and ribose.

In some embodiments, the C6 sugar comprises or alternatively consists essentially of, or yet further consists of, one or more of allose, altrose, glucose, mannose, gulose, idose, talose, galactose, fructose, psicose, sorbose, and tagatose.

In some embodiments, the other carbon source is a feedstock suitable as a carbon source for a microorganism, wherein the feedstock comprises or alternatively consists essentially of, or yet further consists of, amino acids, lipids, corn stover, *miscanthus*, municipal waste, energy cane, sugar cane, bagasse, starch stream, dextrose stream, methanol, formate, or combinations thereof.

In some embodiments, a microorganism is used as a host for the preparation of 1,5-pentanediol, adipic acid, 1,6-hexanediol, or 6-hydroxy hexanoic acid.

In some embodiments, the microorganism has the ability to convert C5 sugars, C6 sugars, glycerol, other carbon sources, or a combination thereof to pyruvate.

In some embodiments, the microorganism is engineered for enhanced sugar uptake, e.g., C5 sugar uptake, simultaneous C6/C5 sugar uptake, simultaneous C6 sugar/glycerol uptake, simultaneous C5 sugar/glycerol uptake, or combinations thereof.

In another aspect, provided herein is a method for producing a 2-keto carboxylic acid of formula:

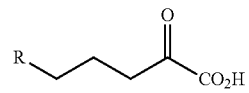

wherein R is H, CH₃, or CH₂OH;

the method comprising, consisting essentially of, or consisting of contacting pyruvate and

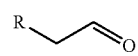

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms.

In another aspect, provided herein is a method for producing a 2-keto carboxylic acid of formula:

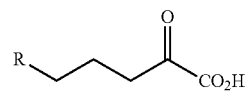

wherein R is H, CH₃, or CH₂OH;

the method comprising, consisting essentially of, or consisting of contacting pyruvate and

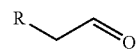

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms, and the method is performed in the presence of the one or more non-naturally occurring microbial organisms.

In another aspect, provided herein is a method for producing a 2-keto carboxylic acid of formula:

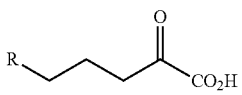

wherein R is H, CH$_3$, or CH$_2$OH;
the method comprising, consisting essentially of, or consisting of contacting pyruvate and

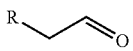

with a trans-o-hydroxybenzylidenepyruvate hydratase-aldolase and a quinone oxidoreductase in a culture comprising one or more non-naturally occurring microbial organisms to produce the 2-keto carboxylic acid; wherein the trans-o-hydroxybenzylidenepyruvate hydratase-aldolase and the quinone oxidoreductase are expressed by the one or more non-naturally occurring microbial organisms, and the method is performed in the presence of the one or more non-naturally occurring microbial organisms.

In another aspect, provided herein is a method for producing a 2-keto carboxylic acid of formula:

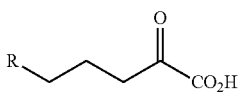

wherein R is H, CH$_3$, or CH$_2$OH;
the method comprising, consisting essentially of, or consisting of contacting pyruvate and

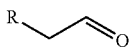

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms; and wherein the pyruvate and

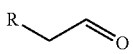

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In another aspect, provided herein is a method for producing a 2-keto carboxylic acid of formula:

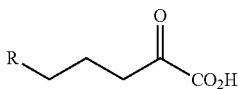

wherein R is H, CH$_3$, or CH$_2$OH;
the method comprising, consisting essentially of, or consisting of contacting pyruvate and

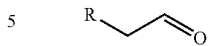

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms, and the method is performed in the presence of the one or more non-naturally occurring microbial organisms; and wherein the pyruvate and

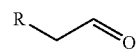

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In another aspect, provided herein is a method for producing a 2-keto carboxylic acid of formula:

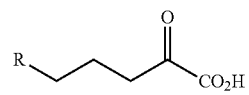

wherein R is H, CH$_3$, or CH$_2$OH;
the method comprising, consisting essentially of, or consisting of contacting pyruvate and

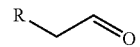

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms.

In another aspect, provided herein is a method for producing a 2-keto carboxylic acid of formula:

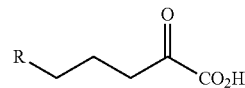

wherein R is H, CH$_3$, or CH$_2$OH;
the method comprising, consisting essentially of, or consisting of contacting pyruvate and

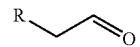

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms, and the method is performed in the presence of the two or more non-naturally occurring microbial organisms.

In another aspect, provided herein is a method for producing a 2-keto carboxylic acid of formula:

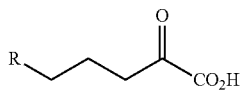

wherein R is H, CH$_3$, or CH$_2$OH;
the method comprising, consisting essentially of, or consisting of contacting pyruvate and

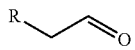

with a trans-o-hydroxybenzylidenepyruvate hydratase-aldolase and a quinone oxidoreductase in a culture comprising two or more non-naturally occurring microbial organisms to produce the 2-keto carboxylic acid; wherein the trans-o-hydroxybenzylidenepyruvate hydratase-aldolase and the quinone oxidoreductase are expressed by the two or more non-naturally occurring microbial organisms, and the method is performed in the presence of the two or more non-naturally occurring microbial organisms.

In another aspect, provided herein is a method for producing a 2-keto carboxylic acid of formula:

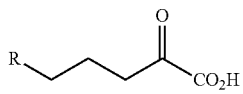

wherein R is H, CH$_3$, or CH$_2$OH;
the method comprising, consisting essentially of, or consisting of contacting pyruvate and

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms; and wherein the pyruvate and

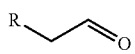

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In another aspect, provided herein is a method for producing a 2-keto carboxylic acid of formula:

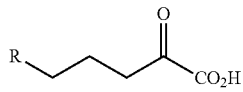

wherein R is H, CH$_3$, or CH$_2$OH;
the method comprising, consisting essentially of, or consisting of contacting pyruvate and

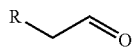

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms, and the method is performed in the presence of the two or more non-naturally occurring microbial organisms; and wherein the pyruvate and

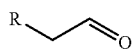

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In some embodiments, the

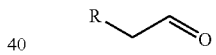

is 3-hydroxy-propanal. In some embodiments, the 3-hydroxy-propanal is produced by dehydration of glycerol by a glycerol dehydratase enzyme exogenously expressed by the one or more non-naturally occurring microbial organisms.

In some embodiments, the method for producing the 2-keto carboxylic acid further comprises separating the 2-keto carboxylic acid from the one or more non-naturally occurring microbial organisms or a culture comprising the one or more non-naturally occurring microbial organisms.

In another aspect, provided herein is a method for producing 1,5-pentanediol, the method comprising
contacting pyruvate and 3-hydroxy-propanal with a hydratase-aldolase and a quinone oxidoreductase to produce a 2-keto carboxylic acid of formula:

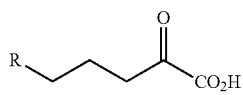

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol, wherein the method is performed in a culture comprising one or more non-naturally occurring microbial organisms.

In another aspect, provided herein is a method for producing 1,5-pentanediol, the method comprising contacting pyruvate and 3-hydroxy-propanal with a hydratase-aldolase and a quinone oxidoreductase to produce a 2-keto carboxylic acid of formula:

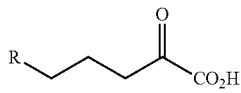

wherein R is CH$_2$OH;

contacting the 2-keto carboxylic acid with a 2-keto-acid-decarboxylase to produce a 5-hydroxy-pentanal; and contacting the 5-hydroxy-pentanal with a primary alcohol dehydrogenase to produce the 1,5-pentanediol, wherein the method is performed in a culture comprising two or more non-naturally occurring microbial organisms.

In another aspect, provided herein is a method for producing 1,6-hexanediol, the method comprising contacting pyruvate and 3-hydroxy-propanal with a hydratase-aldolase and a quinone oxidoreductase to produce a 2-keto carboxylic acid of formula:

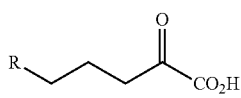

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxy-hexanoyl-CoA transferase to produce 6-hydroxy-hexanoate;

contacting the 6-hydroxy-hexanoate with a 6-hydroxy-hexanoate 1-reductase to produce 6-hydroxy-hexanal; and contacting the 6-hydroxy-hexanal with a 6-hydroxyhexanal 1-reductase to produce the 1,6-hexanediol, wherein the method is performed in a culture comprising one or more non-naturally occurring microbial organisms.

In another aspect, provided herein is a method for producing 1,6-hexanediol, the method comprising contacting pyruvate and 3-hydroxy-propanal with a hydratase-aldolase and a quinone oxidoreductase to produce a 2-keto carboxylic acid of formula:

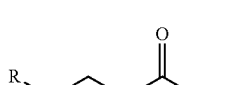

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxy-hexanoyl-CoA transferase to produce 6-hydroxy-hexanoate;

contacting the 6-hydroxy-hexanoate with a 6-hydroxy-hexanoate 1-reductase to produce 6-hydroxy-hexanal; and contacting the 6-hydroxy-hexanal with a 6-hydroxyhexanal 1-reductase to produce the 1,6-hexanediol, wherein the method is performed in a culture comprising two or more non-naturally occurring microbial organisms.

In another aspect, provided herein is a method for producing 6-hydroxy-hexanoate, the method comprising contacting pyruvate and 3-hydroxy-propanal with a hydratase-aldolase and a quinone oxidoreductase to produce a 2-keto carboxylic acid of formula:

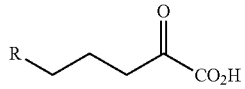

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA; and contacting the 6-hydroxy-hexanoyl-CoA with a 6-hydroxy-hexanoyl-CoA transferase to produce the 6-hydroxy-hexanoate;

wherein the method is performed in a culture comprising one or more non-naturally occurring microbial organisms.

In another aspect, provided herein is a method for producing 6-hydroxy-hexanoate, the method comprising contacting pyruvate and 3-hydroxy-propanal with a hydratase-aldolase and a quinone oxidoreductase to produce a 2-keto carboxylic acid of formula:

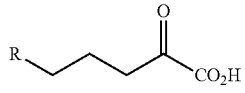

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA; and contacting the 6-hydroxy-hexanoyl-CoA with a 6-hydroxy-hexanoyl-CoA transferase to produce the 6-hydroxy-hexanoate;

wherein the method is performed in a culture comprising two or more non-naturally occurring microbial organisms.

In another aspect, provided herein is a method for producing adipic acid (AA), the method comprising contacting pyruvate and 3-hydroxy-propanal with a hydratase-aldolase and a quinone oxidoreductase to produce a 2-keto carboxylic acid of formula:

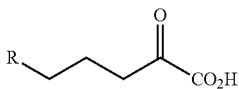

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxy-hexanoyl-CoA transferase to produce 6-hydroxy-hexanoate;

contacting the 6-hydroxy-hexanoate with a 6-hydroxy-hexanoate dehydrogenase to produce 6-oxo-hexanoate; and contacting the 6-oxo-hexanoate with a 6-oxo-hexanoate oxidase to produce the adipic acid, wherein the method is performed in a culture comprising one or more non-naturally occurring microbial organisms.

In another aspect, provided herein is a method for producing adipic acid (AA), the method comprising contacting pyruvate and 3-hydroxy-propanal with a hydratase-aldolase and a quinone oxidoreductase to produce a 2-keto carboxylic acid of formula:

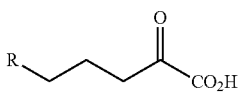

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxy-hexanoyl-CoA transferase to produce 6-hydroxy-hexanoate;

contacting the 6-hydroxy-hexanoate with a 6-hydroxy-hexanoate dehydrogenase to produce 6-oxo-hexanoate; and contacting the 6-oxo-hexanoate with a 6-oxo-hexanoate oxidase to produce the adipic acid, wherein the method is performed in a culture comprising two or more non-naturally occurring microbial organisms.

In some embodiments, the hydratase-aldolase is an enzyme having an EC number 4.1.2.45 or EC number 4.1.2.34 or EC number 4.1.1.4. In some embodiments, the hydratase-aldolase is an enzyme having an EC number 4.1.2.45. In some embodiments, the hydratase-aldolase is a trans-o-hydroxybenzylidenepyruvate hydratase-aldolase having an EC number 4.1.2.45. In some embodiments, the hydratase-aldolase is an enzyme having an EC number 4.1.2.34. In some embodiments, the hydratase-aldolase is an enzyme having an EC number 4.1.1.4.

In some embodiments, the hydratase-aldolase is an enzyme selected from the group of enzymes identified under Genbank or RefSeq or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Genbank or RefSeq or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase is an enzyme selected from Tables 1, 5, 6, 7, and 8. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from Tables 1, 5, 6, 7, and 8.

In some embodiments, the hydratase-aldolase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the quinone oxidoreductase is an enzyme having an EC number 1.6.5. In some embodiments, the quinone oxidoreductase is an enzyme having an EC number 1.6.5.5. In some embodiments, the quinone oxidoreductase is an enzyme selected from the group of enzymes identified under Under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP 012333034.1, or WP_136898000.1. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, at least one of the hydratase-aldolase and the quinone oxidoreductase is exogenously expressed by the one or more non-naturally occurring microbial organisms. In some embodiments, at least one of the hydratase-aldolase and the quinone oxidoreductase is exogenously expressed by the two or more non-naturally occurring microbial organisms.

In some embodiments, at least one of the hydratase-aldolase and the quinone oxidoreductase enzymes are expressed by one or more exogenous genes expressed by the one or more non-naturally occurring microorganisms. In some embodiments, at least one of the hydratase-aldolase and the quinone oxidoreductase enzymes are expressed by one or more exogenous genes expressed by the two or more non-naturally occurring microorganisms. In some embodiments, at least one of the hydratase-aldolase and the quinone oxidoreductase enzymes are expressed by two or more exogenous genes expressed by the one or more non-naturally occurring microorganisms. In some embodiments, at least one of the hydratase-aldolase and the quinone oxidoreductase enzymes are expressed by two or more exogenous genes expressed by the two or more non-naturally occurring microorganisms. One or more exogenous genes includes 1, 2, 3, 4, 5, 6, 7, 8, 9, 10, 11, 12, 13, 14, 15, 16, 17, 18, 19, or 20, or more, exogenous genes. Two or more exogenous genes includes 2, 3, 4, 5, 6, 7, 8, 9, 10, 11, 12, 13, 14, 15, 16, 17, 18, 19, or 20, or more, exogenous genes.

In some embodiments, the hydratase-aldolase is exogenously expressed by the one or more non-naturally occurring microbial organisms. In some embodiments, the hydratase-aldolase is exogenously expressed by the two or more non-naturally occurring microbial organisms.

In some embodiments, the quinone oxidoreductase is exogenously expressed by the one or more non-naturally occurring microbial organisms. In some embodiments, the quinone oxidoreductase is overexpressed by the one or more non-naturally occurring microbial organisms. In some embodiments, the quinone oxidoreductase is exogenously expressed by the two or more non-naturally occurring microbial organisms. In some embodiments, the quinone oxidoreductase is overexpressed by the two or more non-naturally occurring microbial organisms.

In some embodiments, the hydratase-aldolase is exogenously expressed by the one or more non-naturally occurring microbial organisms and the quinone oxidoreductase is overexpressed by the one or more non-naturally occurring microbial organisms. In some embodiments, the hydratase-aldolase is exogenously expressed by the two or more non-naturally occurring microbial organisms and the quinone oxidoreductase is overexpressed by the two or more non-naturally occurring microbial organisms.

In some embodiments, the 2-keto-acid-decarboxylase and the primary alcohol dehydrogenase are expressed by the one or more non-naturally occurring microbial organisms. In some embodiments, the 2-keto-acid-decarboxylase and the primary alcohol dehydrogenase are exogenously expressed by the one or more non-naturally occurring microbial organisms.

In some embodiments, the 2-keto-acid-decarboxylase is an enzyme selected from the group of enzymes identified under EC number 4.1.1.1; EC number 4.1.1.2; EC number 4.1.1.3; EC number 4.1.1.4; EC number 4.1.1.5; EC number 4.1.1.6; EC number 4.1.1.7; EC number 4.1.1.11; EC number 4.1.1.12; EC number 4.1.1.15; EC number 4.1.1.16; EC number 4.1.1.17; EC number 4.1.1.18; EC number 4.1.1.19; EC number 4.1.1.20; EC number 4.1.1.34; EC number 4.1.1.35; EC number 4.1.1.40; EC number 4.1.1.54; EC number 4.1.1.56; EC number 4.1.1.71; EC number 4.1.1.72; EC number 4.1.1.73; EC number 4.1.1.74; EC number 4.1.1.75; or EC number 4.1.1.77. In some embodiments, the 2-keto-acid-decarboxylase is an enzyme selected from the group of enzymes identified under Uniprot ID No. Q6QBS4, A7M7D6, or P20906. In some embodiments, the 2-keto-acid-decarboxylase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot ID Nos. Q6QBS4, A7M7D6, or P20906.

In some embodiments, the 2-keto-acid-decarboxylase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the primary alcohol dehydrogenase is an enzyme having an EC number 1.1.1.61. In some embodiments, the primary alcohol dehydrogenase is an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP 001210625.1, AB067118, AB068223, BAE77068.1, or CAA47743.1. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot or GenBank ID Nos. NP_417279.1, NP_349892.1, NP 349891.1, BAB12273.1, L21902.1, Q94B07, AAB03015.1, NP_014032.1, NP_013892.1, NP_015019.1, NP 010996.2, ABX39192.1, XP_001210625.1, AB067118, AB068223, BAE77068.1, or CAA47743.1. In some embodiments, the primary alcohol dehydrogenase is an enzyme comprising a sequence of SEQ ID NO:70, SEQ ID NO:71, SEQ ID NO:72, SEQ ID NO:73, or SEQ ID NO:74. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70, SEQ ID NO:71, SEQ ID NO:72, SEQ ID NO:73, or SEQ ID NO:74.

In some embodiments, the primary alcohol dehydrogenase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the hydratase-aldolase is an enzyme identified under Uniprot ID No. A0A286PH18; the quinone oxidoreductase is an enzyme identified under Uniprot ID No. P28304; the 2-keto-acid-decarboxylase is an enzyme identified under Uniprot ID No. Q6QBS4; and the primary alcohol dehydrogenase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. A0A286PH18; the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. P28304; the 2-keto-acid-decarboxylase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q6QBS4; and the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the one or more non-naturally occurring microbial organisms.

In some embodiments, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the one or more non-naturally occurring microbial organisms.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxyhexanoate 1-reductase is an enzyme having an EC number 1.2.99.6; and the 6-hydroxyhexanal 1-reductase is an enzyme having an EC number 1.1.1.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC6409; the 2,6-dihydroxy-hexanoate CoA-transferase is an enzyme identified under Uniprot ID No. T4VW93; the 2,6-dihydroxy-hexanoyl-CoA 2-dehydratase is an enzyme identified under Uniprot ID Nos. Q5U924, Q5U925, and Q5U923; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93; the 6-hydroxyhexanoate 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC6409; the 2,6-dihydroxy-hexanoate CoA-transferase is an enzyme identified under Uniprot ID Nos. T4VW93, A0A0C7GD16, A0A175L1W4, or 0A2X3BTQ9; the 2,6-dihydroxy-hexanoyl-CoA 2-dehydratase is an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93, A0A0C7GD16, A0A175L1W4, or A0A2X3BTQ9; the 6-hydroxyhexanoate 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP 036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A0C7GD16, A0A175L1W4, or 0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. T4VW93, A0A0C7GD16, A0A175L1W4, or A0A2X3BTQ9; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP 036338301.1, WP_007472106.1, or A0QWI7; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55, SEQ ID NO:56, SEQ ID NO:57, or SEQ ID NO:58; the 6-hydroxyhexanoate 1-reductase is an enzyme comprising a sequence of SEQ ID NO:66, SEQ ID NO:67, or SEQ ID NO:68; and the 6-hydroxyhexanal 1-reductase is an enzyme comprising a sequence of SEQ ID NO:70.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:66, SEQ ID NO:67, or SEQ ID NO:68; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; and the 6-hydroxyhexanoyl-CoA transferase is an enzyme having an EC number 2.8.3, EC number 2.8.3.1, or EC number 2.8.3.12.

In some embodiments, the 6-hydroxy-2-oxohexanoate-2-reductase is an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme identified under Uniprot ID Nos. T4VW93, A0A2X3BTQ9, A0A0C7GD16, or A0A175L1W4; the 2,6-dihydroxy-hexanoyl-CoA 2-dehydratase is an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase is an enzyme identified under Uniprot ID No. Q73Q47; and the 6-hydroxyhexanoyl-CoA transferase is an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; and the 6-hydroxyhexanoyl-CoA transferase is an enzyme comprising a sequence of SEQ ID NO:55, SEQ ID NO:56, SEQ ID NO:57, or SEQ ID NO:58.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxyhexanoate dehydrogenase is an enzyme having an EC number 1.1.1.258; and the 6-oxo-hexanoate oxidase is an enzyme having an EC number 1.2.1.63.

In some embodiments, the 6-hydroxy-2-oxohexanoate-2-reductase is an enzyme identified under Uniprot ID No. Q5FTU6; the 2,6-dihydroxy-hexanoate CoA-transferase is an enzyme identified under Uniprot ID Nos. T4VW93 or A0A2X3BTQ9; the 2,6-dihydroxy-hexanoyl-CoA 2-dehydratase is an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID Nos. T4VW93 or A0A2X3BTQ9; the 6-hydroxyhexanoate dehydrogenase is an enzyme identified under Uniprot ID Nos. Q7WVD0 or Q84H78; and the 6-oxo-hexanoate oxidase is an enzyme identified under Uniprot ID No. Q9R2F4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q5FTU6; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BKO9, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q7WVD0 or Q84H78; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q9R2F4.

In some embodiments, the 6-hydroxy-2-oxohexanoate-2-reductase is an enzyme comprising a sequence of SEQ ID NO:53; the 2,6-dihydroxy-hexanoate CoA-transferase is an enzyme comprising a sequence of SEQ ID NO:55 or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55 or SEQ ID NO:58; the 6-hydroxyhexanoate dehydrogenase is an enzyme identified comprising a sequence of SEQ ID NO:71 or SEQ ID NO:72; and the 6-oxo-hexanoate oxidase is an enzyme comprising a sequence of SEQ ID NO:75.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified comprising a sequence of SEQ ID NO:71 and SEQ ID NO:72; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:75.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, 6-hydroxyhexanoate dehydrogenase, and the 6-oxo-hexanoate oxidase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag In some embodiments, the pyruvate is produced from carbon sources selected from glycerol, glucose, xylose, arabinose, galactose, mannose, fructose, sucrose, and starch, or a combination of thereof.

In some embodiments, the 3-hydroxy-propanal is produced by dehydration of glycerol by a glycerol dehydratase enzyme exogenously expressed by the one or more non-naturally occurring microbial organisms.

The one or more non-naturally occurring microbial organisms include 1, 2, 3, 4, 5, 6, 7, 8, 9, 10, 11, 12, 13, 14, 15, 16, 17, 18, 19, or 20, or more non-naturally occurring microbial organisms. The two or more non-naturally occurring microbial organisms include 2, 3, 4, 5, 6, 7, 8, 9, 10, 11, 12, 13, 14, 15, 16, 17, 18, 19, or 20, or more non-naturally occurring microbial organisms. In some embodiments, the method disclosed herein is performed in the presence of one non-naturally occurring microbial organism. In some embodiments, the method disclosed herein is performed in the presence of two non-naturally occurring microbial organisms. In some embodiments, the method disclosed herein is performed in the presence of three non-naturally occurring microbial organisms. In some embodiments, the method disclosed herein is performed in the presence of four non-naturally occurring microbial organisms. In some embodiments, the method disclosed herein is performed in the presence of five non-naturally occurring microbial organisms.

Throughout this application various publications have been referenced. The disclosure of these publications in their entireties, including GenBank accession number(s) or Uniprot ID number(s) or RefSeq ID numbers in these publications, are hereby incorporated by reference in this application in order to more fully describe the state of the art to which this present disclosure pertains.

In some embodiments, the present disclosure provides the following Embodiments as examples:

1. A method for producing a 2-keto carboxylic acid of formula:

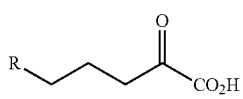

wherein R is H, CH$_3$, or CH$_2$OH;
the method comprising contacting pyruvate and

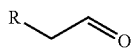

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms.

2. The method of Embodiment 1, wherein at least one of the hydratase-aldolase and the quinone oxidoreductase is exogenously expressed by the one or more non-naturally occurring microbial organisms.

3. The method of Embodiment 1, wherein the hydratase-aldolase is exogenously expressed by the one or more non-naturally occurring microbial organisms.

4. The method of Embodiment 1, wherein the quinone oxidoreductase is exogenously expressed by the one or more non-naturally occurring microbial organisms.

5. The method of Embodiment 1, wherein the quinone oxidoreductase is overexpressed by the one or more non-naturally occurring microbial organisms.

6. The method of Embodiment 1, wherein the hydratase-aldolase is exogenously expressed by the one or more non-naturally occurring microbial organisms and the quinone oxidoreductase is overexpressed by the one or more non-naturally occurring microbial organisms.

7. The method of any one of Embodiments 1-6, wherein

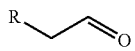

is 3-hydroxy-propanal.

8. The method of Embodiment 7, wherein the 3-hydroxy-propanal is produced by dehydration of glycerol by a glycerol dehydratase enzyme exogenously expressed by the one or more non-naturally occurring microbial organisms.

9. The method of any one of Embodiments 1-8, further comprising separating the 2-keto carboxylic acid from the one or more non-naturally occurring microbial organisms or a culture comprising the one or more non-naturally occurring microbial organisms.

10. A method for producing a 2-keto carboxylic acid of formula:

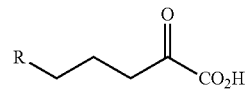

wherein R is H, CH$_3$, or CH$_2$OH;
the method comprising contacting pyruvate and

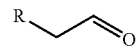

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms.

11. The method of Embodiment 10, wherein at least one of the hydratase-aldolase and the quinone oxidoreductase is exogenously expressed by the two or more non-naturally occurring microbial organisms.

12. The method of Embodiment 10, wherein the hydratase-aldolase is exogenously expressed by the two or more non-naturally occurring microbial organisms.

13. The method of Embodiment 10, wherein the quinone oxidoreductase is exogenously expressed by the two or more non-naturally occurring microbial organisms.

14. The method of Embodiment 10, wherein the quinone oxidoreductase is overexpressed by the two or more non-naturally occurring microbial organisms.

15. The method of Embodiment 10, wherein the hydratase-aldolase is exogenously expressed by the two or more non-naturally occurring microbial organisms and the quinone oxidoreductase is overexpressed by the two or more non-naturally occurring microbial organisms.

16. The method of any one of Embodiments 10-15, wherein

is 3-hydroxy-propanal.

17. The method of Embodiment 16, wherein the 3-hydroxy-propanal is produced by dehydration of glycerol by a glycerol dehydratase enzyme exogenously expressed by the two or more non-naturally occurring microbial organisms.

18. The method of any one of Embodiments 10-17, further comprising separating the 2-keto carboxylic acid from the two or more non-naturally occurring microbial organisms or a culture comprising the two or more non-naturally occurring microbial organisms.

19. The method of any one of Embodiments 1-18, wherein the hydratase-aldolase is an enzyme having an EC number 4.1.2.45 or EC number 4.1.2.34 or EC number 4.1.1.4.

20. The method of any one of Embodiments 1-18, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

21. The method of any one of Embodiments 1-18, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

22. The method of any one of Embodiments 1-18, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

23. The method of any one of Embodiments 1-18, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

24. The method of any one of Embodiments 1-18, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

25. The method of any one of Embodiments 1-18, wherein the hydratase-aldolase is an enzyme selected from Tables 1, 5-8.

26. The method of any one of Embodiments 1-25, wherein the quinone oxidoreductase is an enzyme having an EC number 1.6.5 (e.g., EC 1.6.5.5).

27. The method of any one of Embodiments 1-25, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

28. The method of any one of Embodiments 1-25, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

29. The method of any one of Embodiments 1-25, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

30. The method of any one of Embodiments 1-25, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

31. The method of any one of Embodiments 1-30, wherein one or more of the hydratase-aldolase and quinone oxidoreductase further comprise one or more protein tags.

32. The method of Embodiment 31, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

33. The method of any one of Embodiments 1-32, wherein the pyruvate is produced from carbon sources selected from glycerol, glucose, xylose, arabinose, galactose, mannose, fructose, sucrose, and starch, or a combination of thereof.

34. The method of any one of Embodiments 1-11, wherein R is CH$_2$OH.

35. A method for producing 1,5-pentanediol, the method comprising
contacting pyruvate and 3-hydroxy-propanal with a hydratase-aldolase and a quinone oxidoreductase to produce a 2-keto carboxylic acid of formula:

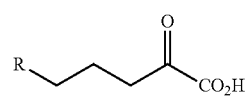

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol,
wherein the method is performed in a culture comprising one or more non-naturally occurring microbial organisms.

36. The method of Embodiment 35, wherein the hydratase-aldolase and the quinone oxidoreductase are expressed by the one or more non-naturally occurring microbial organisms.

37. The method of Embodiment 35, wherein at least one of the hydratase-aldolase and the quinone oxidoreductase is exogenously expressed by the one or more non-naturally occurring microbial organisms.

38. The method of Embodiment 35, wherein the hydratase-aldolase is exogenously expressed by the one or more non-naturally occurring microbial organisms.

39. The method of Embodiment 35, wherein the quinone oxidoreductase is exogenously expressed by the one or more non-naturally occurring microbial organisms.

40. The method of Embodiment 35, wherein the quinone oxidoreductase is overexpressed by the one or more non-naturally occurring microbial organisms.

41. The method of any one of Embodiments 35-40, wherein the 2-keto-acid-decarboxylase and the primary alcohol dehydrogenase are expressed by the one or more non-naturally occurring microbial organisms.

42. The method of any one of Embodiments 35-40, wherein the 2-keto-acid-decarboxylase and the primary alcohol dehydrogenase are exogenously expressed by the one or more non-naturally occurring microbial organisms.

43. The method of any one of Embodiments 35-40, wherein one or more of the 2-keto-acid-decarboxylase and the primary alcohol dehydrogenase are overexpressed by the one or more non-naturally occurring microbial organisms.

44. The method of any one of Embodiments 35-43, further comprising separating the 1,5-pentanediol from the one or more non-naturally occurring microbial organisms or a culture comprising the one or more non-naturally occurring microbial organisms.

45. A method for producing 1,5-pentanediol, the method comprising contacting pyruvate and 3-hydroxy-propanal with a hydratase-aldolase and a quinone oxidoreductase to produce a 2-keto carboxylic acid of formula:

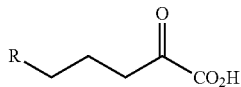

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol,
wherein the method is performed in a culture comprising two or more non-naturally occurring microbial organisms.

46. The method of Embodiment 45, wherein the hydratase-aldolase and the quinone oxidoreductase are expressed by the two or more non-naturally occurring microbial organisms.

47. The method of Embodiment 45, wherein at least one of the hydratase-aldolase and the quinone oxidoreductase is exogenously expressed by the two or more non-naturally occurring microbial organisms.

48. The method of Embodiment 45, wherein the hydratase-aldolase is exogenously expressed by the two or more non-naturally occurring microbial organisms.

49. The method of Embodiment 45, wherein the quinone oxidoreductase is exogenously expressed by the two or more non-naturally occurring microbial organisms.

50. The method of Embodiment 45, wherein the quinone oxidoreductase is overexpressed by the two or more non-naturally occurring microbial organisms.

51. The method of any one of Embodiments 45-50, wherein the 2-keto-acid-decarboxylase and the primary alcohol dehydrogenase are expressed by the two or more non-naturally occurring microbial organisms.

52. The method of any one of Embodiments 45-50, wherein the 2-keto-acid-decarboxylase and the primary alcohol dehydrogenase are exogenously expressed by the two or more non-naturally occurring microbial organisms.

53. The method of any one of Embodiments 45-50, wherein one or more of the 2-keto-acid-decarboxylase and the primary alcohol dehydrogenase are overexpressed by the two or more non-naturally occurring microbial organisms.

54. The method of any one of Embodiments 45-53, further comprising separating the 1,5-pentanediol from the two or more non-naturally occurring microbial organisms or a culture comprising the two or more non-naturally occurring microbial organisms.

55. The method of any one of Embodiments 35-54, wherein the hydratase-aldolase is an enzyme having an EC number 4.1.2.45 or EC number 4.1.2.34 or EC number 4.1.1.4.

56. The method of any one of Embodiments 35-54, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

57. The method of any one of Embodiments 35-54, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

58. The method of any one of Embodiments 35-54, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

59. The method of any one of Embodiments 35-54, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

60. The method of any one of Embodiments 35-54, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

61. The method of any one of Embodiments 35-54, wherein the hydratase-aldolase is an enzyme selected from Tables 1, 5-8.

62. The method of any one of Embodiments 35-61, wherein the quinone oxidoreductase is an enzyme having an EC number 1.6.5 (e.g., EC 1.6.5.5).

63. The method of any one of Embodiments 35-61, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

64. The method of any one of Embodiments 35-61, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

65. The method of any one of Embodiments 35-61, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

66. The method of any one of Embodiments 35-61, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

67. The method of any one of Embodiments 35-66, wherein the 2-keto-acid-decarboxylase is an enzyme having an EC number 4.1.1.1; EC number 4.1.1.2; EC number 4.1.1.3; EC number 4.1.1.4; EC number 4.1.1.5; EC number 4.1.1.6; EC number 4.1.1.7; EC number 4.1.1.11; EC number 4.1.1.12; EC number 4.1.1.15; EC number 4.1.1.16; EC number 4.1.1.17; EC number 4.1.1.18; EC number 4.1.1.19; EC number 4.1.1.20; EC number 4.1.1.34; EC number 4.1.1.35; EC number 4.1.1.40; EC number 4.1.1.54; EC number 4.1.1.56; EC number 4.1.1.71; EC number 4.1.1.72; EC number 4.1.1.73; EC number 4.1.1.74; EC number 4.1.1.75; or EC number 4.1.1.77.

68. The method of any one of Embodiments 35-66, wherein the 2-keto-acid-decarboxylase is an enzyme selected from the group of enzymes identified under Uniprot ID Nos. Q6QBS4, A7M7D6, or P20906.

69. The method of any one of Embodiments 35-66, wherein the 2-keto-acid-decarboxylase has at least 50% identity to an enzyme selected from the group of enzymes identified under Uniprot ID Nos. Q6QBS4, A7M7D6, or P20906.

70. The method of any one of Embodiments 35-66, wherein the 2-keto-acid-decarboxylase has at least 70% identity to an enzyme selected from the group of enzymes identified under Uniprot ID Nos. Q6QBS4, A7M7D6, or P20906.

71. The method of any one of Embodiments 35-66, wherein the 2-keto-acid-decarboxylase has at least 90% identity to an enzyme selected from the group of enzymes identified under Uniprot ID Nos. Q6QBS4, A7M7D6, or P20906.

72. The method of any one of Embodiments 35-71, wherein the primary alcohol dehydrogenase is an enzyme having an EC number 1.1.1.61.

73. The method of any one of Embodiments 35-71, wherein the primary alcohol dehydrogenase is an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP_001210625.1, AB067118, AB068223, BAE77068.1, or CAA47743.1.

74. The method of any one of Embodiments 35-71, wherein the primary alcohol dehydrogenase is an enzyme comprising a sequence of SEQ ID NO:70, SEQ ID NO:71, SEQ ID NO:72, SEQ ID NO:73, or SEQ ID NO:74.

75. The method of any one of Embodiments 35-71, wherein the primary alcohol dehydrogenase has at least 50% identity to an enzyme comprising a sequence of SEQ ID NO:70, SEQ ID NO:71, SEQ ID NO:72, SEQ ID NO:73, or SEQ ID NO:74.

76. The method of any one of Embodiments 35-71, wherein the primary alcohol dehydrogenase has at least 70% identity to an enzyme comprising a sequence of SEQ ID NO:70, SEQ ID NO:71, SEQ ID NO:72, SEQ ID NO:73, or SEQ ID NO:74.

77. The method of any one of Embodiments 35-71, wherein the primary alcohol dehydrogenase has at least 90% identity to an enzyme comprising a sequence of SEQ ID NO:70, SEQ ID NO:71, SEQ ID NO:72, SEQ ID NO:73, or SEQ ID NO:74.

78. The method of any one of Embodiments 35-54, wherein the hydratase-aldolase is an enzyme comprising a sequence of SEQ ID NO:8;
the quinone oxidoreductase is an enzyme comprising a sequence of SEQ ID NO:45;
the 2-keto-acid-decarboxylase is an enzyme comprising a sequence of SEQ ID NO:83; and
the primary alcohol dehydrogenase is an enzyme comprising a sequence of SEQ ID NO:70.

79. The method of any one of Embodiments 35-78, wherein one or more of the hydratase-aldolase, quinone oxidoreductase, 2-keto-acid-decarboxylase, and primary alcohol dehydrogenase further comprise one or more protein tags.

80. The method of Embodiment 79, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

81. The method of any one of Embodiments 35-80, wherein the pyruvate is produced from carbon sources selected from glycerol, glucose, xylose, arabinose, galactose, mannose, fructose, sucrose, and starch, or a combination thereof.

82. The method of any one of Embodiments 35-81, wherein the 3-hydroxy-propanal is produced by dehydration of glycerol by a glycerol dehydratase enzyme exogenously expressed by the one or more non-naturally occurring microbial organisms.

83. A method for producing 1,6-hexanediol, the method comprising
contacting pyruvate and 3-hydroxy-propanal with a hydratase-aldolase and a quinone oxidoreductase to produce a 2-keto carboxylic acid of formula:

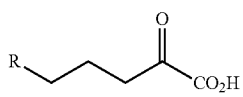

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxy-hexanoyl-CoA transferase to produce 6-hydroxy-hexanoate;
contacting the 6-hydroxy-hexanoate with a 6-hydroxy-hexanoate 1-reductase to produce 6-hydroxy-hexanal; and
contacting the 6-hydroxy-hexanal with a 6-hydroxyhexanal 1-reductase to produce the 1,6-hexanediol,
wherein the method is performed in a culture comprising one or more non-naturally occurring microbial organisms.

84. The method of Embodiment 83, wherein the hydratase-aldolase and the quinone oxidoreductase are expressed by the one or more non-naturally occurring microbial organisms.

85. The method of Embodiment 83, wherein at least one of the hydratase-aldolase and the quinone oxidoreductase is exogenously expressed by the one or more non-naturally occurring microbial organisms.

86. The method of Embodiment 83, wherein the hydratase-aldolase is exogenously expressed by the one or more non-naturally occurring microbial organisms.

87. The method of Embodiment 83, wherein the quinone oxidoreductase is exogenously expressed by the one or more non-naturally occurring microbial organisms.

88. The method of Embodiment 83, wherein the quinone oxidoreductase is overexpressed by the one or more non-naturally occurring microbial organisms.

89. The method of any one of Embodiments 83-88, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the one or more non-naturally occurring microbial organisms.

90. The method of any one of Embodiments 83-88, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the one or more non-naturally occurring microbial organisms.

91. The method of any one of Embodiments 83-88, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are overexpressed by the one or more non-naturally occurring microbial organisms.

92. The method of any one of Embodiments 83-91, further comprising separating the 1,6-hexanediol from the one or more non-naturally occurring microbial organisms or a culture comprising the one or more non-naturally occurring microbial organisms.

93. A method for producing 1,6-hexanediol, the method comprising
contacting pyruvate and 3-hydroxy-propanal with a hydratase-aldolase and a quinone oxidoreductase to produce a 2-keto carboxylic acid of formula:

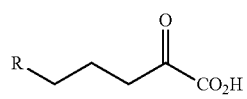

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxy-hexanoyl-CoA transferase to produce 6-hydroxy-hexanoate;
contacting the 6-hydroxy-hexanoate with a 6-hydroxy-hexanoate 1-reductase to produce 6-hydroxy-hexanal; and
contacting the 6-hydroxy-hexanal with a 6-hydroxyhexanal 1-reductase to produce the 1,6-hexanediol,
wherein the method is performed in a culture comprising two or more non-naturally occurring microbial organisms.

94. The method of Embodiment 93, wherein the hydratase-aldolase and the quinone oxidoreductase are expressed by the two or more non-naturally occurring microbial organisms.

95. The method of Embodiment 93, wherein at least one of the hydratase-aldolase and the quinone oxidoreductase is exogenously expressed by the two or more non-naturally occurring microbial organisms.

96. The method of Embodiment 93, wherein the hydratase-aldolase is exogenously expressed by the two or more non-naturally occurring microbial organisms.

97. The method of Embodiment 93, wherein the quinone oxidoreductase is exogenously expressed by the two or more non-naturally occurring microbial organisms.

98. The method of Embodiment 93, wherein the quinone oxidoreductase is overexpressed by the two or more non-naturally occurring microbial organisms.

99. The method of any one of Embodiments 93-98, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the two or more non-naturally occurring microbial organisms.

100. The method of any one of Embodiments 93-98, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the two or more non-naturally occurring microbial organisms.

101. The method of any one of Embodiments 93-98, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are overexpressed by the two or more non-naturally occurring microbial organisms.

102. The method of any one of Embodiments 93-101, further comprising separating the 1,6-hexanediol from the two or more non-naturally occurring microbial organisms or a culture comprising the two or more non-naturally occurring microbial organisms.

103. The method of any one of Embodiments 83-102, wherein the hydratase-aldolase is an enzyme having an EC number 4.1.2.45 or EC number 4.1.2.34 or EC number 4.1.1.4.

104. The method of any one of Embodiments 83-102, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

105. The method of any one of Embodiments 83-102, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

106. The method of any one of Embodiments 83-102, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

107. The method of any one of Embodiments 83-102, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

108. The method of any one of Embodiments 83-102, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

109. The method of any one of Embodiments 83-102, wherein the hydratase-aldolase is an enzyme selected from Tables 1 and 5-8.

110. The method of any one of Embodiments 83-109, wherein the quinone oxidoreductase is an enzyme having an EC number 1.6.5 (e.g., EC 1.6.5.5).

111. The method of any one of Embodiments 83-109, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

112. The method of any one of Embodiments 83-109, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

113. The method of any one of Embodiments 83-109, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

114. The method of any one of Embodiments 83-109, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

115. The method of any one of Embodiments 83-102, wherein
the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;
the 2,6-dihydroxy-hexanoate CoA-transferase is an enzyme having an EC number 2.8.3, EC number 2.8.3.1, or EC number 2.8.3.12;
the 2,6-dihydroxy-hexanoyl-CoA 2-dehydratase is an enzyme having an EC number 4.2.1.167;
the 2,3-dehydro-hexanoyl-CoA 2,3-reductase is an enzyme having an EC number 1.3.1.44;
the 6-hydroxyhexanoyl-CoA transferase is an enzyme having an EC number 2.8.3, EC number 2.8.3.1, or EC number 2.8.3.12;
the 6-hydroxyhexanoate 1-reductase is an enzyme having an EC number 1.2.99.6; and
the 6-hydroxyhexanal 1-reductase is an enzyme having an EC number 1.1.1.

116. The method of any one of Embodiments 83-102, wherein
the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase is an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase is an enzyme comprising a sequence of SEQ ID NO:65;
the 6-hydroxyhexanoyl-CoA transferase is an enzyme comprising a sequence of SEQ ID NO:55, SEQ ID NO:56, SEQ ID NO:57, or SEQ ID NO:58;
the 6-hydroxyhexanoate 1-reductase is an enzyme comprising a sequence of SEQ ID NO:66, SEQ ID NO:67, or SEQ ID NO:68; and
the 6-hydroxyhexanal 1-reductase is an enzyme comprising a sequence of SEQ ID NO:70.

117. The method of any one of Embodiments 83-102, wherein
the 6-hydroxy-2-oxohexanoate-2-reductase has at least 50% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 50% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 50% identity to an enzyme comprising a sequence of SEQ ID NO:65;
the 6-hydroxyhexanoyl-CoA transferase has at least 50% identity to an enzyme comprising a sequence of SEQ ID NO:55, SEQ ID NO:56, SEQ ID NO:57, or SEQ ID NO:58;
the 6-hydroxyhexanoate 1-reductase has at least 50% identity to an enzyme comprising a sequence of SEQ ID NO:66, SEQ ID NO:67, or SEQ ID NO:68; and
the 6-hydroxyhexanal 1-reductase has at least 50% identity to an enzyme comprising a sequence of SEQ ID NO:70.

118. The method of any one of Embodiments 83-102, wherein
the 6-hydroxy-2-oxohexanoate-2-reductase has at least 70% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 70% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 70% identity to an enzyme comprising a sequence of SEQ ID NO:65;
the 6-hydroxyhexanoyl-CoA transferase has at least 70% identity to an enzyme comprising a sequence of SEQ ID NO:55, SEQ ID NO:56, SEQ ID NO:57, or SEQ ID NO:58;
the 6-hydroxyhexanoate 1-reductase has at least 70% identity to an enzyme comprising a sequence of SEQ ID NO:66, SEQ ID NO:67, or SEQ ID NO:68; and
the 6-hydroxyhexanal 1-reductase has at least 70% identity to an enzyme comprising a sequence of SEQ ID NO:70.

119. The method of any one of Embodiments 83-102, wherein
the 6-hydroxy-2-oxohexanoate-2-reductase has at least 90% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 90% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 90% identity to an comprising a sequence of SEQ ID NO:65;
the 6-hydroxyhexanoyl-CoA transferase has at least 90% identity to an enzyme comprising a sequence of SEQ ID NO:55, SEQ ID NO:56, SEQ ID NO:57, or SEQ ID NO:58;
the 6-hydroxyhexanoate 1-reductase has at least 90% identity to an enzyme comprising a sequence of SEQ ID NO:66, SEQ ID NO:67, or SEQ ID NO:68; and
the 6-hydroxyhexanal 1-reductase has at least 90% identity to an enzyme comprising a sequence of SEQ ID NO:70.

120. The method of any one of Embodiments 83-119, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3- dehydro-hexanoyl-CoA 2,3-reductase, the 6-hydroxy-hexanoyl-CoA transferase, the 6-hydroxyhexanoate 1-reductase, and the 6-hydroxyhexanal 1-reductase further comprise one or more protein tags.

121. The method of Embodiment 120, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

122. The method of any one of Embodiments 83-121, wherein the pyruvate is produced from carbon sources is selected from glycerol, glucose, xylose, arabinose, galactose, mannose, fructose, sucrose, and starch, or a combination thereof.

123. The method of any one of Embodiments 83-122, wherein the 3-hydroxy-propanal is produced by dehydration of glycerol by a glycerol dehydratase enzyme exogenously expressed by the one or more non-naturally occurring microbial organisms.

124. A method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

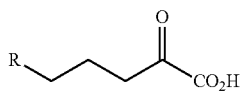

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA; and
contacting the 6-hydroxy-hexanoyl-CoA with a 6-hydroxy-hexanoyl-CoA transferase to produce the 6-hydroxy-hexanoate;
wherein the method is performed in a culture comprising one or more non-naturally occurring microbial organisms.

125. The method of Embodiment 124, wherein the hydratase-aldolase and the quinone oxidoreductase are expressed by the one or more non-naturally occurring microbial organisms.

126. The method of Embodiment 124, wherein at least one of the hydratase-aldolase and the quinone oxidoreductase is exogenously expressed by the one or more non-naturally occurring microbial organisms.

127. The method of Embodiment 124, wherein the hydratase-aldolase is exogenously expressed by the one or more non-naturally occurring microbial organisms.

128. The method of Embodiment 124, wherein the quinone oxidoreductase is exogenously expressed by the one or more non-naturally occurring microbial organisms.

129. The method of Embodiment 124, wherein the quinone oxidoreductase is overexpressed by the one or more non-naturally occurring microbial organisms.

130. The method of any one of Embodiments 124-129, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are expressed by the one or more non-naturally occurring microbial organisms.

131. The method of any one of Embodiments 124-129, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the one or more non-naturally occurring microbial organisms.

132. The method of any one of Embodiments 124-129, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxy-hexanoyl-CoA transferase are overexpressed by the one or more non-naturally occurring microbial organisms.

133. The method of any one of Embodiments 124-132, further comprising separating the 6-hydroxy-hexanoate from the one or more non-naturally occurring microbial organisms or a culture comprising the one or more non-naturally occurring microbial organisms.

134. A method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

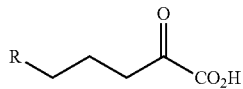

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA; and
contacting the 6-hydroxy-hexanoyl-CoA with a 6-hydroxy-hexanoyl-CoA transferase to produce the 6-hydroxy-hexanoate;
wherein the method is performed in a culture comprising two or more non-naturally occurring microbial organisms.

135. The method of Embodiment 134, wherein the hydratase-aldolase and the quinone oxidoreductase are expressed by the two or more non-naturally occurring microbial organisms.

136. The method of Embodiment 134, wherein at least one of the hydratase-aldolase and the quinone oxidoreductase is exogenously expressed by the two or more non-naturally occurring microbial organisms.

137. The method of Embodiment 134, wherein the hydratase-aldolase is exogenously expressed by the two or more non-naturally occurring microbial organisms.

138. The method of Embodiment 134, wherein the quinone oxidoreductase is exogenously expressed by the two or more non-naturally occurring microbial organisms.

139. The method of Embodiment 134, wherein the quinone oxidoreductase is overexpressed by the two or more non-naturally occurring microbial organisms.

140. The method of any one of Embodiments 134-139, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are expressed by the two or more non-naturally occurring microbial organisms.

141. The method of any one of Embodiments 134-139, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the two or more non-naturally occurring microbial organisms.

142. The method of any one of Embodiments 134-139, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are overexpressed by the two or more non-naturally occurring microbial organisms.

143. The method of any one of Embodiments 134-142, further comprising separating the 6-hydroxy-hexanoate from the two or more non-naturally occurring microbial organisms or a culture comprising the two or more non-naturally occurring microbial organisms.

115. The method of any one of Embodiments 83-102, wherein
the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;
the 2,6-dihydroxy-hexanoate CoA-transferase is an enzyme having an EC number 2.8.3, EC number 2.8.3.1, or EC number 2.8.3.12;
the 2,6-dihydroxy-hexanoyl-CoA 2-dehydratase is an enzyme having an EC number 4.2.1.167;
the 2,3-dehydro-hexanoyl-CoA 2,3-reductase is an enzyme having an EC number 1.3.1.44;
the 6-hydroxyhexanoyl-CoA transferase is an enzyme having an EC number 2.8.3, EC number 2.8.3.1, or EC number 2.8.3.12;
the 6-hydroxyhexanoate 1-reductase is an enzyme having an EC number 1.2.99.6; and
the 6-hydroxyhexanal 1-reductase is an enzyme having an EC number 1.1.1.

116. The method of any one of Embodiments 83-102, wherein
the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase is an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase is an enzyme comprising a sequence of SEQ ID NO:65;
the 6-hydroxyhexanoyl-CoA transferase is an enzyme comprising a sequence of SEQ ID NO:55, SEQ ID NO:56, SEQ ID NO:57, or SEQ ID NO:58;
the 6-hydroxyhexanoate 1-reductase is an enzyme comprising a sequence of SEQ ID NO:66, SEQ ID NO:67, or SEQ ID NO:68; and
the 6-hydroxyhexanal 1-reductase is an enzyme comprising a sequence of SEQ ID NO:70.

117. The method of any one of Embodiments 83-102, wherein
the 6-hydroxy-2-oxohexanoate-2-reductase has at least 50% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 50% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 50% identity to an enzyme comprising a sequence of SEQ ID NO:65;
the 6-hydroxyhexanoyl-CoA transferase has at least 50% identity to an enzyme comprising a sequence of SEQ ID NO:55, SEQ ID NO:56, SEQ ID NO:57, or SEQ ID NO:58;
the 6-hydroxyhexanoate 1-reductase has at least 50% identity to an enzyme comprising a sequence of SEQ ID NO:66, SEQ ID NO:67, or SEQ ID NO:68; and
the 6-hydroxyhexanal 1-reductase has at least 50% identity to an enzyme comprising a sequence of SEQ ID NO:70.

118. The method of any one of Embodiments 83-102, wherein
the 6-hydroxy-2-oxohexanoate-2-reductase has at least 70% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 70% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 70% identity to an enzyme comprising a sequence of SEQ ID NO:65;
the 6-hydroxyhexanoyl-CoA transferase has at least 70% identity to an enzyme comprising a sequence of SEQ ID NO:55, SEQ ID NO:56, SEQ ID NO:57, or SEQ ID NO:58;
the 6-hydroxyhexanoate 1-reductase has at least 70% identity to an enzyme comprising a sequence of SEQ ID NO:66, SEQ ID NO:67, or SEQ ID NO:68; and
the 6-hydroxyhexanal 1-reductase has at least 70% identity to an enzyme comprising a sequence of SEQ ID NO:70.

119. The method of any one of Embodiments 83-102, wherein the 6-hydroxy-2-oxohexanoate-2-reductase has at least 90% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 90% identity to an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 90% identity to an comprising a sequence of SEQ ID NO:65;

the 6-hydroxyhexanoyl-CoA transferase has at least 90% identity to an enzyme comprising a sequence of SEQ ID NO:55, SEQ ID NO:56, SEQ ID NO:57, or SEQ ID NO:58;

the 6-hydroxyhexanoate 1-reductase has at least 90% identity to an enzyme comprising a sequence of SEQ ID NO:66, SEQ ID NO:67, or SEQ ID NO:68; and the 6-hydroxyhexanal 1-reductase has at least 90% identity to an enzyme comprising a sequence of SEQ ID NO:70.

156. The method of any one of Embodiments 124-143, wherein the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;

the 2,6-dihydroxy-hexanoate CoA-transferase is an enzyme having an EC number 2.8.3, EC number 2.8.3.1, or EC number 2.8.3.12;

the 2,6-dihydroxy-hexanoyl-CoA 2-dehydratase is an enzyme having an EC number 4.2.1.167;

the 2,3-dehydro-hexanoyl-CoA 2,3-reductase is an enzyme having an EC number 1.3.1.44; and the 6-hydroxyhexanoyl-CoA transferase is an enzyme having an EC number 2.8.3, EC number 2.8.3.1, or EC number 2.8.3.12.

157. The method of any one of Embodiments 124-143, wherein the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase is an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase is an enzyme comprising a sequence of SEQ ID NO:65; and the 6-hydroxyhexanoyl-CoA transferase is an enzyme comprising a sequence of SEQ ID NO:55, SEQ ID NO:56, SEQ ID NO:57, or SEQ ID NO:58.

158. The method of any one of Embodiments 124-143, wherein the 6-hydroxy-2-oxohexanoate-2-reductase has at least 50% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 50% identity to an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 50% identity to an enzyme comprising a sequence of SEQ ID NO:65; and the 6-hydroxyhexanoyl-CoA transferase has at least 50% identity to an enzyme comprising a sequence of SEQ ID NO:55, SEQ ID NO:56, SEQ ID NO:57, or SEQ ID NO:58.

159. The method of any one of Embodiments 124-143, wherein the 6-hydroxy-2-oxohexanoate-2-reductase has at least 70% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 70% identity to an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 70% identity to an comprising a sequence of SEQ ID NO:65; and the 6-hydroxyhexanoyl-CoA transferase has at least 70% identity to an enzyme comprising a sequence of SEQ ID NO:55, SEQ ID NO:56, SEQ ID NO:57, or SEQ ID NO:58.

160. The method of any one of Embodiments 124-143, wherein the 6-hydroxy-2-oxohexanoate-2-reductase has at least 90% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 90% identity to an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 90% identity to an enzyme comprising a sequence of SEQ ID NO:65; and the 6-hydroxyhexanoyl-CoA transferase has at least 90% identity to an enzyme comprising a sequence of SEQ ID NO:55, SEQ ID NO:56, SEQ ID NO:57, or SEQ ID NO:58.

161. The method of any one of Embodiments 124-160, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase further comprise one or more protein tags.

162. The method of Embodiment 161, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

163. The method of any one of Embodiments 124-162, wherein the pyruvate is produced from carbon sources is selected from glycerol, glucose, xylose, arabinose, galactose, mannose, fructose, sucrose, and starch, or a combination thereof.

164. The method of any one of Embodiments 124-163, wherein the 3-hydroxy-propanal is produced by dehydration of glycerol by a glycerol dehydratase enzyme exogenously expressed by the one or more non-naturally occurring microbial organisms.

165. A method for producing adipic acid, the method comprising
contacting pyruvate and 3-hydroxy-propanal with a hydratase-aldolase and a quinone oxidoreductase to produce a 2-keto carboxylic acid of formula:

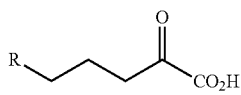

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxy-hexanoyl-CoA transferase to produce 6-hydroxy-hexanoate;
contacting the 6-hydroxy-hexanoate with a 6-hydroxy-hexanoate dehydrogenase to produce 6-oxo-hexanoate; and
contacting the 6-oxo-hexanoate with a 6-oxo-hexanoate oxidase to produce the adipic acid,
wherein the method is performed in a culture comprising one or more non-naturally occurring microbial organisms.

166. The method of Embodiment 165, wherein the hydratase-aldolase and the quinone oxidoreductase are expressed by the one or more non-naturally occurring microbial organisms.

167. The method of Embodiment 165, wherein at least one of the hydratase-aldolase and the quinone oxidoreductase is exogenously expressed by the one or more non-naturally occurring microbial organisms.

168. The method of Embodiment 165, wherein the hydratase-aldolase is exogenously expressed by the one or more non-naturally occurring microbial organisms.

169. The method of Embodiment 165, wherein the quinone oxidoreductase is exogenously expressed by the one or more non-naturally occurring microbial organisms.

170. The method of Embodiment 165, wherein the quinone oxidoreductase is overexpressed by the one or more non-naturally occurring microbial organisms.

171. The method of any one of Embodiments 165-170, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are expressed by the one or more non-naturally occurring microbial organisms.

172. The method of any one of Embodiments 165-170, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are exogenously expressed by the one or more non-naturally occurring microbial organisms.

173. The method of any one of Embodiments 165-170, wherein one or more of 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are overexpressed by the one or more non-naturally occurring microbial organisms.

174. The method of any one of Embodiments 165-173, further comprising separating the adipic acid from the one or more non-naturally occurring microbial organisms or a culture comprising the one or more non-naturally occurring microbial organisms.

175. A method for producing adipic acid, the method comprising
contacting pyruvate and 3-hydroxy-propanal with a hydratase-aldolase and a quinone oxidoreductase to produce a 2-keto carboxylic acid of formula:

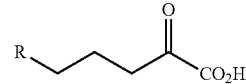

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxy-hexanoyl-CoA transferase to produce 6-hydroxy-hexanoate;
contacting the 6-hydroxy-hexanoate with a 6-hydroxy-hexanoate dehydrogenase to produce 6-oxo-hexanoate; and
contacting the 6-oxo-hexanoate with a 6-oxo-hexanoate oxidase to produce the adipic acid,
wherein the method is performed in a culture comprising two or more non-naturally occurring microbial organisms.

176. The method of Embodiment 175, wherein the hydratase-aldolase and the quinone oxidoreductase are expressed by the two or more non-naturally occurring microbial organisms.

177. The method of Embodiment 175, wherein at least one of the hydratase-aldolase and the quinone oxidoreductase is exogenously expressed by the two or more non-naturally occurring microbial organisms.

178. The method of Embodiment 175, wherein the hydratase-aldolase is exogenously expressed by the two or more non-naturally occurring microbial organisms.

179. The method of Embodiment 175, wherein the quinone oxidoreductase is exogenously expressed by the two or more non-naturally occurring microbial organisms.

180. The method of Embodiment 175, wherein the quinone oxidoreductase is overexpressed by the two or more non-naturally occurring microbial organisms.

181. The method of any one of Embodiments 175-180, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are expressed by the two or more non-naturally occurring microbial organisms.

182. The method of any one of Embodiments 175-180, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are exogenously expressed by the two or more non-naturally occurring microbial organisms.

183. The method of any one of Embodiments 175-180, wherein one or more of 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate dehydrogenase, and the 6-oxo-hexanoate oxidase are overexpressed by the two or more non-naturally occurring microbial organisms.

184. The method of any one of Embodiments 175-183, further comprising separating the adipic acid from the two or more non-naturally occurring microbial organisms or a culture comprising the two or more non-naturally occurring microbial organisms.

185. The method of any one of Embodiments 165-184, wherein the hydratase-aldolase is an enzyme having an EC number 4.1.2.45 or EC number 4.1.2.34 or EC number 4.1.1.4.

186. The method of any one of Embodiments 165-184, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP 034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

187. The method of any one of Embodiments 165-184, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

188. The method of any one of Embodiments 165-184, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

189. The method of any one of Embodiments 165-184, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

190. The method of any one of Embodiments 165-184, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

191. The method of any one of Embodiments 165-184, wherein the hydratase-aldolase is an enzyme selected from Tables 1 and 5-8.

192. The method of any one of Embodiments 165-191, wherein the quinone oxidoreductase is an enzyme having an EC number 1.6.5 (e.g., EC 1.6.5.5).

193. The method of any one of Embodiments 165-191, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

194. The method of any one of Embodiments 165-191, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

195. The method of any one of Embodiments 165-191, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

196. The method of any one of Embodiments 165-191, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

197. The method of any one of Embodiments 165-184, wherein
the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;
the 2,6-dihydroxy-hexanoate CoA-transferase is an enzyme having an EC number 2.8.3, EC number 2.8.3.1, or EC number 2.8.3.12;
the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44;
the 6-hydroxyhexanoyl-CoA transferase is an enzyme having an EC number 2.8.3, EC number 2.8.3.1, or EC number 2.8.3.12;
the 6-hydroxyhexanoate dehydrogenase is an enzyme having an EC number 1.1.1.258; and
the 6-oxo-hexanoate oxidase is an enzyme having an EC number 1.2.1.63.

198. The method of any one of Embodiments 165-184, wherein
the 6-hydroxy-2-oxohexanoate-2-reductase is an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase is an enzyme comprising a sequence of SEQ ID NO:55 or SEQ ID NO:58;
the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase is an enzyme comprising a sequence of SEQ ID NO:65;
the 6-hydroxyhexanoyl-CoA transferase is an enzyme comprising a sequence of SEQ ID NO:55 or SEQ ID NO:58;
the 6-hydroxyhexanoate dehydrogenase is an enzyme identified comprising a sequence of SEQ ID NO:71 or SEQ ID NO:72; and
the 6-oxo-hexanoate oxidase is an enzyme comprising a sequence of SEQ ID NO:75.

199. The method of any one of Embodiments 165-184, wherein
the 6-hydroxy-2-oxohexanoate-2-reductase has at least 50% identity to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 50% identity to an enzyme comprising a sequence of SEQ ID NO:55 or SEQ ID NO:58;
the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 50% identity to an enzyme comprising a sequence of SEQ ID NO:65;
the 6-hydroxyhexanoyl-CoA transferase has at least 50% identity to an enzyme comprising a sequence of SEQ ID NO:55 or SEQ ID NO:58;
the 6-hydroxyhexanoate dehydrogenase has at least 50% identity to an enzyme comprising a sequence of SEQ ID NO:71 or SEQ ID NO:72; and
the 6-oxo-hexanoate oxidase has at least 50% identity to an enzyme comprising a sequence of SEQ ID NO:75.

200. The method of any one of Embodiments 165-184, wherein
the 6-hydroxy-2-oxohexanoate-2-reductase has at least 70% identity to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 70% identity to an enzyme comprising a sequence of SEQ ID NO:55 or SEQ ID NO:58;
the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 70% identity to an comprising a sequence of SEQ ID NO:65;
the 6-hydroxyhexanoyl-CoA transferase has at least 70% identity to an enzyme comprising a sequence of SEQ ID NO:55 or SEQ ID NO:58;
the 6-hydroxyhexanoate dehydrogenase has at least 70% identity to an enzyme comprising a sequence of SEQ ID NO:71 or SEQ ID NO:72; and
the 6-oxo-hexanoate oxidase has at least 70% identity to an enzyme comprising a sequence of SEQ ID NO:75.

201. The method of any one of Embodiments 165-184, wherein
the 6-hydroxy-2-oxohexanoate-2-reductase has at least 90% identity to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 90% identity to an enzyme comprising a sequence of SEQ ID NO:55 or SEQ ID NO:58;
the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 90% identity to an comprising a sequence of SEQ ID NO:65;

the 6-hydroxyhexanoyl-CoA transferase has at least 90% identity to an enzyme comprising a sequence of SEQ ID NO:55 or SEQ ID NO:58;

the 6-hydroxyhexanoate dehydrogenase has at least 90% identity to an enzyme comprising a sequence of SEQ ID NO:71 or SEQ ID NO:72; and the 6-oxo-hexanoate oxidase has at least 90% identity to an enzyme comprising a sequence of SEQ ID NO:75.

202. The method of any one of Embodiments 165-201, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, 6-hydroxyhexanoate dehydrogenase, and the 6-oxo-hexanoate oxidase are further comprise one or more protein tags.

203. The method of Embodiment 202, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

204. The method of any one of Embodiments 165-203, wherein the pyruvate is produced from carbon sources is selected from glycerol, glucose, xylose, arabinose, galactose, mannose, fructose, sucrose, and starch, or a combination thereof.

205. The method of any one of Embodiments 165-204, wherein the 3-hydroxy-propanal is produced by dehydration of glycerol by a glycerol dehydratase enzyme exogenously expressed by the one or more non-naturally occurring microbial organisms.

206. A recombinant microbial organism comprising a first exogenous nucleic acid encoding an aldolase hydratase enzyme, wherein the recombinant microbial organism is further modified to express an increased amount of quinone oxidoreductase as compared to wild-type or the same microbial organism that is not modified, and optionally wherein the microbial organism is *Corynebacterium glutamicum*, a *clostridium* species, or *E. coli*.

207. The recombinant microorganism of Embodiment 206, wherein the organism comprises a second exogenous nucleic acid encoding quinone oxidoreductase.

208. The recombinant microorganism of Embodiment 207, wherein the first and/or second exogenous nucleic acid further comprises a regulatory element that drives expression of the second exogenous nucleic acid.

209. The recombinant microorganism of Embodiment 208, wherein the regulatory element is selected from a promoter or an enhancer.

210. The recombinant microbial organism of any one of Embodiments 206-209, wherein the aldolase hydratase enzyme has an EC number 4.1.2.45 or EC number 4.1.2.34 or EC number 4.1.1.4.

211. The recombinant microbial organism of any one of Embodiments 206-209, wherein the aldolase hydratase enzyme is an enzyme selected from the group of enzymes identified under Genbank or RefSeq or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

212. The recombinant microbial organism of any one of Embodiments 206-209, wherein the aldolase hydratase enzyme is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

213. The recombinant microbial organism of any one of Embodiments 206-209, wherein the aldolase hydratase enzyme has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

214. The recombinant microbial organism of any one of Embodiments 206-209, wherein the aldolase hydratase enzyme has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

215. The recombinant microbial organism of any one of Embodiments 206-209, wherein the aldolase hydratase enzyme has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

216. The recombinant microbial organism of any one of Embodiments 206-209, wherein the aldolase hydratase enzyme is an enzyme selected from Tables 1, 5-8.

217. The recombinant microbial organism of any one of Embodiments 206-216, wherein the first exogenous nucleic acid and the second exogenous nucleic acid are each contained in a vector.

218. The recombinant microbial organism of Embodiment 217, wherein the first exogenous nucleic acid and the second exogenous nucleic acid are each contained in the same vector.

219. The recombinant microbial organism of Embodiment 218, wherein the first exogenous nucleic acid and the second exogenous nucleic acid are each contained in their own separate vectors.

220. The recombinant microbial organism of any one of Embodiments 217-219, wherein the vector is a plasmid.
221. The recombinant microbial organism of any one of Embodiments 206-220, wherein the quinone oxidoreductase is an enzyme having an EC number 1.6.5 (e.g., EC 1.6.5.5).
222. The recombinant microbial organism of any one of Embodiments 206-220, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.
223. The recombinant microbial organism of any one of Embodiments 206-220, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.
224. The recombinant microbial organism of any one of Embodiments 206-220, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.
225. The recombinant microbial organism of any one of Embodiments 206-220, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.
226. The recombinant microbial organism of any one of Embodiments 206-220, wherein one or more of the hydratase-aldolase enzyme and quinone oxidoreductase further comprise one or more protein tags.
227. The recombinant microbial organism of Embodiment 226, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.
228. The recombinant microbial organism of any one of Embodiments 206-227, wherein the recombinant microbial organism is capable of producing a 2-keto carboxylic acid of formula:

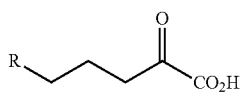

wherein R is H, $CH_3$, or $CH_2OH$.
229. The recombinant microbial organism of any one of Embodiments 206-228, wherein the recombinant microbial organism is capable of producing 1,5-pentanediol, 1,6-hexanediol, adipic acid, or 6-hydroxy hexanoate.
230. The recombinant microbial organism of any one of Embodiments 206-229, wherein the recombinant microbial organism is genetically modified to improve production of pyruvate from a carbon source.
231. The recombinant microbial organism of Embodiment 230, wherein the carbon source is selected from glycerol, glucose, xylose, arabinose, galactose, mannose, fructose, sucrose, and starch, or a combination thereof.
232. A population of recombinant microbial organisms of any one of Embodiments 206-231.
233. The population of Embodiment 232, which is substantially homogenous.
234. A method of producing 1,5-pentanediol, 1,6-hexanediol, adipic acid, or 6-hydroxy hexanoate, comprising culturing the population of Embodiment 232 or Embodiment 233 under suitable conditions.
235. The method of Embodiment 234, further comprising isolating the 1,5-pentanediol, 1,6-hexanediol, adipic acid, or 6-hydroxy hexanoate from the culture or the microbial organisms.
236. A culture comprising the recombinant microbial organisms of any one of Embodiments 206-231.
237. A culture comprising the populations of Embodiment 232 or Embodiment 233.
238. A method comprising:
   contacting pyruvate and an aldehyde with an aldol product biosynthesis polypeptide so that an aldol product is produced, wherein:
   the aldol product is a compound comprising an aldehyde or ketone group and a hydroxyl group attached to a beta-carbon of an aldehyde or ketone carbonyl group.
239. The method of Embodiment 238, wherein a —CHO group of the aldehyde is not conjugated to a double bond, a triple bond or an aromatic group.
240. A method comprising:
   contacting pyruvate and an aliphatic aldehyde with an aldol product biosynthesis polypeptide so that an aldol product is produced, wherein:
   the carbonyl group of the aliphatic aldehyde is not conjugated to a alkenyl, alkynyl, or aromatic group; and
   the aldol product is a compound comprising an aldehyde or ketone group and a hydroxyl group attached to a beta-carbon of an aldehyde or ketone carbonyl group.
241. The method of any one of Embodiments 238-240, wherein the aldol product biosynthesis polypeptide is or comprises an aldolase.
242. The method of any one of Embodiments 238-241, wherein the aldol product biosynthesis polypeptide is in a microbe.
243. The method of Embodiment 242, wherein the microbe is engineered to contain an exogenous nucleic acid that encodes an aldol product biosynthesis polypeptide.
244. The method of Embodiment any one of Embodiments 242-243, wherein the microbe expresses a modulated level of an aldol product biosynthesis polypeptide.
245. The method of Embodiment any one of Embodiments 242-244, wherein the microbe expresses an engineered aldol product biosynthesis polypeptide.
246. The method of any one of Embodiments 238-245, wherein conversion of pyruvate and an aliphatic aldehyde into an aldol product is catalyzed by an aldol product biosynthesis polypeptide.
247. The method of any one of Embodiments 238-246, wherein the method is performed in a culture.
248. The method of any one of Embodiments 238-247, comprising converting an aldol product into an aldol-dehydration product, wherein the aldol-dehydration product is a compound comprising an aldehyde or ketone group and a double bond conjugated with the aldehyde or ketone group.
249. The method of Embodiment 248, wherein the converting comprises contacting an aldol product with a dehydration product biosynthesis polypeptide so that an aldol-dehydration product is produced.
250. The method of any one of Embodiments 248-249, wherein the dehydration product biosynthesis polypeptide is in a microbe.
251. The method of Embodiment 250, wherein the microbe is engineered to contain an exogenous nucleic acid that encodes a dehydration product biosynthesis polypeptide.
252. The method of Embodiment any one of Embodiments 250-251, wherein the microbe expresses a modulated level of a dehydration product biosynthesis polypeptide.
253. The method of Embodiment any one of Embodiments 250-252, wherein the microbe expresses an engineered dehydration product biosynthesis polypeptide.
254. The method of any one of Embodiments 248-253, wherein conversion of an aldol product into an aldol-dehydration product is catalyzed by a dehydration product biosynthesis polypeptide.
255. The method of any one of Embodiments 248-254, wherein the method is performed in a culture.
256. The method of Embodiment 249, wherein a dehydration product biosynthesis polypeptide is a dehydratase.
257. A method comprising:
contacting pyruvate and an aldehyde with an aldol-dehydration product biosynthesis polypeptide so that an aldol-dehydration product is produced, wherein:
the aldol-dehydration product is a compound comprising an aldehyde or ketone group and a double bond conjugated with the aldehyde or ketone group.
258. The method of Embodiment 257, wherein a —CHO group of the aldehyde is not conjugated to a double bond, a triple bond or an aromatic group.
259. A method comprising:
contacting pyruvate and an aliphatic aldehyde with an aldol-dehydration product biosynthesis polypeptide so that an aldol-dehydration product is produced, wherein:
the carbonyl group of the aliphatic aldehyde is not conjugated to a alkenyl, alkynyl, or aromatic group; and
the aldol-dehydration product is a compound comprising an aldehyde or ketone group and a double bond conjugated with the aldehyde or ketone group.
260. The method of any one of Embodiments 257-259, wherein the aldol-dehydration product biosynthesis polypeptide is or comprises a hydratase-aldolase.
261. The method of Embodiment 260, wherein contacting pyruvate and an aliphatic aldehyde with a hydratase-aldolase produces an aldol-dehydration product.
262. The method of any one of Embodiments 257-259, wherein the aldol-dehydration product biosynthesis polypeptide is or comprises an enzyme having an EC number 4.1.2.45 or EC number 4.1.2.34, or EC 4.1.1.4, or is selected from Tables 1 and 5-8.
263. The method of any one of Embodiments 257-259, wherein the aldol-dehydration product biosynthesis polypeptide is or comprises a polypeptide which shares 10%, 15%, 20%, 25%, 30%, 35%, 40%, 45%, 50%, 55%, 60%, 65%, 70%, 75%, 80%, 85%, 90%, 95%, 96%, 97%, 95%, 99% or more homology with an enzyme of Embodiment 262.
264. The method of any one of Embodiments 257-259, wherein the aldol-dehydration product biosynthesis polypeptide is or comprises an aldolase.
265. The method of any one of Embodiments 257-264, wherein the aldol-dehydration product biosynthesis polypeptide is in a microbe.
266. The method of Embodiment 265, wherein the microbe is engineered to contain an exogenous nucleic acid that encodes an aldol-dehydration product biosynthesis polypeptide.
267. The method of Embodiment any one of Embodiments 265-266, wherein the microbe expresses a modulated level of an aldol-dehydration product biosynthesis polypeptide.
268. The method of Embodiment any one of Embodiments 265-267, wherein the microbe expresses an engineered aldol-dehydration product biosynthesis polypeptide.
269. The method of any one of Embodiments 257-268, wherein conversion of pyruvate and an aliphatic aldehyde into an aldol-dehydration product is catalyzed by an aldol-dehydration product biosynthesis polypeptide.
270. The method of any one of Embodiments 257-269, wherein the method is performed in a culture.
271. A method comprising:
contacting an alkene with an alkene reduction product biosynthesis polypeptide so that an alkene reduction product is produced, wherein:
the alkene comprises a double bond conjugated to a carbonyl group; and
a double bond conjugated to a carbonyl group in the alkene is reduced to a single bond to provide an alkene reduction product.
272. The method of Embodiment 271, wherein the alkene is an aldol-dehydration product of any one of Embodiments 257-270.
273. The method of any one of Embodiments 271-272, wherein an alkene reduction product biosynthesis polypeptide is or comprises an enzyme that catalyzes reduction of a 2-oxo-3-enoic acid or a salt thereof.
274. The method of any one of Embodiments 271-272, wherein an alkene reduction product biosynthesis polypeptide is or comprises an enzyme that belongs to EC 1.6.5.
275. The method of any one of Embodiments 271-272, wherein an alkene reduction product biosynthesis polypeptide is or comprises an enzyme that belongs to EC 1.6.5.5 or is selected from Table 9.
276. The method of any one of Embodiments 271-272, wherein the alkene reduction product biosynthesis polypeptide is or comprises a polypeptide which shares 10%, 15%, 20%, 25%, 30%, 35%, 40%, 45%, 50%, 55%, 60%, 65%, 70%, 75%, 80%, 85%, 90%, 95%, 96%, 97%, 95%, 99% or more homology with an enzyme of any one of Embodiments 274-275.
277. The method of any one of Embodiments 271-276, wherein an alkene reduction product biosynthesis polypeptide is in a microbe.
278. The method of Embodiment 277, wherein the microbe is engineered to contain an exogenous nucleic acid that encodes an alkene reduction product biosynthesis polypeptide.
279. The method of Embodiment any one of Embodiments 277-278, wherein the microbe expresses a modulated level of an alkene reduction product biosynthesis polypeptide.
280. The method of Embodiment any one of Embodiments 277-279, wherein the microbe expresses an engineered alkene reduction product biosynthesis polypeptide.
281. The method of any one of Embodiments 271-280, wherein conversion of an alkene into an alkene reduction product is catalyzed by an alkene reduction product biosynthesis polypeptide.

282. The method of any one of Embodiments 271-281, wherein the method is performed in a culture.

283. The method of any one of Embodiments 238-270, comprising a method of any one of Embodiments 271-282.

284. The method of any one of Embodiments 238-283, wherein the aldehyde has the structure of formula A-1 thereof:

R$^a$-L$^2$-L$^1$-C(O)H,  A-1 or a salt thereof, wherein:

R$^a$ is R" or —OR", each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO$_2$R', or —SO$_2$R';

R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

285. The method of any one of Embodiments 238-256 and 284, wherein the aldol product has the structure of formula P-1:

R$^a$-L$^2$-L$^1$-CH(OH)—CH$_2$—C(O)—C(O)OH,  P-1 or a salt thereof, wherein:

R$^a$ is R" or —OR", each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO$_2$R', or —SO$_2$R';

R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

286. The method of any one of Embodiments 257-285, wherein the aldol-dehydration product has the structure of formula P-2:

R$^a$-L$^2$-L$^1$-CH=CH—C(O)—C(O)OH,  P-2 or a salt thereof, wherein:

R$^a$ is R" or —OR", each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO$_2$R', or —SO$_2$R';

R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

287. The method of Embodiment 286, wherein the —CH=CH— is in E configuration.

288. The method of Embodiment 286, wherein the —CH=CH— is in Z configuration.

289. The method of any one of Embodiments 271-288, wherein the alkene reduction product has the structure of formula P-3:

R$^a$-L$^2$-L$^1$-CH$_2$—CH$_2$—C(O)—C(O)OH,  P-3 or a salt thereof, wherein:

R$^a$ is R" or —OR", each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO₂R', or —SO₂R';

R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

290. The method of any one of Embodiments 238-284, comprising converting an alkene reduction product into a compound of formula P-10:

   P-10 or a salt thereof.

291. The method of any one of Embodiments 238-284, comprising converting an alkene reduction product into a compound of formula P-10':

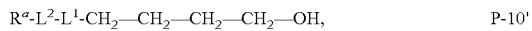   P-10' or a salt thereof.

292. The method of any one of Embodiments 238-291, comprising converting an alkene reduction product into a carbonyl reduction product, wherein:

the alkene reduction product comprises a carbonyl group; and a carbonyl group of the alkene reduction product is converted to —CH(OH)—.

293. The method of any one of Embodiments 238-291, comprising contacting an alkene reduction product with a carbonyl reduction product biosynthesis polypeptide so that a carbonyl reduction product is produced, wherein:

the alkene reduction product comprises a carbonyl group; and a carbonyl group of the alkene reduction product is converted to —CH(OH)—.

294. The method of Embodiment 293, wherein the carbonyl reduction product biosynthesis polypeptide is or comprises a keto reductase or a 2-keto acid-2-reductase.

295. The method of any one of Embodiments 293-294, wherein the carbonyl reduction product biosynthesis polypeptide is in a microbe.

296. The method of Embodiment 295, wherein the microbe is engineered to contain an exogenous nucleic acid that encodes a carbonyl reduction product biosynthesis polypeptide.

297. The method of Embodiment any one of Embodiments 295-296, wherein the microbe expresses a modulated level of a carbonyl reduction product biosynthesis polypeptide.

298. The method of Embodiment any one of Embodiments 295-297, wherein the microbe expresses an engineered carbonyl reduction product biosynthesis polypeptide.

299. The method of any one of Embodiments 290-298, wherein conversion of an alkene reduction product into a carbonyl reduction product is catalyzed by a carbonyl reduction product biosynthesis polypeptide.

300. The method of any one of Embodiments 290-299, wherein the method is performed in a culture.

301. The method of any one of Embodiments 290-300, wherein a carbonyl reduction product has the structure of formula P-4:

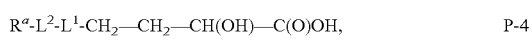   P-4 or a salt thereof, wherein:

R$^a$ is R" or —OR", each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")₂—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)₂—, —S(O)₂N(R")—, —C(O)S—, or —C(O)O—;

-Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO₂R', or —SO₂R';

R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

302. The method of any one of Embodiments 238-301, comprising converting a compound of formula P-4 or a salt thereof into a compound of formula P-5:

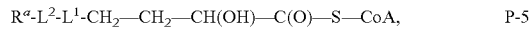   P-5 or a salt thereof.

303. The method of Embodiment 302, wherein the conversion comprises contacting a compound of formula P-4 or a salt thereof with a CoA transfer product biosynthesis polypeptide.

304. The method of any one of Embodiments 238-303, comprising converting a compound of formula P-5 or a salt thereof into a compound of formula P-6:

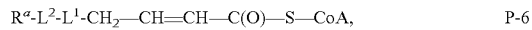   P-6 or a salt thereof.

305. The method of Embodiment 304, wherein the conversion comprises contacting a compound of formula P-5 or a salt thereof with a dehydration product biosynthesis polypeptide.

306. The method of any one of Embodiments 238-305, comprising converting a compound of formula P-6 or a salt thereof into a compound of formula P-7:

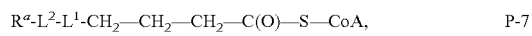   P-7 or a salt thereof.

307. The method of Embodiment 306, wherein the conversion comprises contacting a compound of formula P-6 or a salt thereof with a reduction product biosynthesis polypeptide which is or comprises 2,3-enoyl-CoA reductase.

308. The method of any one of Embodiments 238-307, comprising converting a compound of formula P-7 or a salt thereof into a compound of formula P-8:

   P-8 or a salt thereof.

309. The method of Embodiment 308, wherein the conversion comprises contacting a compound of formula P-7 or a salt thereof with a CoA transfer product biosynthesis polypeptide.

310. The method of any one of Embodiments 238-309, comprising converting a compound of formula P-8, wherein L² is —CH₂-L²'-, or a salt thereof into a compound of formula P-9:

H—C(O)-L²'-L¹-CH₂—CH₂—CH₂—C(O)—OH,     P-9 or a salt thereof, wherein:

L²' is a covalent bond, or a bivalent, optionally substituted, linear or branched C₁₋₁₉ aliphatic or C₁₋₁₉ heteroaliphatic, wherein one or more methylene units are optionally and independently replaced by —C≡C—, —C(R")₂—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)₂—, —S(O)₂N(R")—, —C(O)S—, or —C(O)O—.

311. The method of Embodiment 310, wherein the conversion comprises contacting a compound of formula P-8 or a salt thereof with an oxidation product biosynthesis polypeptide which is or comprises an alcohol dehydrogenase.

312. The method of any one of Embodiments 238-311, comprising converting a compound of formula P-9 or a salt thereof into a compound of formula P-10:

HO—C(O)-L²'-L¹-CH₂—CH₂—CH₂—C(O)—OH,     P-10 or a salt thereof.

313. The method of Embodiment 312, wherein the conversion comprises contacting a compound of formula P-9 or a salt thereof with an aldehyde oxidation product biosynthesis polypeptide.

314. The method of any one of Embodiments 238-312, comprising converting a compound of formula P-8 or a salt thereof into a compound of formula P-9':

Rᵃ-L²-L¹-CH₂—CH₂—CH₂—C(O)—H,     P-9' or a salt thereof.

315. The method of Embodiment 314, comprising contacting a compound of formula P-8 or a salt thereof with a carboxyl reduction product biosynthesis polypeptide.

316. The method of any one of Embodiments 238-315, comprising converting a compound of formula P-9' or a salt thereof into a compound of formula P-10':

Rᵃ-L²-L¹-CH₂—CH₂—CH₂—CH₂—OH,     P-10' or a salt thereof.

317. The method of Embodiment 316, comprising contacting a compound of formula P-9' or a salt thereof with an aldehyde reduction product biosynthesis polypeptide which is or comprises an aldehyde reductase or a primary alcohol dehydrogenase.

318. The method of any one of Embodiments 238-290, comprising converting a compound of formula P-3 or a salt thereof into a compound of formula P-5':

Rᵃ-L²-L¹-CH₂—CH₂—CH₂—OH,     P-5' or a salt thereof.

319. The method of any one of Embodiments 238-290 or 318, comprising converting a compound of formula P-3 or a salt thereof into a compound of formula P-4':

Rᵃ-L²-L¹-CH₂—CH₂—C(O)—H,     P-4' or a salt thereof.

320. The method of Embodiment 319, comprising contacting a compound of formula P-3 or a salt thereof with a decarboxylation product biosynthesis polypeptide.

321. The method of any one of Embodiments 238-290, comprising converting a compound of formula P-4' or a salt thereof into a compound of formula P-5':

Rᵃ-L²-L¹-CH₂—CH₂—CH₂—OH,     P-5' or a salt thereof.

322. The method of Embodiment 321, comprising contacting a compound of formula P-4' or a salt thereof with an aldehyde reduction product biosynthesis polypeptide.

323. The method of any one of Embodiments 301-322, wherein one or more or each converting independently comprises contacting a compound with a suitable biosynthesis polypeptide.

324. The method of Embodiment 323, wherein one or more or all biosynthesis polypeptides are independently in a microbe.

325. The method of Embodiment 324, wherein the microbe is engineered to contain one or more exogenous nucleic acids that encode one or more or all of the biosynthesis polypeptides.

326. The method of Embodiment any one of Embodiments 324-325, wherein the microbe expresses a modulated level of one or more or all of the biosynthesis polypeptides.

327. The method of Embodiment any one of Embodiments 324-326, wherein one or more or all of the biosynthesis polypeptides are independently engineered.

328. The method of any one of Embodiments 324-326, wherein a suitable biosynthesis polypeptide catalyzes a corresponding conversion.

329. The method of any one of Embodiments 285-328, wherein Rᵃ is —H.

330. The method of any one of Embodiments 285-328, wherein Rᵃ is —OH.

331. The method of any one of Embodiments 285-330, wherein L¹ is optionally substituted C₁₋₆ alkylene.

332. The method of any one of Embodiments 285-330, wherein L¹ is unsubstituted C₁₋₆ alkylene.

333. The method of any one of Embodiments 331-332, wherein the alkylene is —CH₂—.

334. The method of any one of Embodiments 331-332, wherein the alkylene is —CH₂CH₂—.

335. The method of any one of Embodiments 331-332, wherein the alkylene is —CH₂CH₂CH₂—.

336. The method of any one of Embodiments 285-330, wherein L¹ is a covalent bond.

337. The method of any one of Embodiments 285-336, wherein L² is a covalent bond.

338. The method of any one of Embodiments 285-336, wherein L² is optionally substituted C₁₋₆ alkylene.

339. The method of any one of Embodiments 285-336, wherein L² is unsubstituted C₁₋₆ alkylene.

340. The method of any one of Embodiments 338-339, wherein the alkylene is —CH₂—.

341. The method of any one of Embodiments 338-339, wherein the alkylene is —CH₂CH₂—.

342. The method of any one of Embodiments 338-339, wherein the alkylene is —CH₂CH₂CH₂—.

343. The method of Embodiment 284, wherein the aliphatic aldehyde is HO—CH₂—CH₂—CHO.

344. The method of Embodiment 285 or 343, wherein the aldol product is HO—CH₂—CH₂—CH(OH)—CH₂—C(O)—COOH or a salt thereof.

345. The method of any one of Embodiments 286 and 343-344, wherein the aldol-dehydration product is HO—CH₂—CH₂—CH=CH—C(O)—COOH or a salt thereof.

346. The method of any one of Embodiments 289 and 343-345, wherein the alkene reduction product is HO—$CH_2$—$CH_2$—$CH_2$—$CH_2$—C(O)—COOH or a salt thereof.

347. The method of any one of Embodiments 301 and 343-346, wherein the carbonyl reduction product is HO—$CH_2$—$CH_2$—$CH_2$—$CH_2$—CH(OH)—COOH or a salt thereof.

348. The method of any one of Embodiments 302 and 343-347, wherein a compound of formula P-5 or a salt thereof is HO—$CH_2$—$CH_2$—$CH_2$—$CH_2$—CH(OH)—CO—S—CoA or a salt thereof.

349. The method of any one of Embodiments 303 and 343-348, wherein a compound of formula P-6 or a salt thereof is HO—$CH_2$—$CH_2$—$CH_2$—CH=CH—CO—S—CoA or a salt thereof.

350. The method of any one of Embodiments 305 and 343-349, wherein a compound of formula P-7 or a salt thereof is HO—$CH_2$—$CH_2$—$CH_2$—$CH_2$—$CH_2$—CO—S—CoA or a salt thereof.

351. The method of any one of Embodiments 308 and 343-350, wherein a compound of formula P-8 or a salt thereof is HO—$CH_2$—$CH_2$—$CH_2$—$CH_2$—$CH_2$—CO—OH or a salt thereof.

352. The method of any one of Embodiments 310 and 343-351, wherein a compound of formula P-9 or a salt thereof is H—C(O)—$CH_2$—$CH_2$—$CH_2$—$CH_2$—CO—OH or a salt thereof.

353. The method of any one of Embodiments 312 and 343-352, wherein a compound of formula P-10 or a salt thereof is HO—CO—$CH_2$—$CH_2$—$CH_2$—$CH_2$—CO—OH or a salt thereof.

354. The method of any one of Embodiments 310 and 343-351, wherein a compound of formula P-9' or a salt thereof is HO—$CH_2$—$CH_2$—$CH_2$—$CH_2$—$CH_2$—C(O)—H or a salt thereof.

355. The method of any one of Embodiments 312 and 343-351 and 354, wherein a compound of formula P-10' or a salt thereof is HO—$CH_2$—$CH_2$—$CH_2$—$CH_2$—$CH_2$—$CH_2$—OH or a salt thereof.

356. The method of any one of Embodiments 317 and 343-346, wherein a compound of formula P-4' or a salt thereof is HO—$CH_2$—$CH_2$—$CH_2$—$CH_2$—C(O)—H or a salt thereof.

357. The method of any one of Embodiments 317 and 343-346 and 356, wherein a compound of formula P-5' or a salt thereof is HO—$CH_2$—$CH_2$—$CH_2$—$CH_2$—$CH_2$—OH or a salt thereof.

358. The method of any one of Embodiments 238-357, wherein a microbe comprises two or more biosynthesis polypeptides in the contacting steps.

359. The method of any one of Embodiments 238-358, comprising performing one or more contacting and/or conversion steps in one type of microbe, and one or more other contacting and/or conversion steps in another type of microbe.

360. The method of any one of Embodiments 238-359, comprising performing one or more contacting and/or conversion steps in one culture, and one or more other contacting and/or conversion steps in another culture.

361. The method of any one of Embodiments 238-359, comprising performing the contacting and/or conversion steps in a single culture.

362. The method of any one of Embodiments 238-361, wherein a microbe comprises all biosynthesis polypeptides recited in the contacting steps.

363. The method of Embodiment 362, comprising performing the contacting and/or conversion steps in a single culture.

364. The method of any one of the preceding Embodiments, wherein the product is produced at about or at least about 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L of culture.

365. The method of any one of the preceding Embodiments, wherein pyruvate utilization for a desired product is about or is at least about 5%, 10%, 15%, 20%, 25%, 30%, 35%, 40%, 45%, 50%, 55%, 60%, 65%, 70%, 75%, 80%, 85%, 90%, or 95%.

366. A preparation prepared by a method of any one of the preceding Embodiments.

367. A preparation of a compound of formula P-1, P-2, P-3, P-4, P-4', P-5, P-5', P-6, P-7, P-8, P-9, P-9', P-10, or P-10', or salt thereof, or a preparation prepared by a method of any one of the preceding Embodiments, which preparation is enriched for $^{14}C$ isotope relative to that observed in a reference preparation of the compound, which reference preparation is prepared using fossil carbon source.

368. A preparation of a polyester, a polyester polyol, a polyurethane, nylon 6, nylon 6,6, a polycarbonate diol, diacrylate ester, or diglycidyl ether, which preparation is manufactured using a preparation prepared by a method of any one of the preceding claims.

369. The preparation of Embodiment 368, wherein the preparation is enriched for $^{14}C$ isotope relative to that observed in a reference preparation of the compound, which reference preparation is prepared using fossil carbon source.

370. An nucleic acid encoding one or more biosynthesis polypeptides of any one of the preceding Embodiments.

371. The nucleic acid of Embodiment 370, wherein the nucleic acid differs from a natural nucleic acid which encodes the same biosynthesis polypeptide.

372. The nucleic acid of Embodiment 370 or 371, wherein the nucleic acid is optimized for expression in a microorganism.

373. An engineered microbe that produces an aldol product of an aliphatic aldehyde, the microbe comprising increased expression or activity of an aldol product biosynthesis polypeptide, wherein:

the carbonyl group of the aliphatic aldehyde is not conjugated to a alkenyl, alkynyl, or aromatic group;

the aldol product is a compound comprising an aldehyde or ketone group and a hydroxyl group attached to a beta-carbon of an aldehyde or ketone carbonyl group.

374. The microbe of Embodiment 373, wherein the aliphatic aldehyde is described in any one of Embodiments 238-363.

375. The microbe of Embodiment 373, wherein the aldol product is described in any one of Embodiments 238-363.

376. An engineered microbe that produces an aldol-dehydration product of an aliphatic aldehyde, the microbe comprising increased expression or activity of an aldol product biosynthesis polypeptide, an aldol-dehydration product biosynthesis polypeptide, a dehydration product biosynthesis polypeptide, or any combination thereof, wherein:

the carbonyl group of the aliphatic aldehyde is not conjugated to a alkenyl, alkynyl, or aromatic group; and the aldol-dehydration product is a compound comprising an aldehyde or ketone group and a double bond conjugated with the aldehyde or ketone group.

377. The microbe of Embodiment 376, wherein the aliphatic aldehyde is described in any one of Embodiments 238-363.

378. The microbe of Embodiment 376, wherein the aldol-dehydration product is described in any one of Embodiments 238-363.

379. An engineered microbe that produces an alkene reduction product, the microbe comprising increased expression or activity of an alkene reduction product biosynthesis polypeptide, wherein:
the alkene comprises a double bond conjugated to a carbonyl group; and
a double bond conjugated to a carbonyl group in the alkene is reduced to a single bond to provide an alkene reduction product.

380. The microbe of Embodiment 379, wherein the alkene is described in any one of Embodiments 271-363.

381. The microbe of Embodiment 379, wherein the alkene reduction product is described in any one of Embodiments 238-363.

382. The microbe of any one of Embodiments 373-381, further comprising increased expression or activity of a biosynthesis polypeptide of any one of Embodiments 271-363.

383. A culture, comprising a microbe of any one of Embodiments 238-382, and one or more compounds independently of formulae P-1 to P-10, P-9', P-10', P-4' or P-5', or a salt thereof.

384. The culture of Embodiment 383, wherein one or more compounds are independently of higher levels compared to a reference culture of comparable microbes without the increased expression or activity of a biosynthesis polypeptide(s).

385. The culture of any one of Embodiments 383-384, wherein each of the compounds of formulae P-1 to P-10, P-9', P-10', P-4' or P-5', or a salt thereof is independently as described in any one of Embodiments 238-363.

386. A method, preparation, compound, organism, microorganism, culture or product as described herein.

EXAMPLES

The following examples are set forth below to illustrate the methods and results according to the disclosed subject matter. These examples are not intended to be inclusive of all aspects of the subject matter disclosed herein, but rather to illustrate certain representative methods and results. These examples are not intended to exclude equivalents and variations of the subject matter described herein which are apparent to one skilled in the art. Throughout the examples, sequences of enzymes or proteins are identified by their Uniprot ID or by their GenBank Accession Numbers (referred to as GenBank ID or GenBank Accession No.) or by their RefSeq ID. In case of Uniprot ID, the sequences are denoted by the primary (citable) accession number. RefSeq protein record represents non-redundant protein sequences within the NCBI database. Non-redundant protein records represent one exact sequence that has been observed once or many times in different strains or species.

Example 1: Enzymes that Catalyze Aldol-Dehydration Product Biosynthesis Using Aliphatic Aldehydes It has not previously been demonstrated that trans-o-hydroxybenzylidenepyruvate hydratase-aldolases (EC 4.1.2.45)[1-5] or 4-(2-carboxyphenyl)-2-oxobut-3-enoate aldolases (E.C. 4.1.2.34; also referred to as trans-2'-carboxybenzalpyruvate hydratase-aldolases)[6], referred cumulatively herein as hydratase-aldolases or Ads-Hyd, possess any aldol addition or aldol condensation activity on aliphatic aldehydes,[1-6] especially those without any unsaturation next to the aldehyde group.[5] Instead, the aldol condensation activity of these enzymes has previously been limited to substrates wherein the newly formed unsaturation can be stabilized via conjugation to unsaturation present within the aldehyde substrate.[1-5] Examples of such aldehyde substrates include aromatic conjugated aldehydes such as benzaldehyde or alkenals (i.e., aliphatic aldehydes with double bonds between C2 and C3). It has been unexpectedly discovered that these hydratase-aldolases are capable of utilizing a number of aliphatic aldehydes, e.g., linear aldehydes of different carbon lengths and different functionalities as substrates and are able to provide aldol-dehydration products, without the intention to be limited by any theory, through carrying out both aldol addition and aldol condensation reactions with pyruvate as the donor (nucleophile) to give the corresponding 4-hydroxy-2-keto-carboxylic acids and 3,4-dehydro-2-keto-carboxylic acids respectively as products. Results for representative trans-o-hydroxybenzylidenepyruvate hydratase-aldolases (e.g., entries Ads-Hyd 2 & 9 in Table 1) and trans-2'-carboxybenzalpyruvate hydratase-aldolases (e.g., entry Ads-Hyd 3 in Table 1) are summarized in Table 1 for aldol-dehydration activity (both aldol addition and aldol condensation), wherein pyruvate is used as donor and acetaldehyde, propionaldehyde, and 3-hydroxy-propanal are used as acceptor aldehydes.

TABLE 1

Provided technologies are active toward various aldehydes.

| Ads-Hyd ID | Uniprot ID or Genbank or RefSeq ID | EC Number | % Identitiy to following Ads-Hyd sequences | | | Activity on Different substrates | | |
|---|---|---|---|---|---|---|---|---|
| | | | A0A286PH18 | P0A144 | Q79EM8 | Acetaldehyde | Propanal | 3-hydroxy-propanal |
| Ads-Hyd 1 | D7C0E5 | UA | 93.6 | ND | ND | + | + | + |
| Ads-Hyd 2 | P0A144 | 4.1.2.45 | ND | 100 | 38.3 | + | + | + |
| Ads-Hyd 3 | Q79EM8 | 4.1.2.34 | ND | 38.3 | 100 | + | + | NA |
| Ads-Hyd 4 | A0A0N0AHI8 | UA | 59.2 | ND | ND | NT | NT | + |
| Ads-Hyd 5 | A0A0N1FRY3 | UA | 93.6 | ND | ND | NT | NT | + |
| Ads-Hyd 6 | M3DYR1 | UA | 59 | ND | ND | NT | + | + |
| Ads-Hyd 7 | W7SU48 | UA | 63 | ND | ND | NT | NT | + |
| Ads-Hyd 8 | A0A286PH18 | UA | 100 | 13.7 | 17 | NT | + | + |
| Ads-Hyd 9 | Q9X9Q6 | 4.1.2.45 | ND | 57 | 36.3 | NT | NT | + |
| Ads-Hyd 10 | Q9WXH7 | UA | ND | 55.6 | 36 | NT | + | + |
| Ads-Hyd 11 | A4XDS1 | UA | ND | 56 | 36.5 | NT | NT | + |
| Ads-Hyd 12 | F2J6N9 | UA | ND | 60.1 | 40.2 | NT | NT | + |

TABLE 1-continued

Provided technologies are active toward various aldehydes.

| Ads-Hyd ID | Uniprot ID or Genbank or RefSeq ID | EC Number | % Identitiy to following Ads-Hyd sequences | | | Activity on Different substrates | | |
|---|---|---|---|---|---|---|---|---|
| | | | A0A286PH18 | P0A144 | Q79EM8 | Acetaldehyde | Propanal | 3-hydroxy-propanal |
| Ads-Hyd 13 | A0A063BFL5 | UA | ND | 63.2 | 34.7 | NT | NT | + |
| Ads-Hyd 14 | Q9ZHH6 | UA | ND | 73.1 | 38.6 | NT | NT | + |
| Ads-Hyd 15 | A0A0C1K853 | UA | ND | 75.2 | 38.6 | NT | NT | + |
| Ads-Hyd 62 | WP_034398482 | UA | ND | 81.7 | 36.8 | NT | NT | + |
| Ads-Hyd 87 | PYK12191 | UA | 50.4 | ND | ND | NT | NT | + |
| Ads-Hyd 96 | A0A370X7D8 | UA | 55.8 | ND | ND | NT | NT | + |
| Ads-Hyd 104 | WP_028222253 | UA | 56.1 | ND | ND | NT | NT | + |
| Ads-Hyd 65 | F2J6L6 | UA | ND | 59.8 | 39.8 | NT | NT | + |
| Ads-Hyd 89 | A0A0N0L9F6 | UA | 54 | ND | ND | NT | NT | + |
| Ads-Hyd 97 | A0A1G9YWG7 | UA | 56.6 | ND | ND | NT | NT | + |
| Ads-Hyd 68 | A0A2U1BT09 | UA | ND | 50.7 | 34.8 | NT | NT | + |
| Ads-Hyd 108 | A0A244DHE8 | UA | 57.4 | ND | ND | NT | NT | + |
| Ads-Hyd 29 | WP_107818191 | UA | ND | 58.3 | 39.8 | NT | NT | + |
| Ads-Hyd 69 | A0A023WZF9 | UA | ND | 91.3 | 37.1 | NT | NT | + |
| Ads-Hyd 93 | PYN48855 | UA | 49.3 | ND | ND | NT | NT | + |
| Ads-Hyd 98 | A0A421PAQ6 | UA | 58.3 | ND | ND | NT | NT | NA |
| Ads-Hyd 99 | WP_028217297 | UA | 56.7 | ND | ND | NT | NT | + |
| Ads-Hyd 100 | WP_034507049 | UA | 56 | ND | ND | NT | NT | NA |
| Ads-Hyd 110 | KMK64081.1 | 4.1.2.45 | ND | 56 | 36 | + | + | + |
| Ads-Hyd 111 | WP_070028041.1 | 4.1.2.45 | ND | 35 | 35 | NT | NT | + |
| Ads-Hyd 112 | KZL92449.1 | 4.1.1.4 | 40 | ND | ND | NT | NT | + |

NT = Not tested;
NA = Not active;
+ = active;
UA = EC number is unassigned;
ND = Actual value is not determined as sequence identity is too blow (~<25%)

Aldol addition and aldol condensation activity on aliphatic unconjugated aldehydes of different carbon lengths and functionalities by a subset of enzymes from Table 1 is summarized in Table 2, further demonstrating the versatility of unconjugated aldehyde substrates suitable for this reaction.

TABLE 2

Provided technologies are active toward various aldehydes.

| Enzyme ID | Aldol Addition | | | | | | Aldol Condensation | | | | | |
|---|---|---|---|---|---|---|---|---|---|---|---|---|
| | A | B | C | D | E | F | A | B | C | D | E | F |
| Ads-Hyd 1 | Yes | Yes | NT | NT | Yes | NT | Yes | Yes | NT | NT | Yes | NT |
| Ads-Hyd 2 | Yes | Yes | NT | NT | Yes | NT | Yes | Yes | NT | Yes | Yes | NT |
| Ads-Hyd 108 | Yes | Yes | NT | NT | Yes | NT | Yes | Yes | NT | NT | Yes | NT |
| Ads-Hyd 3 | Yes | Yes | Yes | Yes | Yes | Yes | Yes | Yes | Yes | Yes | Yes | Yes |
| Ads-Hyd 8 | Yes | Yes | Yes | Yes | Yes | Yes | Yes | Yes | Yes | Yes | Yes | Yes |
| Ads-Hyd 89 | Yes | Yes | NT | Yes | Yes | Yes | Yes | Yes | NT | Yes | Yes | Yes |
| Ads-Hyd 110 | Yes | Yes | Yes | Yes | Yes | Yes | Yes | Yes | Yes | Yes | Yes | Yes |
| Ads-Hyd 112 | NT | NT | NT | Yes | Yes | NT | NT | NT | NT | Yes | Yes | NT |
| HpaI | Yes | Yes | Yes | Yes | Yes | Yes | No | No | No | No | No | No |

NT = Not tested;
A = acetaldehyde;
B = propionaldehyde;
C = butyraldehyde;
D = 2-hydroxy acetaldehyde;
E = 3'-hydroxy-propanal;
F = 4-hydroxy butyraldehyde Among other things, the technologies provide high efficiency, e.g., in terms of product production rate, yield and/or utilization of substrates, e.g., pyruvate. In some embodiments, a biosynthesis polypeptide is about 50%, 100%, or 1.5, 2, 3, 4, 5, 6, 7, 8, 9, 10, 20, 50, 100 fold or more active, as measured by production of comparable products under suitable conditions, compared to a relevant reference biosynthesis polypeptide. In some embodiments, the present disclosure provides highly efficient utilization of a substrate, e.g., pyruvate. In some embodiments, utilization of a substrate, e.g., pyruvate, is about or at least about 5%, 10%, 15%, 20%, 25%, 30%, 35%, 40%, 45%, 50%, 55%, 60%, 65%, 70%, 75%, 80%, 85%, 90%, or 95%. In some embodiments, desired product concentration in a culture is about or is at least about 0.1, 0.2, 0.3, 0.4, 0.5, 0.6, 0.7, 0.8, 0.9, 1, 2, 3, 4, 5, 6, 7, 8, 9, or 10 g/L after a period of production time (e.g., 90 min). In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. For example, Table 3 demonstrates dramatically improved efficiency of provided technologies compared to aldolases known previously to catalyze corresponding reactions: a representative trans-o-hydroxybenzylidenepyruvate hydratase-aldolase in Table 3 outperforms (e.g., >5 times activity) the other aldolases in terms of aldol addition activity on the tested substrates. Among other things, Table 4 demonstrated that Ads-Hyd enzymes can provide improved product yields as well as highly efficient utilization of substrate pyruvate compared to the comparative aldolases. This is particularly notable since pyruvate is a central metabolite and may be consumed by other reactions within a microorganism. As demonstrated herein, provided technologies comprising aldol-dehydration product biosynthesis polypeptides can effectively minimize pyruvate consumption in vivo by undesirable reactions, which is crucial to improve desired product yield in vivo.

see Tables 6-8) have not been assigned an EC number. Additionally, these enzymes have also been annotated in literature or databases (e.g., Uniprot) as acetoacetate decarboxylase or dihydrodipicolinate synthetase or simply as aldolases due to the similarity with these other classes of enzymes. For example, Ads-Hyd 8 enzyme is not annotated as a hydratase-aldolase and is annotated to be an acetoacetate decarboxylase (see Uniprot page for this sequence), when it functions as a hydratase-aldolase (see Table 1). Similarly, Ads-Hyd 11-13 enzymes have been annotated as dihydrodipicolinate synthetase, but they function as a hydratase-aldolase (see Table 1). It is expected that many hydratase-aldolase enzyme sequences are or will be annotated or inferred in public databases as belonging to acetoacetate decarboxylase or dihydrodipicolinate synthetase or aldolases and are not categorized to either belonging to EC 4.1.2.45 or EC 4.1.2.34. Thus, to identify hydratase-aldolase enzyme sequences, homology-based searches to hydratase-aldolase sequences were conducted, and the resultant enzymes were subsequently validated regarding their activ-

TABLE 3

Provided technologies can provide high activity.

| | | | Activity on Different substrates | | |
|---|---|---|---|---|---|
| Enzyme Type | Enzyme ID | Uniprot ID | Acetaldehyde | Propionaldehyde | 3-hydroxy-propanal |
| aldolase | yagE | P75682 | 25000 | NT | NT |
| aldolase | nanA | P0A6L4 | 25000 | NT | NT |
| aldolase | garL | P23522 | 15000 | NT | NT |
| aldolase | eda | P0A955 | 5000 | NT | NT |
| aldolase | dgoA | Q6BF16 | 25000 | NT | NT |
| aldolase | Av-Ads | M9YI86 | NT | 20000 | NT |
| aldolase | Cg-Ads | Q8NMD2 | NT | 45000 | NT |
| aldolase | Cj-Ads | A0A1J6QD42 | NT | 5000 | NT |
| aldolase | Mt-Ads | Q8RBI5 | NT | 5000 | NT |
| aldolase | Ps-Ads | A3LZU9 | NT | 25000 | NT |
| aldolase | Sa-Ads | Q4JC35 | NT | 30000 | NT |
| hydratase-aldolase | Ads-Hyd 1 | D7C0E5 | 270000 | 405000 | NT |
| aldolase | Ss-Ads | O54288 | NT | 25000 | NT |
| aldolase | St-Ads | F9VPG1 | NT | 25000 | NT |
| aldolase | HpaI | Q47098 | 15000 | 25000 | NT |

NT = Not tested. For activity determination, pyruvate (20 g/L) was incubated with either acetaldehyde (40 g/L) or propionaldehyde (40 g/L) for 12 hr aerobically.

TABLE 4

Provided technologies can provide high yields and highly efficient substrate utilization.

| Enzyme | | Product Formation (g/L) After 90 mins | | | % Pyruvate Used For Production | | |
|---|---|---|---|---|---|---|---|
| Name | Enzyme ID | A | B | C | A | B | C |
| Sb Ads-Hyd | Ads-Hyd 1 | >3 | >3 | + | 25 | 57 | NT |
| G12 Ads-Hyd | Ads-Hyd 108 | NT | NT | + | + | NT | Not applicable |
| Aldolase | HpaI | 0.2 | 0.7 | + | 1 | 4 | Not applicable |

NT = Not tested;
+ = activity confirmed but not quantified;
A = acetaldehyde;
B = propionaldehyde;
C = 3'-hydroxy-propanal Although a few hydratase-aldolases have been categorized as belonging to EC 4.1.2.45 or EC 4.1.2.34 (see Table 5), most enzyme sequences reported in Table 1 and sequences identified by homology searches (using BLAST;

ity using methods described herein. An exemplary, homology-based search using (a) one sequence belonging to EC 4.1.2.34 (Ads-Hyd 3; results in Table 8); (b) one sequence belonging to an unassigned enzyme with extremely low homology to enzymes belonging to EC 4.1.2.34 and EC 4.1.2.45 (Ads-Hyd 8; results in Table 6) and (c) one sequence belonging to an unassigned enzyme show moderate homology to enzymes belonging to EC 4.1.2.34 and EC 4.1.2.45 (Ads-Hyd 10; results in Table 7) revealed >500 enzymes, some of which are listed in the tables below, and many of which upon testing were confirmed to be active for aldol addition and condensation (data in Table 1). For example, 13 sequences identified in Table 6 (see underlined sequences in Table 6 with data for those sequence in Table 1), and 11 sequences identified in Table 7 (see underlined sequences in Table 7 with data for those sequence in Table 1) were confirmed to be functional Ads-Hyd enzymes. Among other things, the present disclosure demonstrated that Ads-Hyd 112, which is classified as belonging to E.C 4.1.1.4 and annotated as an acetetoacetate decarboxylase, was also found to catalyze aldol addition and aldol condensation reactions with a number of different aldehydes (Table 2). In some embodiments, enzymes annotated as acetoacetate decarboxylases as well as those belonging to E.C 4.1.1.4 are useful for catalyzing aldol condensation and addition reactions as well. Enzymes with identities ranging from as low as 35% (Ads-Hyd 68 in Table 1), 38% (Ads-Hyd 3 in Table 1) and 49% (Ads-Hyd 93 in Table 1) to Ads-Hyd 3 belonging to EC 4.1.2.34, Ads-Hyd 2 belonging to EC 4.1.2.45, and Ads-Hyd 8 enzymes respectively, were confirmed to have hydratase-aldolase activity.

TABLE 5

Certain biosynthesis polypeptides.

| Uniprot ID | Genbank ID | EC Number | Protein names |
| --- | --- | --- | --- |
| Q9X9Q6 | AAD45417.1 | 4.1.2.45 | Trans-O-hydroxybenzylidenepyruvate hydratase-aldolase (2'-hydroxybenzalpyruvate aldolase) |
| P0A144 | AAB62713.1 | 4.1.2.45 | Trans-O-hydroxybenzylidenepyruvate hydratase-aldolase (2'-hydroxybenzalpyruvate aldolase) |
| P0A142 | BAA12246.1 | 4.1.2.45 | Trans-O-hydroxybenzylidenepyruvate hydratase-aldolase (2'-hydroxybenzalpyruvate aldolase) |
| Q79EM8 | BAA23263.1 | 4.1.2.34 | Trans-2'-carboxybenzalpyruvate hydratase-aldolase |
| Q51947 | AAA66357.1 | 4.1.2.45 | Trans-O-hydroxybenzylidenepyruvate hydratase-aldolase (2'-hydroxybenzalpyruvate aldolase) |
| P0A143 | AAA16132.1 | 4.1.2.45 | Trans-O-hydroxybenzylidenepyruvate hydratase-aldolase (2'-hydroxybenzalpyruvate aldolase) |
| A0A0J5Q5D8 | KMK64081.1 | 4.1.2.45 | Dihydrodipicolinate synthase/N-acetylneuraminate lyase |
| A0A1Y5PJE4 | SBS78822.1 | 4.1.2.34 | Trans-2'-carboxybenzalpyruvate hydratase-aldolase |
| A0A2H5YJ14 | GBD13407.1 | 4.1.2.34 | Trans-2'-carboxybenzalpyruvate hydratase-aldolase |
| A0A1V6C3X5 | OQB71622.1 | 4.1.2.45 | Trans-O-hydroxybenzylidenepyruvate hydratase-aldolase (2'-hydroxybenzalpyruvate aldolase) |
| A0A2H5YYR5 | GBD18589.1 | 4.1.2.45 | Trans-O-hydroxybenzylidenepyruvate hydratase-aldolase (2'-hydroxybenzalpyruvate aldolase) |
| A0A2H5VLK1 | GBC77546.1 | 4.1.2.45 | Trans-O-hydroxybenzylidenepyruvate hydratase-aldolase (2'-hydroxybenzalpyruvate aldolase) |
| A0A1K2FZU3 | SFY52690.1 | 4.1.2.45 | Trans-O-hydroxybenzylidenepyruvate hydratase-aldolase (2'-hydroxybenzalpyruvate aldolase) |
| A0A2H5W1Y6 | GBC82821.1 | 4.1.2.45 | Trans-O-hydroxybenzylidenepyruvate hydratase-aldolase (2'-hydroxybenzalpyruvate aldolase) |

TABLE 6

Certain biosynthesis polypeptides - enzymes that show homology to Ads-Hyd 8.

| Genbank ID (Enzyme ID if verified) | Protein names |
| --- | --- |
| KZL92449.1 (Ads-Hyd 112) | Acetoacetate decarboxylase (EC 4.1.1.4) |
| AOS64057.1 | Acetoacetate decarboxylase (ADC) (EC 4.1.1.4) |
| GBC87126.1 | Acetoacetate decarboxylase (EC 4.1.1.4) |
| AKL97316.1 | Acetoacetate decarboxylase (EC 4.1.1.4) |
| PZG10242.1 | Acetoacetate decarboxylase |
| AEB44722.1 | Acetoacetate decarboxylase |
| ABG04000.1 | Acetoacetate decarboxylase |
| KPH00942.1 (Ads-Hyd 89) | Acetoacetate decarboxylase |
| EMF26762.1 (Ads-Hyd 6) | Acetoacetate decarboxylase |
| PVY06388.1 | Acetoacetate decarboxylase |
| AOJ06649.1 | Acetoacetate decarboxylase |
| KOX08160.1 (Ads-Hyd 4) | Acetoacetate decarboxylase |
| OPG13060.1 | Enduracididine biosynthesis enzyme MppR |
| SDQ34954.1 | Acetoacetate decarboxylase |
| OIJ66442.1 | Acetoacetate decarboxylase |
| GCE00545.1 | Acetoacetate decarboxylase |
| ACK51122.1 | Acetoacetate decarboxylase |
| PJJ78777.1 | Acetoacetate decarboxylase |
| GAU76561.1 | Acetoacetate decarboxylase |
| SEM36970.1 | Acetoacetate decarboxylase |
| REK87553.1 | Enduracididine biosynthesis enzyme MppR |

TABLE 6-continued

Certain biosynthesis polypeptides - enzymes that show homology to Ads-Hyd 8.

| Genbank ID (Enzyme ID if verified) | Protein names |
| --- | --- |
| KPI02092.1 (Ads-Hyd 5) | Acetoacetate decarboxylase |
| KPC94750.1 | Acetoacetate decarboxylase (Fragment) |
| AEF90707.1 | Acetoacetate decarboxylase |
| OPC78676.1 | Acetoacetate decarboxylase |
| OPY57828.1 | Acetoacetate decarboxylase |
| KUL75432.1 | Acetoacetate decarboxylase |
| OEV06324.1 | Acetoacetate decarboxylase |
| PVX87320.1 | Acetoacetate decarboxylase |
| PIG16285.1 | Acetoacetate decarboxylase |
| POR47715.1 | Acetoacetate decarboxylase |
| SFH06339.1 | Acetoacetate decarboxylase |
| KUM42217.1 | Acetoacetate decarboxylase |
| PZT77592.1 | Acetoacetate decarboxylase |
| KYC38950.1 | Acetoacetate decarboxylase |
| RKS77249.1 | Acetoacetate decarboxylase |
| OIJ92678.1 | Acetoacetate decarboxylase |
| BAU27837.1 | Acetoacetate decarboxylase |
| QAV71426.1 | Acetoacetate decarboxylase |
| PQZ48703.1 | Uncharacterized protein |
| EXU61971.1 | Acetoacetate decarboxylase |
| SHN38127.1 | Acetoacetate decarboxylase |
| KGT73177.1 | Acetoacetate decarboxylase |
| SIO29145.1 | Acetoacetate decarboxylase |
| KGT73210.1 | Acetoacetate decarboxylase |
| SIO27946.1 | Acetoacetate decarboxylase |
| OSJ25700.1 | Acetoacetate decarboxylase |
| RMD31380.1 | Acetoacetate decarboxylase |
| SIO53681.1 | Acetoacetate decarboxylase |
| RFU48568.1 | Acetoacetate decarboxylase |
| OSJ25816.1 | Acetoacetate decarboxylase |
| HCV33217.1 | Acetoacetate decarboxylase |
| KPD20047.1 | Acetoacetate decarboxylase |
| OFW57075.1 | Uncharacterized protein |
| HCW00147.1 | Acetoacetate decarboxylase |
| EIM94241.1 | Acetoacetate decarboxylase |
| OYV58956.1 | Acetoacetate decarboxylase |
| REK15702.1 | Acetoacetate decarboxylase |
| MBV14559.1 | Acetoacetate decarboxylase |
| HAN36693.1 | Acetoacetate decarboxylase |
| HAP74745.1 | Acetoacetate decarboxylase |
| PYR38950.1 | Acetoacetate decarboxylase (Fragment) |
| PYR49219.1 | Acetoacetate decarboxylase |
| PTB41031.1 | Uncharacterized protein |
| EHK39542.1 | Uncharacterized protein |
| SYX90497.1 | Acetoacetate decarboxylase |
| RKN45560.1 | Acetoacetate decarboxylase |
| KJC40693.1 | Uncharacterized protein |
| RKR91249.1 | Acetoacetate decarboxylase |
| EJL77881.1 | Acetoacetate decarboxylase |
| PIG41119.1 | Acetoacetate decarboxylase |
| KJC40569.1 | Acetoacetate decarboxylase |
| KGF80061.1 | Acetoacetate decarboxylase |
| SON57276.1 | Acetoacetate decarboxylase (ADC) |
| KYO55945.1 | Acetoacetate decarboxylase |
| RFC69939.1 | Acetoacetate decarboxylase |
| RPE56489.1 | Acetoacetate decarboxylase |
| SFQ35591.1 | Acetoacetate decarboxylase |
| SCD72996.1 | Acetoacetate decarboxylase |
| RQO46864.1 | Acetoacetate decarboxylase |
| RLK57997.1 | Enduracididine biosynthesis enzyme MppR |
| ACZ90180.1 | Acetoacetate decarboxylase |
| GCD42233.1 | Uncharacterized protein |
| PIF96550.1 | Enduracididine biosynthesis enzyme MppR |
| PBC93106.1 | Acetoacetate decarboxylase |
| SIO44972.1 | Acetoacetate decarboxylase |
| OYD73530.1 | Acetoacetate decarboxylase |
| SEC28728.1 | Enduracididine biosynthesis enzyme MppR |
| RFC78087.1 | Acetoacetate decarboxylase |
| PWC35104.1 | Acetoacetate decarboxylase |
| AWL33917.1 | Enduracididine biosynthesis enzyme MppR |
| SED37560.1 | Acetoacetate decarboxylase |
| KOG37070.1 | Acetoacetate decarboxylase |
| SDJ19059.1 | Enduracididine biosynthesis enzyme MppR |
| PHX81843.1 | Acetoacetate decarboxylase |
| MBJ31847.1 | Acetoacetate decarboxylase |
| RPJ15459.1 | Acetoacetate decarboxylase |

TABLE 6-continued

Certain biosynthesis polypeptides - enzymes that show homology to Ads-Hyd 8.

| Genbank ID (Enzyme ID if verified) | Protein names |
|---|---|
| ABD65946.1 | Enduracididine biosynthesis enzyme MppR |
| RSM78635.1 | Acetoacetate decarboxylase |
| RSM86524.1 | Acetoacetate decarboxylase |
| AUG07753.1 | Acetoacetate decarboxylase |
| SHG60447.1 | Acetoacetate decarboxylase |
| SMC73048.1 | Acetoacetate decarboxylase |
| PKR44685.1 | Enduracididine biosynthesis enzyme MppR |
| AUC95510.1 | Acetoacetate decarboxylase |
| SUZ73052.1 | Uncharacterized protein (Fragment) |
| SNS52433.1 | Acetoacetate decarboxylase (ADC) |
| MMZ55024.1 | Acetoacetate decarboxylase |
| MNQ33472.1 | Acetoacetate decarboxylase |
| KJC46837.1 | Acetoacetate decarboxylase |
| SDL38666.1 | Acetoacetate decarboxylase |
| ONI74756.1 | Acetoacetate decarboxylase |
| SOD30619.1 | Acetoacetate decarboxylase |
| KJC46838.1 | Acetoacetate decarboxylase |
| RUL62263.1 | Acetoacetate decarboxylase |
| RMI93268.1 (Ads-Hyd 98) | Acetoacetate decarboxylase |
| RKR21285.1 | Acetoacetate decarboxylase |
| SDK87733.1 | Acetoacetate decarboxylase |
| PZS29802.1 | Acetoacetate decarboxylase |
| AAU34211.1 | Uncharacterized protein |
| CNE94443.1 | Acetoacetate decarboxylase |
| CDR14781.1 | Acetoacetate decarboxylase |
| OGI63453.1 | Acetoacetate decarboxylase |
| SDW59396.1 | Enduracididine biosynthesis enzyme MppR |
| MBE40108.1 | Acetoacetate decarboxylase |
| RPI20925.1 | Acetoacetate decarboxylase |
| AVZ77933.1 | Acetoacetate decarboxylase |
| CRK83612.1 | Acetoacetate decarboxylase |
| AOP51678.1 | Enduracididine biosynthesis enzyme MppR |
| KJC56449.1 | Uncharacterized protein |
| POX38729.1 | Acetoacetate decarboxylase |
| RDS84232.1 (Ads-Hyd 96) | Acetoacetate decarboxylase |
| ABK52869.1 | Acetoacetate decarboxylase |
| ERI08645.1 | Putative acetoacetate decarboxylase |
| SED02700.1 | Acetoacetate decarboxylase |
| SED57674.1 | Acetoacetate decarboxylase |
| AJQ29697.1 | Acetoacetate decarboxylase |
| AUS77184.1 | Enduracididine biosynthesis enzyme MppR |
| OEV05744.1 | Enduracididine biosynthesis enzyme MppR |
| SHJ82744.1 | Acetoacetate decarboxylase (ADC) |
| PDQ21702.1 | Acetoacetate decarboxylase |
| MBF06178.1 | Acetoacetate decarboxylase |
| SDI62088.1 | Acetoacetate decarboxylase |
| SES42580.1 | Enduracididine biosynthesis enzyme MppR |
| OAN53209.1 | Acetoacetate decarboxylase |
| CUU19651.1 | Acetoacetate decarboxylase CDS |
| PIG70517.1 | Acetoacetate decarboxylase |
| GAT80125.1 | Acetoacetate decarboxylase |
| RMI45923.1 | Acetoacetate decarboxylase |
| RFS83293.1 | Acetoacetate decarboxylase |
| RUL90134.1 | Enduracididine biosynthesis enzyme MppR |
| CEH29276.1 | Putative acetoacetate decarboxylase |
| KJC56043.1 | Acetoacetate decarboxylase |
| KJC56044.1 | Acetoacetate decarboxylase |
| AWE54161.1 | Acetoacetate decarboxylase |
| ADI03636.1 (Ads-Hyd 1) | Acetoacetate decarboxylase |
| GAT84669.1 | Acetoacetate decarboxylase |
| RUQ72183.1 | Acetoacetate decarboxylase |
| RSN12399.1 | Acetoacetate decarboxylase |
| RKD49684.1 | Acetoacetate decarboxylase |
| RKR34606.1 | Acetoacetate decarboxylase |
| PIG06713.1 | Acetoacetate decarboxylase |
| ROQ34846.1 | Enduracididine biosynthesis enzyme MppR |
| KXU84461.1 | Acetoacetate decarboxylase |
| OUL77098.1 (Ads-Hyd 108) | Acetoacetate decarboxylase |
| PYK12191.1 (Ads-Hyd 87) | Acetoacetate decarboxylase |
| RUL72479.1 | Acetoacetate decarboxylase |
| PWK86305.1 | Enduracididine biosynthesis enzyme MppR |
| GCD34260.1 | Uncharacterized protein |
| SOE90358.1 | Acetoacetate decarboxylase |
| SDG84621.1 | Enduracididine biosynthesis enzyme MppR |

TABLE 6-continued

Certain biosynthesis polypeptides - enzymes that show homology to Ads-Hyd 8.

| Genbank ID (Enzyme ID if verified) | Protein names |
|---|---|
| EWM12399.1 (Ads-Hyd 7) | Acetoacetate decarboxylase |
| SDG23054.1 | Acetoacetate decarboxylase |
| AFK55453.1 | Uncharacterized protein |
| AUT62680.1 | Acetoacetate decarboxylase |
| RPE37958.1 | Acetoacetate decarboxylase |
| EWM12653.1 | Acetoacetate decarboxylase |
| RSN04866.1 | Enduracididine biosynthesis enzyme MppR |
| KQV82686.1 | Acetoacetate decarboxylase |
| RKF38182.1 | Acetoacetate decarboxylase |
| REE27044.1 | Acetoacetate decarboxylase |
| PJN40277.1 | Enduracididine biosynthesis enzyme MppR |
| SDN12921.1 | Acetoacetate decarboxylase |
| PYG36199.1 | Acetoacetate decarboxylase |
| RKQ65112.1 | Acetoacetate decarboxylase |
| SDN12891.1 (Ads-Hyd 97) | Acetoacetate decarboxylase |
| EIW19392.1 | Acetoacetate decarboxylase |
| RSN99590.1 | Acetoacetate decarboxylase |
| PON28167.1 | Uncharacterized protein |
| PNP43262.1 | Uncharacterized protein |
| PON20078.1 | Uncharacterized protein |
| AEM85455.1 | Acetoacetate decarboxylase |
| AOT70611.1 | Acetoacetate decarboxylase |
| OPF83246.1 | Acetoacetate decarboxylase |
| PYN48855.1 (Ads-Hyd 93) | Acetoacetate decarboxylase |
| SFH92960.1 | Acetoacetate decarboxylase |
| SME92731.1 | Acetoacetate decarboxylase |
| RKQ67404.1 | Acetoacetate decarboxylase |
| RAK24761.1 | Acetoacetate decarboxylase |
| ALV48823.1 | Acetoacetate decarboxylase |
| SHG57166.1 | Acetoacetate decarboxylase |
| SHI09865.1 | Acetoacetate decarboxylase |
| RLV76922.1 | Acetoacetate decarboxylase |
| SHG57190.1 | Acetoacetate decarboxylase |
| KXU84652.1 | Acetoacetate decarboxylase |
| SIO27627.1 | Acetoacetate decarboxylase |
| AXQ55553.1 | Enduracididine biosynthesis enzyme MppR |
| AOJ04944.1 | Acetoacetate decarboxylase |
| ARH95437.1 | Enduracididine biosynthesis enzyme MppR |
| REH48625.1 | Acetoacetate decarboxylase |
| RLJ42250.1 | Acetoacetate decarboxylase |
| SHN71285.1 | Acetoacetate decarboxylase |
| SHN71288.1 | Acetoacetate decarboxylase |
| SHI09851.1 | Acetoacetate decarboxylase |
| SHN71296.1 | Acetoacetate decarboxylase |
| SIO27636.1 | Acetoacetate decarboxylase |
| REH35177.1 | Acetoacetate decarboxylase |
| SOE93021.1 | Acetoacetate decarboxylase |
| ALO91482.1 | Acetoacetate decarboxylase |
| AKJ70148.1 | Acetoacetate decarboxylase |
| EJL71335.1 | Acetoacetate decarboxylase |
| KMS76577.1 | Acetoacetate decarboxylase |
| SAL51447.1 | Acetoacetate decarboxylase |
| MBA77131.1 | Acetoacetate decarboxylase |
| MAM76769.1 | Acetoacetate decarboxylase |
| AXL50798.1 | Acetoacetate decarboxylase |
| SOE99541.1 | Acetoacetate decarboxylase |
| PIF38354.1 | Acetoacetate decarboxylase |
| GAX58847.1 | Acetoacetate decarboxylase |
| SFN30008.1 | Acetoacetate decarboxylase |
| KUL58863.1 | Enduracididine biosynthesis enzyme MppR |
| KOG74850.1 | Acetoacetate decarboxylase |
| AEY87061.1 | Acetoacetate decarboxylase |
| RDS66140.1 | Acetoacetate decarboxylase |
| ONI72521.1 | Acetoacetate decarboxylase |
| AHH95455.1 | Carboxy-lyase |
| SOE19480.1 | Acetoacetate decarboxylase (ADC) |
| ROO80377.1 | Acetoacetate decarboxylase |
| SAL27032.1 | Acetoacetate decarboxylase |
| HAM27991.1 | Acetoacetate decarboxylase |
| KDN75868.1 | Acetoacetate decarboxylase |
| AEW99245.1 | Uncharacterized protein |
| AAR35773.1 | Acetoacetate decarboxylase family protein |
| PMR61960.1 | Acetoacetate decarboxylase |
| OXL32653.1 | Acetoacetate decarboxylase |
| KUN27737.1 | Acetoacetate decarboxylase |
| EPR75769.1 | Acetoacetate decarboxylase |

TABLE 6-continued

Certain biosynthesis polypeptides - enzymes that show homology to Ads-Hyd 8.

| Genbank ID (Enzyme ID if verified) | Protein names |
|---|---|
| SFT90048.1 | Acetoacetate decarboxylase |
| RFU39638.1 | Acetoacetate decarboxylase |
| SMG22616.1 | Acetoacetate decarboxylase |

TABLE 7

Certain biosynthesis polypeptides - enzymes that show homology to Ads-Hyd 10.

| Genbank ID (Enzyme ID) | Protein names |
|---|---|
| SBS78822.1 | Trans-2'-carboxybenzalpyruvate hydratase-aldolase (EC 4.1.2.34) |
| GBD13407.1 | Trans-2'-carboxybenzalpyruvate hydratase-aldolase (EC 4.1.2.34) |
| BAA23263.1 (Ads-Hyd 3) | Trans-2'-carboxybenzalpyruvate hydratase-aldolase (EC 4.1.2.34) |
| AAD45417.1 (Ads-Hyd 9) | Trans-O-hydroxybenzylidenepyruvate hydratase-aldolase (EC 4.1.2.45) |
| AAA16132.1 | Trans-O-hydroxybenzylidenepyruvate hydratase-aldolase (EC 4.1.2.45) |
| BAA12246.1 | Trans-O-hydroxybenzylidenepyruvate hydratase-aldolase (EC 4.1.2.45) |
| AAB62713.1 (Ads-Hyd 2) | Trans-O-hydroxybenzylidenepyruvate hydratase-aldolase (EC 4.1.2.45) |
| AAA66357.1 | Trans-O-hydroxybenzylidenepyruvate hydratase-aldolase (EC 4.1.2.45) |
| KMK64081.1 | Dihydrodipicolinate synthase/N-acetylneuraminate lyase (EC 4.1.2.45) |
| GBD18589.1 | Trans-O-hydroxybenzylidenepyruvate hydratase-aldolase (EC 4.1.2.45) |
| GBC82821.1 | Trans-O-hydroxybenzylidenepyruvate hydratase-aldolase (EC 4.1.2.45) |
| ART89851.1 | 4-hydroxy-tetrahydrodipicolinate synthase (EC 4.3.3.7) |
| SJM52860.1 | 4-hydroxy-tetrahydrodipicolinate synthase (EC 4.3.3.7) |
| ART58441.1 | Aldolase |
| BAA76332.1 (Ads-Hyd 10) | Hydratase-aldolase |
| AEF88788.1 | Dihydrodipicolinate synthetase |
| ART51183.1 | Aldolase |
| KLU36881.1 | Aldolase |
| AKM12047.1 | Aldolase |
| CCA93880.1 | Dihydrodipicolinate synthetase |
| EZP70093.1 | Putative 2-hydroxy-benzylpyruvate aldolase |
| EHJ58034.1 | Putative 2-hydroxy-benzylpyruvate aldolase |
| ART40746.1 | L352 |
| ATW03328.1 | Aldolase |
| CCA92467.1 | Dihydrodipicolinate synthetase |
| ABM79813.1 | Aldolase (Hydratase-aldolase) |
| BAC65452.1 | Putative 2-hydroxy-benzylpyruvate aldolase |
| GAM16817.1 | Hydratase-aldolase |
| PBN41471.1 | Trans-o-hydroxybenzylidenepyruvate hydratase-aldolase |
| OWQ92810.1 | Aldolase |
| SHN54758.1 | Dihydrodipicolinate synthase/N-acetylneuraminate lyase |
| KDA01194.1 | Dihydrodipicolinate synthetase |
| KJS38380.1 | Aldolase |
| AKQ42951.1 | 1,2-dihydroxybenzylpyruvate aldolase |
| PNU02635.1 | Aldolase |
| EJU12841.1 | 1,2-dihydroxybenzylpyruvate aldolase |
| OAP30848.1 | Aldolase |
| ETI62764.1 | Aldolase |
| KKW89821.1 | Aldolase |
| PNQ03402.1 | Aldolase |
| AGZ63484.1 | NahE |
| PKB13561.1 | Dihydrodipicolinate synthase/N-acetylneuraminate lyase |
| PEQ10932.1 | Aldolase |
| AYO76044.1 | Aldolase |
| ABP64082.1 (Ads-Hyd 11) | Dihydrodipicolinate synthetase |
| KHS42353.1 | Dihydrodipicolinate synthetase |
| AAD03976.1 | 1,2-dihydroxybenzylpyruvate aldolase |
| KTE40403.1 | Aldolase |
| KTE22766.1 | Aldolase |
| RJG53082.1 | Aldolase |
| PQM29276.1 | Aldolase |
| KTE33221.1 | Aldolase |
| KGB52059.1 | Putative 2-hydroxy-benzylpyruvate aldolase |
| ART37867.1 | F474 |
| ODU68266.1 | Aldolase (Fragment) |
| PXV63448.1 | Trans-o-hydroxybenzylidenepyruvate hydratase-aldolase |
| AJP47897.1 | Aldolase |
| ADZ72499.1 (Ads-Hyd 65) | Dihydrodipicolinate synthetase |
| AER08042.1 | Hydratase-aldolase |
| EIF28466.1 | Dihydrodipicolinate synthase/N-acetylneuraminate lyase |
| ALE55172.1 | Aldolase |
| OWJ56339.1 | Aldolase |

TABLE 7-continued

Certain biosynthesis polypeptides - enzymes that show homology to Ads-Hyd 10.

| Genbank ID (Enzyme ID) | Protein names |
|---|---|
| PJJ06708.1 | Trans-o-hydroxybenzylidenepyruvate hydratase-aldolase |
| AKM10279.1 | Aldolase |
| ART40122.1 | K159 |
| ART38154.1 | F222 |
| PWJ76345.1 | Trans-o-hydroxybenzylidenepyruvate hydratase-aldolase |
| PTQ67744.1 | Trans-o-hydroxybenzylidenepyruvate hydratase-aldolase |
| KGB81035.1 | Aldolase |
| PTQ65074.1 | Trans-o-hydroxybenzylidenepyruvate hydratase-aldolase |
| ADZ72522.1 (Ads-Hyd 12) | Dihydrodipicolinate synthetase |
| ALG92322.1 | Aldolase |
| KEP68746.1 | Aldolase |
| AMM86059.1 | Aldolase |
| MAM12073.1 | Aldolase |
| EIT71336.1 | Dihydrodipicolinate synthetase |
| AEF05081.1 | Dihydrodipicolinate synthetase |
| PAL23311.1 | Aldolase |
| PWJ76353.1 | Trans-o-hydroxybenzylidenepyruvate hydratase-aldolase |
| RVT39492.1 | Aldolase |
| SEP74235.1 | Trans-o-hydroxybenzylidenepyruvate hydratase-aldolase |
| BAA20397.1 | Hydratase-aldolase |
| AAL07266.1 | 2-hydroxybenzalpyruvate aldolase |
| ETI60157.1 | Aldolase |
| ART36295.1 | C905 |
| BAF34962.1 | Trans-o-hydrobenzylidenepyruvate hydratase aldolase |
| BAF34972.1 | Trans-o-hydrobenzylidenepyruvate hydratase aldolase |
| AAP44192.1 | 1,2-dihydroxybenzyl pyruvate aldolase |
| EXF90974.1 | Aldolase |
| OPK08859.1 | Trans-o-hydroxybenzylidenepyruvate hydratase-aldolase |
| APV43293.1 | Aldolase (Trans-o-hydroxybenzylidenepyruvate hydratase-aldolase) |
| AAO64280.1 | Trans-o-hydroxybenzylidenepyruvate hydratase-aldolase |
| ALC77286.1 | Trans-O-hydroxybenzylidenepyruvate hydratase-aldolase |
| ACQ63497.1 | Trans-o-hydroxybenzylidenepyruvate hydratase-aldolase |
| ASW04047.1 | Aldolase |
| KKC26031.1 | Aldolase |
| AEV45882.1 | Trans-o-hydroxybenzylidenepyruvate hydratase-aldolase NahE |
| BAE92162.1 | Trans-o-hydroxybenzylidenepyruvate hydratase-aldolase NahE |
| BAF30942.1 | Trans-ohydrobenzylidenepyruvate hydratase aldolase |
| APP18116.1 | Trans-o-hydroxybenzylidenepyruvate hydratase-aldolase |
| AEV41420.1 | Trans-o-hydroxybenzylidenepyruvate hydratase-aldolase |
| AAD02141.1 | 1, 2-dihydroxybenzylpyruvate aldolase |
| OCX93212.1 | Aldolase |
| EPL61966.1 | Trans-o-hydroxybenzylidenepyruvate hydratase-aldolase |
| AFM32586.1 | Trans-o-hydroxybenzylidenepyruvate hydratase-aldolase |
| AAD12616.1 | Trans-o-hydroxybenzylidenepyruvate hydratase-aldolase |
| MAS13884.1 | Aldolase |
| EWC41257.1 | Aldolase |
| AHY45199.1 (Ads-Hyd 69) | Aldolase |
| AJE45066.1 | Dihydrodipicolinate synthetase |
| VBB16389.1 | Aldolase |
| AAZ93394.1 | Dihydrodipicolinate synthetase (Trans-o-hydroxybenzylidenepyruvate hydratase-aldolase) |
| SAL31848.1 | Dihydrodipicolinate synthetase family protein |
| ALE55136.1 | Aldolase |
| OWJ56143.1 | Aldolase |
| AAD09869.1 (Ads-hyd 14) | Hydratase/aldolase PhnE |
| ACT53260.1 | Hydratase/aldolase |
| ANI13636.1 | Aldolase |
| EZQ14085.1 | Aldolase |
| PRF53899.1 | Aldolase |
| EHJ59545.1 | Hydratase-aldolase |
| ODU66836.1 | Aldolase |
| AZI70977.1 | 1,2-dihydroxybenzylpyruvate aldolase (Trans-o-hydroxybenzylidenepyruvate hydratase-aldolase) |
| KIC79255.1 (Ads-Hyd 15) | Aldolase |
| AMK37583.1 | Trans-o-hydroxybenzylidenepyruvate hydratase-aldolase |
| KGH10186.1 | Aldolase |
| PHR55511.1 | Aldolase |
| RAK18497.1 | Trans-o-hydroxybenzylidenepyruvate hydratase-aldolase |
| EHJ59565.1 | 2-hydroxybenzalpyruvate aldolase |
| PVY51792.1 (Ads-Hyd 68) | Dihydrodipicolinate synthase/N-acetylneuraminate lyase |
| KDB08187.1 (Ads-Hyd 13) | Dihydrodipicolinate synthetase |
| APP18130.1 | Hydratase-aldolase |
| EHJ59532.1 | Hydratase/aldolase |
| EIE49938.1 | Trans-o-hydroxybenzylidenepyruvate hydratase-aldolase NahE |
| KHK92942.1 | Aldolase |

TABLE 7-continued

Certain biosynthesis polypeptides - enzymes that show homology to Ads-Hyd 10.

| Genbank ID (Enzyme ID) | Protein names |
|---|---|
| ART39436.1 | J508 |
| RSM40400.1 | Aldolase |
| HAC32985.1 | Aldolase |
| SED12223.1 | Dihydrodipicolinate synthase/N-acetylneuraminate lyase |
| ART36910.1 | D219 |
| HCO44328.1 | Aldolase |
| OUR88246.1 | Aldolase |
| ANX02865.1 | Aldolase |
| PCI67543.1 | Aldolase |
| SHJ43395.1 | Trans-o-hydroxybenzylidenepyruvate hydratase-aldolase |
| AGS39599.1 | Dihydrodipicolinate synthase/N-acetylneuraminate lyase |
| MBG95280.1 | Aldolase |
| AFT67194.1 | Dihydrodipicolinate synthetase |
| PHS71704.1 | Aldolase |
| HAI96648.1 | Aldolase |
| EHJ59569.1 | Dihydrodipicolinate synthetase |
| AIN43768.1 | Hydratase-aldolase (Fragment) |
| ART35398.1 | A220 |
| SDM13008.1 | Trans-o-hydroxybenzylidenepyruvate hydratase-aldolase |
| SDG98718.1 | Trans-o-hydroxybenzylidenepyruvate hydratase-aldolase |
| EKX84573.1 | Trans-o-hydroxybenzylidenepyruvate hydratase-aldolase NahE |
| RTL66015.1 | Aldolase |
| KPK20478.1 | Uncharacterized protein |
| SEH64089.1 | Dihydrodipicolinate synthase/N-acetylneuraminate lyase |
| ART37041.1 | D408 |
| PYC47978.1 | Aldolase |
| OUS22376.1 | Uncharacterized protein |
| ANX03747.1 | Uncharacterized protein |
| KDE97295.1 | Aldolase |
| OPX10770.1 | Uncharacterized protein |
| ODQ85801.1 | Aldolase |
| ORB11495.1 | Aldolase |
| ORA58811.1 | Aldolase |
| ABL90862.1 | Dihydrodipicolinate synthetase |
| ADT96876.1 | Dihydrodipicolinate synthase/N-acetylneuraminate lyase |
| ABM11316.1 | Dihydrodipicolinate synthetase |
| BBA72532.1 | Dihydrodipicolinate synthetase |
| GAT12856.1 | Dihydrodipicolinate synthetase |
| ARV80195.1 | Aldolase (Dihydrodipicolinate synthase/N-acetylneuraminate lyase) |
| ABP43078.1 | Dihydrodipicolinate synthetase |
| AKK27886.1 | Aldolase |
| SEH58270.1 | 4-(2-carboxyphenyl)-2-oxobut-3-enoate aldolase |
| APE19406.1 | Aldolase |
| AAT51742.1 | PhdJ |
| BBA72542.1 | Dihydrodipicolinate synthetase |
| BBA72825.1 | Dihydrodipicolinate synthetase |
| AEV73682.1 | Dihydrodipicolinate synthase/N-acetylneuraminate lyase |
| ORB61988.1 | Aldolase |
| RDH74327.1 | Aldolase |
| ACN38282.1 | Trans-2'-carboxybenzalpyruvate hydratase-aldolase |
| KLU36867.1 | Aldolase |
| OUS03890.1 | Uncharacterized protein |
| ORW27057.1 | Uncharacterized protein |
| OAR05193.1 | 4-hydroxy-tetrahydrodipicolinate synthase (Aldolase) |
| CQD18686.1 | Dihydrodipicolinate synthetase |
| ORB04914.1 | Uncharacterized protein |
| AJP48436.1 | Uncharacterized protein |
| ACM06757.1 | Aldolase |
| HCO44883.1 | Aldolase |
| ANX04975.1 | Uncharacterized protein |
| SPM40709.1 | Dihydrodipicolinate synthase/N-acetylneuraminate lyase |
| SPM34880.1 | Dihydrodipicolinate synthase/N-acetylneuraminate lyase |
| OLT42115.1 | Aldolase |
| HAC33263.1 | Aldolase |
| RFU95674.1 | Dihydrodipicolinate synthetase |
| OGQ80071.1 | Uncharacterized protein |
| SFB53516.1 | Dihydrodipicolinate synthase/N-acetylneuraminate lyase |
| PVY51809.1 | Dihydrodipicolinate synthase/N-acetylneuraminate lyase |
| PVY51803.1 | Dihydrodipicolinate synthase/N-acetylneuraminate lyase |
| ORB07056.1 | Aldolase |
| PVY51800.1 | Dihydrodipicolinate synthase/N-acetylneuraminate lyase |
| RIA44335.1 | Dihydrodipicolinate synthase/N-acetylneuraminate lyase |
| EHJ59573.1 | Uncharacterized protein |
| PVY51825.1 | Dihydrodipicolinate synthase/N-acetylneuraminate lyase |
| AIJ21944.1 | Putative aldolase |

TABLE 7-continued

Certain biosynthesis polypeptides - enzymes that show homology to Ads-Hyd 10.

| Genbank ID (Enzyme ID) | Protein names |
| --- | --- |
| ORB38363.1 | Aldolase |
| AWK75959.1 | Aldolase |
| EID78824.1 | Putative aldolase NarC |
| ACV96860.1 | Putative aldolase |
| HAC33092.1 | Aldolase |
| AKM10259.1 | Uncharacterized protein |
| ART40134.1 | K171 |
| ELB89137.1 | Putative aldolase NarC |
| BAH47216.1 | Putative aldolase NarC |
| AAR05117.1 | Putative aldolase |
| EKT84398.1 | Putative aldolase NarC |
| KDE09923.1 | Aldolase |
| BAE53379.1 | Aldolase |
| AAR05109.1 | Putative aldolase |
| AQW45620.1 | Putative aldolase |
| API60260.1 | Uncharacterized protein |
| RLA50226.1 | Aldolase |
| OUZ12202.1 | Aldolase |
| RLV57233.1 | Aldolase |
| BAA94711.1 | Hydratase-aldolase |
| AFC42746.1 | Dihydrodipicolinate synthetase |
| ASW94610.1 | Aldolase |
| ORW23722.1 | Aldolase |
| ORB75698.1 | Aldolase |
| AAG53397.1 | 1,2-dihydroxybenzylpyruvate aldolase 2 (Fragment) |
| CRL08851.1 | 2-carboxybenzalpyruvate hydratase aldolase |
| OSC27070.1 | Aldolase |
| RKO19521.1 | Aldolase |
| ADX75098.1 | Dihydrodipicolinate synthase/N-acetylneuraminate lyase |
| RTL66022.1 | Dihydrodipicolinate synthetase |
| AAG53396.1 | 1,2-dihydroxybenzylpyruvate aldolase 1 (Fragment) |
| ADK82461.1 | Dihydrodipicolinate synthetase |
| OLT33718.1 | Aldolase |
| ADX73348.1 | Dihydrodipicolinate synthase/N-acetylneuraminate lyase |
| PSQ18743.1 | Aldolase |
| APA86915.1 | Aldolase |
| RAW15463.1 | Aldolase |
| AYY15006.1 | Aldolase |
| SEH58300.1 | Hydratase-aldolase |
| ORB22843.1 | Aldolase |

TABLE 8

Certain biosynthesis polypeptides - enzymes that show homology to Ads-Hyd 3.

| Genbank ID | Protein names |
| --- | --- |
| WP_013601270.1 | aldolase [*Pseudarthrobacter phenanthrenivorans*] |
| WP_013602982.1 | aldolase [*Pseudarthrobacter phenanthrenivorans*] |
| WP_127127049.1 | aldolase [*Georgenia* sp. SYP-B2076] |
| WP_075839590.1 | aldolase [*Rhodococcus* sp. CUA-806] |
| WP_086725852.1 | aldolase [*Streptomyces carpinensis*] |
| WP_137144035.1 | aldolase [*Mycolicibacterium* sp. CR10] |
| WP_047330709.1 | aldolase [*Mycobacterium* sp. EPa45] |
| WP_011559036.1 | MULTISPECIES: aldolase [Mycobacteriaceae] |
| WP_036349078.1 | aldolase [*Mycolicibacterium aromaticivorans*] |
| RTL66015.1 | aldolase [Pseudonocardiaceae bacterium] |
| WP_087139803.1 | aldolase [*Mycobacterium chimaera*] |
| WP_011777788.1 | aldolase [*Mycolicibacterium vanbaalenii*] |
| WP_011891552.1 | aldolase [*Mycolicibacterium gilvum*] |
| WP_069416983.1 | aldolase [*Mycolicibacterium flavescens*] |
| WP_083043896.1 | aldolase [*Mycolicibacterium elephantis*] |
| WP_083410401.1 | aldolase [*Mycolicibacterium rutilum*] |
| BBA72542.1 | dihydrodipicolinate synthetase [*Mycobacterium* sp. PO1] |
| WP_042910008.1 | MULTISPECIES: aldolase [*Mycobacterium avium* complex (MAC)] |
| WP_067396827.1 | aldolase [*Mycolicibacterium novocastrense*] |
| WP_083128714.1 | aldolase [*Mycolicibacterium tusciae*] |
| AAT51742.1 | PhdJ [*Mycolicibacterium vanbaalenii* PYR-1] |
| WP_114740710.1 | aldolase [*Mycolicibacterium moriokaense*] |
| WP_071950246.1 | aldolase [*Mycobacterium* sp. WY10] |
| GAT12856.1 | dihydrodipicolinate synthetase [*Mycolicibacterium novocastrense*] |
| WP_094286221.1 | aldolase [*Mycobacterium lehmannii*] |

TABLE 8-continued

Certain biosynthesis polypeptides - enzymes that show homology to Ads-Hyd 3.

| Genbank ID | Protein names |
| --- | --- |
| BBA72532.1 | dihydrodipicolinate synthetase [*Mycobacterium* sp. PO1] |
| WP_041303477.1 | aldolase [*Mycolicibacterium rhodesiae*] |
| AEV73682.1 | dihydrodipicolinate synthase/N-acetylneuraminate lyase [*Mycolicibacterium rhodesiae* NBB3] |
| 6DAQ_A | Chain A, PhdJ [*Mycolicibacterium vanbaalenii*] |
| WP_099039075.1 | aldolase [*Mycobacterium* sp. CECT 8778] |
| ACN38282.1 | trans-2'-carboxybenzalpyruvate hydratase-aldolase [*Mycobacterium* sp. CH1] |
| CRL08851.1 | 2-carboxybenzalpyruvate hydratase aldolase [*Mycobacterium* sp. 6PY1] |
| WP_096699239.1 | aldolase [*Polaromonas* sp. AER18D-145] |
| WP_047824912.1 | MULTISPECIES: aldolase [Massilia] |
| KPK20478.1 | hypothetical protein AMJ67_01080 [*Betaproteobacteria* bacterium SG8_41] |
| WP_027197771.1 | aldolase [*Paraburkholderia sprentiae*] |
| SDR61564.1 | Dihydrodipicolinate synthase/N-acetylneuraminate lyase [*Paraburkholderia tuberum*] |
| WP_090812328.1 | aldolase [*Paraburkholderia tuberum*] |
| WP_077079464.1 | MULTISPECIES: aldolase [*Mycobacterium*] |
| WP_090422646.1 | aldolase [*Mycobacterium europaeum*] |
| WP_062895341.1 | aldolase [*Mycobacterium avium*] |
| WP_011856608.1 | MULTISPECIES: aldolase [Mycobacteriaceae] |
| WP_123787007.1 | aldolase [*Achromobacter denitrificans*] |
| WP_083173134.1 | aldolase [*Mycobacterium paraseoulense*] |
| WP_071394168.1 | hypothetical protein [*Bacillus tuaregi*] |
| WP_083094487.1 | aldolase [*Mycobacterium mantenii*] |
| ETZ38018.1 | trans-2'-carboxybenzalpyruvate hydratase-aldolase [*Mycobacterium intracellulare* MIN_061107_1834] |
| WP_009953931.1 | MULTISPECIES: aldolase [*Mycobacterium*] |
| WP_085290658.1 | aldolase [*Mycolicibacterium vulneris*] |
| RLA50226.1 | aldolase [Gammaproteobacteria bacterium] |
| WP_107764147.1 | dihydrodipicolinate synthetase [*Coprothermobacter proteolyticus*] |
| WP_007179239.1 | aldolase [*Burkholderia* sp. Ch1-1] |
| WP_067464354.1 | aldolase [*Actinomadura macra*] |
| WP_083829069.1 | aldolase [*Delftia* sp. Cs1-4] |
| AEF88778.1 | dihydrodipicolinate synthetase [*Delftia* sp. Cs1-4] |
| WP_086911711.1 | aldolase [*Acidovorax carolinensis*] |
| WP_036562639.1 | aldolase [*Oceanicola* sp. MCTG156(1a)] |
| TAD90455.1 | aldolase [Alphaproteobacteria bacterium] |
| WP_047824930.1 | MULTISPECIES: aldolase [Massilia] |
| WP_018963718.1 | hypothetical protein [*Coprothermobacter platensis*] |
| OGB50545.1 | aldolase [*Burkholderiales* bacterium RIFOXYD12_FULL_59_19] |
| GBD13407.1 | Trans-2'-carboxybenzalpyruvate hydratase-aldolase [bacterium HR24] |
| WP_066198397.1 | aldolase [*Hydrogenibacillus schlegelii*] |
| WP_007298126.1 | MULTISPECIES: aldolase [*Rhodococcus*] |
| WP_051423516.1 | hypothetical protein [*Arthrobacter* sp. MA-N2] |
| WP_117329621.1 | dihydrodipicolinate synthetase [*Sphaerochaeta halotolerans*] |
| WP_128644286.1 | dihydrodipicolinate synthetase [*Rhodococcus opacus*] |
| WP_087561951.1 | MULTISPECIES: dihydrodipicolinate synthetase [*Rhodococcus*] |
| WP_012642744.1 | aldolase [*Thermomicrobium roseum*] |
| WP_017681823.1 | MULTISPECIES: aldolase [*Rhodococcus*] |
| WP_124259333.1 | aldolase [*Rhodococcus ruber*] |
| TAN29949.1 | hypothetical protein EPN30_01545 [*Actinobacteria* bacterium] |
| WP_005570095.1 | MULTISPECIES: aldolase [*Rhodococcus*] |
| WP_005253631.1 | aldolase [*Rhodococcus opacus*] |
| WP_079931448.1 | hypothetical protein [*Gordonia* sp. i37] |
| AAR05109.1 | putative aldolase [*Rhodococcus* sp. P400] |
| OUS22376.1 | hypothetical protein A9Q95_05145 [Rhodobacterales bacterium 59_46_T64] |
| WP_013602975.1 | aldolase [*Pseudarthrobacter phenanthrenivorans*] |
| GBD18589.1 | Trans-O-hydroxybenzylidenepyruvate hydratase-aldolase [bacterium HR27] |
| WP_110795628.1 | aldolase [Rhodobacteraceae bacterium FSX-11] |
| WP_013255920.1 | dihydrodipicolinate synthetase [*Sediminispirochaeta smaragdinae*] |
| WP_075849231.1 | aldolase [*Saccharomonospora* sp. CUA-673] |
| WP_020501058.1 | aldolase [*Sciscionella marina*] |
| OUS03890.1 | hypothetical protein A9Q96_17015 [Rhodobacterales bacterium 52_120_T64] |
| WP_091675950.1 | MULTISPECIES: aldolase [*Amycolatopsis*] |
| WP_038532000.1 | aldolase [*Amycolatopsis methanolica*] |
| WP_087059681.1 | aldolase [Actinomycetales bacterium JB111] |
| WP_092817818.1 | hypothetical protein [*Halopenitus malekzadehii*] |
| WP_065123170.1 | aldolase [*Mycobacterium asiaticum*] |
| WP_107447362.1 | aldolase [*Streptomyces* sp. P3] |
| WP_067937422.1 | aldolase [*Mycobacterium* sp. E2479] |
| WP_027943869.1 | aldolase [*Amycolatopsis taiwanensis*] |
| WP_078947647.1 | aldolase [*Streptomyces griseus*] |
| WP_121792642.1 | aldolase [*Aeromicrobium* sp. 9W16Y-2] |
| WP_010204520.1 | aldolase [*Salinibacterium* sp. PAMC 21357] |
| AMK37583.1 | trans-o-hydroxybenzylidenepyruvate hydratase-aldolase [*Pseudomonas* sp. C5pp] |
| WP_087622569.1 | aldolase [*Aeromicrobium* sp. PE09-221] |

TABLE 8-continued

Certain biosynthesis polypeptides - enzymes that show homology to Ads-Hyd 3.

| Genbank ID | Protein names |
| --- | --- |
| WP_032395674.1 | MULTISPECIES: aldolase [*Rhodococcus*] |
| WP_039615401.1 | MULTISPECIES: aldolase [*Pseudomonas*] |

Cloning, and expression: DNA encoding heterologous aldolase hydratase enzymes were codon-optimized for expression in *E. coli* and synthesized by a commercial DNA synthesis company. Using standard cloning methods, each gene was cloned downstream of the T7 RNA polymerase promoter and upstream of the T7 terminator sequence in pB11 backbone plasmid. Additionally, for experiments wherein the aldehyde selected was 3-hydroxy-propionaldehyde a glycerol dehydratase enzyme that is a B12-dependent enzyme (*Lactococcus reuteri* glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned on a second compatible plasmid to enable production of 3-hydroxy-propionaldehyde from glycerol using this enzyme. The plasmids were transformed in *E. coli* BL21*(DE3) AldhA. Starter cultures for each clone were grown overnight in tubes containing 5 mL 2×YT media with 1 g/L D-glucose and appropriate antibiotics. Cell cultures for expression were carried out in 2 mL growth medium in 96 well plates. Complex (2×YT) growth medium was used and supplemented with 2 g/L D-glucose, 0.5 g/L potassium phosphate buffer (pH 7.2), and 100 mg/L ferric ammonium citrate. Pre-induction growth was carried out for 2 hours under aerobic conditions and at 30° C. Recombinant protein expression was induced at an OD600 of 0.2-0.4 with 250 µM IPTG. Post-induction expression was carried out for 30-180 minutes at 30° C. and under aerobic conditions followed by 0-60 mins under anaerobic conditions.

Enzyme assay: Post expression, cells were harvested and re-suspended in 0.4 mL fresh medium (OD600 ~30) containing 15 g/L potassium phosphate buffer (pH 7.2) with substrates for the reaction. For activity determination, pyruvate (10-20 g/L) was incubated with 5-40 g/L aldehydes (e.g., acetaldehyde, propionaldehyde, butyraldehyde, 2-hydroxy-acetaldehyde, or 4-hydroxy-butyraldehyde) for 12 hr aerobically. For activity determination with 3-hydroxy-propanal, post expression cells were harvested and re-suspended in 0.4 mL fresh medium (OD600 ~30) containing 15 g/L potassium phosphate buffer (pH 7.2) with 10-20 g/L glucose, 5-10 g/L glycerol, and 10 g/L pyruvate for 15 hr under anaerobic conditions. The reaction mix was also supplemented with 10 µM vitamin B12 and 1 g/L glutathione. After incubation at room temperature, the cells were centrifuged, and the supernatant was filtered and analyzed via HPLC.

Analysis of product: Isocratic HPLC was primarily used to detect and quantify production of enzyme products, aldol addition products (4-hydroxy-2-keto-carboxylic acids), aldol condensation products (3,4-dehydro-2-keto-carboxylic acids). One method employed a Bio-Rad Aminex HPX-87 column, 0.7 mL/min of 0.05% formic acid (or 5 mM sulfuric acid) at 35° C. Detection was carried out using an RID (refractive index detector) and UV detector, the latter of which was used to measure signals at 210 and 260 nm. Additionally, aldol addition and aldol condensation products were also confirmed by LC-MS, by measuring the masses of the respective peaks identified previously via HPLC (data not included herein).

Example 2: Enzymes that Catalyze Reduction of Aldol-Dehydration Products

Figure 6:
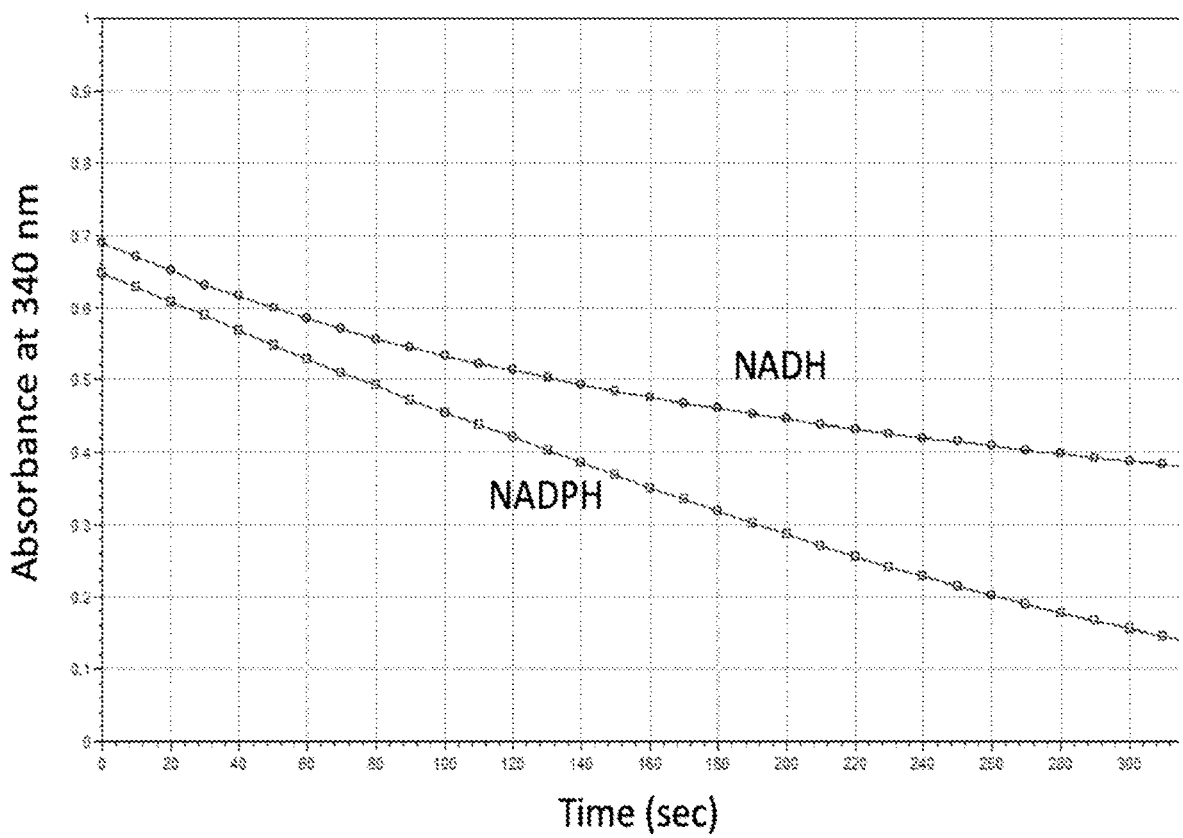
FIG. 6 shows the activity of the quinone oxidoreductase-1 (Qor-1) for reducing 6-hydroxy-3,4-dehydro-2-keto-hexenoate to 6-hydroxy-2-keto-hexenoate with cofactor NADH and NADPH.

As demonstrated herein, reduction of activated double bonds, i.e., double bonds next to a carbonyl or carboxylate group, can be catalyzed by enzymes. Aldol-dehydration products, e.g., 2-oxo-3-enoic acids, can be further reduced using enzymes, to give the corresponding 2-oxo-carboxylic acids. It was unexpectedly discovered that oxidoreductases belonging to EC 1.6.5 (e.g., EC 1.6.5.5) that utilize NADH and/or NADPH for reduction of quinones are capable of catalyzing this reaction. For example, when Ads-Hyd enzymes (see Example 1) were recombinantly expressed in *E. coli* BL21 or *E. coli* MG1655 strains for the production of 2-keto-carboxylic acids as described in Example 1, it was discovered that a portion of the Ads-Hyd enzyme product (i.e., 2-oxo-3-enoic acids) was converted to the corresponding 2-keto-carboxylic acid. This led to the possibility that some natively expressed enzyme or enzymes within these *E. coli* strains was responsible for carrying out the reduction of 2-oxo-3-enoic acids. A survey of known oxidoreductases that could conceivably carry out reduction of activated double bonds (i.e., EC 1.3.- and EC 1.6.-) within these strains was carried out. Seventeen such promising enzymes were identified within *E. coli* MG1655 and *E. coli* BL21 each. Knock-out strains for each of these enzymes in both of these hosts were prepared using known methods in the art. Subsequently each such knockout strain was tested for its ability to produce both of 2-oxo-3-enoic acid and its product of 2-keto-carboxylic acid using methods described above and using recombinantly expressed Ads-Hyd enzymes. This led to identification that knocking out the gorA gene or quinone oxidoreductase-1 led to production of 2-oxo-3-enoic acid and no 2-keto-carboxylic acid. This confirmed that the enzyme encoded by the gorA was likely responsible for natively carrying out this reaction. Subsequently, a N-terminal His6 tagged QorA enzyme ("His6" disclosed as SEQ ID NO: 106) was overexpressed and purified, and it was confirmed that it was indeed active for carrying out the desired reaction (FIG. 6). This unequivocally confirmed for the first time that quinone oxidoreductase enzyme from *E. coli* belonging to EC 1.6.5 (e.g., EC 1.6.5.5) is capable of functioning on substrates that are very different from their natural substrates, which are cyclic in structure. Furthermore, it was confirmed that this enzyme is able to utilize both NADH and NADPH as cofactors during the reaction (FIG. 6), which is very advantageous as it enables use of this enzyme under both aerobic and anaerobic conditions during bioproduction.

Various biosynthesis polypeptides belonging to EC 1.6.5 can be utilized in accordance with the present disclosure, e.g., as alkene reduction product biosynthesis polypeptides and/or for reduction of aldol-dehydration products. For example, a number of quinone oxidoreductases of EC 1.6.5.5 were assessed for their activities in accordance with the present disclosure, including eighteen enzymes (see Table 9) whose identities to *E. coli* Qor-1 enzyme ranged from 37-90%. All enzymes selected were confirmed to be active on at least one substrate (Table 9), further confirming the generality of this class of enzymes to carry out this reaction.

Enzyme assay: Same as Example 1 of in vivo activity measurement of the different quinone oxidoreductases. For in vitro activity measurement shown FIG. 6, the Qor-1 enzyme (0.3 mg/ml) was incubated with ~10 mM of 6-hydroxy-3,4-dehydro-2-oxohexanoate (synthesized in house), 0.5 mM of either NADH or NADPH in 100 mM pH 7 phosphate buffer.

TABLE 9

Certain useful biosynthesis polypeptides - reductase.

| Enzyme Name | Enzyme ID | % Identity to Qor-1 | Uniprot ID or Genbank ID | Activity on Different substrates | | |
|---|---|---|---|---|---|---|
| | | | | 3,4-dehydro-2-oxopentanoate | 3,4-dehydro-2-oxohexanoate | 6-hydroxy-3,4-dehydro-2-oxohexanoate |
| Ec QorA | Qor-1 | 100 | P28304 | + | + | + |
| Stm Qor | Qor-2 | 90 | P40783 | NT | NT | + |
| Reh Qor1 | Qor-3 | 43 | Q0K2I0 | NT | NT | + |
| Pvl Qor | Qor-4 | 67 | A0A1Z1SRY9 | NT | NT | + |
| Pae Qor | Qor-5 | 59 | P43903 | NT | NT | + |
| Msg Qor | Qor-6 | 44 | I7G8G0 | NT | NT | + |
| Bxb Qor | Qor-7 | 48 | Q142L2 | NT | NT | + |
| Bcep Qor | Qor-8 | 48 | ALK19324.1 | NT | NT | + |
| Aalbi Qor | Qor-9 | 42 | A0A1G9R408 | NT | NT | + |
| Ain Qor | Qor-10 | 29 | G4Q8R5 | NT | NT | + |
| Mche Qor | Qor-11 | 37 | ANA98723.1 | NT | NT | + |
| Nbr Qor | Qor-12 | 42 | K0EUQ3 | NT | NT | + |
| Pole Qor | Qor-13 | 60 | A0A061CRS8 | NT | NT | + |
| Ccr Qor | Qor-14 | 46 | Q9A212 | NT | NT | + |
| Sflav Qor | Qor-15 | 42 | A0A1I6RWW2 | NT | NT | + |
| Smari Qor | Qor-16 | 44 | WP_026197277.1 | NT | NT | + |
| Zmo Qor | Qor-17 | 37 | Q5NKZ3 | NT | NT | + |
| Met Qor | Qor-18 | 48 | WP_012333034.1 | NT | NT | + |
| Tri Qor | Qor-19 | 47 | WP_136898000.1 | NT | NT | + |

NT = Not tested;
NA = Not active;
+ = activity confirmed but not quantified

Other reduction product biosynthesis polypeptides, e.g., those belonging to various subclasses of EC 1.6.5 such as various quinone oxidoreductase enzymes belonging to EC 1.6.5.5 may also carry out this reaction.

Cloning and expression: DNA encoding heterologous aldolase hydratase (Ads-Hyd 1) and quinone oxidoreductase enzymes shown in Table 5 were codon-optimized for expression in *E. coli* and synthesized by a commercial DNA synthesis company. For in vitro activity measurements, and N-terminal His6 tag (SEQ ID NO: 106) was added onto Qor-1 enzyme. Using standard cloning methods, each gene was cloned downstream of the T7 RNA polymerase promoter and upstream of the T7 terminator sequence in single pB11 backbone plasmid. Additionally, for experiments wherein the aldehyde selected was 3-hydroxy-propionaldehyde a glycerol dehydratase enzyme that is a B12-dependent enzyme (*Lactococcus reuteri* glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned on a second compatible plasmid to enable production of 3-hydroxy-propionaldehyde from glycerol using this enzyme. The plasmids were transformed in *E. coli* BL21*(DE3) ΔldhA ΔgorA. Recombinant protein expression was carried out as described above in Example 1. For in vitro studies, the Qor-1 enzyme was induced at an OD600 of 0.2-0.4 with 250 µM IPTG. Post-induction expression was carried out for 180 minutes at 30° C. and under aerobic conditions. Post induction the enzyme was purified using Ni-NTA affinity chromatography using standard methods in art.

Analysis of product: Isocratic HPLC method described in Example 1 was used to detect and quantify production of enzyme product, i.e., 2-keto-carboxylic acids. For in vitro activity measurement, the decrease in absorbance at 340 nm was used to measure depletion of NADH or NADPH cofactor and thus Qor-1 activity.

Example 3: A Two-Enzyme System for the Production of 2-Keto-Carboxylic Acids from Pyruvate and Aliphatic Aldehydes The use of aldolase-hydratase enzyme(s) in combination with quinone oxidoreductase enzymes for the production of a range of 2-keto acids was examined. This combination enables the production of a range of 2-keto acids, which are precursors for the production of a number of industrially desirable products such as 1,5-pentanediol, 1,6-hexanediol, adipic acid, caprolactam, caprolactone, 6-hydroxy hexanoic acid, 6-amino caproic acid, amino acids, and many different fatty molecules. A number of different combinations of aldolase-hydratase enzymes and oxidoreductases were confirmed to be active for the production of different 2-keto acids (Table 10). As demonstrated herein, provided technologies can provide high products concentration, e.g., about or at least about 1, 2, 3, 4, 5, 6, 7, 8, 9, 10, 11, 12, 13, 14, 15, 16, 15, 17, 18, 20, 21, 22, 23, 24, 25, 30, 35, 40, 45, 50, 55, 60, 70, 80, 90, 100, 200, 300, 400, 500, 600, 700, 800, 900, 1000, 1200, 1500, 2000, 2500, 3000u.

TABLE 10

Provided technologies comprising multiple biosynthesis polypeptides generate desired products.

| Ads-Hyd ID | Reductase ID | Activity on Different substrates | | |
|---|---|---|---|---|
| | | mM of 2-keto pentanoic acid product | mM of 2-keto hexanoic acid product | mM of 6-hydroxy-2-keto hexanoic acid product |
| Ads-Hyd 1 | Qor-1 | + | + | 3.2 |
| Ads-Hyd 2 | Qor-1 | NT | NT | + |
| Ads-Hyd 3 | Qor-1 | NT | NT | NA |
| Ads-Hyd 4 | Qor-1 | NT | NT | 7.1 |
| Ads-Hyd 5 | Qor-1 | NT | NT | NA |
| Ads-Hyd 6 | Qor-1 | NT | NT | + |
| Ads-Hyd 7 | Qor-1 | NT | NT | + |
| Ads-Hyd 8 | Qor-1 | NT | NT | 5.8 |
| Ads-Hyd 9 | Qor-1 | NT | NT | + |
| Ads-Hyd 10 | Qor-1 | NT | NT | 12.3 |
| Ads-Hyd 11 | Qor-1 | NT | NT | + |
| Ads-Hyd 12 | Qor-1 | NT | NT | + |
| Ads-Hyd 13 | Qor-1 | NT | NT | + |
| Ads-Hyd 14 | Qor-1 | NT | NT | + |
| Ads-Hyd 15 | Qor-1 | NT | NT | + |
| Ads-Hyd 62 | Qor-1 | NT | NT | 20.0 |
| Ads-Hyd 87 | Qor-1 | NT | NT | 28.4 |
| Ads-Hyd 96 | Qor-1 | NT | NT | 28.3 |
| Ads-Hyd 104 | Qor-1 | NT | NT | 24.6 |
| Ads-Hyd 65 | Qor-1 | NT | NT | 18.9 |
| Ads-Hyd 89 | Qor-1 | NT | NT | 8.5 |
| Ads-Hyd 97 | Qor-1 | NT | NT | 26.1 |
| Ads-Hyd 68 | Qor-1 | NT | NT | 18.5 |
| Ads-Hyd 108 | Qor-1 | NT | NT | 33.8 |
| Ads-Hyd 29 | Qor-1 | NT | NT | 18.3 |
| Ads-Hyd 69 | Qor-1 | NT | NT | 8.9 |
| Ads-Hyd 93 | Qor-1 | NT | NT | 40.5 |
| Ads-Hyd 8 | Qor-1 | NT | NT | 5.8 |
| Ads-Hyd 8 | Qor-2 | NT | NT | + |
| Ads-Hyd 8 | Qor-3 | NT | NT | + |
| Ads-Hyd 8 | Qor-4 | NT | NT | + |
| Ads-Hyd 8 | Qor-5 | NT | NT | + |
| Ads-Hyd 8 | Qor-6 | NT | NT | + |
| Ads-Hyd 8 | Qor-7 | NT | NT | + |
| Ads-Hyd 8 | Qor-8 | NT | NT | + |
| Ads-Hyd 8 | Qor-9 | NT | NT | + |
| Ads-Hyd 8 | Qor-10 | NT | NT | + |
| Ads-Hyd 8 | Qor-11 | NT | NT | + |
| Ads-Hyd 8 | Qor-12 | NT | NT | + |
| Ads-Hyd 8 | Qor-13 | NT | NT | + |
| Ads-Hyd 8 | Qor-14 | NT | NT | + |
| Ads-Hyd 8 | Qor-15 | NT | NT | + |
| Ads-Hyd 8 | Qor-16 | NT | NT | + |
| Ads-Hyd 8 | Qor-17 | NT | NT | + |
| Ads-Hyd 8 | Qor-18 | NT | NT | + |
| Ads-Hyd 8 | Oor-19 | NT | NT | + |

NT = Not tested;
NA = Not active;
+ = activity confirmed but not quantified

Various biosynthesis polypeptides, particularly those belonging to EC 1.6.5, may be utilized for a reduction. For example, quinone oxidoreductases belonging to EC 1.6.5.5. are reported to be involved in electron carrier activity and are reported to be ubiquitous enzymes as they are reported to be present in, e.g., mammals, fungi, and bacteria (see entry for this EC class on Brenda.org). Although the native expression levels of these enzymes across various hosts are not known, it has been postulated previously that the expression level of this class of enzymes natively can be affected by the oxidative stress faced by the microbial host. It was discovered that *E. coli* (MG1655 and BL 21 strains) QorA gene (Qor-1) is natively expressed, especially under conditions described in Example 2. It was demonstrated that even native enzyme levels of Qor-1 in *E. coli* can be sufficient for production of 2-keto acids when Ads-Hyd enzymes (e.g., Ads-Hyd 8) are overexpressed in *E. coli*. For example, when Ads-Hyd 8 is overexpressed in *E. coli* BL 21*(DE3) ΔldhA, this resulted in the production of ~3 mM 6-hydroxy 2-keto hexanoate. However, overexpression of Qor-1 from plasmids in addition to Ads-Hyd 8, led to ~2× improved production (~5.8 mM 6-hydroxy 2-keto hexanoate). Based on this result, the in vitro kinetics data gathered in-house, and typical enzyme levels discovered in *E. coli*, it is estimated that in some embodiments, the native amounts of Qor-1 enzyme expressed under these conditions is <100 µM, and likely in the range of 0.1-100 µM.

Compared to a three-enzyme system, wherein aldol addition, dehydration, and subsequent reduction are carried out by three separate enzymes, provided technologies using two-enzyme systems provided significant improvement, for example: (1) only two enzymes need to be expressed rather than three enzymes—thus reducing catalysts required, and reducing cell resources for protein production when reaction are conducted in vivo, and (2) by having a single biosynthesis polypeptide carry out both the aldol addition and condensation reactions, reaction equilibrium is shifted towards the direction of production of desired products, which can be favorable to overall yields feasible through the process.

Cloning, and expression: DNA encoding heterologous aldolase hydratases and quinone oxidoreductase enzymes shown in Table 5 were codon-optimized for expression in *E. coli* and synthesized by a commercial DNA synthesis company. Using standard cloning methods, each gene was cloned downstream of the T7 RNA polymerase promoter and upstream of the T7 terminator sequence on two compatible plasmids. Additionally, for experiments wherein the aldehyde selected was 3-hydroxy-propionaldehyde, a glycerol dehydratase enzyme that is a B12-dependent enzyme (*Lactococcus reuteri* glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned on a third compatible plasmid to enable production of 3-hydroxypropionaldehyde from glycerol using this enzyme. The plasmids were transformed in *E. coli* MG1655 (DE3) rne131 ΔldhA ΔadhE ΔfrdBC ΔpoxB ΔpflB ΔackA-pta ΔyghD, ΔadhP, ΔeutG, ΔgldA, ΔyiaY, ΔfucO. Recombinant protein expression was carried out as described above in Example 1.

Enzyme assay: Same as Example 1.

Analysis of product: Isocratic HPLC method described in Example 1 was used to detect and quantify production of enzyme product, i.e., 2-keto-carboxylic acids.

Example 4: Biosynthetic Pathway for the Production of 1,5-Pentanediol

Figure 2:
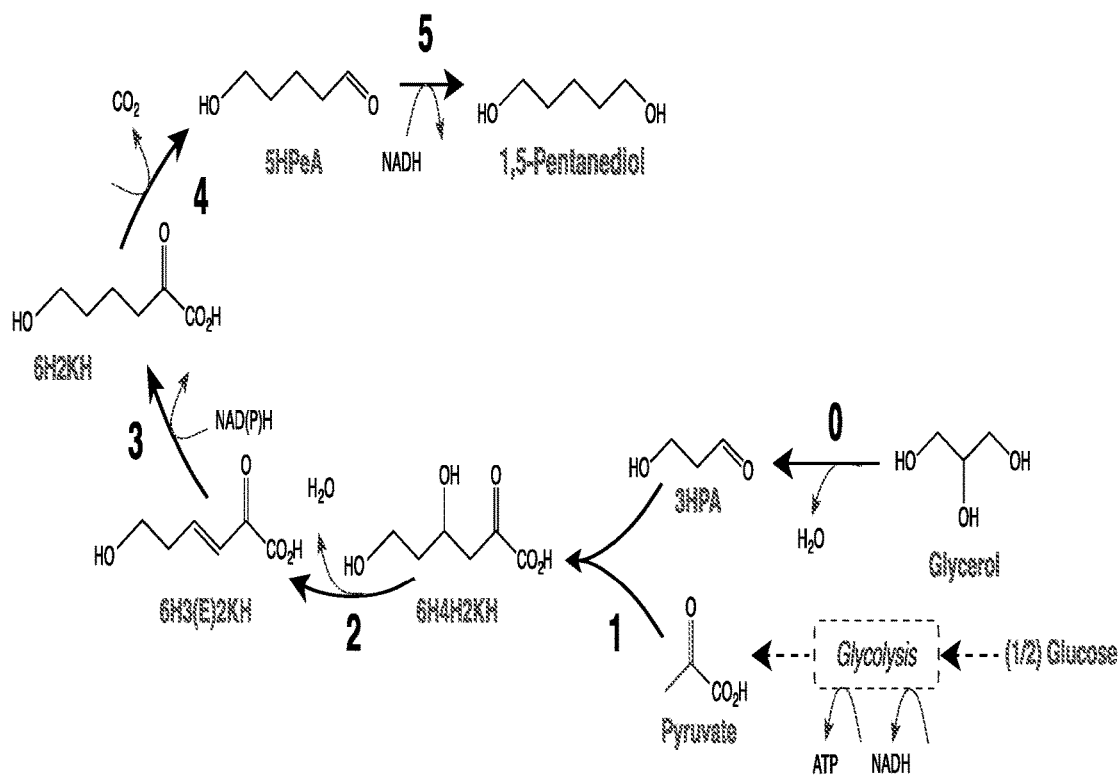
FIG. 2 shows a biosynthetic pathway for production of 1,5-pentanediol via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; and 5HPeA refers to 5-hydroxy pentanal. NADH is depicted as the cofactors for many reduction steps of the pathway for illustrative purposes. Either NADPH or NADH could be a cofactor.

This example describes a biosynthetic pathway for the production of 1,5-pentanediol from pyruvate and 3-hydroxypropionaldehyde. As shown in FIG. 2, the biosynthetic pathway from pyruvate and 3-hydroxy-propionaldehyde includes five reactions. The first three reactions are described in Example 3, which involve converting pyruvate and 3-hydroxy-propionaldehyde to 6-hydroxy-2-ketohexanoate. Described below are both known enzymes from the remaining two steps of the pathway. Notably, enzymes have been validated for all five reactions, which included demonstrating the complete pathway in vivo (see Example 5).

Steps 1-3: Conversion of pyruvate and 3-hydroxy-propionaldehyde to 6-hydroxy-2-oxo-hexanoate. See Example 3 for details.

Step 4: Conversion of 6-hydroxy-2-oxo-hexanoate to 5-hydroxy-pentanal. Exemplary enzymes are shown in Table 11. 2-Keto-acid decarboxylases (EC 4.1.1.7) catalyze the thiamine diphosphate (TPP) dependent decarboxylation of ($C_n$) 2-keto acids to give the corresponding ($C_{n-1}$) aldehydes. Enzymes that possess high-activity towards long-chain 2-oxo-acids with minimal or no activity on pyruvate are desired since cross-reactivity with pyruvate can dramatically affect yields of this pathway. Z. mobilis pyruvate decarboxylase (PDC) has been mutated (I472A/I476F) to significantly modify its active site for increased efficiency towards long-chain 2-oxo-acids along with a dramatic reduction (>2000 fold) in its activity towards pyruvate.[7] Z. mobilis PDC mutant I472A/I476F also shows excellent kinetic properties on 2-oxo-hexanoate which is structurally similar to desired substrate. Another promising enzyme candidate for catalyzing this step is L. lactis branched chain keto-acid decarboxylase KdcA (ketoacid decarboxylase), and P. putida benzoyl formate decarboxylase (BFD) mutant A460I.[8-10] The Pseudomonas putida BFD and L. lactis KdcA show >50 and 500-fold selectivity towards long-chain 2-oxo-acids compared to pyruvate for decarboxylation. In particular, L. lactis KdcA has specific activity towards 2-oxo-hexanoic acid and can tolerate substitutions on C3 and C4 positions. This enzyme was confirmed to be active for catalyzing the decarboxylation reaction (Table 14).

TABLE 11

Exemplary enzymes.

| Uniprot ID | Protein Name | Gene Name | Organism | E.C. Number |
|---|---|---|---|---|
| Q6QBS4 | Branched-chain alpha-ketoacid decarboxylase | kdcA | Lactococcus lactis | 4.1.1.72 |
| A7M7D6 | Pyruvate decarboxylase | pdc | Zymomonas mobilis | 4.1.1.1 |
| P20906 | benzoyl formate decarboxylase | mdlc | Pseudomonas putida | 4.1.1.7 |

Decarboxylases having other BC numbers are also suitable for carrying out this reaction. A representative list is shown in Table 12.

TABLE 12

Exemplary decarboxylases.

| E.C. Number | Name |
|---|---|
| 4.1.1.1 | Pyruvate decarboxylase |
| 4.1.1.2 | Oxalate decarboxylase |
| 4.1.1.3 | oxaloacetate decarboxylase |
| 4.1.1.4 | acetoacetate decarboxylase |
| 4.1.1.5 | acetolactate decarboxylase |
| 4.1.1.6 | aconitate decarboxylase |
| 4.1.1.7 | benzyl formate decarboxylase |
| 4.1.1.11 | aspartate-1-decarboxylase |
| 4.1.1.12 | aspartate-4-decarboxylase |
| 4.1.1.15 | glutamate decarboxylase |
| 4..1.1.16 | hydroxyglutamate decarboxylase |
| 4.1.1.17 | ornithine decaraboxylase |
| 4.1.1.18 | lysine decarboxylase |
| 4.1.1.19 | arginine decarboxylase |
| 4.1.1.20 | diaminopimelate decarboxylase |

TABLE 12-continued

Exemplary decarboxylases.

| E.C. Number | Name |
|---|---|
| 4.1.1.34 | dehydro-L-gulonate decarboxylase |
| 4.1.1.35 | UDP-glucuronate decarboxylase |
| 4.1.1.40 | hydroxypyruvate decarboxylase |
| 4.1.1.54 | dihydroxyfumarate decarboxylase |
| 4.1.1.56 | 3-oxolaurate decarboxylase |
| 4.1.1.71 | 2-oxoglutarate decarboxylase |
| 4.1.1.72 | branched chain 2-oxo-acid decarboxylase |
| 4.1.1.73 | tartarate decarboxylase |
| 4.1.1.74 | indolepyruvate decarboxylase |
| 4.1.1.75 | 5-guanidino-2-oxopentanoate decarboxylase |
| 4.1.1.77 | 2-oxo-3-hexnedioate decarboxylase |

Step 5: Conversion of 5-hydroxy-pentaldehyde to 1,5-pentanediol. Primary alcohol dehydrogenases catalyze the NAD(P)H-dependent reduction of aldehydes to primary alcohols.

Many primary alcohol dehydrogenases are known in literature, and exemplary candidates to catalyze this step are described below and shown in Table 13 below. A number of E. coli alcohol-aldehyde dehydrogenases are known including AdhE, adhP, eutG, yiaY, yghD, fucO, and yjgB.[11] Recently, 44 aldehyde reductases have been identified in E. coli. Butanol dehydrogenases[12] from C. acetobutylicum are of interest to catalyze these transformations. A number of S. cerevisiae alcohol dehydrogenases have been shown to reduce a range of different aldehydes including, ADH2-6. Of particular interest is ADHI-ADHII from two alkyl alcohol dehydrogenase (ADH) genes[13] from the long-chain alkane-degrading strain Geobacillus thermodenitrificans NG80-2. Other promiscuous ADH include AlrA which encodes a medium-chain alcohol dehydrogenase.[14] Also of interest are 4-hydroxy butyrate dehydrogenases (EC 1.1.1.61) that catalyze reduction of 4-oxo butyrate that have been found in A. thaliana[15], E. coli (yihu)[16], and as well as C. eluyveri.[17] A. thaliana enzyme as well as A. terrus enzyme (ATEG in Table 13) can reduce glutarate semialdehyde (WO 2010/068953A2, WO 2010/068953A2). Although a number of alcohol dehydrogenase are of interest for carrying out this reaction, a specific enzyme of particular interest due to its high level of activity for reducing 5-hydroxy pentanal is alcohol dehydrogenase from Leifsonia sp. S749 (GenBank ID No. AB213459.1). This enzyme and four other alcohol dehydrogenases were validated (Table 14) to carry out this reaction.

TABLE 13

Exemplary dehydrogenases.

| Gene | GenBank ID or Uniprot ID | Name | Organism |
|---|---|---|---|
| fucO | NP_417279.1 | Alcohol Dehydrogenase | Escherichia coli |
| bdh I | NP_349892.1 | Alcohol Dehydrogenase | Clostridium acetobutylicum |
| bdh II | NP_349891.1 | Alcohol Dehydrogenase | Clostridium acetobutylicum |
| alrA | BAB12273.1 | Alcohol Dehydrogenase | Acinetobacter sp. strain |
| 4hbd | L21902.1 | 4-hydroxy butyrate dehydorgenase | Clostridium kluyveri |
| 4hbd | Q94B07 | 4-hydroxy butyrate dehydorgenase | Arabidopsis thaliana |
| yihu | AAB03015.1. | 4-hydroxy butyrate dehydorgenase | Escherichia coli |
| ADH2 | NP_014032.1 | Alcohol Dehydrogenase | Saccharomyces cerevisiae |
| ADH3 | NP_013892.1 | Alcohol Dehydrogenase | Saccharomyces cerevisiae |
| ADH4 | NP_015019.1 | Alcohol Dehydrogenase | Saccharomyces cerevisiae |
| ADH5 | NP_010996.2 | Alcohol Dehydrogenase | Saccharomyces cerevisiae |
| ADH6 | ABX39192.1 | Alcohol Dehydrogenase | Saccharomyces cerevisiae |
| ATEG | XP_001210625.1 | Alcohol Dehydrogenase | Aspergillus terreus |
| ADHI | ABO67118 | Alcohol Dehydrogenase | Geobacillus thermodenitrificans NG80-2 |
| ADHII | ABO68223 | Alcohol Dehydrogenase | Geobacillus thermodenitrificans NG80-2 |
| YqhD | BAE77068.1 | Alcohol Dehydrogenase | Escherichia coli |
| bdh CLJU_c23460 | D8GL45 | butanol dehydrogenase | Clostridium ljungdahlii |
| bdhA CA_C3299 | Q04944 | butanol dehydrogenase A | Clostridium acetobutylicum |
| chnD | Q84H78 | 6-hydroxyhexanoate dehydrogenase | Rhodococcus sp. Phi2 |
| chnD | Q7WVD0 | 6-hydroxyhexanoate dehydrogenase | Acinetobacter sp. NCIMB9871 |
| lsadh | AB213459.1 | Short chain alcohol dehydrogenase | Leifsonia sp. S749 |
| Adhe | CAA47743.1 . | Alcohol Dehydrogenase | Escherichia coli |

Cloning, and expression: DNA encoding heterologous 2-keto acid decarboxylase and alcohol dehydrogenase enzymes shown in Table 14 below were codon-optimized for expression in E. coli and synthesized. Using standard cloning methods, each gene was cloned downstream of the T7 RNA polymerase promoter and upstream of the T7 terminator sequence on a single plasmid. The plasmid was transformed in E. coli MG1655 (DE3) rne131 ΔldhA ΔadhE ΔfrdBC. Recombinant protein expression was carried out as described above in Example 1.

TABLE 14

Production of 1,5-pentanediol.

| Example No: | Uniprot ID of Keto acid decarboxylase | Uniprot ID of primary alcohol dehydrogenase* | 1,5-pentanediol produced (g/L) |
|---|---|---|---|
| 4A | Q6QBS4 | D8GL45 | 0.6 |
| 4B | Q6QBS4 | Q04944 | 0.8 |
| 4C | Q6QBS4 | Q84H78 | 1.4 |
| 4D | Q6QBS4 | Q7WVD0 | 1.4 |
| 4E | Q6QBS4 | AB213459.1 | 1.4 |

*In this case, this enzyme also can be referred to as 5-hydroxy-pentanal 1-reductase.

Activity Assay: Observation of the production of 1,5-pentanediol from externally fed 6-hydroxy-2-keto-hexanoate indicated successful activity of the 2-keto acid decarboxylase and alcohol dehydrogenase enzymes. Thus post expression, cells were harvested and re-suspended in 0.4 mL fresh medium (OD600 ~30) containing 15 g/L potassium phosphate buffer (pH 7.2) with 6-hydroxy-2-keto-hexanoate (~5 g/L) and 10 g/L glucose, for 15 hr under anaerobic conditions. After incubation at room temperature, the cells were centrifuged, and the supernatant was filtered and analyzed via HPLC for the formation of 1,5-pentanediol from 6-hydroxy-2-keto-hexanoate.

HPLC analysis of 1,5-pentanediol production: Isocratic HPLC was used to detect and quantify 1,5-pentanediol. The method employed a Bio-Rad Aminex HPX-87 column, 0.7 mL/min of 0.05% formic acid (or 5 mM sulfuric acid) at 35° C. Detection was carried out using an RID (refractive index detector) and UV detector, the latter of which was used to measure signals at 210 and 260 nm. The HPLC results showed production of 1,5-pentanediol; results of certain preparations were presented in Table 14.

Example 5: Preparation and Use of Microbial Organism for Production of 1,5-Pentanediol from Different Carbon Sources Via 6-Hydroxy-2-Keto-Hexanoate Intermediate In some embodiments, the present disclosure provides technologies for producing 1,5-pentanediol. In some embodiments, glycerol is utilized as a carbon source. In some embodiments, one or more, or all, biosynthesis steps are performed in one organism (e.g., bacterium) and culture. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L.

E. coli was used as an exemplary organism to engineer the production of 1,5-pentanediol from carbon sources such as glycerol and/or glucose via metabolic precursor pyruvate and 3-hydroxy-propionaldehyde that are derived from these carbon sources, using the metabolic pathway which is shown in FIG. 2, and which is also described in Example 4. To generate E. coli capable of making 1,5-pentanediol via this pathway from desired carbon sources (e.g. glycerol and/or glucose), the nucleic acid encoding each individual enzyme in the pathway and other enzymes necessary for 3-hydroxy-propionaldehyde production were either codon-optimized for E. coli and synthesized commercially or obtained via PCR amplification using E. coli genomic DNA. Genes were cloned into plasmids, which were transformed in E. coli. In vivo expression of all of the pathway enzymes resulted in production of 1,5-pentanediol.

Cloning of 1,5-pentanediol pathway genes: DNA encoding heterologous enzymes in the 1,5-pentanediol pathway were codon-optimized for expression in E. coli and synthesized by a commercial DNA synthesis company (e.g., Twist Biosciences). DNA encoding native enzymes in the 1,5-pentanediol pathway were amplified from E. coli genomic DNA via PCR. Using standard cloning methods, each gene was cloned downstream of the T7 RNA polymerase promoter and upstream of a terminator sequence. Compatible plasmids harboring expression cassettes for the genes contained one of the following combinations of a marker and replicon: (1) chloramphenicol maker+P15A replicon, (2) ampicillin marker+ColE1 replicon, and (3) kanamycin marker+COLA replicon. Examples of genes used include the following: Ads-Hyd 8 (Uniprot ID No. A0A286PH18), Qor-1 (Uniprot ID No. P28304), 6-hydroxy-2-oxo-hexanoate decarboxylase (Uniprot ID No. Q6QBS4), primary alcohol dehydrogenase also referred to as 5-hydroxy-pentanal 1-reductase (GenBank ID No. AB213459.1). Additionally, glycerol dehydratase enzyme that is vitamin B12-independent (e.g. Clostridium butyricum glycerol dehydratase that is comprised of two subunits as follows: DhaB1 [Uniprot ID No. Q8GEZ8]; DhaB2 [Uniprot ID No. Q8GEZ7]) or glycerol dehydratase enzyme that is a B12-dependent enzyme (Lactococcus reuteri glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned to enable production of 3-hydroxy-propionaldehyde—a 1,5-pentanediol pathway precursor that can be made from glycerol using this enzyme. All five genes encoding the Lactococcus reuteri glycerol dehydratase were cloned as a single gene operon.

Construction of strain(s) for the production of 1,5-pentanediol: The E. coli strain BL21* (DE3) ΔldhA was used as the background strain for testing of the 1,5-pentanediol pathway enzymes. Plasmids harboring the genes encoding the pathway enzymes were transformed using standard electroporation methods associated with transforming E. coli.

Production of 1,5-pentanediol: The following expression strains were obtained after sequentially transforming the following plasmids into E. coli.

Strain PeDO1: Plasmid 1 (COLA replicon, kanamycin marker): Gene 1 (Glycerol dehydratase—DhaB1), Gene 2 (Glycerol dehydratase—DhaB2), Gene 3 (Qor 1). Plasmid 2 (ColE1 replicon, ampicillin marker): Gene 1 (6-hydroxy-2-oxo-hexanoate decarboxylase), Gene 2 (Ads-Hyd 8). Plasmid 3 (P15A replicon, chloramphenicol marker): Gene 1 (5-hydroxy-pentanal 1-reductase).

Strain PeDO2: Plasmid 1 (COLA replicon, kanamycin marker): Gene 1 (Glycerol dehydratase—DhaB1), Gene 2 (Glycerol dehydratase—DhaB2), Gene 3 (Qor 1). Plasmid 2 (ColE1 replicon, ampicillin marker): Gene 1 (6-hydroxy-2-oxo-hexanoate decarboxylase), Gene 2 (Ads-Hyd 8).

Strain PeDO3: Plasmid 1 (COLA replicon, kanamycin marker): Gene 1 (Glycerol dehydratase—pduCDEGH). Plasmid 2 (ColE1 replicon, ampicillin marker): Gene 1 (6-hydroxy-2-oxo-hexanoate decarboxylase), Gene 2 (Ads-Hyd 8), Gene 3 (5-hydroxy-pentanal 1-reductase). Plasmid 3 (P15A replicon, chloramphenicol marker): Gene 1 (Qor 1).

Strain PeDO4: Plasmid 1 (COLA replicon, kanamycin marker): Gene 1 (Glycerol dehydratase—pduCDEGH). Plasmid 2 (ColE1 replicon, ampicillin marker): Gene 1 (6-hydroxy-2-oxo-hexanoate decarboxylase), Gene 2 (Ads-Hyd 8). Plasmid 3 (P15A replicon, chloramphenicol marker): Gene 1 (5-hydroxy-pentanal 1-reductase).

Culturing for Strain PeDO1 and PeDO2: Starter cultures were grown overnight in tubes containing 5 mL 2×YT media with 1 g/L D-glucose and appropriate antibiotics. Cell cultures for the expression and the 1,5-pentanediol pathway enzymes were carried out in 40 mL growth medium using 125 mL baffled flasks. Complex (2×YT) growth medium was used and supplemented with 2 g/L D-glucose, 0.5 g/L potassium phosphate buffer (pH 7.2), and 100 mg/L ferric ammonium citrate. Pre-induction growth was carried out for 2 hours under aerobic conditions and at 30° C. Recombinant protein expression was induced at an OD600 of 0.2-0.4 with 250 μM IPTG. Post-induction expression was carried out for 30 minutes at 30° C. and under aerobic conditions. Cell cultures were then transferred to 100 mL glass bottles, L-cysteine-HCl-monohydrate was added to the growth medium (1 g/L final concentration), and the bottles were sealed within an anaerobic glove box (Coy Laboratory). Cultures were then grown in the glass bottles for 2 hours at 30° C. and under anaerobic conditions. Afterwards, cells were harvested and re-suspended in 0.4 mL fresh medium (OD600 ~30) containing 8 g/L glucose, 4 g/L glycerol, and 15 g/L potassium phosphate buffer (pH 7.2). After incubation under anaerobic conditions for 24 hours and at room temperature, the cells were centrifuged, and the supernatant was filtered and analyzed via HPLC.

Culturing for Strain PeDO3 and PeDO4: Production medium contains following composition: 1×MOPS minimal medium, 5 g/L yeast extract, 10 g/L glycerol, 20 g/L glucose, and 10 uM of Cyanocobalamin (pH7.2). The 1×MOPS minimal medium is composed of 40 mM MOPS, 4 mM tricine, 0.01 mM $FeSO_4$, 9.5 mM $NH_4Cl$, 0.276 mM $K_2SO_4$, 0.5 μM $CaCl_2$, 0.525 mM $MgCl_2$, 50 mM NaCl, $2.92E^{-7}$ mM $(NH4)2MoO4$, $4.0E^{-5}$ mM $H_3BO_3$, $3.02E^{-6}$ mM $CoCl_2$, $9.62E^{-7}$ mM $CuSO_4$, $8.08E^{-6}$ mM $MnCl_2$, $9.74E^{-7}$ mM $ZnSO_4$, and 1.32 mM $K_2PO_4$. Seed cultures were grown overnight in tubes containing 10 mL 2×YT media and appropriate antibiotics. Cell cultures for 1,5-pentanediol production were prepared using 10 mL production medium with appropriate antibiotics in 125 mL flask with a stopper, 1 mL of seed culture was inoculated and allow cell to grow at 37° C. for 2 hr before induction. After 2 hr, cell culture was induced with 0.1 mM IPTG and the culture was transferred to 26° C. to start the production. Samples were taken every 12 hr aerobically with final sample taken at 72 hr, and the supernatant was filtered and analyzed via HPLC.

HPLC analysis of 1,5-pentanediol production: Isocratic HPLC was used to detect and quantify 1,5-pentanediol. The method employed a Bio-Rad Aminex HPX-87 column, 0.7 mL/min of 0.05% formic acid (or 5 mM sulfuric acid) at 35° C. Detection was carried out using an RID (refractive index detector) and UV detector, the latter of which was used to measure signals at 210 and 260 nm. The HPLC results showed evidence 1,5-pentanediol production at a final titer of 800 mg/L (Strain PeDO1), 400 mg/L (PeDO2), 212 mg/L (PeDO3), and 41 mg/L (PeDO4).

Additional Working Examples for 1,5-Pentanediol Production

Based on the success of producing 1,5-pentanediol using the above-described strains, the use of alternative quinone oxidoreductases identified in Examples 2 & 3 for the production of 1,5-pentanediol was assessed. Briefly, the plasmid combination of Strain PeDO3 in the above-described example was used, wherein the plasmid 3 contained different Qor enzymes namely Qor-1 (Uniprot ID No. P28304), Qor-2 (Uniprot ID No. P40783), and Qor-5 (Uniprot ID No. P43903). The strain construction, production, and analytical methods were identical to those described above. Strain PeDO5 (containing Qor-1), Strain PeDO6 (containing Qor-2), and Strain PeDO6 (containing Qor-5) led to the production of ~2 g/L, 2.2 g/L and 2.4 g/L 1,5-pentanediol respectively under production conditions described above

Figure 3:
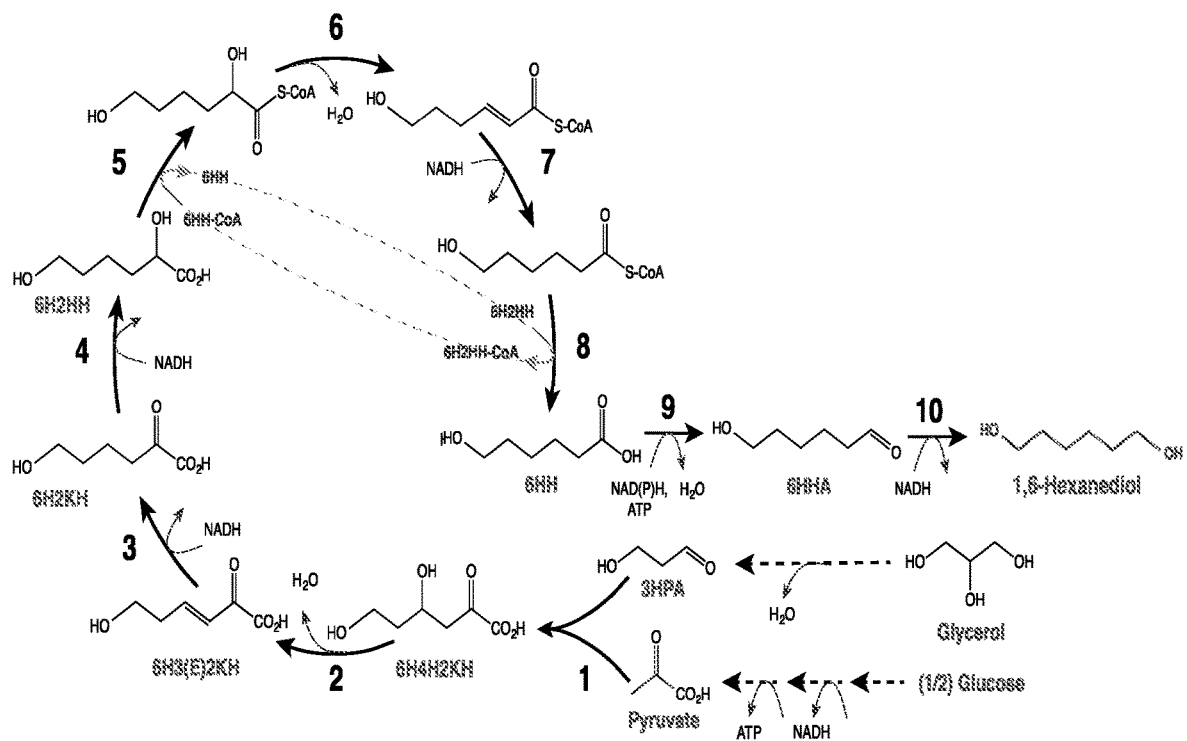
FIG. 3 shows a biosynthetic pathway for production of 1,6-hexanediol via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; 6H2HH refers to 2,6-dihydroxy-hexanoate; 6HH-CoA refers to 6-hydroxy-hexanoyl-CoA; 6HH refers to 6-hydroxy hexanoate; 6H2HH-CoA refers to 2,6-dihydroxy-hexanoyl-CoA; and 6HHA refers to 6-hydroxy hexanal. Either NADPH or NADH could be a cofactor. Step 5 and 8 are catalyzed by a single CoA-transferase enzyme. 6HH-CoA is depicted as donor for Step 5 reaction and 6H2HH as the acceptor for illustrative purposes. Other CoA-esters or carboxylic acids can serve as donors and acceptors for this enzyme in vivo.

Example 6: Preparation and Use of Microbial Organism for Production of 1,6-Hexanediol from 6-Hydroxy-Hexanoate Intermediate In some embodiments, the present disclosure provides technologies for preparing 6HH and HDO. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 1,6-hexanediol from 6-hydroxy-hexanoate (6HH) intermediate is shown in FIG. 3. Shown below are examples incorporating the use of different enzymes for each step of this pathway to validate the production of 1,6-hexanediol from 6HH. Examples of genes and corresponding enzymes from which they are encoded that were used to carry out each step of the 1,6-hexanediol biosynthetic pathway from 6HH intermediate are shown in Table 15 below. Each enzyme therein may be substituted with homologous enzymes that belong to the same E.C. class.

TABLE 15

Production of HDO.

| ENTRY No: | Gene 1 Uniprot ID or Genbank ID | Gene 2 Uniprot ID or Genbank ID | Gene 3 Uniprot ID or Genbank ID |
|---|---|---|---|
| 1 | D6Z860 | P39135 | AB213459.1 |
| 2 | YP_001705436.1 | P39135 | AB213459.1 |
| 3 | ANO06407.1 | P39135 | AB213459.1 |
| 4 | AAR91681.1 | P39135 | AB213459.1 |
| 5 | AHH98121.1 | P39135 | AB213459.1 |
| 6 | ANB00612.1 | P39135 | AB213459.1 |
| 7 | ANO04655.1 | P39135 | AB213459.1 |
| 8 | A0R484 | P39135 | AB213459.1 |
| 9 | AFP42026.1 | P39135 | AB213459.1 |
| 10 | GAJ86510.1 | P39135 | AB213459.1 |
| 11 | YP_001704097.1 | P39135 | AB213459.1 |
| 12 | ANA99315.1 | P39135 | AB213459.1 |
| 13 | GAJ83027.1 | P39135 | AB213459.1 |
| 14 | ANA98925.1 | P39135 | AB213459.1 |
| 15 | ANA98924.1 | P39135 | AB213459.1 |
| 16 | ANO04656.1 | P39135 | AB213459.1 |
| 17 | YP_001703694.1 | P39135 | AB213459.1 |
| 18 | WP_036338301.1 | P39135 | AB213459.1 |
| 19 | WP_007472106.1 | P39135 | AB213459.1 |
| 20 | A0QWI7 | P39135 | AB213459.1 |

Reaction catalyzed by enzyme named 6-hydroxyhexanoate 1-reductase, which is coded by gene 1: 6-hydroxy-hexanoate --> 6-hydroxy-hexanal. Enzyme coded by gene 2: 6-hydroxyhexanoate 1-reductase activator. Reaction catalyzed by enzyme named 6-hydroxy-hexanal 1-reductase, which is coded by gene 3: 6-hydroxy-hexanal --> 1,6-hexanediol (i) Preparation of Plasmids for HDO Production:

The HDO production pathway genes were cloned on a two plasmids shown below.

Synthetic genes were obtained from commercial vendors, and each gene was codon optimized for expression in *E. coli*. Each gene was cloned under its own T7 promoter and terminator using standard molecular biology methods. *Escherichia coli* was used as a target organism to engineer the 1,6-hexanediol production. The expression strains were obtained after co-transforming all two plasmids in electro competent *E. coli* MG1655 (DE3) Δrne131, ΔldhA.

Plasmid 1 (ColE1 replicon, ampicillin marker): Gene 1.
Plasmid 2 (COLA replicon, kanamycin marker): Gene 2, and Gene 3

(ii) Cell Culturing, Protein Expression, and HDO Production Analysis:

Starter cultures were grown overnight in tubes containing 10 mL. LB media with appropriate antibiotics. Cell cultures for the expression and HDO production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 μM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing ~10 g/L glucose, 6-hydroxy-hexanoate (~5 g/L), and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 0.1 to 2.5 g/L of 1,6-hexanediol for all examples in Table 15.

enzymes for each step of this pathway to validate the production of 1,6-hexanediol via this pathway. Examples of genes and corresponding enzymes from which they are encoded that were used to carry out each step of the 1,6-hexanediol biosynthetic pathway from 6-hydroxy-2-keto-hexanoate intermediate are shown in Table 16 below. Each enzyme therein may be substituted with homologous enzymes that belong to the same E.C. class. Additionally, the example below highlights the confirmation of multiple enzymes for carrying out both the CoA-transfer reaction and the 2,6-dihidroxy-hexanoyl-CoA dehydration reaction.

(i) Preparation of Plasmids for HDO Production:

TABLE 16

Biosynthesis polypeptides for HDO production.

| Reaction Catalyzed | Enzyme Name | Gene Number | Example 7A Uniprot ID or Genbank ID | Example 7B Uniprot ID or Genbank ID | Example 7C Uniprot ID or Genbank ID | Example 7D Uniprot ID or Genbank ID | Example 7E Uniprot ID or Genbank ID |
|---|---|---|---|---|---|---|---|
| 6-hydroxy-2-oxohexanoate- → 2,6-dihydroxy-hexanoate | 6-hydroxy-2-oxohexanoate 2-reductase | Gene 1 | Q5FTU6 | Q5FTU6 | Q5FTU6 | Q5FTU6 | Q5FTU6 |
| 2,6-dihydroxy-hexanoate → 2,6-dihydroxy-hexanoyl-CoA | 2,6-dihydroxy-hexanoate CoA-transferase | Gene 2 and Gene 3 | T4VW93* | T4VW93** | T4VW93 + A0A0C7GD16 | T4VW93 + A0A175L1W4 | T4VW93 + A0A2X3BTQ9 |
| 2,6-dihydroxy-hexanoyl-CoA → 6-hydroxy-2,3-dehydro-hexanoyl-CoA | 2,6-dihydroxy-hexanoyl-CoA 2-dehydratase - Subunit A | Gene 4 | Q5U924 | A0A2X3BK09 | A0A2X3BK09 | A0A2X3BK09 | A0A2X3BK09 |
|  | 2,6-dihydroxy-hexanoyl-CoA 2-dehydratase - Subunit B | Gene 5 | Q5U925 | A0A2X3BU19 | A0A2X3BU19 | A0A2X3BU19 | A0A2X3BU19 |
|  | 2,6-dihydroxy-hexanoyl-CoA 2-dehydratase - Subunit C | Gene 6 | Q5U923 | A0A1V9IXA9 | A0A1V9IXA9 | A0A1V9IXA9 | A0A1V9IXA9 |
| 6-hydroxy-2,3-dehydro-hexanoyl-CoA → 6-hydroxy-hexanoyl-CoA | 2,3-dehydro-hexanoyl-CoA 2,3-reductase | Gene 7 | Q73Q47 | Q73Q47 | Q73Q47 | Q73Q47 | Q73Q47 |
| 6-hydroxy-hexanoyl-CoA → 6-hydroxy-hexanoate | 6-hydroxyhexanoyl-CoA transferase | Gene 8 | Same as Gene 2 & Gene 3 | Same as Gene 2 & Gene 3 | Same as Gene 2 & Gene 4 | Same as Gene 2 & Gene 5 | Same as Gene 2 & Gene 6 |
| 6-hydroxy-hexanoate → 6-hydroxy-hexanal | 6-hydroxyhexanoate 1-reductase | Gene 9 | A0R484 | A0R484 | A0R484 | A0R484 | A0R484 |
|  | 6-hydroxyhexanoate 1-reductase activator | Gene 10 | P39135 | P39135 | P39135 | P39135 | P39135 |
| 6-hydroxy-hexanal → 1,6-hexanediol | 6-hydroxyhexanal 1-reductase | Gene 11 | AB213459.1 | AB213459.1 | AB213459.1 | AB213459.1 | AB213459.1 |

*single copy of the same gene;
**dual copy of the same gene

Example 7: Preparation and Use of Microbial Organism for Production of 1,6-Hexanediol from 6-Hydroxy-2-Keto-Hexanoate Intermediate In some embodiments, the present disclosure provides technologies for preparing 6HH and HDO. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 1,6-hexanediol from 6-hydroxy-2-keto-hexanoate intermediate is shown in FIG. 3. Shown below are examples incorporating the use of different The HDO production pathway genes were cloned on two separate compatible plasmids shown below. Each plasmid had a different origin of replication and antibiotic marker, as indicated. Synthetic genes were obtained from commercial vendors, and each gene was codon optimized for expression in *E. coli*. Each gene was cloned under its own T7 promoter and terminator using standard molecular biology methods. *Escherichia coli* was used as a target organism to engineer the 1,6-hexanediol production. The expression strains were obtained after co-transforming all three plasmids in electro competent *E. coli* BL21*(DE3) Δldh, ΔadhE, ΔfrdA.

Plasmid 1 (COLA replicon, kanamycin marker): Gene 10, Gene 9,

Plasmid 2 (ColE1 replicon, ampicillin marker): Gene 1, Gene 2, Gene 3, and Gene 4

Plasmid 3 (P15A replicon, chloramphenicol marker): Gene 5, Gene 6, Gene 7, Gene 8, and Gene 11.

(ii) Cell Culturing, Protein Expression, and HDO Production Analysis:

Starter cultures were grown overnight in tubes containing 10 mL LB media with appropriate antibiotics. Cell cultures for the expression and HDO production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 µM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing ~10 g/L glucose, 6-hydroxy-2-keto-hexanoate (~5 g/L), and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 700 mg/L, 1.2 g/L, 1.1 g/L, 1.1 g/L, and 1 g/L of 1,6-hexanediol for Examples 7A-7E from Table 16, respectively.

Example 8: Preparation and Use of Microbial Organism for Production of 1,6-Hexanediol from Different Carbon Sources Via 6-Hydroxy-2-Keto-Hexanoate Intermediate In some embodiments, the present disclosure provides technologies for preparing 6HH and HDO. In some embodiments, the present disclosure provides technologies for producing HDO using glycerol as a carbon source. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for HDO production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 1,6-hexanediol from pyruvate and 3-hydroxy-propanal through the 6-hydroxy-2-keto-hexanoate intermediate is shown in FIG. 3. Shown below are examples (8a and 8b) incorporating the use of aldolase-hydratase based two enzyme system for production of 1,6-hexanediol via this pathway. A glycerol dehydratase enzyme that is vitamin B12-independent or glycerol dehydratase enzyme that is a B12-dependent enzyme can be cloned to enable production of 3-hydroxy-propionaldehyde—a 1,6-hexanediol pathway precursor that can be made from glycerol using this enzyme. The B12-dependent glycerol dehydratase was used herein. Examples of genes and corresponding enzymes they encode that were used to carry out each step of the 1,6-hexanediol biosynthetic pathway as well as production of 3-hydroxy-propionaldehyde are shown in Table 17. It is important to note that each enzyme herein could be substituted with homologous enzymes that belong to the same E.C class.

TABLE 17

Biosynthesis of HDO.

| Reaction Catalyzed | Enzyme Name | Enzyme ID | Gene Number | Uniprot ID or Genbank ID |
|---|---|---|---|---|
| Pyruvate + 3-hydroxy propanal → 6-hydroxy-3,4-dehydro-2-oxohexanoate | Trans-o-hydroxybenzylidenepyruvate hydratase-aldolases | Ads-Hyd 8 | Gene 1 | A0A286PH18 |
| 6-hydroxy-3,4-dehydro-2-oxohexanoate → 6-hydroxy-2-oxohexanoate | Quinone oxidoreductase | Qor 1 | Gene 2 | P28304 |
| 6-hydroxy-2-oxohexanoate- → 2,6-dihydroxy-hexanoate | 6-hydroxy-2-oxohexanoate 2-reductase | | Gene 3 | Q5FTU6 |
| 2.6-dihydroxy-hexanoate → 2,6-dihydroxy-hexanoyl-CoA | 2,6-dihydroxy-hexanoate CoA-transferase | | Gene 4 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase - Subunit A | | Gene 5 | Q5U924 |
| | 2,6-dihydroxy-hexanoyl-CoA 2-dehydratase - Subunit B | | Gene 6 | Q5U925 |
| | 2,6-dihydroxy-hexanoyl-CoA 2-dehydratase - Subunit C | | Gene 7 | Q5U923 |
| 6-hydroxy-2,3-dehydro-hexanoyl-CoA → 6-hydroxy-hexanoyl-CoA | 2.3-dehydro-hexanoyl-CoA 2.3-reductase | | Gene 8 | Q73Q47 |
| 6-hydroxy-hexanoyl-CoA → 6-hydroxy-hexanoate | 6-hydroxyhexanoyl-CoA transferase | | Gene 4 | T4VW93 |

TABLE 17-continued

Biosynthesis of HDO.

| Reaction Catalyzed | Enzyme Name | Enzyme ID | Gene Number | Uniprot ID or Genbank ID |
|---|---|---|---|---|
| 6-hydroxy-hexanoate → 6-hydroxy-hexanal | 6-hydroxyhexanoate 1-reductase | | Gene 9 | A0R484 |
| | 6-hydroxyhexanoate 1-reductase activator | | Gene 10 | P39135 |
| 6-hydroxy-hexanal → 1,6-hexanediol | 6-hydroxyhexanal 1-reductase | | Gene 11 | AB213459.1 |
| Glycerol dehyration | Glyerol dehydratase | | Gene 12 | Q8GEZ8 |
| | Glyerol dehydratase activator | | Gene 13 | Q8GEZ7 |

Example 8a: Production of 1,6-Hexanediol (HDO) in a Single *E. coli* Strain (i) Preparation of Plasmids for HDO Production:

The HDO production pathway genes were cloned on three separate compatible plasmids shown below. Each plasmid had a different origin of replication and antibiotic marker, as indicated. Synthetic genes were obtained from commercial vendors, and each gene was codon optimized for expression in *E. coli*. Each gene was cloned under its own T7 promoter and terminator using standard molecular biology methods. *Escherichia coli* was used as a target organism to engineer the 1,6-hexanediol production. The expression strains were obtained after co-transforming all three plasmids in electro competent *E. coli* BL21*(DE3) Δldh, ΔadhE, ΔfrdA.

Plasmid 1 (COLA replicon, kanamycin marker): Gene 12, Gene 13, Gene 2, Gene 10

Plasmid 2 (ColE1 replicon, ampicillin marker): Gene 3, Gene 4, Gene 1, and Gene 9

Plasmid 3 (P15A replicon, chloramphenicol marker): Gene 5, Gene 6, Gene 7, Gene 8, and Gene 11.

(ii) Cell Culturing, Protein Expression, and HDO Production Analysis:

Starter cultures were grown overnight in tubes containing 10 mL LB media with appropriate antibiotics. Cell cultures for the expression and HDO production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 μM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 m/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 25-100 mg/L of 1,6-hexanediol. To illustrate that alternate enzymes previously validated to carry out specific steps of the pathway can be used for HDO production using this methodology, an alternate HDO production strain wherein genes 5-7 were encoded by Uniport IDs A0A2X3BKO9, A0A2X3BU19, and A0A1V9IXA9 respectively was constructed and evaluated using above methods. This production strain also led to production of >10 mg/L of of 1,6-hexanediol.

Example 8b: Production of 1,6-Hexanediol (HDO) in Two *E. coli* Strains (i) Preparation of Plasmids & Strains for HDO Production:

To minimize the number of HDO production pathway genes expressed from plasmids, *E. coli* expression strain was constructed wherein certain pathway genes were integrated in the genome. Specifically, HDO production strain BL21*(DE3) Δldh, ΔadhE, ΔfrdA containing HDO pathway genes (Gene 12, Gene 13) at the arsB location with expression of each gene controlled by its own T7 promoter. The remaining HDO production pathway genes were cloned on four separate plasmids shown below using techniques described in example above. Identity of Genes was as described in Example 8a. Two *E. coli* based expression strains were constructed. Expression strain 1 was obtained after co-transforming plasmids 1, and plasmid 2 in *E. coli*; and Expression strain 2 was obtained after co-transforming plasmid 3 and plasmid 4 in *E. coli*.

Plasmid 1 (ColE1 replicon, ampicillin marker): Gene 4, gene 3, and gene 1.

Plasmid 2 (P15A replicon, chloramphenicol marker): Gene 5, Gene 6, Gene 7, Gene 8, and Gene 2.

Plasmid 3 (RSF replicon, kanamycin marker): Gene 4, and gene 11.

Plasmid 4 (ColE1 replicon, ampicillin marker): Gene 9 and gene 10.

(ii) Cell culturing, protein expression, and HDO production analysis:

Starter cultures were grown overnight in tubes containing 10 mL LB media with appropriate antibiotics for each expression strain separately. Cell cultures for the expression and HDO production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 μM IPTG and was carried out separately for each expression strain.

Post-induction expression was carried out at 30° C. under aerobic conditions for 30 minutes followed by 2-3 hours of anaerobic conditions for each expression strain separately. Afterwards, cells from both expression strains were mixed in equal amounts, after which they were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 100-550 mg/L of 1,6-hexanediol.

Figure 4:
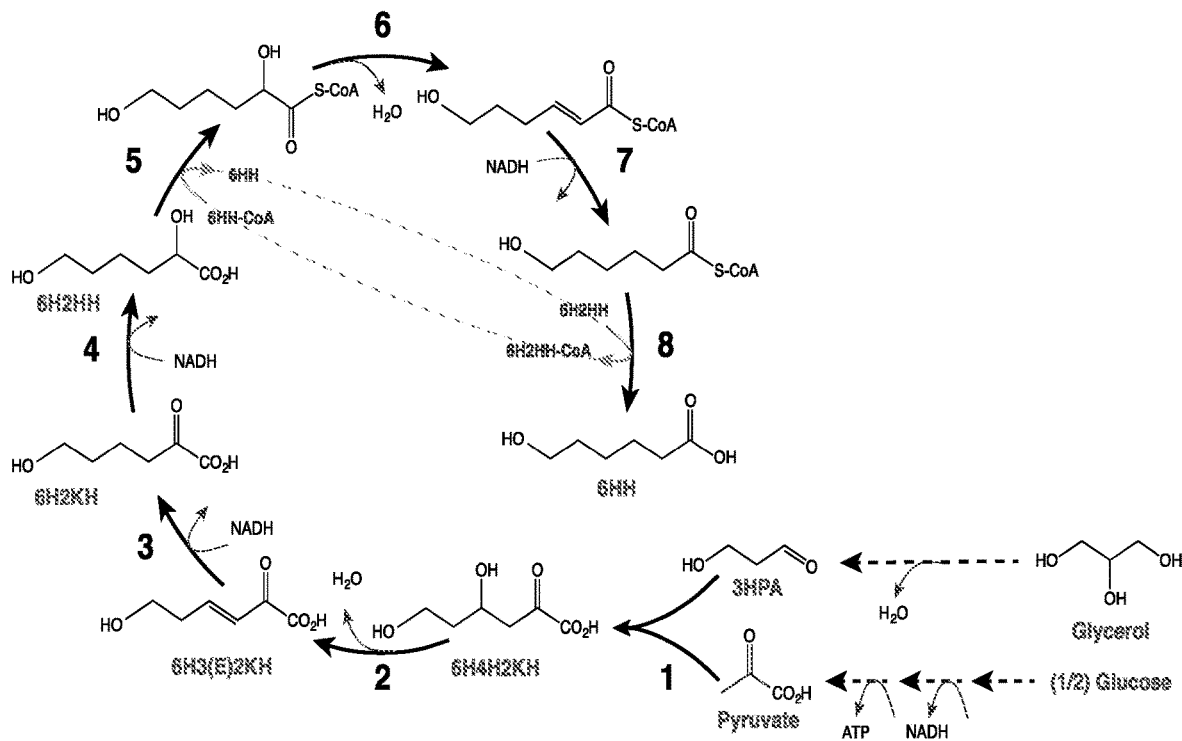
FIG. 4 shows a biosynthetic pathway for production of 6-hydroxy hexanoate via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; 6H2HH refers to 2,6-dihydroxy-hexanoate; 6HH-CoA refers to 6-hydroxy-hexanoyl-CoA; 6HH refers to 6-hydroxy hexanoate; and 6H2HH-CoA refers to 2,6-dihydroxy-hexanoyl-CoA. Either NADPH or NADH could be a cofactor. Step 5 and 8 are catalyzed by a single CoA-transferase enzyme. 6HH-CoA is depicted as donor for Step 5 reaction and 6H2HH as the acceptor for illustrative purposes. Other CoA-esters or carboxylic acids can serve as donors and acceptors for this enzyme in vivo.

Example 9: Preparation and Use of Microbial Organism for Production of 6-Hydroxyhexanoate from 6-Hydroxy-2-Keto-Hexanoate Intermediate In some embodiments, the present disclosure provides technologies for preparing 6HH. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for 6HH production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L 6HH. A biosynthetic pathway for the production of 6-hydroxyhexanoate (6HH) from 6-hydroxy-2-keto-hexanoate intermediate is shown in FIG. 4. Shown below are examples incorporating the use of different enzymes for each step of this pathway to validate the production of 6HH via this pathway. Examples of genes and corresponding enzymes from which they are encoded that were used to carry out each step of the 6HH biosynthetic pathway from 6-hydroxy-2-keto-hexanoate intermediate are shown in Table 18. Each enzyme therein may be substituted with homologous enzymes that belong to the same E.C. class. Additionally, the example below highlights the confirmation of multiple enzymes for carrying out both the CoA-transfer reaction and the 2,6-dihidroxy-hexanoyl-CoA dehydration reaction.

(i) Preparation of Plasmids for 6HH Production:

The 6HH production pathway genes were cloned on two separate compatible plasmids shown below. Each plasmid had a different origin of replication and antibiotic marker, as indicated. Synthetic genes were obtained from commercial vendors, and each gene was codon optimized for expression in *E. coli*. Each gene was cloned under its own T7 promoter and terminator using standard molecular biology methods. *Escherichia coli* was used as a target organism to engineer the 6HH production. The expression strains were obtained after co-transforming all three plasmids in electro competent *E. coli* BL21*(DE3) ΔldhA, ΔadhE, ΔfrdA.

Plasmid 1 (ColE1 replicon, ampicillin marker): Gene 1, Gene 2, and Gene 3 (only examples 6 & 7)

Plasmid 3 (P15A replicon, chloramphenicol marker): Gene 4, Gene 5, Gene 6, and Gene 7.

TABLE 18

Biosynthesis polypeptides for 6HH production.

| Enzyme Name | Gene Number | Example 9A Uniprot ID | Example 9B Uniprot ID | Example 9C Uniprot ID | Example 9D Uniprot ID |
|---|---|---|---|---|---|
| 6-hydroxy-2-oxohexanoate 2-reductase | Gene 1 | Q5FTU6 | Q5FTU6 | Q5FTU6 | Q5FTU6 |
| 2,6-dihydroxy-hexanoate CoA-transferase | Gene 2 and Gene 3* | A0A2X3BTQ9 | A0A2X3BTQ9 | A0A0C7GD16 | T4VW93 |
| 2,6-dihydroxy-hexanoyl-CoA 2-dehydratase -Subunit A | Gene 4 | Q5U924 | A0A2X3BK09 | A0A2X3BK09 | A0A2X3BK09 |
| 2,6-dihydroxy-hexanoyl-CoA 2-dehydratase -Subunit B | Gene 5 | Q5U925 | A0A2X3BU19 | A0A2X3BU19 | A0A2X3BU19 |
| 2,6-dihydroxy-hexanoyl-CoA 2-dehydratase -Subunit C | Gene 6 | Q5U923 | A0A1V9IXA9 | A0A1V9IXA9 | A0A1V9IXA9 |
| 2,3-dehydro-hexanoyl-CoA 2,3-reductase | Gene 7 | Q73Q47 | Q73Q47 | Q73Q47 | Q73Q47 |
| 6-hydroxyhexanoyl-CoA transferase | Gene 2 and Gene 3* | A0A2X3BTQ9 | A0A2X3BTQ9 | A0A0C7GD16 | T4VW93 |

| Enzyme Name | Example 9E Uniprot ID | Example 9F Uniprot ID | Example 9G Uniprot ID |
|---|---|---|---|
| 6-hydroxy-2-oxohexanoate 2-reductase | Q5FTU6 | Q5FTU6 | A0A1V9IP73 |
| 2,6-dihydroxy-hexanoate CoA-transferase | A0A175L1W4 | T4VW93 + A0A175L1W4* | T4VW93 + A0A175L1W4* |
| 2,6-dihydroxy-hexanoyl-CoA 2-dehydratase -Subunit A | A0A2X3BK09 | A0A2X3BK09 | A0A2X3BK09 |
| 2,6-dihydroxy-hexanoyl-CoA 2-dehydratase -Subunit B | A0A2X3BU19 | A0A2X3BU19 | A0A2X3BU19 |
| 2,6-dihydroxy-hexanoyl-CoA 2-dehydratase -Subunit C | A0A1V9IXA9 | A0A1V9IXA9 | A0A1V9IXA9 |

TABLE 18-continued

| Biosynthesis polypeptides for 6HH production. | | | |
|---|---|---|---|
| 2,3-dehydro-hexanoyl-CoA 2,3-reductase | Q73Q47 | Q73Q47 | Q73Q47 |
| 6-hydroxyhexanoyl-CoA transferase | A0A175L1W4 | T4VW93 + A0A175L1W4 | T4VW93 + A0A175L1W4 |

*present only for Examples 9F and 9G (ii) Cell Culturing, Protein Expression, and 6HH Production Analysis:

Starter cultures were grown overnight in tubes containing 10 mL LB media with appropriate antibiotics. Cell cultures for the expression and 6HH production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 µM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing ~10 g/L glucose, 6-hydroxy-2-keto-hexanoate (5-10 g/L), and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of ~0.4-5 g/L of 6HH from strains of Examples 9A-9G of Table 18.

Example 10: Preparation and Use of Microbial Organism for Production of 6-Hydroxy Hexanoic Acid (6HH) from Different Carbon Sources Via 6-Hydroxy-2-Keto-Hexanoate Intermediate In some embodiments, the present disclosure provides technologies for preparing 6HH. In some embodiments, the present disclosure provides technologies for producing 6HH using glycerol as a carbon source. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for 6HH production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 6HH from pyruvate and 3-hydroxy-propanal through the 6-hydroxy-2-keto-hexanoate intermediate is shown in FIG. 4. Shown below are examples incorporating the use of aldolase-hydratase based two enzyme system for production of 6HH via this pathway. A glycerol dehydratase enzyme that is vitamin B12-independent or glycerol dehydratase enzyme that is a B12-dependent enzyme can be cloned to enable production of 3-hydroxy-propionaldehyde—a 6HH pathway precursor that can be made from glycerol using this enzyme. Although both types of glycerol dehydratases were used herein, entries shown in Table 19 focus on examples that use the B12-independent glycerol dehydratase enzyme. Each enzyme therein may be substituted with homologous enzymes that belong to the same E.C. class to yield 6HH, and Examples 10B and 10C in Table 19 demonstrate this point wherein enzymes catalyzing both CoA-transfer reactions and the 2,6-dihidroxy-hexanoyl-CoA dehydration reactions have been substituted with homologous enzymes.

(i) Preparation of Plasmids & Strains for 6HH Production:

To minimize the number of 6HH production pathway genes expressed from plasmids, E. coli expression strain was constructed wherein certain pathway genes were integrated in the genome. Specifically, 6HH production strain BL21* (DE3) ΔldhΔadhE, ΔfrdA containing 6HH pathway genes (Gene 12, Gene 13) at the arsB location with expression of each gene controlled by its own T7 promoter. The remaining 6HH production pathway genes were cloned on two separate plasmids shown below using techniques described in example above.

Plasmid 1 (ColE1 replicon, ampicillin marker): Gene 4, gene 3, and gene 1.

Plasmid 2 (P15A replicon, chloramphenicol marker): Gene 5, Gene 6, Gene 7, Gene 8, and Gene 2.

(ii) Cell Culturing, Protein Expression, and 6HH Production Analysis:

Starter cultures were grown overnight in tubes containing 10 mL LB media with appropriate antibiotics for each expression strain separately. Cell cultures for the expression and HDO production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 µM IPTG and was carried out separately for each expression strain. Post-induction expression was carried out at 30° C. under aerobic conditions for 30 minutes followed by 2-3 hours of anaerobic conditions for each expression strain separately. Afterwards, cells were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

TABLE 19

Biosynthesis polypeptides for 6HH.

| Reaction Catalyzed | Enzyme Name | Enzyme ID | Gene Number | Example 10A Uniprot ID or Genbank ID | Example 10B Uniprot ID or Genbank ID | Example 10C Uniprot ID or Genbank ID |
|---|---|---|---|---|---|---|
| Pyruvate + 3-hydroxy propanal → 6-hydroxy-3,4-dehydro-2-oxohexanoate | Trans-o-hydroxybenzylidenepyruvate hydratase -aldolases | Ads-Hyd 8 | Gene 1 | A0A286PH18 | A0A286PH18 | A0A286PH18 |
| 6-hydroxy-3,4-dehydro-2-oxohexanoate → 6-hydroxy-2-oxohexanoate | Quinone oxidoreductase | Qor-1 | Gene 2 | P28304 | P28304 | P28304 |
| 6-hydroxy-2-oxohexanoate → 2,6-dihydroxy-hexanoate | 6-hydroxy-2-oxohexanoate 2-reductase | | Gene 3 | Q5FTU6 | Q5FTU6 | Q5FTU6 |
| 2,6- dihydroxy-hexanoate → 2,6- dihydroxy-hexanoyl-CoA | 2,6-dihydroxy-hexanoate CoA-transferase | | Gene 4 | T4VW93 | A0A2X3BTQ9 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase -Subunit A | | Gene 5 | Q5U924 | A0A2X3BK09 | A0A2X3BK09 |
| | 2,6-dihydroxy-hexanoyl-CoA 2-dehydratase -Subunit B | | Gene 6 | Q5U925 | A0A2X3BU19 | A0A2X3BU19 |
| | 2,6-dihydroxy-hexanoyl-CoA 2-dehydratase -Subunit C | | Gene 7 | Q5U923 | A0A1V9IXA9 | A0A1V9IXA9 |
| 6-hydroxy-2,3-dehydro-hexanoyl-CoA → 6-hydroxy-hexanoyl-CoA | 2,3-dehydro-hexanoyl-CoA 2,3-reductase | | Gene 8 | Q73Q47 | Q73Q47 | Q73Q47 |
| 6-hydroxy-hexanoyl-CoA → 6-hydroxy-hexanoate | 6-hydroxyhexanoyl-CoA transferase | | Gene 4 | T4VW93 | A0A2X3BTQ9 | T4VW93 |
| Glycerol dehydration | Glycerol dehydratase | | Gene 12 | Q8GEZ8 | Q8GEZ8 | Q8GEZ8 |
| | Glycerol dehydratase activator | | Gene 13 | Q8GEZ7 | Q8GEZ7 | Q8GEZ7 |

(iii) HPLC analysis of 6HH production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of ~50-800 mg/L of 6HH from strains of Examples 10A-10C in Table 19. An alternative example is where B12-dependent glycerol dehydratase pduCDEGH was used (encoded as a single gene operon on a third plasmid with COLA replicon, kanamycin marker) instead of B12-independent glycerol dehydratase, wherein the rest of the enzymes of the pathway were identical to Example 10A. Such a system also led to production of ~350 mg/L of 6HH using culture conditions described for strains PeDO3 and PeDO4 containing B12-dependent enzymes in Example 5.

Figure 5:
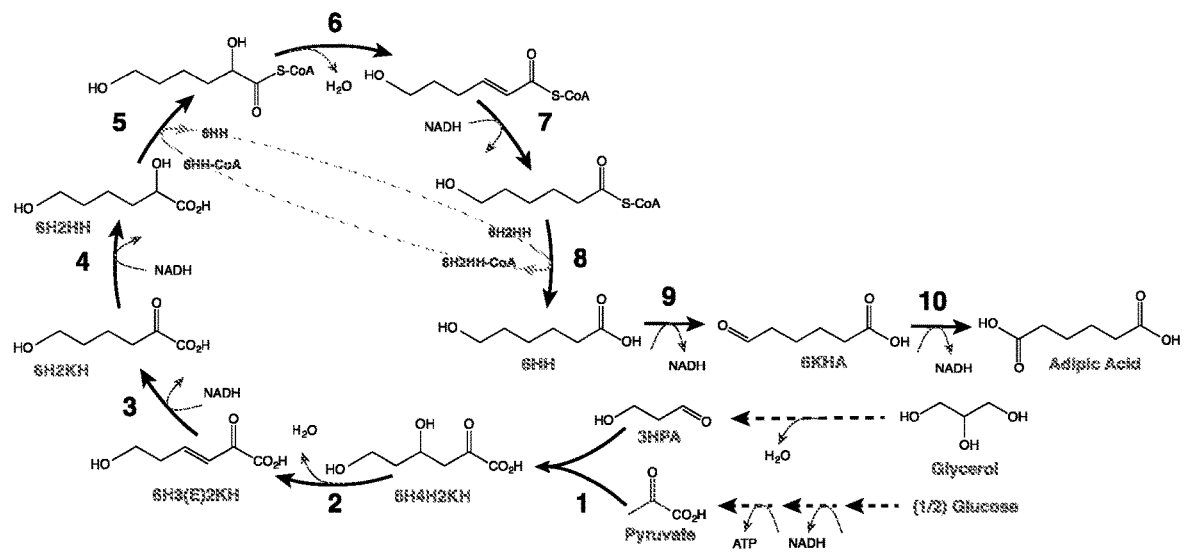
FIG. 5 shows biosynthetic pathway for production of adipic acid via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; 6H2HH refers to 2,6-dihydroxy-hexanoate; 6HH-CoA refers to 6-hydroxy-hexanoyl-CoA; 6HH refers to 6-hydroxy hexanoate; 6H2HH-CoA refers to 2,6-dihydroxy-hexanoyl-CoA; and 6KHA refers to 6-oxo-hexanoate. Either NADPH or NADH could be a cofactor. Step 5 and 8 are catalyzed by a single CoA-transferase enzyme. 6HH-CoA is depicted as donor for Step 5 reaction and 6H2HH as the acceptor for illustrative purposes. Other CoA-esters or carboxylic acids can serve as donors and acceptors for this enzyme in vivo.

Example 11: Preparation and Use of Microbial Organism for Production of Adipic Acid (AA) from 6-Hydroxy-Hexanoate (6HH) Intermediate In some embodiments, the present disclosure provides technologies for preparing AA. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of AA from pyruvate and 3-hydroxy-propanal through the 6-hydroxy-hexanoate intermediate is shown in FIG. 5. Shown in Table 20 are examples of enzymes that enable the conversion of 6HH to AA. It is important to note that each enzyme herein could be substituted with homologous enzymes that belong to the same E.C class to yield AA.

TABLE 20

Biosynthesis polypeptides for AA.

| Reaction Catalyzed | Enzyme Name | Gene Number | Example 11A Uniprot ID or Genbank ID | Example 11B Uniprot ID or Genbank ID |
|---|---|---|---|---|
| 6-hydroxy-hexanoate → 6-oxo-hexanoate | 6-hydroxyhexanoate dehydrogenase | Gene 1 | Q7WVD0 | Q84H78 |
| 6-oxo-hexanoate → Adipic acid | 6-oxo-hexanoate oxidase | Gene 2 | Q9R2F4 | Q9R2F4 |

(i) Preparation of plasmids & strains for AA production from 6HH: The AA production pathway genes were cloned on a single plasmid shown below using techniques described in examples before. BL21*(DE3) Δldh, ΔadhE, ΔfrdA was used as the production strain.

Plasmid 1 (ColE1 replicon, ampicillin marker): Gene 1, and gene 2.

(ii) Cell culturing, protein expression, and AA production analysis: Starter cultures were grown overnight in tubes containing 10 mL LB media with appropriate antibiotics for each expression strain separately. Cell cultures for the expression and AA production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 μM IPTG and was carried out separately for each expression strain. Post-induction expression was carried out at 30° C. under aerobic conditions for 30-120 minutes followed by 2-3 hours of anaerobic conditions for each expression strain separately. Afterwards, cells were harvested, concentrated, and re-suspended in 0.5 ml volume at OD600 of ~40 in fresh medium containing 5-10 g/L glucose, 5 g/L 6HH, and 15 g/L potassium phosphate buffer (pH 7.2). After incubation for 3 hours at room temperature, the cells were centrifuged, and supernatant was filtered and analyzed via HPLC.

(iii) HPLC analysis of AA production: Isocratic HPLC was used to detect and quantify AA. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 500-1500 mg/L of AA for Examples 11A and 11B of Table 20.

Example 12: Preparation and Use of Microbial Organism for Production of Adipic Acid (AA) from 6-Hydroxy-2-Keto-Hexanoate Intermediate In some embodiments, the present disclosure provides technologies for preparing AA from 6H2KH. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of AA from pyruvate and 3-hydroxy-propanal through the 6-hydroxy-2-keto-hexanoate intermediate is shown in FIG. 5. Shown below are examples incorporating the use of different enzymes for each step of this pathway to validate the production of AA via this pathway. Examples of genes and corresponding enzymes from which they are encoded that were used to carry out each step of the AA biosynthetic pathway from 6-hydroxy-2-keto-hexanoate intermediate are shown in Table 21 below. Each enzyme therein may be substituted with homologous enzymes that belong to the same E.C. class. Examples 12A and 12B in Table 21 highlight the confirmation of multiple enzymes for carrying out both CoA-transfer reaction and the 2,6-dihidroxy-hexanoyl-CoA dehydration reaction to enable successful production of AA via this pathway.

(i) Preparation of plasmids & strains for AA production from 6-hydroxy-2-keto-hexanoate: The AA production pathway genes were cloned on two separate compatible plasmids shown below. Each plasmid had a different origin of replication and antibiotic marker, as indicated. Synthetic genes were obtained from commercial vendors, and each gene was codon optimized for expression in *E. coli*. Each gene was cloned under its own T7 promoter and terminator using standard molecular biology methods. *Escherichia coli* was used as a target organism to engineer the 6HH production. The expression strains were obtained after co-transforming both plasmids in electro competent *E. coli* MG1655 (DE3) rne131 ΔldhA ΔadhE ΔfrdBC.

Plasmid 1 (ColE1 replicon, ampicillin marker): Gene 3, Gene 4, Gene 9, and Gene 10

Plasmid 3 (P15A replicon, chloramphenicol marker): Gene 5, Gene 6, Gene 7, and Gene 8

(ii) Cell culturing, protein expression, and AA production analysis: Same as example 11 except 10 g/L 6-hydroxy-2-keto-hexanoate was used (instead of 6HH used in example 11) as the substrate.

(iii) HPLC analysis of AA production: Isocratic HPLC was used to detect and quantify AA as described above. The results showed production of 100-800 mg/L of AA for Examples 12A-12C of Table 21.

TABLE 21

Biosynthesis polypeptides for AA.

| Reaction Catalyzed | Enzyme Name | Gene Number | Example 12A Uniprot ID or Genbank ID | Example 12B Uniprot ID or Genbank ID | Example 12C Uniprot ID or Genbank ID |
|---|---|---|---|---|---|
| 6-hydroxy-2-oxohexanoate → 2,6-dihydroxy-hexanoate | 6-hydroxy-2-oxohexanoate 2-reductase | Gene 3 | Q5FTU6 | Q5FTU6 | Q5FTU6 |
| 2,6-dihydroxy-hexanoate → 2,6-dihydroxy-hexanoyl-CoA | 2,6-dihydroxy-hexanoate CoA-transferase | Gene 4 | T4VW93 | A0A2X3BTQ9 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase -Subunit A | Gene 5 | Q5U924 | A0A2X3BK09 | A0A2X3BK09 |
| | 2,6-dihydroxy-hexanoyl-CoA 2-dehydratase -Subunit B | Gene 6 | Q5U925 | A0A2X3BU19 | A0A2X3BU19 |
| | 2,6-dihydroxy-hexanoyl-CoA 2-dehydratase -Subunit C | Gene 7 | Q5U923 | A0A1V9IXA9 | A0A1V9IXA9 |
| 6-hydroxy-2,3-dehydro-hexanoyl-CoA → 6-hydroxy-hexanoyl-CoA | 2,3-dehydro-hexanoyl-CoA 2,3-reductase | Gene 8 | Q73Q47 | Q73Q47 | Q73Q47 |
| 6-hydroxy-hexanoyl-CoA → 6-hydroxy-hexanoate | 6-hydroxyhexanoyl-CoA transferase | Gene 4 | T4VW93 | A0A2X3BTQ9 | T4VW93 |
| 6-hydroxy-hexanoate → 6-oxo-hexanoate | 6-hydroxyhexanoate dehydrogenase | Gene 9 | Q84H78 | Q84H78 | Q84H78 |
| 6-oxo-hexanoate → Adipic acid | 6-oxo-hexanoate oxidase | Gene 10 | Q9R2F4 | Q9R2F4 | Q9R2F4 |

Example 13: Preparation and Use of Microbial Organism for Production of Adipic Acid (AA) from Different Carbon Sources Via 6-Hydroxy-2-Keto-Hexanoate Intermediate In some embodiments, the present disclosure provides technologies for preparing AA. In some embodiments, the present disclosure provides technologies for producing AA using 3HPA and pyruvate. In some embodiments, the present disclosure provides technologies for producing AA using glycerol as a carbon source. In some embodiments, production is carried out in one organism. In some embodiments, that is a B12-dependent enzyme can be cloned to enable production of 3-hydroxy-propionaldehyde —a 6HH pathway precursor that can be made from glycerol using this enzyme. The B12-dependent glycerol dehydratase was used herein. Examples of genes and corresponding enzymes they encode that were used to carry out each step of AA biosynthetic pathway as well as production of 3-hydroxy-propionaldehyde are shown in Table 22. Each enzyme therein may be substituted with homologous enzymes that belong to the same E.C. class.

TABLE 22

Biosynthesis polypeptides for AA.

| Reaction Catalyzed | Enzyme Name | Enzyme ID | Gene Number | Uniprot ID or Genbank ID |
|---|---|---|---|---|
| Pyruvate + 3-hydroxy propanal → 6-hydroxy-3,4-dehydro-2-oxohexanoate | Trans-o-hydroxybenzylidenepyruvate hydratase-aldolases | Ads-Hyd 8 | Gene 1 | A0A286PH18 |
| 6-hydroxy-3,4-dehydro-2-oxohexanoate → 6-hydroxy-2-oxohexanoate | Quinone oxidoreductase | Qor 1 | Gene 2 | P28304 |
| 6-hydroxy-2-oxohexanoate → 2,6-dihydroxy-hexanoate | 6-hydroxy-2-oxohexanoate 2-reductase | | Gene 3 | Q5FTU6 |
| 2,6-dihydroxy-hexanoate → 2,6-dihydroxy-hexanoyl-CoA | 2,6-dihydroxy-hexanoate CoA-transferase | | Gene 4 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase -Subunit A | | Gene 5 | Q5U924 |
| | 2,6-dihydroxy-hexanoyl-CoA 2-dehydratase -Subunit B | | Gene 6 | Q5U925 |
| | 2,6-dihydroxy-hexanoyl-CoA 2-dehydratase -Subunit C | | Gene 7 | Q5U923 |
| 6-hydroxy-2,3-dehydro-hexanoyl-CoA → 6-hydroxy-hexanoyl-CoA | 2.3-dehydro-hexanoyl-CoA 2.3-reductase | | Gene 8 | Q73Q47 |
| 6-hydroxy-hexanoyl-CoA → 6-hydroxy-hexanoate | 6-hydroxyhexanoyl-CoA transferase | | Gene 4 | T4VW93 |
| 6-hydroxy-hexanoate → 6-oxo-hexanoate | 6-hydroxyhexanoate dehydrogenase | | Gene 9 | Q84H78 |
| 6-oxo-hexanoate → Adipic acid | 6-oxo-hexanoate oxidase | | Gene 10 | Q9R2F4 |
| Glycerol dehydration | Glycerol dehydratase | | Gene 12 | Q8GEZ8 |
| | Glycerol dehydratase activator | | Gene 13 | Q8GEZ7 | production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for AA production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of AA from pyruvate and 3-hydroxy-propanal through the 6-hydroxy-2-keto-hexanoate intermediate is shown in FIG. 5. Shown below are examples incorporating the use of aldolase-hydratase-based two-enzyme system for production of AA via this pathway. A glycerol dehydratase enzyme that is vitamin B12-independent or a glycerol dehydratase enzyme (i) Preparation of Plasmids & Strains for AA Production:

To minimize the number of AA production pathway genes expressed from plasmids, E. coli expression strain was constructed wherein certain pathway genes were integrated in the genome. Specifically, AA production strain BL21* (DE3) ΔldH, ΔadhE, ΔfrdA containing pathway genes (Gene 12, Gene 13) at the arsB location with expression of each gene controlled by its own T7 promoter. Two E. coli based expression strains were constructed. Expression strain 1 was obtained after co-transforming plasmids 1, and plasmid 2 in E. coli; and Expression strain 2 was obtained after transforming plasmid 3 in E. coli.

Plasmid 1 (ColE1 replicon, ampicillin marker): Gene 4, gene 3, and gene 1.

Plasmid 2 (P15A replicon, chloramphenicol marker): Gene 5, Gene 6, Gene 7, Gene 8, and Gene 2.

Plasmid 3 (ColE1 replicon, ampicillin marker): Gene 9, gene 10, and gene 3.

(ii) Cell Culturing, Protein Expression, and AA Production Analysis:

Starter cultures were grown overnight in tubes containing 10 mL. LB media with appropriate antibiotics for each expression strain separately. Cell cultures for the expression and AA production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 µM IPTG and was carried out separately for each expression strain. Post-induction expression was carried out at 30° C. under aerobic conditions for 30 minutes followed by 2-3 hours of anaerobic conditions for each expression strain separately. Afterwards, cells were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

(iii) HPLC analysis of AA production: Isocratic HPLC was used to detect and quantify AA. The method employed a Bio-Rad Aminex HPX-87 column, 0.7 m/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 20-350 mg/L of AA.

Example 14: Multi-Strain and Multi-Pot Production of 6-Hydroxyhexanoate

In some embodiments, production of a product e.g., 6HH, is carried out in one strain. In some embodiments, production is carried out in two or more strains. In some embodiments, the two or more strains together express all biosynthesis polypeptides utilized in a production. In some embodiments, a product of a biosynthesis polypeptide in one strain is a substrate of a biosynthesis polypeptide of another strain. In some embodiments, products of two or more biosynthesis polypeptides of one strain are independently substrates of two or more biosynthesis polypeptides in one or more other strains. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L of 6-hydroxyhexanoate.

Example 10 above describes the production of a 6HH in a single *E. coli* strain, wherein all the biosynthetic pathway enzymes necessary for converstion of pyruvate and 3-hydroxy propanal (and its production from glycerol) are all expressed simultaneously within a single *E. coli* strain. In some embodiments, it might be advantageous to pursue a multistrain approach, wherein the entire biosynthetic pathway is split into smaller sections called modules, wherein each module comprises a series of sequential enzymes of the biosynthetic pathway that are expressed in its own unique *E. coli* strain. For example, it was demonstrated that it was feasible to split the entire 6HH biosynthetic pathway into two modules. Specifically, described in Example 3 above is a construction of the first module, which allows for production of 6-hydroxy-2-keto-hexanoate—an intermediate of the 6HH biosynthetic pathway in a single *E. coli* strain, wherein all enzymes necessary for conversion of pyruvate and 3-hydroxy propanal (and its production from glycerol) were all expressed simultaneously within a single *E. coli* strain. Described in Example 9 above is a construction of the second module, which allows for production of 6HH from 6-hydroxy-2-keto-hexanoate in a second (separate) *E. coli* strain, wherein all enzymes necessary for conversion of 6-hydroxy-2-keto-hexanoate to 6HH are all expressed simultaneously within this single *E. coli* strain. Use of both modules leads to a complete biosynthetic pathway for production of 6HH in two separate *E. coli* strains. Such a multistrain approach can be advantageous for a number of reasons such as, but not limited to: a) constructing and testing plasmids for developing extensive biosynthetic pathways like these can result in large libraries, and conventional brute-force methods of screening for functional (or the best) genetic constructs can be inefficient and expensive; b) enzyme expression may be simplified and balanced across the pathway leading to substantially faster development cycles; c) genetic background of *E. coli* strains for each separate module may be tailored to suit redox, ATP, and other needs to maximize production for each module (since a single strain optimization may not be efficient for the entire pathway). Results summarized in Table 23 below demonstrate the successful use of this multi-strain approach for the production of 6HH either in simultaneous (i.e., one-pot) or via sequential production methodology.

TABLE 23

Production of 6-hydroxyhexanoate.

|  | Example 14A | Example 14B |
| --- | --- | --- |
| Growth: | multi-pot | multi-pot |
| Production: | one-pot | sequential |
| Titer: | 350 mg/L 6HH | 1.1 g/L 6HH |

| Reaction Catalyzed | Gene Number | Uniprot ID | Host |
| --- | --- | --- | --- |
| Pyruvate + 3-hydroxy propanal → 6-hydroxy-3,4-dehydro-2-oxohexanoate | Gene 1 | A0A286PH18 | strain 1 |
| 6-hydroxy-3,4-dehydro-2-oxohexanoate → 6-hydroxy-2-oxohexanoate | Gene 2 | P28304 | strain 1 |
| 6-hydroxy-2-oxohexanoate → 2,6-dihydroxy-hexanoate | Gene 3 | Q5FTU6 | strain 2 |
| 2,6-dihydroxy-hexanoate → 2,6-dihydroxy-hexanoyl-CoA | Gene 4 | A0A2X3BTQ9 | strain 2 |

TABLE 23-continued

| Production of 6-hydroxyhexanoate. | | | |
|---|---|---|---|
| 2,6-dihydroxy-hexanoyl-CoA → 6-hydroxy-2,3-dehydro-hexanoyl-CoA | Gene 5 | A0A2X3BK09 | strain 2 |
|  | Gene 6 | A0A2X3BU19 | strain 2 |
|  | Gene 7 | A0A1V9IXA9 | strain 2 |
| 6-hydroxy-2,3-dehydro-hexanoyl-CoA → 6-hydroxy-hexanoyl-CoA | Gene 8 | Q73Q47 | strain 2 |
| 6-hydroxy-hexanoyl-CoA → 6-hydroxy-hexanoate | Gene 4 | A0A2X3BTQ9 | strain 2 |
| Glycerol dehydratase (B12-dependent) | Gene 9 | Lre PduCDEGH* | strain 1 |

*Lre PduCDEGH is a vitamin B-12 dependent glycerol dehydratase and its corresponding activator from *Lactococcus reuteri*. It is encoded by a single gene operon encoded that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]).

(i) Preparation of Plasmids & Strains for 6HH Production:

The entire 6HH biosynthetic pathway was split into two *E. coli* strains (or modules) as described above. Two *E. coli* based expression strains were constructed. Expression strain 1 was obtained after co-transforming plasmids 1, and plasmid 2 in *E. coli* MG1655 (DE3) rne131 ΔldhA ΔadhE ΔfrdBC ΔpoxB ΔpflB ΔackA-pta ΔyghD, ΔadhP, ΔeutG, ΔgldA, ΔyiaY, ΔfucO; and Expression strain 2 was obtained after transforming plasmid 3 and 4 in *E. coli* MG1655 (DE3) rne131 ΔldhA ΔadhE ΔfrdBC.

Plasmid 1 (ColE1 replicon, ampicillin marker): Gene 1, gene 2, and gene 1.

Plasmid 2 (P15A replicon, chloramphenicol marker): Gene 9.

Plasmid 3 (ColE1 replicon, ampicillin marker): Gene 4.

Plasmid 4 (P15A replicon, chloramphenicol marker): Gene 5, Gene 6, Gene 7, Gene 8, and Gene 3.

(ii) Cell Culturing, Protein Expression, and 6HH Production Analysis:

Starter cultures were grown overnight in tubes containing 10 mL LB media with appropriate antibiotics for each expression strain separately. Cell cultures for the expression and 6HH production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 µM IPTG and was carried out separately for each expression strain. Post-induction expression was carried out at 30° C. under aerobic conditions for 30 minutes followed by 2-3 hours of anaerobic conditions for each expression strain separately. Afterwards, cells from both expression strains were harvested, concentrated, and re-suspended in 0.5 ml volume at OD600 of ~40. For Example 14A, equal number cells from both strains were re-suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC. For Example 14B, cells from expression strain 1 was suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and mixed with cells from expression strain 2. After incubation for 24 hours at room temperature, the cells were centrifuged, and supernatant was filtered and analyzed by HPLC.

(iii) HPLC analysis of 6HH production: This was carried out as mentioned before. The results showed production of 350-1100 mg/L of 6HH.

Example 15: Multi-Strain and Multi-Pot Production of 1,6-Hexanediol

In some embodiments, the present disclosure provides technologies for preparing HDO. In some embodiments, the present disclosure provides technologies for producing HDO from 3HPA and pyruvate. In some embodiments, the present disclosure provides technologies for producing HDO using glycerol as a carbon source. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for HDO production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. Examples 8 above describe the production of HDO in a single or dual *E. coli* strain, wherein all the biosynthetic pathway enzymes necessary for conversion of pyruvate and 3-hydroxy propanal (and its production from glycerol) are all expressed simultaneously within a single *E. coli* strain or two separate *E. coli* strains. Such a multi-strain approach can be advantageous for a number of reasons mentioned in Example 14. Results summarized in Table 24 demonstrate another successful use of this multi-strain approach for the production of HDO either in simultaneous (i.e., one-pot) or via sequential production methodology.

TABLE 24

Production of 1,6-hexanediol.

|  | Example 15A | Example 15B |
|---|---|---|
| Growth: | multi-pot | multi-pot |
| Production: | one-pot | sequential |
| Titer: | 400 mg/L 16HDO | 800 mg/L 16HDO |

| Reaction Catalyzed | Gene Number | Uniprot ID or Genbank ID | Host |
|---|---|---|---|
| Pyruvate + 3-hydroxy propanal → 6-hydroxy-3,4-dehydro-2-oxohexanoate | Gene 1 | A0A286PH18 | strain 1 |
| 6-hydroxy-3,4-dehydro-2-oxohexanoate → 6-hydroxy-2-oxohexanoate | Gene 2 | P28304 | strain 1 |
| 6-hydroxy-2-oxohexanoate → 2,6-dihydroxy-hexanoate | Gene 3 | Q5FTU6 | strain 2 |
| 2,6-dihydroxy-hexanoate → 2,6-dihydroxy-hexanoyl-CoA | Gene 4 | A0A2X3BTQ9 | strain 2 |
| 2,6-dihydroxy-hexanoyl-CoA → 6-hydroxy-2,3-dehydro-hexanoyl-CoA | Gene 5 | A0A2X3BK09 | strain 2 |
|  | Gene 6 | A0A2X3BU19 | strain 2 |
|  | Gene 7 | A0A1V9IXA9 | strain 2 |
| 6-hydroxy-2,3-dehydro-hexanoyl-CoA → 6-hydroxy-hexanoyl-CoA | Gene 8 | Q73Q47 | strain 2 |
| 6-hydroxy-hexanoyl-CoA → 6-hydroxy-hexanoate | Gene 4 | A0A2X3BTQ9 | strain 2 |
| 6-hydroxy-hexanoate → 6-hydroxy-hexanal | Gene 9 | A0R484 | strain 2 |
|  | Gene 10 | P39135 | strain 2 |
| 6-hydroxy-hexanal → 1,6-hexanediol | Gene 11 | AB213459.1 | strain 2 |
| Glyerol dehydratase (B12-dependent) | Gene 12 | Lre PduCDEGH* | strain 1 |

*Lre PduCDEGH is a vitamin B-12 dependent glycerol dehydratase and its corresponding activator from *Lactococcus reuteri*. It is encoded by a single gene operon encoded that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]).

(i) Preparation of Plasmids & Strains for HDO Production:

The entire HDO biosynthetic pathway was split into two *E. coli* strains (or modules) as described above. Two *E. coli* based expression strains were constructed. Expression strain 1 was obtained after co-transforming plasmids 1, and plasmid 2 in *E. coli* MG1655 (DE3) rne131 ΔldhA ΔadhE ΔfrdBC ΔpoxB ΔpflB ΔackA-pta ΔyghD, ΔadhP, ΔeutG, ΔgldA, ΔyiaY, ΔfucO; and Expression strain 2 was obtained after transforming plasmid 3 and 4 in *E. coli* MG1655 (DE3) rne131 ΔldhA ΔadhE ΔfrdBC.

Plasmid 1 (ColE1 replicon, ampicillin marker): Gene 1, gene 2, and gene 1.

Plasmid 2 (P15A replicon, chloramphenicol marker): Gene 12.

Plasmid 3 (ColE1 replicon, ampicillin marker): Gene 3, Gene 9, Gene 4, Gene 11, and Gene 10.

Plasmid 4 (P15A replicon, chloramphenicol marker): Gene 5, Gene 6, Gene 7, Gene 8, and Gene 4.

(ii) Cell Culturing, Protein Expression, and HDO Production Analysis:

Starter cultures were grown overnight in tubes containing 10 mL LB media with appropriate antibiotics for each expression strain separately. Cell cultures for the expression and 6HH production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 μM IPTG and was carried out separately for each expression strain. Post-induction expression was carried out at 30° C. under aerobic conditions for 30 minutes followed by 2-3 hours of anaerobic conditions for each expression strain separately. Afterwards, cells from both expression strains were harvested, concentrated, and re-suspended in 0.5 ml volume at OD600 of ~40. For Example 15A, equal number cells from both strains were re-suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC. For Example 15B, cells from expression strain 1 was suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and mixed with cells from expression strain 2. After incubation for 24 hours at room temperature, the cells were centrifuged, and supernatant was filtered and analyzed by HPLC.

(iii) HPLC analysis of HDO production: This was carried out as mentioned before. The results showed production of 400-800 mg/L of HDO.

Example 16: Synthesis of 3-Hydroxy-Propanal from Glycerol

3-Hydroxy-propanal is synthesized from glycerol using glycerol dehydratases. Glycerol dehydratases can catalyze the dehydration in a coenzyme B12-dependent or coenzyme B12-independent manner in the presence of a reactivator protein. Coenzyme B12-dependent dehydratase is composed of three subunits: the large or "α" subunit, the medium or "β" subunit, and the small or "γ" subunit. These subunits assemble in an α2β2γ2 structure to form the apoenzyme.

Coenzyme B12 (the active cofactor species) binds to the apoenzyme to form the catalytically active holoenzyme. Coenzyme B12 is required for catalytic activity as it is involved in the radical mechanism by which catalysis occurs. Biochemically, both coenzyme B12-dependent glycerol and coenzyme B12-dependent diol dehydratases are known to be subject to mechanism-based suicide inactivation by glycerol and other substrates (Daniel et al., *FEMS Microbiology Reviews* 22:553-566 (1999); Seifert, et al., *Eur. J. Biochem.* 268:2369-2378 (2001)). Inactivation can be overcome by relying on dehydratase reactivation factors to restore dehydratase activity (Toraya and Mori (*J. Biol. Chem.* 274:3372 (1999); and Tobimatsu et al. (*J. Bacteria* 181:4110 (1999)). Both the dehydratase reactivation and the coenzyme B12 regeneration processes require ATP. Shown below are a few examples of glycerol dehydratases, diol dehydratases and reactivating factors. One skilled in the art will recognize that glycerol dehydratases of *Citrobacter freundii*, *Lactococcus reuteri*, *Clostridium pasteurianum*, *Clostridium butyricum*, *K. pneumoniae* or their strains; diol dehydratase of *Salmonella typhimurium*, *Klebsiella oxytoca* or *K. pneumoniae*; and other dehydratase enzymes belonging to E.C. groups listed in Table 25 below or homologous enzymes of these sequences can also be used to carry out this step. Mutants of these enzymes (U.S. Pat. Nos. 8,445,659 & 7,410,754) can also be used herein to increase the efficiency of the process. In particular, coenzyme B12-independent-dehydratases (Raynaud, C., et al., *Proc. Natl. Acad. Sci. U.S.A.* 100, 5010-5015 (2003)) are favored for the industrial process due to the high cost of vitamin-B12.

glycerol is dehydrogenated to dihydroxyacetone which, after phosphorylation (using phosphoenol pyruvate or ATP), is converted to dihydroxyacetone phosphate a glycolytic pathway intermediate (Dharmadi, et al., *Biotechnol. Bioeng.* 94:821-829 (2006)). The respiratory pathway for glycerol conversion involves phosphorylation (by ATP) of glycerol followed by oxidation (quinone as electron acceptors) to give dihydroxyacetone phosphate that can be converted to pyruvate via glycolysis (Booth I R. Glycerol and methylglyoxal metabolism. Neidhardt F C, et al., editors. In: *Escherichia coli* and *Salmonella*: Cellular and molecular biology (web edition). 2005, Washington, D.C., ASM Press; Durnin et al., *Biotechnol Bioeng.* 103(1):148-161 (2009)).

Example 18: Preparation and Use of Microbial Organism for Production of 2,6-Dihydroxy-Hexanoate from 6-Hydroxy-2-Keto-Hexanoate Intermediate In some embodiments, the present disclosure provides technologies for producing 2,6-dihydroxy-hexanoate from 6-hydroxy-2-keto-hexanoate. Certain examples are described below.

Shown in FIG. 4 is a biosynthetic pathway for the production of 2,6-dihydroxy-hexanoate (6H2HH) from 6-hydroxy-2-keto-hexanoate intermediate. Shown below are examples incorporating the use of different 2-keto reductase enzymes for reduction of 6l H2KH to 6H2HH i.e. 6-hydroxy-2-oxohexanoate 2-reductase. Examples of genes and corresponding enzymes from which they are encoded that were used to this step are shown in Table 26. Each enzyme therein may be substituted with homologous enzymes that belong to the same E.C. class.

TABLE 25

Exemplary biosynthesis polypeptides.

| Genbank ID | EC Number | Name | Organism |
| --- | --- | --- | --- |
| BAA08099.1 | 4.2.1.28 | Diol dehydrase alpha subunit | *Klebsiella oxytoca* |
| BAA08100.1 | 4.2.1.28 | Diol dehydrase beta subunit | *Klebsiella oxytoca* |
| BAA08101.1 | 4.2.1.28 | Diol dehydrase gamma subunit | *Klebsiella oxytoca* |
| ABR24274.1 | 4.2.1.30 | Glycerol dehydratase large subunit | *Klebsiella pneumoniae* |
| ABR24275.1 | 4.2.1.30 | Glycerol dehydratase medium subunit | *Klebsiella pneumoniae* |
| ABR24276.1 | 4.2.1.30 | Glycerol dehydratase small subunit | *Klebsiella pneumoniae* |
| AAM54728.1 | 4.2.1.30 | Glycerol dehydratase | *Clostridium butyricum* |
| AAM54729.1 | — | glycerol dehydratase activator | *Clostridium butyricum* |
| ACI39932.1 | 4.2.1.30 | B12-independent glycerol dehydratase | *Clostridium diolis* |
| ACI39933.1 | — | glycerol dehydratase activator | *Clostridium diolis* |
| ABQ83986.1 | 4.2.1.30 | Glyerol dehydratase (B12-dependent) large subunit | *Lactococcus* reuteri |
| ABQ83985.1 | 4.2.1.30 | Glyerol dehydratase (B12-dependent) medium subunit | *Lactococcus* reuteri |
| ABQ83984.1 | 4.2.1.30 | Glyerol dehydratase (B12-dependent) small subunit | *Lactococcus* reuteri |
| ABQ83983.1 | — | Glyerol dehydratase (B12-dependent) activator large subunit | *Lactococcus* reuteri |
| ABQ83982.1 | — | Glyerol dehydratase (B12-dependent) activator small subunit | *Lactococcus* reuteri |

Example 17: Synthesis of Pyruvate

Conversion of Sugars to Pyruvate.

Conversion of sugars to pyruvate through glycolysis is very well known. In glycolysis, each mole of glucose gives 2 moles of ATP, 2 moles of reducing equivalents in the form of NAD(P)H and 2 moles of pyruvate.

Conversion of Glycerol to Pyruvate.

Glycerol can be converted to glycolysis intermediates both anaerobically and micro-aerobically. Anaerobically, (i) Preparation of Plasmids for 6H2HH Production:

The gene encoding 6-hydroxy-2-oxohexanoate 2-reductase was cloned on a plasmid with expression driven by T7 promoter using standard molecular biology methods. *Escherichia coli* was used as a target organism to engineer the 6H2HH production. The expression strains were obtained after co-transforming all three plasmids in electro competent *E. coli* BL21*(DE3) Δldh.

TABLE 26

Exemplary biosynthesis polypeptides.

| Name | Annotated Name | EC Number | Uniprot ID or Genbank ID of 6-hydroxy-2-oxohexanoate 2-reductases | 6H2HH Produced |
|---|---|---|---|---|
| 1 | D-2-hydroxyacid dehydrogenase | 1.1.99.6 | WP_003431407.1 | Yes |
| 2 | ketopantoate reductase | 1.1.1.169 | BAL51292.1 | Yes |
| 3 | 2-ketogluconate reductase | 1.1.1.215 | Q5FTU6 | Yes |
| 4 | D-lactate dehydrogenase | 1.1.1.28 | AKC64094.1 | Yes |
| 5 | D-2-hydroxyacid dehydrogenase | 1.1.99.6 | WP_002876862.1 | Yes |
| 6 | D-lactate dehydrogenase | 1.1.1.28 | AGP69017.1 | Yes |
| 7 | D-2-hydroxyacid dehydrogenase | 1.1.99.6 | WP_003640741.1 | Yes |
| 8 | phenyllactate dehydrogenase | 1.1.1.110 | AKC64095.1 | Yes |
| 9 | D-lactate dehydrogenase | 1.1.1.28 | AKC64094.1 | Yes |

(ii) Cell Culturing, Protein Expression, and 6H2HH Production Analysis:

Starter cultures were grown overnight in tubes containing 10 mL LB media with appropriate antibiotics. Cell cultures for the expression and 6H2HH production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 µM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing ~10 g/L glucose, 6-hydroxy-2-keto-hexanoate (5-10 g/L), and 15 g/L potassium phosphate buffer (pH 7.2). After incubation for 24 hours at room temperature, the cells were centrifuged, and supernatant was filtered and analyzed via HPLC.

(iii) HPLC analysis of 6H2HH production: Isocratic HPLC was used to detect and quantify 6H2HH. The method employed a Bio-Rad Aminex HPX-87 column, 0.7 mL/min of 0.5% formic acid (or 5 mM sulfuric acid) at 35° C. Detection was carried out using an RID (refractive index detector). The results showed production of 6H2HH from all strains of Examples 1-9 of Table 26.

Example 19: Preparation and Use of Microbial Organism for Production of 2,6-Dihydroxy-Hexanoate from Different Carbon Sources Via 6-Hydroxy-2-Keto-Hexanoate Intermediate In some embodiments, the present disclosure provides technologies for producing 2,6-dihydroxy-hexanoate from various carbon sources. Certain examples are described below. In some embodiments, the present disclosure provides technologies for producing 2,6-dihydroxy-hexanoate from pyruvate and 3HPA. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L.

A biosynthetic pathway for the production of 6H2HH from pyruvate and 3-hydroxy-propanal through the 6-hydroxy-2-keto-hexanoate intermediate is shown in FIG. 4. Shown below are examples incorporating the use of aldolase-hydratase based two enzyme system for production of 6H2HH via this pathway. A glycerol dehydratase enzyme that is vitamin B12-independent or glycerol dehydratase enzyme that is a B12-dependent enzyme can be cloned to enable production of 3-hydroxy-propionaldehyde—a 6H2HH pathway precursor that can be made from glycerol using this enzyme. Although both types of glycerol dehydratases can be used herein, example shown herein uses the B12-dependent glycerol dehydratase enzyme. Each enzyme therein may be substituted with homologous enzymes that belong to the same E.C. class to yield 6H2HH.

(i) Preparation of plasmids & strains for 6H2HH production: MG1655(DE3) Δrne131, ΔldhA, Δ[frdB, frdC], ΔadhE, ΔpoxB, ΔpflB, Δ[ackA, pta] was used as the strain with the following plasmid comninations: Plasmid 1 (COLA replicon, kanamycin marker): Gene 1 (Glycerol dehydratase—pduCDEGH). Plasmid 2 (ColE1 replicon, ampicillin marker): Gene 2 (Ads-Hyd 8), Gene 2 (Qor-1), and Gene 3 (6-hydroxy-2-oxohexanoate 2-reductase—Q5FTU6).

(ii) Cell Culturing, Protein Expression, and 6H2HH Production Analysis:

Cell culturing (with appropriate antibiotics), and protein expression was similar to that described in Example 1 for 3-hydroxy propanal. After incubation for 24 hours at room temperature, the cells were centrifuged, and supernatant was filtered and analyzed via HPLC.

(iii) HPLC analysis of 6H2HH production: Analysis was carried as our as mentioned in example 18. The strain was able to produce >1 g/L of 6H2HH under these conditions.

EQUIVALENTS

Unless otherwise defined, all technical and scientific terms used herein have the same meaning as commonly understood by one of ordinary skill in the art to which this present disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

It is to be understood that while the present technology has been described in conjunction with the above aspects, that the foregoing description and examples are intended to illustrate and not limit the scope of the present technology. Other aspects, advantages and modifications within the scope of the present technology will be apparent to those skilled in the art to which the present technology pertains.

REFERENCES

1. Eaton, R. W., & Chapman, P. J. (1992). Journal of Bacteriology, 174, 7542-7554.
2. Eaton, R. W. (2000). Applied and Environmental Microbiology, 66, 2668-2672.
3. Ferrara, S., Mapelli, E., Sello, G., & Di Gennaro, P. (2011). Biochimica et Biophysica Acta, 1814, 622-629.
4. Guido Sello, & Patrizia Di Gennar (2013). Appl Biochem Biotechnol, 170:1702-1712
5. Mueller, L. S., Hoppe, R. W., Ochsenwald, J. M., Berndt, R. T., Severin, G. B., Schwabacher, A. W. & Silvaggi, N. R. (2015). Biochemistry, 54, 3978-3988.
6. Iwabuchi, T., and Harayama, S. (1998). J. Bacteriol. 180, 945-949.
7. Siegert P, McLeish M J, Baumann M, Iding H, Kneen M M, Kenyon G L, Pohl M: *Protein Eng Des Sel* 2005, 18(7):345-357.
8. de la Plaza M, Fernandez de Palencia P, Pelaez C, Requena T. *FEMS Microbiol Lett* 2004, 238(2):367-374.
9. Gocke Dr, Graf T, Brosi H, Frindi-Wosch I, Walter L, M. *Journal of Molecular Catalysis B: Enzymatic* 2009, 61(1, Å12):30-35.
10. Andrews F H, McLeish M J. *Bioorg Chem* 2012, 43:26-36.
11. G. M. Rodriguez, S. Atsumi, Microb. Cell Factories 11 (2012) 90.
12. D. J. Petersen, R. W. Welch, F. B. Rudolph, G. N. Bennett, J. Bacteriol. 173 (1991)1831.
13. X. Liu, Y. Dong, J. Zhang, A. Zhang, L. Wang, L. Feng, Microbiol. Read. Engl. 155 (2009) 2078.
14. A. Tani, Y. Sakai, T. Ishige, N. Kato, Appl. Environ. Microbiol. 66 (2000) 5231.
15. K. E. Breitkreuz, W. L. Allan, O. R. Van Cauwenberghe, C. Jakobs, D. Talibi, B. Andre, B. J. Shelp, J. Biol. Chem. 278(2003) 41552.
16. N. Saito, M. Robert, H. Kochi, G. Matsuo, Y. Kakazu, T. Soga, M. Tomita, J. Biol. Chem. 284 (2009) 16442.
17. R. A. Wolff, W. R. Kenealy, Protein Expr. Purif. 6 (1995)206.

```
                          Certain Sequences

Uniprot or    Sequence
Genbank ID    ID Number   Sequence Information

D7C0E5        SEQ ID      MKGYTVPLSPRGIANLAPAPPWHYAGTVVGVEFFTDPAAAAATLPEGLTPDPDSAGRGVAMFIDWQY
              NO: 1       SSTGLEYLDPARSQYREFLITLDAHCNGAPVAWCPYIYVDNDAAMARGWVQGFPKKLGAVHQTRAYS
                          VGGPGTPVLGPGGQFGATASSAGQRIAEAKITLEQPVPDPAALMSRPVINLRHFPRLAAGQHDQPAV
                          HELVMSVLDDTAVSDAWVGTADLAFLPAHGEELADLPVRRTGKGFHFDLAYTVTDLMTLADHSA

P0A144        SEQ ID      MSNKIMKTSRLTAEDINGAWTIMPTPSTPDASDWRSTATVDLEETARIVEELIAAGVNGILSMGTFG
              NO: 2       ECATLTWDEKRDYVSTIVETIRGRVPYFCGTTALNTREVIRQTRELIDIGANGTMLGVPMWVKMDLP
                          TAVQFYRDVADAVPEAAIAIYANPEAFKFDFPRPFWAEMSKIPQVVTAKYLGIGMLDLDLRLAPNIR
                          FLPHEDDYYAAARINPERITAFWSSGAMCGPATAIMLRDEVVRAKSTGDWAKAKAISDDMRAADSTL
                          FPRGDFSEFSKYNIGLEKARMDAAGWLKAGPCRPPYNLVPEDYLAGAQKSGKAWAALHAKYSNELK

Q79EM8        SEQ ID      MTSPAVTSADITGLVGIVPTPSKPGSEAPDAVDTVDLDETARMVELIVASGVDVLLTNGTFGEVATL
              NO: 3       TYEELLAFNDTVIRTVANRIPVFCGASTLNTRDTIARSLALMGLGANGLFVGRPMWLPLDDEQLVSY
                          YAAVCDAVPAAAVVVYDNTGVFKGKISSAAYAALAEIPQIVASKHLGVLSGSDAYASDLAAVKGRFP
                          LLPTADNWLPSLEAFPGEVPAAWSGDVACGPEPVMALRRAIAEGLWDDARAVHEDIAWATEPLFPGG
                          DISKFMPYSIQIDRAEFEAAGYIVPGPSRHPYGTAPAAYLEGGAEVGRRWAGIRQKYVATLAEP

A0A0N0AHI8    SEQ ID      MKGYTYPLSPRGVANLAGKPPWHYVGDAVGVEFWTSPEAAAASLPTGLDPDPANPGHGYAVFIDWQF
              NO: 4       NGATDDYLDPPFSQYSEFLVLLDAQWQGTPVAWCPFIWVDNDASLARGWVQGFPKKMGSIRQTRAFA
                          IDSPAAPTVGKGGRFAAVMSAGGRRLAETTVTLDRTTDRLPALTRPLVNLRHFPRLSAGQHDNPAVH
                          ELTMSVLANLKFANTWIGTGELRFLPAPREELADLTPRRVGVGFRGSLSYTVNDLRIL

A0A0N1FRY3    SEQ ID      MKGYTVPLSPRGVANLAPAPPWHYAGTVVGVEFFTDPAAAAALPEGLSSDPDSAGRGVAMFIDWQY
              NO: 5       SSTDLEYLDPARSQYREFLVTLDAHYYGAPVAWCPYIYVDNDSAMARGWVQGFPKKLGAVHQTRAYS
                          VGGQGTPVLGPGGQFGATASAAGQRIAEAKITLEQAVPDPAALMSRPVVNLRHFPRLTAGQHHKPAV
                          HELVMSVLDGAAVSDAWAGTADLAFLPARGEELADLPIQRTGRGFHFDLAYTVTDLKTLIDHSN

M3DYR1        SEQ ID      MLKGYTVPLSPKGEANIAPTPPWHYAGDIVGVEFFTEPAAAEATLPEGLDPDPDTSGRVVAFFVDWQ
              NO: 6       FNGERDEYLDPVRSQYREFFVLVDARHQGRPVSWCPYIYVDNHHALARGWIQGFPKKAGNVHQTRVF
                          ASPGKASPTLSPGARFGASVSSDERTLAEARVTLEAPMEDPSALLSRDTINLRHFPTLEAGRYDKPA
                          VHELVRMDYADQQVADVWTGTSEITLFPAVGEELADLAPVRSGMGFRASMSYNVTQVEPLL

W7SU48        SEQ ID      MLGYSLPLSANGTANVVPAPPWHYAGDVVGVEFWTTPAAAAATLPSGLTPDPTTSGHAYALFVDQW
              NO: 7       AGSHQEYLDPVRSQYSEFLILMDAQFQGRAVAWCPYIWVDNDAALARGWFQGFPKKLGAIRQTRAFS
                          VPGQASPVVGPGGQFGASLSAAGRRLAEAQITLQAPSATLPALGRPIVNLRHFPRLIAGQYDNPSVH
                          ELTQSVLDTPVVGNNWTGTSTLNFFTAPGEELADLQPVRTGSGFRGSLSYTVTTLKMLSGPDA

A0A286PH18    SEQ ID      MKGYTVPLSPRGIANLAPAPPWHYAGTVVGVEFFTDPAAAAATLPEGLTPDPDSAGRGVAMFIDWQY
              NO: 8       SSTGLEYLDPARSQYREFLLTLDAHYNGTPVAWCPYIYVDNDSAMARGWVQGFPKKLGAVHQTRAYS
                          VGGPGTPVLGPGGQFGATASAAGQRIAEAKVTLEQPVPDPAALMSRPVVNLRHFPRLAAGQHDKPAV
                          HELVMSVLDGVAVSDAWAGTADLAFLPAHGEELADLPVQRTGRGFHFDLAYTVTDLKTLIDRSN

Q9X9Q6        SEQ ID      MARTLMKPDDVKGAWAIIPTPAKDDASDWRATKTVDLDETARVVNGLIDAGINGILSMGTLGEAATM
              NO: 9       THDEKLDFIKALVDAAAGRVPIFVGTTCLNTRDTIALTRQALDIGADGTMLGVPMWCAPSVDVAVQF
                          YKDLAEAVPEMNIAIYANPEAFKFDFPRSFWAQVAEIPQVVTAKYIGVAHLLPDLAAIRGRIKLLPI
                          DFDYYGAARMDESIDAFWSSGAVCDPLVTTTLRDLVSQARATGDWSAARAFMGRLGPTAAPLFPNGS
                          FKEFSTYNIALEKARMNAGGWMNAGPVRPPYHLCPEPYLEGARLSGRMWAELGKALAAEK
```

-continued

Certain Sequences

| Uniprot or Genbank ID | Sequence ID Number | Sequence Information |
|---|---|---|
| Q9WXH7 | SEQ ID NO: 10 | MAKSGLLNASDIHGVWSILPTPSKPDASDWRATNTVDLDETARAVEGLIAAGANGILSMGTLGECES LTWEEKKVFMQTIVETARGRVPVFVGTTTLNTRDTIEQTRYAHSIGADGTMLGIPMWCNPCVDMAVQ YYKDVAEAVPEMNIAIYANTEAFKFDFPRAFWARVSEIRQVVAAKYIGIEFLLQDLHLTKHRMKLLP LDYQYYAAARMDDFVDAFWSSGTVCGPLVSTTLRDKVIAARRTKDWTDAHAFQGRLVKTAAPPPEDS FKTFSIYNVALEKGRIDAAGWMNAGPVRPPYNDICPASYLDSWKASGQRWAELHKQLETESSGK |
| A4XDS1 | SEQ ID NO: 11 | MARELLTAADVKGAWAIVPTPAKEGASDWRAADTVNVEEAARMIDGLIEAGVDGILSMGTLGEAATM TLDEKLVFMKTIVDTAAGRVPVFVGTTCINTRDTIALTRKAVDIGATGTMLGVPMWCAPSVDVAVQF YRDVAEAVPDINIAIYANPEAFKFDFPRTFWGQVAEIPQVVTAKYIGVGTLLPDLAAIKGRIKLLPI DFDYYGAARMDDSIDAFWTSGAVCHPLVSTTLRDVVAAARASGDWSAAKAFMGRLAPTAATLFPNGS FKEFSTYNIPLEKARMTAGGWMNAGPCRPPYHLCPENYLEGARNSGRMWAELGKALEAER |
| F2J6N9 | SEQ ID NO: 12 | MTRKLLTVDDVNGCWAIMPTPSKPGASDPNAVDTVDLEETARAAEALVAAGVDGILSLGTFGEAATT TWEEKQAFMRTLVETVRGRVPVFGGTTSLNTRDTIRMTRAAREIGVDGVMLGLPMWVQPDLATAVQF FRDVASACPDVAICAYANPEAFKFEFPRAFWAQIADIPQIVSAKYIHTAGLYADLNLTKRRIRLMPL DVDYYAAARIDPDACTAFWTSGAVCGPAPAIQLRDLVSKAKKTGDWTGAKKLTDRIGQTYRTLFPNG SFKDFSVYNIGIEKARMDAAGWMKAGPCRAPYSLVPEPYLEGARESGRQWAKLAAELATERAE |
| A0A063BFL5 | SEQ ID NO: 13 | MIHPKLRIDASGINGLWPILPTPAKPNASDWRERSTVDLDETARIVESLIDAGVDGLLSLGTYGEAH SLLWEEKKAFVGCVLETIRGRIPFFTGTTALNTREVVEQTRAMHDMGVSGTMLGVPMWCKTDLATAV QFFRDVTEACPDTALAIYANTEAFKFEFPRPFWAEIGKMPQAVACKYLGIGMLAVDLELAPNMRFLP NEQDYYAAARIDPERVTAFWSSGALCGPLPALTLRDRVARAKSSNDWTSAKEIADRMRACDVGFFPK GEFSEFSKFNAPLEKARMNTAGYVNAGPCRPPYHVIPQEYLAGAERSGRAHAALNAELKQAEHSI |
| Q9ZHH6 | SEQ ID NO: 14 | MSKQRKQRLGTEDVNGAWVIMPTPAKPEASDWRATDTVDLDETARIVEALIDSGVNGILSLGTFGEC ATLTWEEKQAFIGAVVETTRGRVPFFCGTTALNTREVVRQTRAALDIGVDGTMLGVPMWSRMEVPAA VQFYRDVAEACPEAAIAVYANADAFKFEFPRAFWAQVAQIPQVVTAKYLGIGMLDLDLTLAPGIRFL PHEDDYYAAARVAPERVTAFWSSGAMCGPATAIRLRDEVAKAKQTGDWRLAKELSDAMRRADATLFP RGDFAEFSKYNIAIEKERMNAAGWLRAGPCRPPYHIAPEEYLDGARQSGRAWAELHQQYSDL |
| A0A0C1K853 | SEQ ID NO: 15 | MMSDMVKPRMTADDVNGVWVIMPTPAKPDASDWRVENTVDLDETVRIVENLLASGVNGIMSNGTFGE CATLTWDEKRDFIATVAETIKGRVPFFCGTTALHTREVIRQTREVMRLGADGVMLGLPMWCKMETPS AIQFYRDVAEAVPDAAIAVYANPEAFKYEFPREFWAQVSEIPQVVTAKYLGIGMLDLDLRLASSIRF LPHEDDYYAAARINPERMTAFWSSAAMCGPATPLKLRDAVADAKVTGKWSVAKAISDEMRKADSMLF PKGDFSEFSKYNIGLEKARMDEAGWLKAGPCRPPYHVIPEMYLEGARKSGRAWAELHAKYSAEG |
| WP_034398482 | SEQ ID NO: 16 | MAKQKKSRMTAEDIHGAWVIMPTPATPDASDWRVQHTVDLEETARIVEALIAAGVNGIFSNGTFGEC ATLTWEEKRDFIATVVETARGRVPFFCGTTALHTREVIRQTREAMDIGASGTMLGVPMWCKMEVPTA VQFYRDVAEAVPEAAIAIYANPEAFKFDFPRSFWAQIPQVITAKYLGIGMLDLDLDLRLAPSIRFL PHEDDYYAAARIDPERMTAFWSSGAMCGPATAIRLRDTVGAAKRSGDWTDAKAISDAMRQADSTLFP RGDFSEFSKFNIGLEKARMDAAGWLKAGPCRPPYHIVPEEHLAGARKSGEAWAALHARYATLD |
| PYK12191 | SEQ ID NO: 17 | MNTAKLIGFNYPLTPKGKSTLNPPPPWYYSSDFLDVEFWAQPAAVASLLPNGLEPDPAANGHCNALF YDWQFSGDNEEYLDPARYQYREFFILVDALFEGRSVSYCPYIFVDNDAALARGWTQGYPKRLGQVFQ TRYYAATSKAGPALAPGSKFAGSLTAAGQLIAEAVVTLRQAVTDPSLLKQKPVINLLHVPRLAADKH DKPAIHELVENVPSSVKIEQAWIGEGSLTLPVCRGEEISDLAPLRCGKGIRASMAYVVDDLKTLKDL RN |
| A0A370X7D8 | SEQ ID NO: 18 | MKSNFFVPMTPRGLSNISPPPPWHYAGDFLIIDFWARPDAVASLLPAELQPDVKAEGHAQAYFIDWQ YTAAHDEFLDPARYQYREFFVLVDALFQGKPVAFCPYIFVDNDAAIARGWAQGFPKRYGTILQTRLF AASGPASPKLAPGGRFGASASTAGQRIARGLVTLEKAVTDPAALGSRPTINLRHFPRLAAGQWERPA VHELVESVMDNFTVADAWMGKGELTLPECENEELSDLAPVRCGNGYRMSVSYSVTDLKTLVDHSAK |
| WP_028222253 | SEQ ID NO: 19 | MLKGYMAPLSPLGKASINPPPPWHYSGDVIGAEFWAEPEATAATLPPGLDPDPSTAGHGVVLFIDWQ FTAQDDEFLDPARYQYRECLFLVDAVHKGTPVMWCPYIYVDNDAALARGWAQGFPKKLASVYQTRTF AAPSAAAAPVASGSRFGASLSAHGERLAEARITLRQPVADPKSLLARPTVNRRYFASLVAGLHDKPA VDELVLSVTDNLSVADAWAGDAELLFPDARGEEICAFGPVKVGGGRFSLAYSVTDLKLLEDLTRLG K |
| F2J6L6 | SEQ ID NO: 20 | MKRDMLTVDDVTGCWAIMPTPSKPNASDPSATDTVDLDETARVAEALVAAGVDGILSLGTLGECATT TWDEKQAYMRTLVETLRGRIPVFGGTTGLNTRDSIAMTRAAREIGVDGVMLGLPMWVQPDVPTAVQF YRDVAAACPDVAICVYANPEAFKFEFPRAFWAQIAEIPQVVSAKYINIAALYTDLNLTRRRIRLMPL DVDYYAAARVDPEACSAFWTSGAVCGPAPAIQLRDLVLEARQSGDWSKAKALTDRIGMTYRTLFPNG SFKEFSVYNIGIEKARMDAAGWMTAGPVRPPYHIVPEAILEGGRESGRQWAKLAAELEREAGR |
| A0A0N0L9F6 | SEQ ID NO: 21 | MTQSYTTPLTPRGLSSIAPPPPWHYSGDFLVVEFWADPIAVANTLPAGLTVDSASPGHASAVFVDWQ FTGENDELLDPARYQYREFFILLDALHEGQPVSYCPYIFVDNDSALMRGLIQGFPKRLGAVHQTRTF SAPSRAAAQVEPGARFAATASTAGQRIARGEVQLQHKIDDVSKLGFGARPLINLRHFPRLATGQHND PAVHELVSVMDNPNIVDAWAGEGNLVFPQAEGEEVSDLAPTRVGAGFRASMSYTVTDLKALPNATI ER |

-continued

Certain Sequences

| Uniprot or Genbank ID | Sequence ID Number | Sequence Information |
|---|---|---|
| A0A1G9YWG7 | SEQ ID NO: 22 | MLRGFTVPKSPFGQAALTPPPPWHYAGDVVGVEFWTDPEATAATLPNGLSPDPNSNGHAVMMFLDWQ FTAQDDEYLEPARYQYREAFILVDAMYRDEPVMWCPYIYVDNDAALARGWTQGFPKKMGSIFQTRSF AASGPAAAPVASGSRFGASLSAHGQRLAEACVTLHRPVENGLSLLSRPTVLLRYFPRLAAGYQDKPA VNELAMSITDNLTVAGAWIGKGELNFPEASGEELNALAPKRIESGFRYSLSYSVSDLKILEDHGSQ |
| A0A2U1BT09 | SEQ ID NO: 23 | MSTKRTLMTANDVQGAWAIMPTSAKDGSESWRMTDSLDLDATVAAINGLIDSGVDGILTMGTYGEAA TLTVDEKKRFMACLVETVAGRVPCFVGTTTLNTRDTIELTRYAADLGADGTMLGLPMWCAPTLPAAV RFYRDVAEACPDMAQCIYANPEAFRFDFPPPPFWAQVADIPQVVSAKFTSVGHLIQNLEITRGKVRAL PIELDYYAATRVDDDVCAFWSSGAVCGPTPTIALRDEITRAKTSGDWTKAKELTDKMWAAVTPMFPA GGFREFSMYNIAIDKMRMQTAGWMRVGPTRPPYDMMPDHIRGGAVEAGKLWAELAKATVLAGA |
| A0A244DHE8 | SEQ ID NO: 24 | MSKQYAVPLSPRGLSSIAPPPPWHYSGDFLIVEFWADPAAVAATLPAGLSVDPSSPGHATALFVDWQ FTGQNDELLDPARYQYREFFLLVDALYEGQPVAYCPYIFVDNDSAMMRGLIQGFPKRLGAVHQTRTF AAPSLAAAQVAPGARFAATASTAGORIARAEVKLTGKVDDPSTVSLAGRPIVNLRHFPRLAAGQHET PAVHELVMSIMDDPRMADVWAGEGQLSLPVAEGEEISDLAPVRVGAGYRLSMSYTVTDLKTLSDGTQ AA |
| WP_107818191 | SEQ ID NO: 25 | MKKPLLTVDDVTGCWAIMPTPSKPNGSDINATDTVDLDETARAAEALVASGVNGILSQGTFGEAATT TWEEKQAFLRTLVETVDGRVPVFGGTTSLNTRDTIRMTKAVREIGVDGVMLGPPMWCQPDVPTAVQF FRDVAEACPDTAICAYANPEAFKFDFPRAFWAQIAEIPQVVSAKYMNIAALYMDLNLTGRKIRLMPL DMDYYAAARMDPEACTAFWTSGAICGPEPVIQLRDLVAEAHKTGDWGKAKALTDRIAATYRTLFPNG SFKEFSVYNIGIEKARIDAAGWMTAGPCRPPYHVIPEPILDGAREAGLQWAKLVSALESEKTA |
| A0A023WZF9 | SEQ ID NO: 26 | MSNKTMKPARLTAEDIHGVWAIMPTPATPDASNWRSTNTVDLNETARIVEEELIAAGVNGILSMGTFG ECATLTWEEKRDYVSTIVETIRGRVPYFCGTTALNTREVIRQTREFMDMGASGTMLGVPMWVKMDLN TAVQFYRDVAEAVPEAAIAIYANPEAFKFDFPRPFWAEMSKIPQVVTAKYLGIGMLDLDLKLAPNIR FLPHEDDYYAAARINPERMTAFWSSGSMCGPATAIMLRDAVDQAKSSGDWIKAKAISDDMRAADSTL FPRGDFSEFSKYNIGLEKARMDAAGWLTAGPCRPPYNIVPEDYIAGALKSGKAWAALHAKYSKELK |
| PYN48855 | SEQ ID NO: 27 | MLKGFNYPLTPKGKSTLNPSPPWHYSADFLDIEFWSEPSAVTAVLPAGLDPDPAANGHGHALFYDWQ FAGENEEYLDPARYQYREFFLLVDALYEGQPISYCPYIFVDNDAAIARGWTQGYPKRLGQVFQTRYY AATGKAGPALAPGSKFAGSLTAGGQRLAEALVTLKEPVTDPALLKQRPIVNLLHYPQLAADKQDEPA IHQLVENVPHDLKIEQAWIGDGSLTLPVCRSEELSDLAPVRCGKGIRASMAYIVDDLKTLKDLTKGF SLLA |
| A0A421PAQ6 | SEQ ID NO: 28 | MLKGYTVPLSPKGEANIAPTPPWHYAGDIVGVEFFTEPSAAEATLPEGLDPDPDTSGRVVAFFVDWQ FNGEQDEYLDPVRSQYREFFVLVDARHQGRPVSWCPYIYVDNHHALARGWIQGFPKKAGNVHQTRVF ASPGKASPTLSPGARFGATVSSDERTLAEARVTLEAPMEDPSALLARDTINLRHFPTLEVGKYDKPA VHELVRMDYADQQVADVWTGTSEITLFPAVGEELADLAPVRPGMGFRASMSYNVTQVEPLG |
| WP_028217297 | SEQ ID NO: 29 | MNKPYAVPLSPRGLSSIAPPPPWHYAGDFILVEFWADPAAAAVLPKGLSLDPASPGHATALFIDWQ FTGSNDEMLDPARYQYREFFVLVDALHEGKPVSFCPYIFVDNDSAMMRGLIQGFPKRYGQIHQTRTF AALSPAAAPVTAGTRFAATASAAGQRLAHAEVKLEAAVQDVSKLGIAGRPVVNQRYFPRLAAGQHDT PAVNELVLSIMDNAQIADVWAGEGKLTFPPFAQGEEIADLQPVRVGAGFRGSMAYSVTDLKTLVDHTK |
| WP_034507049 | SEQ ID NO: 30 | MLKGFTLPKSPFGQAALTPPPPWHYSGDVIGVEFRTDPSATAATLPNGLSPDPKSNGHAVMMFVDWQ FTAQNDEYLDPARYRYREAFVLLDAVYRNAPVMWCPYVFVDNDAALARGWTQGFPKKIGSIFQTRTY AAASPAAAPVAPGGRFGASLSAHGQRLAEARITLQEPVEDGLSLLSRPTVLLRYFPRLAAGYQDKPA VNELTMAITDNLTVADAWIGDGELNLPEVHGEELHGLAPIAIESGFRYSLSYSVTDLKILEDHAS |
| Q47098 | SEQ ID NO: 31 | MENSFKAALKAGRPQIGLWLGLSSSYSAELLAGAGFDWLLIDGEHAPNNVQTVLTQLQAIAPYPSQP VVRPSWNDPVQIKQLLDVGTQTLLVPMVQNADEAREAVRATRYPPAGIRGVGSALARASRWNRIPDY LQKANDQMCVLVQIETREAMKNLPQILDVEGVDGVFIGPADLSADMGYAGNPQHPEVQAAIEQAIVQ IRESGKAPGILIANEQLAKRYLELGALFVAVGVDTTLLARAAEALAARFGAQATAVKPGVY |
| P75682 | SEQ ID NO: 32 | MPQSALFTGIIPPVSTIFTADGQLDKPGTAALIDDLIKAGVDGLFFLGSGGEFSQLGAEERKAIARF AIDHVDRRVPVLIGTGGTNARETIELSQHAQQAGADGIVVINPYYWKVSEANLIRYFEQVADSVTLP VMLYNFPALTGQDLTPALVKTLADSRSNIIGIKDTIDSVAHLRSMIHTVKGAHPFTVLCGYDDHLF NTLLLGGDGAISASGNFAPQVSVNLLKAWRDGDVAKAAGYHQTLLQIPQMYQLDTPFVNVIKEAIVL CGRPVSTHVLPPASPLDEPRKAQLKTLLQQLKLC |
| P0A6L4 | SEQ ID NO: 33 | MATNLRGVMAALLTPFDQQQALDKASLRRLVQFNIQQGIDGLYVGGSTGEAFVQSLSEREQVLEIVA EEAKGKIKLIAHVGCVSTAESQQLAASAKRYGFDAVSAVTPFYYPFSFEEHCDHYRAIIDSADGLPM VVYNIPALSGVKLTLDQINTLVTLPGVGALKQTSGDLYQMEQIRREHPDLVLYNGYDEIFASGLLAG ADGGIGSTYNIMGWRYQGIVKALKEGDIQTAQKLQTECNKVIDLLIKTGVFRGLKTVLHYMDVVSVP LCRKPFGPVDEKYLPELKALAQQLMQERG |
| P23522 | SEQ ID NO: 34 | MNNDVFPNKFKAALAAKQVQIGCWSALSNPISTEVLGLAGFDWLVLDGEHAPNDISTFIPQLMALKG SASAPVVRVPTNEPVIIKRLLDIGFYNFLIPFVETKEEAELAVASTRYPPEGIRGVSVSHRANMFGT VADYFAQSNKNITILVQIESQQGVDNVDAIAATEGVDGIFVGPSDLAAALGHLGNASHPDVQKAIQH IFNRASAHGKPSGILAPVEADARRYLEWGATFVAVGSDLGVFRSATQKLADTFKK |

-continued

Certain Sequences

| Uniprot or Genbank ID | Sequence ID Number | Sequence Information |
|---|---|---|
| P0A955 | SEQ ID NO: 35 | MKNWKTSAESILTTGPVVPVIVVKKLEHAVPMAKALVAGGVRLEVTLRTECAVDAIRAIAKEVPEA IVGAGTVLNPQQLAEVTEAGAQFAISPGLTEPLLKAATEGTIPLIPGISTVSELMLGMDYGLKEFKF FPAEANGGVKALQAIAGPFSQVRFCPTGGISPANYRDYLALKSVLCIGGSWLVPADALEAGDYDRIT KLAREAVEGAKL |
| Q6BF16 | SEQ ID NO: 36 | MQWQTKLPLIAILRGITPDEALAHVGAVIDAGFDAVEIPLNSPQWEQSIPAIVDAYGDKALIGAGTV LKPEQVDALARMGCQLIVTPNIHSEVIRRAVGYGMTVCPGCATATEAFTALEAGAQALKIFPSSAFG PQYIKALKAVLPSDIAVFAVGGVTPENLAQWIDAGCAGAGLGSDLYRAGQSVERTAQQAAAFVKAYR EAVQ |
| M9YI86 | SEQ ID NO: 37 | MPAPVLAATSPGAGRAIHLINPAMPAFRAAFEETLMKMPHNAFKAALQRPETQYGIWAGFASGYAAE IVAGTGYDWMLIDGEHAPNSVPTILAQLQSVAPYPTQPVVRPVCGDPVLIKQLLDIGAQTLMVPMVE SAEQARALVRAMRYPPHGIRGVGGGLARATRWDGVPDYLNTAHEELCLIVQVESRAGVENVEAIAAV EGVDAVFIGPADLSIGLGHPGDPGHPQVQELIHHAIEATRAAGKACGILAPHEEDARRYREWGCRFI AVAIDISLLRQGALAGLARFRDTPASDAPSRTY |
| Q8NMD2 | SEQ ID NO: 38 | MASATFTGVIPPVMTPLHADGSVDVESLRKLVDHLINGGVDGLFALGSSGEAAFLTRAQRKLALTTI IEHTAGRVPVTAGVIETTTARVIELVEDALEAGAEGLVATAPFYTRTHDVEIEEHFRKIHAAAPELP LFAYNIPVSVHSNLNPVMLLTLAKDGVLAGTKDSSGNDGAIRSLIEARDDAGLTEQFKILTGSETTV DFAYLAGADGVVPGLGNVDPAAYAALAKLCLDGKWAEAAALQKRINHLFHIVFVGDTSHMSGSSAGL GGFKTALAHLGIIESNAMAVPHQSLSDEETARIHAIVDEFLYTA |
| A0A1J6QD42 | SEQ ID NO: 39 | MDKNIIIGAMTALITPFKNGKVDEQSYARLIKRQIENGIDAVVPVGTTGESATLTHEEHRTCIEIAV ETCKETKVKVLAGAGSNATHEAVGLAKFAKEHGADGILSVAPYYNKPTQQGLYEHYKAIAQSVDIPV LLYNVPGRTGCEISTDTIIKLFRDCENIYGVKEASGNIDKCVDLLAHEPRMMLISGEDAINYPILSN GGKGVISVTSNLLPDMISTLTHFALDENYKEAKKINDELYNINKILFCESNPIPIKTAMYIAGLIES LEFRLPLCPPSKENFAKIEEVMKKYKIKGF |
| Q8RBI5 | SEQ ID NO: 40 | MPVFKGSCVAIVTPFTENGVNFDKLGELIEWHIKEGTDAILICGTTGEASTMTDEEQKEAIKFTVEK VAKRIPVIAGTGSNNTAHAIELSEYAQSVGADALLVITPYYNKTTQKGLVAHFTEIARHVDIPIIIY NVPSRTSLNMLPETYLEVKKKAENVVGVKEASGDISQIAEIARIMGKSFEIYSGNDDQVIPIMSLGG LGVISVTANIIPAKIHEMTTAYLNGDIEKARDMQLELNPLNKALFIETNPIPVKTAMNLMGFGVGPL RLPLVEMSEKNLEYLKSVLRQYGLLKEEN |
| A3LZU9 | SEQ ID NO: 41 | MTISAALPKRGVYTPVPTFFKKDLHTIDYDSQIEHAKFLQQNGITGLVLLGSTGENSHLTRKERIEL VSTIHEELPDFPLMAGVAQNSVEDAIEEILQLKNAGAQHALVLPSSYFGASIKQQGIIDWYTEVADN ASLPVLIYVYPGVSNNISIDPRTIKKLSAHPNIVGAKISHGDVSHHAIIGLDQEIAANQFITLTGLG QILLPVLVVGIQGTVDALCGAFPKIYVKLLENYDKGDLRAAAELQLVISRAEELVVKFGVVGIKKAI HFATGIGETYLGRAPLTQDVNDADWKSYNDYLLGIVSVESTL |
| Q4JC35 | SEQ ID NO: 42 | MEIISPIITPFDKQGKVNVDALKTHAKNLLEKGIDAIFVNGTTGLGPALSKDEKRQNLNALYDVTHK LIFQVGSLNLNDVMELVKFSNEMDILGVSSHSPYYFPRLPEKFLAKYYEEIARISSHSLYIYNYPAA TGYDIDPPSILKSLPVKGIKDTNQDLAHSLEYKLNLPGVKVYNGSNTLIYYSLLSLDGVVASFTNFIP EVIVKQRDLIKQGKLDDALRLQELINRLADILRKYGSISAIYVLVNEFQGYDVGYPRPPIFPLTDEE ALSLKREIEPLKRKIQELVH |
| O54288 | SEQ ID NO: 43 | MPEIITPIITPFTKDNRIDKEKLKIHAENLIRKGIDKLFVNGTTGLGPSLSPEEKLENLKAVYDVTN KIIFQVGGLNLDDAIRLAKLSKDFDIVGIASYAPYYYPRMSEKHLVKYFKTLCEVSPHPVYLYNYPT ATGKDIDAKVAKEIGCFTGVKDTIENIIHTLDYKRLNPNMLVYSGSDMLIATVASTGLDGNVAAGSN YLPEVTVTIKKLAMERKIDEALKLQFLHDEVIEASRIFGSLSSNYVLTKYFQGYDLGYPRPPIFPLD DEEERQLIKKVEGIRAKLVELKILKE |
| F9VPG1 | SEQ ID NO: 44 | MDIVTPILTPFTKEGKIDVEKLKAHAKFLIDNGIDLLFVNGTTGLGPALSKEEKLTTLKTIYDVTNK VIFQVGSLNINDVIDLVKASKDFDIVGIASYPPFYFPRLPEKFLLKYFTTIANYSPHSLYIYNYPLA TGYDISAKIVYQMKDLITGLKDTNQDLSHSLEYKILMPNLKVYNGSDSLVFYSLTSLDGSVTAASNY LPHVMKKMKEHITSGQVSKAIELQKLINKALDISRKYGQLSAIYYLVKEFLGYDVGYPRGPIFPLEE DEVKALLSEIQPVKKEIERAVS |
| P28304 | SEQ ID NO: 45 | MATRIEFHKHGGPEVLQAVEFTPADPAENEIQVENKAIGINFIDTYIRSGLYPPPSLPSGLGTEAAG IVSKVGSGVKHIKAGDRVVYAQSALGAYSSVHNIIADKAAILPAAISFEQAAASFLKGLTVYYLLRK TYEIKPDEQFLFHAAAGGVGLIACQWAKALGAKLIGTVGTAQKAQSALKAGAWQVINYREEDLVERL KEITGGKKVRVVYDSVGRDTWERSLDCLQRRGLMVSFGNSSGAVTGVNLGILNQKGSLYVTRPSLQG YITTREELTEASNELFSLIASGVIKVDVAEQQKYPLKDAQRAHEILESRATQGSSLLIP |
| P40783 | SEQ ID NO: 46 | MATRIEFHKHGGPEVLQTVEFTPAEPAEHEIQVENKAIGINFIDTYIRSGLYPPPSLPAGLGTEAAG VVSKVGNGVEHIRVGDRVVYAQSTLGAYSSVHNVTADKAAILPDAISFEQAAASFLKGLTVFYLLRK TYEVKPDEPFLFHAAAGGVGLIACQWAKALGAKLIGTVGSAQKAQRALDAGAWQVINYREESIVERV KEITGGKKVRVVYDSVGKDTWEASLDCLQRRGLMVSFGNASGPVTGVNLGILNQKGSLYATRPSLQG YITTREELTEASNELFSLIASGVIKVDVAENQRYALKDARRAHEVLESRATQGSSLLIP |

-continued

| Uniprot or Genbank ID | Sequence ID Number | Sequence Information |
|---|---|---|
| Q0K2I0 | SEQ ID NO: 47 | MPRHGCLTIVTVAPMIAARAGHDNQETALAKAIRMYETGGPEVLRYEDAEVGDPGPGEVRIRHAAVG<br>LNYADTYFRNGTYPVPLPGGMGVEAAGVVQAVGPGVTHVAEGDRVTYTGFINTLGAYSTERLVPAAP<br>LIRLPEAISFETAAAMTRGLTSAYLMRRIYPFQGGEAILLHAAAGGVGLIVSQWARLLGLTVIGTV<br>STEAKAEVARAHGCDHIINYSHEDVAKRVRELTDGAGVSVVFDSVGKSTFMASLDSLKRRGLMVCVG<br>TASGTIPPFDPQLLARKGSVYLTRPALADYIADPAEKAELAAEVFGHVAAGRIRIEINQRYALQDAV<br>QAHRDLESRKTTGSSIFVL |
| A0A1Z1SRY9 | SEQ ID NO: 48 | MAKRIQFAAHGNADVLELTSFTPAPLGDNEVQVANKAIGINYIDTYVRSGLYPVEHFPSGLGTEAAG<br>VVIKTGAHVTSLKEGDRVVYAQSPLGAYSDTHNVPENKVARLPDNISFEQAAASFLKGLTVYYLFNE<br>TYKLRAGETFLFHAAAGGVGLIASQWAKAIGAKMIGTAGSDEKVAKAKAAGAWKVINYQTESIVERV<br>LALTNNQKVPVVYDSVGKATWLDSLHCLQRRGLMVSFGNASGAVTGVDLGILNKLGSLYVTRPSISG<br>YITTREELDAASEALFTLIGRGKIDVSVPDNQKFALADAKAAHRYLESRQSQGSSLLIP |
| P43903 | SEQ ID NO: 49 | MAKRIQFAAYGGPEVLEYRDYQPAEPGPREVRVRNRAIGLNFIDTYYRSGLYPAPGLPSGLGSEGAG<br>EVEAVGSEVTRFKVGDRVAYATGPLGAYSELHVLAEEKLVHLPDGIDFEQAAAVMLKGLTTQYLLRQ<br>TYELRGGETILFHAAAGGVGLFACQWAKALGVQLIGTVSSPEKARLARQHGAWETIDYSHENVARRV<br>LELTDGKKCPVVYDSVGKDTWETSLDCVAPRGLLVSFGNASGPVTGVNLGILSQKGSLYVTRPTLGS<br>YADTPEKLQAMADELFGLIERGDIRIEINQRFALAEEAARAHTELAARRTTGSTVLLP |
| I7G8G0 | SEQ ID NO: 50 | MHAIEVAETGGPEVLNYIERPEPSPGPGEVLIKADAIGVNFIDTYFRSGLYPRELPFVVGTEVCGTV<br>AAIGNDVAALKVGDRVVTANAVGAYADYCVAPADFVAYVPDGVAPEAVASALLKGMTAHYLLKSTYP<br>VQPSDTVLVHAGAGGVGLILTQWATSLGTRVITTASTPEKAELSRQAGAVEVLDYPDPDDPQPFASR<br>VRELTGGAGVAVYDGVGATTFDASLASLAVRGTLALFGASSGPVPPFDPQRLNAAGSVFLTRPTLA<br>HHTRTADEFSWRAGELINAIADGSIKITVGGTYPLAEASRAHTDLQGRKTVGSIVLIP |
| Q142L2 | SEQ ID NO: 51 | MVKAIRFDKTGGPEVMKWVDVEVGEPGAGEIRVRQTAVGLNYIDVYFRTGLYPLPLPGGLGMEAAGE<br>VTALGSGVSGLKVGDRIAYVARPPGAYAQERVLQAAQVVKVPDALTDEQAASVMLQGLTAQYLLRRT<br>YPVKAGDTILIQAAAGGVGLLVCQWAKALGATVIGTVGSDEKAEIATAHGCDHAIVYTRENFTRRVR<br>EITNGAGVPVVYDSIGKDTFTGSLDCLAPLGMFVSFGNASGPLPPIDSSEFAGRGSLFFTRPTLFTY<br>IAKRSDYEAMSTELFDVLVSGKVKTSINQRYALADVGRAHADLEGRRTTGSTVLLP |
| ALK19324.1 | SEQ ID NO: 52 | MPKAIRYDQPGGPDVMKWVDVEVGEPKAGEVRIRQHAVGLNYIDVYFRTGLYSQPLPGGLGMEAAGE<br>VTAVGEGVTALKAGDRVAYVGQPGAYAQERVMPAERLVKLPDGISYDDAASVMLQGLTAHYLLRRT<br>YPVKAGDTILIHAAAGGVGLLVCQWAKALGATVIGTVGSDEKAALAKAHGCDHPIVYTRENFTQRVK<br>EITNGAGVPVVYDSIGKDTYIGSLDCLAPLGYFVSFGNASGPLPAIDSKEFSSRGSLFFTRPTLFSY<br>IAKRADLESAAAELFDVILSGKVKTSINQRYPLAEVGRAHADLESRNTTGSTILVP |
| Q5FTU6 | SEQ ID NO: 53 | MSSKPDILTIDPLVPVMKERLEKSFTLHPYTSLENLKNIAPAIRGITTGGGSGVPSEIMDALPNLEV<br>ISVNGVGTDRINLDEARRNIGVAITQNTLTDDVADMAVALMMAVMRSIVTNDAFVRAGKWPSATAP<br>LGRSLTRKKVGIAGFGHIGQAIAKRVSAFGMEVAYFNSHARPESTCHFEPDLKALATWCDVLILAVS<br>GGPRSANMIDRDTLDALGKDGFLVNIARGTVVDEAALLSALQEKRIAGAGLDVFQNEPNINPAFLSL<br>PNTVLQAHQASATVETRTTMANLVVDNLIAYFTDKTLLTPVI |
| A0A1V9IP73 | SEQ ID NO: 54 | MKILAYCVRPDEIDSFKNFSEKYGHTVDLIPDSFGPSVAHLAKGYDGISILGNDTCNREALEKIKDC<br>GIKYLATRTAGVNNIDFDAAKEFGINVANVPAYSPNSVSEFTVGLALSLTRKIPFALKRVELNNFAL<br>GGLIGVELRNLTLGVIGTGRIGLKVIEGFSGFGMKKMIGYDIFENEKAKEYIEYKSLDEVYKEADII<br>TLHAPLTDDNYHMIGKESIAKMKDGVFIINAARGALIDSEALIEGLKSGKIAGAALDSYEYEQGVFH<br>NNKMNEIMKDDTLARLKSFPNVVITPHLGFYTDEAVSNMVEITLMNLQEFELKGTCKNQRVCK |
| T4VW93 | SEQ ID NO: 55 | MDNKALLKGVRVVELSSFVAAPCCAKLLGDWGAEVIKIEPLGGDGIRVMGGTFKSPCTDEENPMFEL<br>ENGNKKGISVNVKTKEGVEIIHKLLAKADIFITNVREQALSKIGLTYDQLKDEFPALIHAHILGYGE<br>NGPLKDKPGFDYTAYFARGGVSQSLMEKGTSPCNTAAAFGDHYAGVSLTAGILAALYKKQMTGEGDR<br>VTVSLYHTALYGMGMMITTAQYGNKMPISRANPNSPLMTTYKCKDGKWIQLALIQYNKWLPKFCNVI<br>NRPEIMEDERFNDIKVMPLHVDEMVEIVGEAMLEKTLDEWSALLEEADLPFEKVQSCEDILEDEQAW<br>ANDFLFKTKYANGNEGVLVNGPVKFKTMGIKEYTPAPRVGEHTEEVLKELGYTEEEILNMVNSQAVK<br>LDDSKELV |
| A0A0C7GD16 | SEQ ID NO: 56 | MDNRALLKGVRVVELSSFVAAPCCAKLLADWGAEVIKIEPLGGDGIRVMGGTFKSPCTDDENPMFEL<br>ENGNKKGISVNVKTKEGVEILHKLLSKSDIFVTNVREKALAKMGLTYDQLKDDFPGLIHAHILGYGE<br>EGPLKDKPGFDYTAYFARGGVSQSLMEKGTSPCNTAAGFGDHYAGISLTAGILAALYKKQITGEGDR<br>VTVSLFHTALYGMGMMITTSQYGNEMPISRTEPNSPLMTTYKCKDGKWIQLALIQYNKWLPKFCEVI<br>NRPEIMKDDRFNDIKVMPLHVDEMVKIVEKAMLEKTLDEWSDLLEEADLPFEKVQSCEDIINDDQAW<br>ANDFLFKTTYENGNEGVLVNGPVKFKTMGIKEYEPAPRLGQHTEEVLKSIGYTEEEILDMVNSQAIK<br>LDDAKELV |
| A0A175L1W4 | SEQ ID NO: 57 | MTKEGLALEGVKVVELSSFVAAPSCSKLLADWGADVIKIEPIQGDNIRVVGGVYNSPARDDENPMFE<br>LENGNKRGIAINTRSEKGKEVLGKLLKDADVFVTNVREKALQRSGLSYDQLKDKYPSLIHAHILGYG<br>EKGPLKDKPGFDYTAYFARGAVSTSLMEKGTSPANTNAGFGDHYAGMSLAAGILAALHRKTLTGKGD<br>RVTVSLYHTAIFGMGLMITTAQYGNKMPLSRRTPNNPLATTYRCKDDRWIQLALLKYDAWFPKFCKE<br>VINRPDLIEDLRFNKQSEVVKHVETFVGILEEEFIKKDLKEWADLLDKADLPYEKLQYCEDILEDEQ<br>AWANDYLFKTTYDSGNTGVLVNSPVKFSEAGMRTYKAAPKIGEDTEVVLTSLGYSKEEIEEMRKEES<br>IK |

-continued

Certain Sequences

| Uniprot or Genbank ID | Sequence ID Number | Sequence Information |
|---|---|---|
| A0A2X3BTQ9 | SEQ ID NO: 58 | MTKEGLALEGVKVVELSSFVAAPSCSKLLADWGADVIKIEPIQGDNIRVVGGVYNSPARDDENPMFE LENGNKRGVAINTRSEKGKEVLGKLLKDADVFVTNVREKALQRSGLSYDQLKDKYPSLIHAHILGYG EKGPLKDKPGFDYTAYFARGAVSTSLMEKGTSPANTNAGFGDHYAGMSLAAGILAALHRKTLTGKGD RVTVSLYHTAIFGMGLMITTAQYGNKMPLSRRTPNNPLATTYRCKDDRWIQLALLKYDAWFPKFCKE VINRPDLIEDSRFNKQSEVVKHVETFVGVLEGEFIKKDLKEWADLLDKADLPYEKLQYCEDILEDEQ AWANDYLFKTTYDSGNTGVLVNSPVKFSEAGMRPYKAAPKIGEDTEAILTSLGYSKEEIEEMRKENA IK |
| Q5U924 | SEQ ID NO: 59 | MSEKKEARVVINDLLAEQYANAFKAKEEGRPVGWSTSVFPQELAEVFDLNVLYPENQAAGVAAKKGS LELCEIAESKGYSIDLCAYARTNFGLLENGGCEALDMPAPDFLLCCNNICNQVIKWYENISRELDIP LIMIDTTFNNEDEVTQSRIDYIKAQFEEAIKQLEIISGKKFDPKKFEEVMKISAENGRLWKYSMSLP ADSSPSPMNGFDLFTYMAVIVCARGKKETTEAFKLLIEELEDNMKTGKSSFRGEEKYRIMMEGIPCW PYIGYKMKTLAKFGVNMTGSVYPHAWALQYEVNDLDGMAVAYSTMFNNVNLDRMTKYRVDSLVEGKC DGAFYHMNRSCKLMSLIQYEMQRRAAEETGLPYAGFDGDQADPRAFTNAQFETRIQGLVEVMEERKK LNRGEI |
| A0A2X3BK09 | SEQ ID NO: 60 | MADKKEVKKNAAKMINGILAKSYADAWKAKEEGKPVGWSTSVFPQELVETFGLDVLYPENQAAGVAA KKESLSLCEAAESAGYSIDLCAYARTNFGLLEKGGSENLNMPKPDFICCCNNICNQVIKWYENIAKE LDIPLIMIDTTFNNEDEVTENRIKYLRAQFEEAIKQLEKISGKKFDPKKFEEVMKISAENGLWKYS MSLPSGSFPSPMNGFDLFTYMAVIVCYRGKKETTEAFKLLISELEDNIKNKATSFRGEEKYRIMMEG IPCWPYIGYKMRTLAGYGVNMTGSVYPHAWALQYEVNDLDGMAKAYSTMFNNVNLETMCKYRIDSLI DGNCDGAFYHMNRSCKLMSFIQYEMERKVFEETGIPYAGFDGDQADPRNFSKAQFETRLQGLVEVME ERKKGGNK |
| Q5U925 | SEQ ID NO: 61 | MYTMGLDIGSTASKGVILKNGEDIVASETISSGTGTTGPSRVLEKLYGKTGLAREDIKKVVVTGYGR MNYSDADKQISELSCHARGVNFIIPETRTIIDIGGQDAKVLKLDNNGRLLNFLMNDKCAAGTGRFLD VMAKIIEVDVSELGSISMNSQNEVSISSTCTVFAESEVISHLSENAKIEDIVAGIHTSVAKRVSSLV KRIGVQRNVVMVGGVARNSGIVRAMAREINTEIIVPDIPQLTGALGAALYAFDEAKESQKEVKNI |
| A0A2X3BU19 | SEQ ID NO: 62 | MDNIKNILSKLEGIVKNPKKVVSDYKERTGNKVIGCFPVYTPEEIVYAADMLPIGIWGGDVEANLAK QYYPAFCCSIMQSCMEFGLKGIYEGLSAVIIPGMCDTLNCMGGQNWKFAIKDIPYIALVHPQNRKLEA GVEYLVEEYKHVCAKIEEIRGKEITEEEMQNSIDIYNEHRKVMRSFVDEAAKHPNTINNYQRNLVIK SGFFMRKDEHTKIVKELNELLAVLPEEKYDGKKVLVTGILLDSKEMLDVFEENKLRIVADDLAQESR QFRTDVPEGKNALDRLARQWSNIEGCSLAYDPKKIRGSMIAKEAKAKGIDGVVFAMMKFCDPEEYDY PIVKKDIEKEDIPTTMIEVDQQNKSVEQIRTRIQTFSEIL |
| Q5U923 | SEQ ID NO: 63 | MEAILSKMKEVVENPNAAVKKYKSETGKKAIGCFPVYCPEEIIHAAGMLPVGIWGGQTELDLAKQYF PAFACSIMQSCLEYGLKGAYDELSGVIIPGMCDTLICLGQNWKSAVPHIKYISLVHPQNRKLEAGVK YLISEYKGVKRELEEICGYEIEEAKIHESIEVYNEHRKTMRDFVEVAYKHSNTIKPSIRSLVIKSGF FMRKEEHTELVKDLIAKLNAMPEEVCSGKKVLLTGILADSKDILDILEDNNISVVADDLAQETRQFR TDVPAGDDALERLARQWSNIEGCSLAYDPKKKRGSLIVDEVKKKDIDGVIFCMMKFCDPEEYDYPLV RKDIEDSGIPTLYVEIDQQTQNNEQARTRIQTFAEMMSLA |
| A0A1V9IXA9 | SEQ ID NO: 64 | MYTMGLDIGSTTSKGVIIKDGEEIVASVLVPVGTGTSGPLKLIKELKEKSNLTEKDIEKTVVTGYGR IQYKDADKQISELSCHAKGVAFLIPGARTIIDIGGQDAKAMKLNDKGKLINFIMNDKCAAGTGRFLD VMAGVLETDVSKLGEISEKSTKEVSISSTCTVFAESEVISHLSANAKKEDIVAGIHTSVVRRVSTLA MRVGIEDQVVMVGGVARNKGIVKAMEKELGHDIKVPELAQLTGALGAAIYAFEETK |
| Q73Q47 | SEQ ID NO: 65 | MIVKPMVRNNICLNAHPQGCKKGVEDQIEYTKKRITAEVKAGAKAPKNVLVLGCSNGYGLASRITAA FGYGAATIGVSFEKAGSETKYGTPGWYNNLAFDEAAKREGLYSVTIDGDAFSDEIKAQVIEEAKKKG IKFDLIVYSLASPVRTDPDTGIMHKSVLKPFGKTFTGKTVDPFTGELKEISAEPANDEEAAATVKVM GGEDWERWIKQLSKEGLLEEGCITLAYSYIGPEATQALYRKGTIGKAKEHLEATAHRLNKENPSIRA FVSVNKGLVTRASAVIPVIPLYLASLFKVMKEKGNHEGCIEQITRLYAERLYRKDGTIPVDEENRIR IDDWELEEDVQKAVSALMEKVTGENAESLTDLAGYRHDFLASNGFDVEGINYEAEVERFDRI |
| A0R484 | SEQ ID NO: 66 | MTSDVHDATDGVTETALDDEQSTRRIAELYATDPEFAAAAPLPAVVDAAHKPGLRLAEILQTLFTGY GDRPALGYRARELATDEGGRTVTRLLPRFDTLTYAQVWSRVQAVAAALRHNFAQPIYPGDAVATIGF ASPDYLTLDLVCAYLGLVSVPLQHNAPVSRLAPILAEVEPRILTVSAEYLDLAVESVRDVNSVSQLV VFDHHPEVDDHRDALARAREQLAGKGIAVTTLDAIADEGAGLPAEPIYTADHDQRLAMILYTSGSTG APKGAMYTEAMVARLWTMSFITGDPTPVINVNFMPLNHLGGRIPISTAVQNGGTSYFVPESDMSTLF EDLALVRPTELGLVPRVADMLYQHHLATVDRLVTQGADELTAEKQAGAELREQVLGGRVITGFVSTA PLAAEMRAFLDITLGAHIVDGYGLTETGAVTRDGVIVRPPVIDYKLIDVPELGYFSTDKPYPRGELL VRSQTLTPGYYKRPEVTASVFDRDGYYHTGDVMAETAPDHLVYVDRRNNVLKLAQGEFVAVANLEAV FSGAALVRQIFVYGNSERSFLLAVVVPTPEALEQYDPAALKAALADSLQRTARDAELQSYEVPADFI VETEPFSAANGLLSGVGKLLRPNLKDRYGQRLEQMYADIAATQANQLRELRRAAATQPVIDTLTQAA ATILGTGSEVASDAHFTDLGGDSLSALTLSNLLSDFFGFEVPVGTIVNPATNLAQLAQHIEAQRTAG DRRPSFTTVHGADATEIRASELTLDKFIDAETLRAAPGLPKVTTEPRTVLLSGANGWLGRFLTQWL ERLAPVGGTLITIVRGRDDAAARARLTQAYDTDPELSRRFAELADRHLRVVAGDIGDPNLGLTPEIW HRLAAEVDLVVHPAALVNHVLPYRQLFGPNVVGTAEVIKLALTERIKPVTYLSTVSVAMGIPDFEED GDIRTVSPVRPLDGGYANGYGNSKWAGEVLLREAHDLCGLPVATFRSDMILAHPRYRGQVNVPDMFT RLLLSLLITGVAPRSFYIGDGERPRAHYPGLTVDFVAEAVTTLGAQQREGYVSYDVMNPHDDGISLD VFVDWLIRAGHPIDRVDDYDDWVRRFETALTALPEKRRAQTVLPLLHAFRAPQAPLRGAPEPTEVFH AAVRTAKVGPGDIPHLDEALIDKYIRDLREFGLI |

-continued

| Uniprot or Genbank ID | Sequence ID Number | Sequence Information |
|---|---|---|
| A0QWI7 | SEQ ID NO: 67 | MTIETREDRFNRRIDHLFETDPQFAAARPDEAISAAAADPELRLPAAVKQILAGYADRPALGKRAVE FVTDEEGRTTAKLLPRFDTITYRQLAGRIQAVTNAWHNHPVNAGDRVAILGFTSVDYTTIDIALLEL GAVSVPLQTSAPVAQLQPIVAETEPKVIASSVDFLADAVALVESGPAPSRLVVFDYSHEVDDQREAF EEAAKGKLAGTGVVVETITDALDRGRSLADAPLYVPDEADPLTLLIYTSGSTGTPKGAMYPESKTATM WQAGSKARWDETLGVMPSITLNFMPMSHVMGRGILCSTLASGGTAYFAARSDLSTFLEDLALVRPTQ LNFVPRIWDMLFQEYQSRLDNRRAEGSEDRAEEAAVLEEVRTQLLGGRFVSALTGSAPISAEMKSWVE DLLDMHLLEGYGSTEAGAVFIDGQIQRPPVIDYKLVDVPDLGYFATDRPYPRGELLVKSEQMFPGYY KRPEITAEMFDEDGYYRTGDIVAELGPDHLEYLDRRNNVLKLSQGEFVTVSKLEAVFGDSPLVRQIY VYGNSARSYLLAVVVPTEEALSRWDGDELKSRISDSLQDAARAAGLQSYEIPRDFLVETTPFTLENG LLTGIRKLARPKLKAHYGERLEQLYTDLAEGQANELRELRRNGADRPVVETVSRAAVALLGASVTDL RSDAHFTDLGGDSLSALSFSNLLHEIFDVDVPVGVIVSPATDLAGVAAYIEGELRGSKRPTYASVHG RDATEVRARDLALGKFIDAKTLSAAPGLPRSGTEIRTVLLTGATGFLGRYLALEWLERMDLVDGKVI CLVRARSDDEARARLDATFDTGDATLLEHYRALAADHLEVIAGDKGEADLGLDHDTWQRLADTVDLI VDPAALVNHVLPYSQMFGPNALGTAELIRIALTTTIKPYVYVSTIGVGQGISPEAFVEDADIREISA TRRVDDSYANGYGNSKWAGEVLLREAHDWCGLPVSVFRCDMILADTTYSGQLNLPDMFTRLMLSLVA TGIAPGSFYELDADGNRQAHYDGLPVEFIAEAISTIGSQVTDGFETFPHVMNPYDDGIGLDEYVDWL IEAGYPVHRVDDYATWLSRFETALRALPERQRQASLLPLLHNYQQPSPPVCGAMAPTDRFRAAVQDA KIGPDKDIPHVTADVIVKYISNLQMLGLL |
| D6Z860 | SEQ ID NO: 68 | MTQSHTQGPQASAAHSRLARRAAELLATDPQAAATLPDPEVVRQATRPGLRLAERVDAILSGYADRP ALGQRSFQTVKDPITGRSSVELLPTFDTITYRELRERATAIASDLAHHPQAPAKPGDFLASIGFISV DYVAIDIAGVFAGLTAVPLQTGATLATLTAITAETAPTLFAASIEHLPTAVDAVLATPSVRRLLVFD YRAGSDEDREAVEAAKRKIADAGSSVLVDVLDEVIARGKSAPKAPLPPATDAGDDSLSLLIYTSGST GTPKGAMYPERNVAHFWGGVWAAAFDEDAAPPVPAINITFLPLSHVASRLSLMPTLARGGLMHFVAK SDLSTLFEDLKLARPTNLFLVPRVVEMLYQHYQSELDRRGVQDGTREAEAVKDDLRTGLLGGRILTA GFGSAPLSAELAGFIESLLQIHLVDGYGSTEAGPVWRDGYLVKPPVTDYKLIDVPELGYFSTDSPHP RGELAIKTQTILPGYYKRPETTAEVFDEDGFYLTGDVVAQIGPEQFAYVDRRKNVLKLSQGEFVTLA KLEAAYSSSPLVRQLFVYGSSERSYLLAVIVPTPDALKKFGVGEAAKAALGESLQKIARDEGLQSYE VPRDFIIETDPFTVENGLLSDARKSLRPKLKEHYGERLEAMYKELADGQANELRDIRRGVQQRPTLE TVRRAAAMLGASAAEIKPDAHFTDLGGDSLSALTFSNFLHDLFEVDVPVGVIVSAANTLGSVAEHI DAQLAGGRARPTFATVHGKGSTTIKASDLTLDKFIDEQTLEAAKHLPKPADPPRTVLLTGANGWLGR FLALEWLERLAPAGGKLITIVRGKDAAQAKARLDAAYESGDPKLAGHYQDLAATTLEVLAGDFSEPR LGLDEATWNRLADEVDFISHPGALVNHVLPYNQLFGPNVAGVAEIIKLAITTRIKPVTYLSTVAAA GVEPSALDEDGDIRTVSAERSVDEGYANGYGNSKWGGEVLLREAHDRTGLPVRVFRSDMILAHQKYT GQVNATDQFTRLVQSLLATGLAPKSFYELDAQGNRQRAHYDGIPVDFTAESITTLGGDGLEGYRSYN VFNPHRDGVGLDEFVDWLIEAGHPITRIDDYDQWLSRFETSLRGLPESKRQASVLPLLHAFARPGPA VDGSPFRNTVFRTDVQKAKIGAEHDIPHLGKALVLKYADDIKQLGLL |
| P39135 | SEQ ID NO: 69 | MKIYGIYMDRPLSQEENERFMSFISPEKREKCRRFYHKEDAHRTLLGDVLVRSVISRQYQLDKSDIR FSTQEYGKPCIPDLPDAHFNISHSGRWVICAFDSQPIGIDIEKTKPISLEIAKRFFSKTEYSDLLAK DKDEQTDFYHLWSMKESFIKQEGKGLSLPLDSFSVRLHQDGQVSIELPDSHSPCYIKTYEVDPGYK MAVCAAHPDFPEDITMVSYEELL |
| AB213459.1 | SEQ ID NO: 70 | MAQYDVADRSAIVTGGGSGIGRAVALTLAASGAAVLVTDLNEEHAQAVVAEIEAAGGKAAALAGDVT DPAFGEASVAGANALAPLKIAVNNAGIGGEAATVGDYSLDSWRTVIEVNLNAVFYGMQPQLKAMAAN GGGAIVNMASILGSVGFANSSAYVTAKHALLGLTQNAALEYAADKVRVVAVGPGFIRTPLVEANLSA DALAFLEGKHALGRLGEPEEVASLVAFLASDAASFITGSYHLVDGGYTAQ |
| Q84H78 | SEQ ID NO: 71 | MRVFAVQPEDTTIHDLQVPTPSPEGREVLLRVVRAGVCHTDTHLRAGGYDLGSRGMMSMKERGIEYP MVLGHEVVGVVEKVGDGVESVQVGDIRLIYPWIGCGECRQCRAGHDNRCAAGKNLGVARHGGYAENI LVPDEKYLVDIDGLDPSWAATLACSGLTAYSAVDKALPLEPDEPVVVFGAGGLGLTAIAILRSRGHR NICAVDVAERNLALARDMGASSTVLSGTGSGADDIRGAAGGPAGAVIDFVNNGATATTAFEVLAKAG IMIQVGLFGGEVTLPTALLALRMIRIEGSFVGTLVQMQDLVRLAQRGELPHIPVVERSLSAAAVSQA LDDLTAGGVAGRIVLTA |
| Q7WVD0 | SEQ ID NO: 72 | MHCYCVTHHGQPLEDVEKEIPQPKGTEVLLHVKAAGLCHTDLHLWEGYYDLGGGKRLSLADRGLKPP LTLSHEITGQVVAVGPDAESVKVGMVSLVHPWIGCGECNYCKRGEENLCAKPQQLGIAKPGGFAEYI IVPHPRYLVDIAGLDLAEAAPLACAGVTTYSALKKFGDLIQSEPVVIIGAGGLGLMALELLKAMQAK GAIVVDIDDSKLEAARAAGALSVINSRSEDAAQQLIQATDGGARLILDLVGSNPTLSLALASAARGG HIVICGLMGGEIKLSIPVIPMRPLTIQGSYVGTVEELRELVELVKETHMSAIPVKKLPISQINSAFG DLKDGNVIGRIVLMHEN |
| D8GL45 | SEQ ID NO: 73 | MENFIFKNATEIIFGKDTENLVGSKVKEYSKSDKILFCYGGGSIKRSGLYDRVIKSLKENGIEFIEL PGIKPNPRLGPVKEGIRLCRENNIKFVLSVGGGSSADTAKAIAVGVPYKGDVWDFYTGKAEVKEALP VGVVITLPATGTESSNSSVIMNEDGWFKKGLNTVLIRPAFSIMNPELTFTLPEYQTACGACDIMAHI MERYFTNVKHVDITDRLCEAALRNVINNAPIVLKDPKNYDARAEIMWTGTIAHNDVLSAGRIGDWAS HKIEHELSGETDIAHGAGLAIVFPPAWMKYVYKHDINRFVQFAVRVWDVDLSYSSCEDIVLEGIRRMT AFFKSMGLPVTLKEGSIGEDKIEEMANKCTDNGTKTVGQFVKLNKDDIVKILNLAK |

-continued

Certain Sequences

| Uniprot or Genbank ID | Sequence ID Number | Sequence Information |
|---|---|---|
| Q04944 | SEQ ID NO: 74 | MLSFDYSIPTKVFFGKGKIDVIGEEIKKYGSRVLIVYGGGSIKRNGIYDRATAILKENNIAFYELSG VEPNPRITTVKKGIEICRENNVDLVLAIGGGSAIDCSKVIAAGVYYDGDTWDMVKDPSKITKVLPIA SILTLSATGSEMDQIAVISNMETNEKLGVGHDDMRPKFSVLDPTYTFTVPKNQTAAGTADIMSHTFE SYFSGVEGAYVQDGIAEAILRTCIKYGKIAMEKTDDYEARANLMWASSLAINGLLSLGKDRKWSCHP MEHELSAYYDITHGVGLAILTPNWMEYILNDDTLHKFVSYGINVWGIDKNKDNYEIAREAIKNTREY FNSLGIPSKLREVGIGKDKLELMAKQAVRNSGGTIGSLRPINAEDVLEIFKKSY |
| Q9R2F4 | SEQ ID NO: 75 | MNYPNIPLYINGEFLDHTNRDVKEVFNPVNHECIGLMACASQADLYALESSQQAFLRWKKTSPITR SEILRTFAKLAREKAAEIGRNITLDQGKPLKEAIAEVTVCAEHAEWHAEECRRIYGRVIPPRNPNVQ QLVVREPLGVCLAFSPWNFPFNQAIRKISAAIAAGCTIIVKGSGDTPSAVYAIAQLFHEAGLPNGVL NVIWGDSNFISDYMIKSPIIQKISFTGSTPVGKKLASQASLYMKPCTMELGGHAPVIVCDDADIDAA VEHLVGYKFRNAGQVCVSPTRFYVQEGIYKEFSEKVVLRAKQIKVGCGLDASSDMGPLAQARRMHAM QQIVEDAVHKGSKLLLGGNKISDKGNFFEPTVLGDLCNDTQFMNDEPFGPIIGLIPFDTIDHVLEEA NRLPFGLASYAFTTSSKNAHQISYGLEAGMVSINHMGLALAETPFGGIKDSGFGSEGGIETFDGYLR TKFITQLN |
| Q8GEZ8 | SEQ ID NO: 76 | MISKGFSTQTERINILKAQILNAKPCVESERAILITESFKQTEGQPAILRRALALKHILENIPITIR DQELIVGSLTKEPRSSQVFPEFSNKWLQDELDRLNKRTGDAFQISEESKEKLKDVFEYWNGKTTSEL ATSYMTEETREAVNCDVFTVGNYYYNGVGHVSVDYGKVLRVGFNGIINEAKEQLEKNRSIDPDFIKK EKFLNSVIISCEAAITYVNRYAKKAKEIADNTSDAKRKAELNEIAKICSKVSGEGAKSFYEACQLFW FIHAIINIESNGHSISPARFDQYMYPYYENDKNITDKFAQELIDCIWIKLNDINKVRDEISTKHFGG YPMYQNLIVGGQNSEGKDATNKVSYMALEAAVHVKLPQPSLSVRIWNKTPDEFLLRAAELTREGLGL PAYYNDEVIIPALVSRGLTLEDARDYGIIGCVEPQKPKGTEGWHDSAFFNLARIVELTINSGFDKNK QIGPKTQNFEEMKSFDEFMKAYKAQMEYFVKHMCCADNCIDIAHAERAPLPFLSSMVDNCIGKGKSL QDGGAEYNFSGPQGVGVANIGDSLVAVKKIVFDENKITPSELKKTLNNDFKNSEEIQALLKNAPKFG NDIDEVDNLAREGALVYCREVNKYTNPRGGNFQPGLYPSSINVYFGSLTGATPDGRKSGQPLADGVS PSRGCDVSGPTAACNSVSKLDHFIASNGTLFNQKFHPSALKGDNGLMNLSSLIRSYFDQKGFHVQFN VIDKKILLAAQKNPEKYQDLIVRVAGYSAQFISLDKSIQNDIIARTEHVM |
| Q8GEZ7 | SEQ ID NO: 77 | MSKEIKGVLFNIQKFSLHDGPGIRTIVFFKGCSMSCLWCSNPESQDIKPQVMFNKNLCTKCGRCKSQ CKSAAIDMNSEYRIDKSKCTECTKCVDNCLSGALVIEGRNYSVEDVIKELKKDSVQYRRSNGGITLS GGEVLLQPDFAVELLKECKSYGWHTAIETAMYVNSESVKKVIPYIDLAMIDIKSMNDEIHRKFTGVS NEIILQNIKLSDELAKEIIIRIPVIEGFNADLQSIGAIAQFSKSLTNLKRIDLLPYHNYGENKYQAI GREYSLKELKSPSKDKMERLKALVEIMGIPCTIGAE |
| A5VMB2 | SEQ ID NO: 78 | MKRQKRFEELEKRPIHQDTFVKEWPEEGFVAMMGPNDPKPSVKVENGKIVEMDGKKLEDFDLIDLYI AKYGINIDNVEKVMNMDSTKIARMLVDPNVSRDEIIEITSALTPAKAEEIISKLDFGEMIMAVKKMR PRRKPDNQCHVTNTVDNPVQIAADAADAALRGFPEQETTTAVARYAPFNAISILIGAQTGRPGVLTQ CSVEEATELQLGMRGFTAYAETISVYGTDRVFTDGDDTPWSKGFLASCYASRGLKMRFTSGAGSEVL MGYPEGKSMLYLEARCILLTKASGVQGLQNGAVSCIEIPGAVPNGIREVLGENLLCMMCDIECASGC DQAYSHSDMRRTERFIGQFIAGTDYINSGYSSTPNYDNTFAGSNTDAMDYDDMYVMERDLGQYYGIH PVKEETIIKARNKAAKALQAVFEDLGLPKITDEEVEAATYANTHDDMPKRDMVADMKAAQDMMDRGI TAIDIIKALYNHGFKDVAEAILNLQKQKVVGDYLQTSSIFDKDWNVTSAVNDGNDYQGPGTGYRLYE DKEEWDRIKDLPFALDPEHLEL |
| A5VMB1 | SEQ ID NO: 79 | MADIDENLLRKIVKEVLSETNQIDTKIDFDKSNDSTATATQEVQQPNSKAVPEKKLDWFQPVGEAKP GYSKDEVVIAVGPAFATVLDKTETGIPHKEVLRQVIAGIEEEGLKARVVKVYRSSDVAFCAVQGDHL SGSGIAIGIQSKGTTVIHQKDQDPLGNLELFPQAPVLTPETYRAIGKNAAMYAKGESPEPVPAKNDQ LARIHYQAISAIMHIRETHQVVVGKPEEEIKVTFD |
| A5VMB0 | SEQ ID NO: 80 | MMSEVDDLVAKIMAQMGNSSSANSSTGTSTASTSKEMTADDYPLYQKHRDLVKTPKGHNLDDINLQK VVNNQVDPKELRITPEALKLQGEIAANAGRPAIQKNLQRAAELTRVPDERVLEMYDALRPFRSTKQE LLNIAKELRDKYDANVCAAWFEEAADYYESRKKLKGDN |
| A5VMA9 | SEQ ID NO: 81 | MATEKVIGVDIGNSSTEVALADVSDSGQVHFINSGIAPTTGIKGTKQNLVGIRDSITQVLNKSNLTI DDIDLIRINEATPVIGDVAMETITETVVTESTMIGHNPNTPGGIGTGAGITVRLLDDLLKKTDKSKNY IVVVPKDIDFEDVAKLINAYVASGYKITAAILRNDDGVLVDNRLNHKIPIVDEVAMIDKVPLNMLAA VEVAGPGQVISQLSNPYGIATLFGLTPEETKNIVPVSRALIGNRSAVVIKTPAGDVKARVIPAGKII INGDTGKEEVGVSEGADAIMKKVSSFRHINNITGESGTNVGGMLENVRQTMADLTGKKNDEIAIQDL LAVDTQVPVEVRGGLAGEFSNESAVGIAAMVKSDHLQMEVIAKLIEKEFNTKVEIGGAEVESAIRGA LTTPGTDKPIAILDLGAGSTDASIINKENNTVAIHLAGAGDMVTMIINSELGLNDIHLAEDIKRYPL AKVENLFQIRHEDGSVQFFKDPLPSSLFAKVVVIKPDGYEPVTGNPSIEKIKLVRQSAKKRVFVTNA LRALKYVSPTGNIRDIPFVVIVGGSALDFEIPQLVTDELAHFNLVAGRGNVRGVEGPRNAVATGLIL RYGEERRKRYEQR |
| A5VMA8 | SEQ ID NO: 82 | MNNDDSQRPSIVVGLENGITIPDSVKPLFYGIEEEQIPVSVRKININDTVERAYQSALASRLSVGIA FEGDHFIVHYKNLKENQPLFDMTINDKKQLRILGANAARLVKGIPFKEMANR |
| Q6QBS4 | SEQ ID NO: 83 | MYTVGDYLLDRLHELGIEEIFGVPGDYNLQFLDQIISREDMKWIGNANELNASYMADGYARTKKAAA FLTTFGVGELSAINGLAGSYAENLPVVEIVGSPTSKVQNDGKFVHHTLADGDFKHFMKMHEPVTAAR TLLTAENATYEIDRVLSQLLKERKPVYINLPVDVAAAKAEKPALSLEKESSTTNTTEQVILSKIEES LKNAQKPVVIAGHEVISFGLEKTVTQFVSETKLPITTLNFGKSAVDESLPSFLGIYNGKLSEISLKN FVESADFILMLGVKLTDSSTGAFTHHLDENKMISLNIDEGIIFNKVVEDFDFRAVVSSLSELKGIEY EGQYIDKQYEEFIPSSAPLSQDRLWQAVESLTQSNETIVAEQGTSFFGASTIFLKSNSRFIGQPLWG |

-continued

Certain Sequences

| Uniprot or Genbank ID | Sequence ID Number | Sequence Information |
|---|---|---|
| | | SIGYTFPAALGSQIADKESRHLLFIGDGSLQLTVQELGLSIREKLNPICFIINNDGYTVEREIHGPT<br>QSYNDIPMWNYSKLPETFGATEDRVVSKIVRTENEFVSVMKEAQADVNRMYWIELVLEKEDAPKLLK<br>KMGKLFAEQNK |
| KMK64081.1 | SEQ ID NO: 84 | MSAKRTLLTVDDVTGCWAIMPTPAKDDASDWRTEFSVDLDETARVANALVESGVDGILALGTFGEGA<br>TLTWEEKEAYVRTVVDAVAGRVPFFAGTTSLNTRETIRQMRIVRDIGVDGVMLGIPMWVEADTATAV<br>QFYRDVTEACPDVAICAYANPEAFKYEFGRAFWAQVSDLPQIVSAKYLNMGGLYPDLNLSKRRIRLM<br>PLDVDYYAAARIDPDHCTAFWTSGAVCGPEPAILLRDLMEKARKSGDWAEAKALTDRIGMTYKTLFP<br>NGSFKEFSRYNISIEKIRMDAAGWMKAGPCRPPYHVTPEPILEGGRIAGQKWAELAESLRAGN |
| WP_070028041.1 | SEQ ID NO: 85 | MITAAEINGMYGIIPTPALPGAERLDARDTVDVDETARVVDRLIRDGVSGIIALGTTGECPALSEDD<br>FDVVTDTVVEAVAGRVPVFVGATGAGGHGTARRLRKVAASGATGALLGLPMWQPLTTAMAVEYYAQA<br>SAAFPDLALMVYANARAFRYTFPVEFWQGVSSQAPTVTSAKVSRAPQLERMLEVTGKKVNFIPSDMV<br>VHDFAARAPQTTTACWATAAGMGPEPSIALMDALRRGDSEAAGRAVAGIAWANEPLAHLFADQEIFA<br>SYNTQIEKSRIAAAGYCRPGPVRSPYHHLPEEYAAASAVCGQRWRELRERIAAGTNDQK |
| KZL92449.1 | SEQ ID NO: 86 | MIKGYSLPLTPKGTSNIVPAPPWHYVGNVLAIEYEAYAENIAAFLPEGLEFSSNQCAIYFIEWQYCS<br>EFGEEHLDPVNSQYKETIVLVSANYKGTPVSYCPFIWVDQDLSLMRGLIQGWPKQLGETYITRPYNL<br>PSKAASNLEKGGKLGATLSVKGRRLVDARITVNKKTETLPNPTFAQAINLRHPPELVLGRHNQPLIH<br>ELVQLKSRDLHISPIWKGDAILNFFDHPFIELSDLKPTKVKNSYYFSAALTVDDLSQLEV |
| A0A1G9R408 | SEQ ID NO: 87 | MRAVVVRSHGGPEVLVAEELDRPEPGPGAVLVDVAAAGVNYIDTYHREGVYPIPTPFTLGLEGAGTV<br>AALGEGVTEFAVGDRVAWASAIGSYAQQVAAPAAQLVPVPSTVDLEIAAGAMLQGMTAHYLTASTHP<br>IAEGDVALVHAAAGGMGLLLTQMIKARGGRVIGTVSTAEKEKLAREAGADEVIRYTEQDVAQRVREL<br>TDGVGVHVVYDGVGKDTFDASLASLRPRGLLALYGAASGAVPPFDAQRLNAGGSLFLTRPSLGHHTA<br>TREELLWRAGEVFDAIQAGELDIAIGGRYALDSARQAHEDLQGRRTTGKLLLTTS |
| G4Q8R5 | SEQ ID NO: 88 | MKAIVMKEFGGPEVLKYVDVPDPVPEANEVLIKLAFCGVNPNETYVRTGTYNFYKPELPYTPGYDGA<br>GVIEKVGAGVTHVKVGDRVFVAALLAKRNTGTYAQKVVCDADSVHKLPDFISFEEGASFGIPAMAAY<br>RALFHRAHIKAGEIVMIHGAEGGVGSLAVQMAKAVGAIVIGTGTTPEGLDIVRSFGADYAIYHLKAD<br>NQDELMELTKGKGPDVIIEFLANVNLQTDLKVIAKYGRIVVVGNRGTIEINPRLAMANESTILGMAL<br>WNAPANEYRESLFALRAFMQSGAVRAKVGKQLLLKDAAQAHNEIINGLAKGKMILKIE |
| ANA98723.1 | SEQ ID NO: 89 | MRAIEVPVTGGPEVLTLVEKTAPTPGPGEVLIDVDAVGVNFRDIYLRNGSYAAPLPHIPGSEVTGVV<br>SAVGEGVENLAPGDRVASPVAAWGYAESTTAPADYTAKVPAGLSSEVAASALLQGITAHYLLTSVYP<br>VAAGDTVLVHAGAGGMGLLLTQWASHRGVRVITTVSSAAKEKLSREAGAAEVLPYPDPTDPAEFAEK<br>ILELTSGEGVAVAYDGVGKSTFEASLAAVRVRGLIALYGAASGQVPPFDPQRLTAKSAVLTRPTMGH<br>FIRTPAEFAWRADDVLDLVSRGTLKITVGASYPLEQAAQAHIDLEARKTTGSVVLVP |
| K0EUQ3 | SEQ ID NO: 90 | MRAIQVSEHGGPEVLHHVELPDPTIDADQLLVDVQATGINFIDTYIRTGRYPQDVPYVPGSEATGVV<br>AEVGANVTEFAVGDRVAWASAPGSYAERVAVRADVAVEVPDGVEPPVAASALLQGMTAHYLLESIYT<br>PEPGETVLVHAGAGGVGLILTQLAVARGARVITTVSSDVKEKLSREAGATEVLRYGDDLADEVRTLT<br>DGVGVAAVYDGVGASTFEASLRSLRVRGMLALFGAASGPVPPFDLQRLNGAGSLFVTRPSLAFYTRD<br>RAELLWRATDIFTAIAEGTLQIRIGATYPLAEAEQAHRDLESRKTTGSIVLLP |
| A0A061CRS8 | SEQ ID NO: 91 | MAKRIQFSQHGGSEVLEYRDYQPAAPGPREVRVANKAIGLNFIDTYFRSGLYQPPALPSSLGTEGAG<br>VVEAIGSEVEGLKVGDRVAYATGPLGAYSELHVLPADNLVHLPDSISFEQAAAVMLKGLTVQYLLRQ<br>TYELKGGETILFHAAAGGVGSFACQWAKALGVNLIGTVSSAKKAALAKELGAWETIDYSHENVVQRV<br>LELTDGAKCPVVVYDGVGKDTWETSLDCVAPRGLLVSFGNASGAVTGVNLGILAQKGSLYVTRPTLAS<br>YANTPQNLQAMADELFAMISSGKLQVDISNRYALKDAAAAQDALSSRQTTGSTILLP |
| Q9A212 | SEQ ID NO: 92 | MLAVQAVRTGGPEVLEVVDLPLPSPGPGQILVRHQAVGLNYIDTYHRSGLYPVKTPLVIGLEAAGVV<br>ESVGEAVTRFKVGDRVAYNGTMGAYAQAAVVPAERAVLVPDGVSLEVAAAALLKGMTAEFLVRRCFH<br>VKQGDWVLVHAAAGGVGQILVQWCKALGATVVATVGSTAKATIARDLGADHVIDYSHEDVAARVAEL<br>TGGRGVAVVYDGVGKDTWEASLASLARRGMLVTFGNASGPAPAFPPLALAPKSAFVTRPKLFDYIVT<br>TEELDESAQALFAVIASGAIKIDIGQTFPLAEARAAHEALEGRRTTGATLLLP |
| A0A1I6RWW2 | SEQ ID NO: 93 | MRAIRVTSHGGPEALEVSEVEVPEPGPGQLLVDVAASGVNFIDTYQRSGVYSVPLPFTPGSEGAGEI<br>VAVGPDVDGFAVGERVAWAMTPGSYAEKALVPARAAVKIPDGVDTRTAAAATLQGMTAHFLVTSTHE<br>IKTGETALVHAAAGGMGLLLTQLIKSKGGNVIGTVSTDEKERLAREAGADEIIRYTEADVAAEVKDL<br>TDGRGVDVVYDGVGKSTFEASLASLRPRGTLALFGGASGQVPPFDPQRLNGAGSLFLTRPSLAHHVL<br>TREELEWRAGEVFGWISSGALHIRVSGTYSLEDAARAHEDLEGRRTTGKLLILP |
| WP_026197277.1 | SEQ ID NO: 94 | MTNAIRVHETGGPEVLRLDEVTREAGAGQLLVRVEAAGVNFIDTYQRSGVYSVELPHALGLEGAGTV<br>EAVGDEASFDTPGDRVAWVAAGSYAEHTVVPVERAVRIPDDVDTKTAGALMLQGLTAHYLLRSTYR<br>VDETDTVLVHAAAGGVGLLLVQLAKSLGARVIATASTAEKRALATGAGADEVLGYEGFDTKLRELTG<br>GIGVSVVYDGVGKDTFDASLASIRPRGYLVLFGGSSGQVPPFDLQRLNAAGSLFVTRPSLGPYIADR<br>TEYEWRVGELFEAVGNGSLNVRIGGSYPLAEAANAHRDLEGRKTTGKLLLVP |
| Q5NKZ3 | SEQ ID NO: 95 | MSEAYAIIAEKAGGPEVLVKKPLDLGKMKPEAGQVLLRHQAIGLNFIDIYHRSGLYKQDFPANLGCE<br>AAGVIEVGDKVKGFKAGDRVAVFTSKPGAYATHRIVDASELVALPDDISAETAAAVLLKGMTSWML<br>AEKCLAHAAIEGEAPKVMVLAAAGGVGSLLIPWLKYLGVTVFAHTSTEEKAAKVKANGADYVTTLPY<br>SDLPDWVRKQNHGEGVHAVLDSVGADSWKSSIASLRKKGLWVVYGNASGPVPALSPLELSKAGSIYT<br>SRPRLIDYVDNSVDLTTASQKLFALLRKNILKVEINQRFPLTEVAKAHQLLESRKTTGSTVLIP |

Certain Sequences

| Uniprot or Genbank ID | Sequence ID Number | Sequence Information |
|---|---|---|
| WP_012333034.1 | SEQ ID NO: 96 | MPKAIRVHEYGGPEVMRYEEVDLPAPGPGQIRVRQRAVGVNFIDIYFRSGLYKAPQLPFTPGNEGTG<br>EVVAVGEGVAGLAVGDRVAYGSAAQTYAQEAVIEARMAVKVPDGIDDATAAAMMLKGLTAQYLLRKT<br>YRVQPGDTILFHAAAGGVGLIATQWAKHLGATVIGTVGSRDKAELAKQHGCDHVILYRDEDFAARVK<br>EITGGKGCAVVYDGVGQATYPASLDCLRPFGMFVSFGNASGVIENFNIGLLGPKGSLYATRPTLFTH<br>VAERASLEAMADDLFGVVGSGAVRIPVHSRVPLAEAAQVHRDLAGRQTTGATVLIP |
| WP_136898000.1 | SEQ ID NO: 97 | MAKAIRFEKTGGPEVMQWVDVEVGDPSGGEVRIKQHAVGLNYIDVYFRTGLYPMPLPGGLGMEAAGE<br>VTAVGPDVEGLRVGDRVAYVARPPGAYAQERVLPAAALVKLPGALGYDDAASAMLQGLTAQYLLRRT<br>YRVKAGDTILIQAAAGGVGLFVCQWAKALGATVIGTVSSDEKAELAKAHGCDYPIVYTRESFTKRVK<br>EITGGAGVPVVYDSIGKDTFTGSLDCLAPLGLFVSFGNASGPLPPIDSSEFAGRGSLFFTRPTLFTH<br>IAKRSDYDAMAAELFDVIVSGKVKTMIRQRFPLAEVGQAHADLEARRTTGSTILIP |
| WP_003431407.1 | SEQ ID NO: 98 | MKILVFGARDYEEPVIKKWSEEHKDVQVDIYPENMTEENVVKAKGYDGISIQQTNYIDNPYIYETLK<br>DAGVKVIASRTAGVDMIHFDLVNENGLIVTNVPSYSPNAIAELAVTQAMNLLRKTPLVKKKVCEGDY<br>RWIAELLGTEVRSITVGVIGTGKIGATSAKLFKGLGANVIAFDQYPNSDLNDILTYKDSLEDLLKEA<br>DLITLHTPLLEGTKHMINKDTLAIMKDGAYINTGRGGLINTGDLIEALESGKIRAAALDTFETEGL<br>FLNKKMNPGELTDPEINKLLSMEQVIFTHHLGFFTSTAIENIVYSSLSSAVEVIKTGTATNRVN |
| BAL51292.1 | SEQ ID NO: 99 | MRITIAGAGAMGSRFGLMLHKGGNEVTLIDGWPEHVKAIKDHGLRANYNGEELTAHLSVELQSEISS<br>KEKTDLIILFTKAMQLDKMLQDIKPLIDEHTKVLCLLNGIGHEDTIEKYVSKNIFIGNTMWTAGLE<br>GPGKAKLFGDGSVELQNLISGEEETAKKLAEILSESGLNAKYSNNIHYSIYRKACVNGTMNGLCTIL<br>DTNMAGLGETKPAHDMVVTIVNEFAAVAKFENVNLDIAEVVQHVETCFDPATIGLHYPSMYQDLIKN<br>NRLTEIDYINGAVSRKGKKYNVATPYCDFLTQLVHSKEELLKAK |
| AKC64094.1 | SEQ ID NO: 100 | MKILMYSVREHEKPAIKKWLEANPGVQIDLSDEALSEDTVCKVKDYDGIAIQQTNSIGGETVYSTLK<br>KYGIRQIASRTAGVDMIDLKMASENNIIVTNVPAYSPNAIAELAVTHTMNLLRNIKTVNKRIAFGDY<br>RWSADLIAREVRSITVGVVGTGKIGRTSAKLFKGLGANVIGYDAYPDKKLEENNLLTYKDSLEDLLK<br>EADVVTLHTPLLESTKHMINKNNLKYMKPNAFIVNTGRGGIINTEDLIEALEENKIAGAALDTFENE<br>GLFLNKVIDPTKIPDPQLDKLLKMDQVLITHHVGFFTTTAVQNMVDTSLDSVMEVLKTNDSVNKAN |
| WP_002876862.1 | SEQ ID NO: 101 | MTKIAMYNVSPIEVPYIEDWAKKNDVEIKTTDQALTSATVDLAEGCSSVSLKPLGPVDEEVVYQKLS<br>EYGVKCIGLRIVGFNTINFDWTKKYNLLVTNVPVYSPRAIAEMTVTQAMYLLRKIGEFRYRMDHDHD<br>FTWPSNLISNEIYNLTVGLIGVGHIGSAVAEIFSAMGAKVIAYDVAYNPEFEPPLTYTDFDTVLKEA<br>DIVSLHTPLLPSTENMIGEKQLKEMKKSAYLINCARGELVDTGALIKALQDGEIAGAGLDTLAGESS<br>YFGHTGLTDSEIPEDYKTLAKMPNVVITPHSAFYTETSIRNMVQICLTDQLTIAKGGRPRSIVNL |
| AGP69017.1 | SEQ ID NO: 102 | MTKILMYTVRPDERAAIDAWVAANDIQVDTNTVEFGPDTVDLAKGYDGVVIQQHGAIPEEMVYQKLK<br>AFGIKQLTLRITGYDIVNLDAATANGLVVTNVPAYSPRSVSELVLAQVMRLIRHLGEASAREAKDDY<br>SWTGLEAPEIHNLTVGIIGAGKIGSAVARIFRALGATVIVSDPVKRPELADTVSYVDLNTLLTTSDV<br>VTVHTPLDGLTTHLIDADALRKMKSTAYLINAARGPIVDTEALIKALNDHTIAGAALDTIEGEAGIF<br>GEDRSQTLVDNQTLETLKAMPNVEISPHIGFYTDAAVKNMIDISLDDVKTILEGGKSAHQVN |
| WP_003640741.1 | SEQ ID NO: 103 | MKIIAYAVRDDERPFFDTWMKENPDVEVKLVPELLTEDNVDLAKGFDGADVYQQKDYTAEVLNKLAD<br>EGVKNISLRNVGVDNLDVPTVKARGLNISNVPAYSPNAIAELSVTQLMQLLRQTPLFNKKLAKQDFR<br>WAPDIAKELNTMTVGVIGTGRIGRAAIDIFKGFGAKVIGYDVYRNAELEKEGMVYDTLDELYAQADV<br>ITLHVPALKDNYHMLNADAFSKMKDGAYILNFARGTLIDSEDLIKALDSGKVAGAALDTYEYETKIF<br>NKDLEGQTIDDKVFMNLFNRDNVLITPHTAFYTETAVHNMVHVSMNSNKQFIETGKADTQVKFD |
| AKC64095.1 | SEQ ID NO: 104 | MKILAYCVRPDEIDSFKNFSEKYGHTVDLIPDSFGPSVAHLAKGYDGISILGNDTCNREALEKIKDC<br>GIKYLATRTAGVNNIDFDAAKEFGINVANVPAYSPNSVSEFTVGLALSLTRKIPFALKRVELNNFAL<br>GGLIGVELRNLTLGVIGTGRIGLKVIEGFSGFGMKKMIGYDIFENEKAKEYIEYKSLDEVYKEADII<br>TLHAPLTDDNYHMIGKESIAKMKDGVFIINAARGALIDSEALIEGLKSGKIAGAALDSYEYEQGVFH<br>NNKMNEIMKDDTLARLKSFPNVVITPHLGFYTDEAVSNMVEITLMNLQEFELKGTCKNQRVCK |
| AKC64094.1 | SEQ ID NO: 105 | MKILMYSVREHEKPAIKKWLEANPGVQIDLSDEALSEDTVCKVKDYDGIAIQQTNSIGGETVYSTLK<br>KYGIRQIASRTAGVDMIDLKMASENNIIVTNVPAYSPNAIAELAVTHTMNLLRNIKTVNKRIAFGDY<br>RWSADLIAREVRSITVGVVGTGKIGRTSAKLFKGLGANVIGYDAYPDKKLEENNLLTYKDSLEDLLK<br>EADVVTLHTPLLESTKHMINKNNLKYMKPNAFIVNTGRGGIINTEDLIEALEENKIAGAALDTFENE<br>GLFLNKVIDPTKIPDPQLDKLLKMDQVLITHHVGFFTTTAVQNMVDTSLDSVMEVLKTNDSVNKAN |

SEQUENCE LISTING

```
Sequence total quantity: 106
SEQ ID NO: 1           moltype = AA  length = 265
FEATURE                Location/Qualifiers
source                 1..265
                       mol_type = protein
                       organism = Streptomyces bingchenggensis
SEQUENCE: 1
```

```
MKGYTVPLSP RGIANLAPAP PWHYAGTVVG VEFFTDPAAA AATLPEGLTP DPDSAGRGVA    60
MFIDWQYSST GLEYLDPARS QYREFLITLD AHCNGAPVAW CPYIYVDNDA AMARGWVQGF   120
PKKLGAVHQT RAYSVGGPGT PVLGPGGQFG ATASSAGQRI AEAKITLEQP VPDPAALMSR   180
PVINLRHFPR LAAGQHDQPA VHELVMSVLD DTAVSDAWVG TADLAFLPAH GEELADLPVR   240
RTGKGFHFDL AYTVTDLMTL ADHSA                                        265

SEQ ID NO: 2            moltype = AA  length = 334
FEATURE                 Location/Qualifiers
source                  1..334
                        mol_type = protein
                        organism = Pseudomonas putida
SEQUENCE: 2
MSNKIMKTSR LTAEDINGAW TIMPTPSTPD ASDWRSTATV DLEETARIVE ELIAAGVNGI    60
LSMGTFGECA TLTWDEKRDY VSTIVETIRG RVPYFCGTTA LNTREVIRQT RELIDIGANG   120
TMLGVPMWVK MDLPTAVQFY RDVADAVPEA AIAIYANPEA FKFDFPRPFW AEMSKIPQVV   180
TAKYLGIGML DLDLRLAPNI RFLPHEDDYY AAARINPERI TAFWSSGAMC GPATAIMLRD   240
EVVRAKSTGD WAKAKAISDD MRAADSTLFP RGDFSEFSKY NIGLEKARMD AAGWLKAGPC   300
RPPYNLVPED YLAGAQKSGK AWAALHAKYS NELK                              334

SEQ ID NO: 3            moltype = AA  length = 332
FEATURE                 Location/Qualifiers
source                  1..332
                        mol_type = protein
                        organism = Nocardioides sp.
SEQUENCE: 3
MTSPAVTSAD ITGLVGIVPT PSKPGSEAPD AVDTVDLDET ARMVELIVAS GVDVLLTNGT    60
FGEVATLTYE ELLAFNDTVI RTVANRIPVF CGASTLNTRD TIARSLALMG LGANGLFVGR   120
PMWLPLDDEQ LVSYYAAVCD AVPAAAVVVY DNTGVFKGKI SSAAYAALAE IPQIVASKHL   180
GVLSGSDAYA SDLAAVKGRF PLLPTADNWL PSLEAFPGEV PAAWSGDVAC GPEPVMALRR   240
AIAEGLWDDA RAVHEDIAWA TEPLFPGGDI SKFMPYSIQI DRAEFEAAGY IVPGPSRHPY   300
GTAPAAYLEG GAEVGRRWAG IRQKYVATLA EP                                332

SEQ ID NO: 4            moltype = AA  length = 259
FEATURE                 Location/Qualifiers
source                  1..259
                        mol_type = protein
                        organism = Micromonospora sp.
SEQUENCE: 4
MKGYTYPLSP RGVANLAGKP PWHYVGDAVG VEFWTSPEAA AASLPTGLDP DPANPGHGYA    60
VFIDWQFNGA TDDYLDPPFS QYSEFLVLLD AQWQGTPVAW CPIWVDNDA SLARGWVQGF   120
PKKMGSIRQT RAFAIDSPAA PTVGKGGRFA AVMSAGGRRL AETTVTLDRT TDRLPALTRP   180
LVNLRHFPRL SAGQHDNPAV HELTMSVLAN LKFANTWIGT GELRFLPAPR EELADLTPRR   240
VGVGFRGSLS YTVNDLRIL                                               259

SEQ ID NO: 5            moltype = AA  length = 265
FEATURE                 Location/Qualifiers
REGION                  1..265
                        note = Description of Unknown:Actinobacteria bacterium
                         sequence
source                  1..265
                        mol_type = protein
                        organism = unidentified
SEQUENCE: 5
MKGYTVPLSP RGVANLAPAP PWHYAGTVVG VEFFTDPAAA AALPEGLSS DPDSAGRGVA    60
MFIDWQYSST DLEYLDPARS QYREFLVTLD AHYYGAPVAW CPYIYVDNDA AMARGWVQGF   120
PKKLGAVHQT RAYSVGGQGT PVLGPGGQFG ATASAAGQRI AEAKITLEQA VPDPAALMSR   180
PVVNLRHFPR LTAGQHHKPA VHELVMSVLD GAAVSDAWAG TADLAFLPAR GEELADLPIQ   240
RTGRGFHFDL AYTVTDLKTL IDHSN                                        265

SEQ ID NO: 6            moltype = AA  length = 262
FEATURE                 Location/Qualifiers
source                  1..262
                        mol_type = protein
                        organism = Streptomyces gancidicus
SEQUENCE: 6
MLKGYTVPLS PKGEANIAPT PPWHYAGDIV GVEFFTEPAA AEATLPEGLD PDPDTSGRVV    60
AFFVDWQFNG ERDEYLDPVR SQYREFFVLV DARHQGRPVS WCPYIYVDNH HALARGWIQG   120
FPKKAGNVHQ TRVFASPGKA SPTLSPGARF GASVSSDERT LAEARVTLEA PMEDPSALLS   180
RDTINLRHFP TLEAGRYDKP AVHELVRMDY ADQQVADVWT GTSEITLFPA VGEELADLAP   240
VRSGMGFRAS MSYNVTQVEP LL                                           262

SEQ ID NO: 7            moltype = AA  length = 264
FEATURE                 Location/Qualifiers
source                  1..264
                        mol_type = protein
                        organism = Kutzneria sp.
SEQUENCE: 7
MLGYSLPLSA NGTANVVPAP PWHYAGDVVG VEFWTTPAAA AATLPSGLTP DPTTSGHAYA    60
LFVDWQWAGS HQEYLDPVRS QYSEFLILMD AQFQGRAVAW CPYIWVDNDA ALARGWFQGF   120
```

```
PKKLGAIRQT RAFSVPGQAS PVVGPGGQFG ASLSAAGRRL AEAQITLQAP SATLPALGRP    180
IVNLRHFPRL IAGQYDNPSV HELTQSVLDT PVVGNNWTGT STLNFFTAPG EELADLQPVR    240
TGSGFRGSLS YTVTTLKMLS GPDA                                           264

SEQ ID NO: 8              moltype = AA   length = 265
FEATURE                   Location/Qualifiers
source                    1..265
                          mol_type = protein
                          organism = Streptomyces olivochromogenes
SEQUENCE: 8
MKGYTVPLSP RGIANLAPAP PWHYAGTVVG VEFFTDPAAA AATLPEGLTP DPDSAGRGVA     60
MFIDWQYSST GLEYLDPARS QYREFLLTLD AHYNGTPVAW CPYIYVDNDS AMARGWVQGF    120
PKKLGAVHQT RAYSVGGPGT PVLGPGGQFG ATASAAGQRI AEAKVTLEQP VPDPAALMSR    180
PVVNLRHFPR LAAGQHDKPA VHELVMSVLD GVAVSDAWAG TADLAFLPAH GEELADLPVQ    240
RTGRGFHFDL AYTVTDLKTL IDRSN                                          265

SEQ ID NO: 9              moltype = AA   length = 328
FEATURE                   Location/Qualifiers
source                    1..328
                          mol_type = protein
                          organism = Sphingobium xenophagum
SEQUENCE: 9
MARTLMKPDD VKGAWAIIPT PAKDDASDWR ATKTVDLDET ARVVNGLIDA GINGILSMGT     60
LGEAATMTHD EKLDFIKALV DAAAGRVPIF VGTTCLNTRD TIALTRQALD IGADGTMLGV    120
PMWCAPSVDV AVQFYKDLAE AVPEMNIAIY ANPEAFKFDF PRSFWAQVAE IPQVVTAKYI    180
GVAHLLPDLA AIRGRIKLLP IDFDYYGAAR MDESIDAFWS SGAVCDPLVT TTLRDLVSQA    240
RATGDWSAAR AFMGRLGPTA APLFPNGSFK EFSTYNIALE KARMNAGGWM NAGPVRPPYH    300
LCPEPYLEGA RLSGRMWAEL GKALAAEK                                       328

SEQ ID NO: 10             moltype = AA   length = 332
FEATURE                   Location/Qualifiers
source                    1..332
                          mol_type = protein
                          organism = Alcaligenes faecalis
SEQUENCE: 10
MAKSGLLNAS DIHGVWSILP TPSKPDASDW RATNTVDLDE TARAVEGLIA AGANGILSMG     60
TLGECESLTW EEKKVFMQTI VETARGRVPV FVGTTTLNTR DTIEQTRYAH SIGADGTMLG    120
IPMWCNPCVD MAVQYYKDVA EAVPEMNIAI YANTEAFWRS EIRQVVAAKY              180
IGIEFLLQDL HLTKHRMKLL PLDYQYYAAA RMDDFVDAFW SSGTVCGPLV STTLRDKVIA    240
ARRTKDWTDA HAFQGRLVKT AAPFFEDSFK TFSIYNVALE KGRIDAAGWM NAGPVRPPYN    300
DICPASYLDS WKASGQRWAE LHKQLETESS GK                                  332

SEQ ID NO: 11             moltype = AA   length = 328
FEATURE                   Location/Qualifiers
source                    1..328
                          mol_type = protein
                          organism = Novosphingobium aromaticivorans
SEQUENCE: 11
MARELLTAAD VKGAWAIVPT PAKEGASDWR AADTVNVEEA ARMIDGLIEA GVDGILSMGT     60
LGEAATMTLD EKLVFMKTIV DTAAGRVPVF VGTTCINTRD TIALTRKAVD IGATGTMLGV    120
PMWCAPSVDV AVQFYRDVAE AVPDINIAIY ANPEAFKFPD PRTFWGQVAE IPQVVTAKYI    180
GVGTLLPDLA AIKGRIKLLP IDFDYYGAAR MDDSIDAFWT SGAVCHPLVS TTLRDVAAA    240
RASGDWSAAK AFMGRLAPTA ATLFPNGSFK EFSTYNIPLE KARMTAGGWM NAGPCRPPYH    300
LCPENYLEGA RNSGRMWAEL GKALEAER                                       328

SEQ ID NO: 12             moltype = AA   length = 331
FEATURE                   Location/Qualifiers
source                    1..331
                          mol_type = protein
                          organism = Polymorphum gilvum
SEQUENCE: 12
MTRKLLTVDD VNGCWAIMPT PSKPGASDPN AVDTVDLEET ARAAEALVAA GVDGILSLGT     60
FGEAATTTWE EKQAFMRTLV ETVRGRVPVF GGTTSLNTRD TIRMTRAARE IGVDGVMLGL    120
PMWVQPDLAT AVQFFRDVAS ACPDVAICAY ANPEAFKFEF PRAFWAQIAD IPQIVSAKYI    180
HTAGLYADLN LTKRRIRLMP LDVDYYAAAR IDPDACTAFW TSGAVCGPAP AIQLRDLVSK    240
AKKTGDWTGA KKLTDRIGQT YRTLFPNGSF KDFSVYNIGI EKARMDAAGW MKAGPCRAPY    300
SLVPEPYLEG ARESGRQWAK LAAELATERA E                                   331

SEQ ID NO: 13             moltype = AA   length = 333
FEATURE                   Location/Qualifiers
source                    1..333
                          mol_type = protein
                          organism = Burkholderia sp.
SEQUENCE: 13
MIHPKLRIDA SGINGLWPIL PTPAKPNASD WRERSTVDLD ETARIVESLI DAGVDGLLSL     60
GTYGEAHSLL WEEKKAFVGC VLETIRGRIP FFTGTTALNT REVVEQTRAM HDMGVSGTML    120
GVPMWCKTDL ATAVQFFRDV TEACPDTALA IYANTEAFKF EFPRPFWAEI GKMPQAVACK    180
YLGIGMLAVD LELAPNMRFL PNEQDYYAAA RIDPERVTAF WSSGALCGPL PALTLRDRVA    240
RAKSSNDWTS AKEIADRMRA CDVGFFPKGE FSEFSKFNAP LEKARMNTAG YVNAGPCRPP    300
```

```
YHVIPQEYLA GAERSGRAHA ALNAELKQAE HSI                                            333

SEQ ID NO: 14            moltype = AA  length = 330
FEATURE                  Location/Qualifiers
source                   1..330
                         mol_type = protein
                         organism = Paraburkholderia sartisoli
SEQUENCE: 14
MSKQRKQRLG TEDVNGAWVI MPTPAKPEAS DWRATDTVDL DETARIVEAL IDSGVNGILS               60
LGTFGECATL TWEEKQAFIG AVVETTRGRV PFFCGTTALN TREVVRQTRA ALDIGVDGTM              120
LGVPMWSRME VPAAVQFYRD VAEACPEAAI AVYANADAFK FEFPRAFWAQ VAQIPQVVTA              180
KYLGIGMLDL DLTLAPGIRF LPHEDDYYAA ARVAPERVTA FWSSGAMCGP ATAIRLRDEV              240
AKAKQTGDWR LAKELSDAMR RADATLFPRG DFAEFSKYNI AIEKERMNAA GWLRAGPCRP              300
PYHIAPEEYL DGARQSGRAW AELHQQYSDL                                              330

SEQ ID NO: 15            moltype = AA  length = 332
FEATURE                  Location/Qualifiers
source                   1..332
                         mol_type = protein
                         organism = Pseudomonas sp.
SEQUENCE: 15
MMSDMVKPRM TADDVNGVWV IMPTPAKPDA SDWRVENTVD LDETVRIVEN LLASGVNGIM               60
SNGTFGECAT LTWDEKRDFI ATVAETIKGR VPFFCGTTAL HTREVIRQTR EVMRLGADGV              120
MLGLPMWCKM ETPSAIQFYR DVAEAVPDAA IAVYANPEAF KYEFPREFWA QVSEIPQVVT              180
AKYLGIGMLD LDLRLASSIR FLPHEDDYYA AARINPERMT AFWSSAAMCG PATPLKLRDA              240
VADAKVTGKW SVAKAISDEM RKADSMLFPK GDFSEFSKYN IGLEKARMDE AGWLKAGPCR              300
PPYHVIPEMY LEGARKSGRA WAELHAKYSA EG                                           332

SEQ ID NO: 16            moltype = AA  length = 331
FEATURE                  Location/Qualifiers
source                   1..331
                         mol_type = protein
                         organism = Comamonas thiooxydans
SEQUENCE: 16
MAKQKKSRMT AEDIHGAWVI MPTPATPDAS DWRVQHTVDL EETARIVEAL IAAGVNGIFS               60
NGTFGECATL TWEEKRDFIA TVVETARGRV PFFCGTTALH TREVIRQTRE AMDIGASGTM              120
LGVPMWCKME VPTAVQFYRD VAEAVPEAAI AIYANPEAFK FDFPRSFWAQ VSNIPQVITA              180
KYLGIGMLDL DLRLAPSIRF LPHEDDYYAA ARIDPERMTA FWSSGAMCGP ATAIRLRDTV              240
GAAKRSGDWT DAKAISDAMR QADSTLFPRG DFSEFSKFNI GLEKARMDAA GWLKAGPCRP              300
PYHIVPEEHL AGARKSGEAW AALHARYATL D                                            331

SEQ ID NO: 17            moltype = AA  length = 270
FEATURE                  Location/Qualifiers
REGION                   1..270
                         note = Description of Unknown:Verrucomicrobia bacterium
                          sequence
source                   1..270
                         mol_type = protein
                         organism = unidentified
SEQUENCE: 17
MNTAKLIGFN YPLTPKGKST LNPPPPWYYS SDFLDVEFWA QPAAVASLLP NGLEPDPAAN               60
GHCNALFYDW QFSGDNEEYL DPARYQYREF FILVDALFEG RSVSYCPYIF VDNDAALARG              120
WTQGYPKRLG QVFQTRYYAA TSKAGPALAP GSKFAGSLTA AGQLIAEAVV TLRQAVTDPS              180
LLKQKPVINL LHVPRLAADK HDKPAIHELV ENVPSSVKIE QAWIGEGSLT LPVCRGEEIS              240
DLAPLRCGKG IRASMAYVVD DLKTLKDLRN                                              270

SEQ ID NO: 18            moltype = AA  length = 267
FEATURE                  Location/Qualifiers
source                   1..267
                         mol_type = protein
                         organism = Dyella psychrodurans
SEQUENCE: 18
MKSNFFVPMT PRGLSNISPP PPWHYAGDFL IIDFWARPDA VASLLPAELQ PDVKAEGHAQ               60
AYFIDWQYTA AHDEFLDPAR YQYREFFVLV DALFQGKPVA FCPYIFVDND AAIARGWAQG              120
FPKRYGTILQ TRLFAASGPA SPKLAPGGRF GASASTAGQR IARGLVTLEK AVTDPAALGS              180
RPTINLRHFP RLAAGQWERP AVHELVESVM DNFTVADAWM GKGELTLPEC ENEELSDLAP              240
VRCGNGYRMS VSYSVTDLKT LVDHSAK                                                 267

SEQ ID NO: 19            moltype = AA  length = 269
FEATURE                  Location/Qualifiers
source                   1..269
                         mol_type = protein
                         organism = Paraburkholderia oxyphila
SEQUENCE: 19
MLKGYMAPLS PLGKASINPP PPWHYSGDVI GAEFWAEPEA TAATLPPGLD PDPSTAGHGV               60
VLFIDWQFTA QDDEFLDPAR YQYRECLFLV DAVHKGTPVM WCPYIYVDND AALARGWAQG              120
FPKKLASVYQ TRTFAAPSAA AAPVASGSRF GASLSAHGER LAEARITLRQ PVADPKSLLA              180
RPTVNRRYFA SLVAGLHDKP AVDELVLSVT DNLSVADAWA GDAELLFPDA RGEEICAFGP              240
VKVGGGFRFS LAYSVTDLKL LEDLTRLGK                                               269
```

```
SEQ ID NO: 20            moltype = AA  length = 331
FEATURE                  Location/Qualifiers
source                   1..331
                         mol_type = protein
                         organism = Polymorphum gilvum
SEQUENCE: 20
MKRDMLTVDD VTGCWAIMPT PSKPNASDPS ATDTVDLDET ARVAEALVAA GVDGILSLGT    60
LGECATTTWD EKQAYMRTLV ETLRGRIPVF GGTTGLNTRD SIAMTRAARE IGVDGVMLGL   120
PMWVQPDVPT AVQFYRDVAA ACPDVAICVY ANPEAFKFEF PRAFWAQIAE IPQVVSAKYI   180
NIAALYTDLN LTRRRIRLMP LDVDYYAAAR VDPEACSAFW TSGAVCGPAP AIQLRDLVLE   240
ARQSGDWSKA KALTDRIGMT YRTLFPNGSF KEFSVYNIGI EKARMDAAGW MTAGPVRPPY   300
HIVPEAILEG GRESGRQWAK LAAELEREAG R                                  331

SEQ ID NO: 21            moltype = AA  length = 270
FEATURE                  Location/Qualifiers
source                   1..270
                         mol_type = protein
                         organism = Pseudomonas sp.
SEQUENCE: 21
MTQSYTTPLT PRGLSSIAPP PPWHYSGDFL VVEFWADPIA VANTLPAGLT VDSASPGHAS    60
AVFVDWQFTG ENDELLDPAR YQYREFFILL DALHEGQPVS YCPYIFVDND SALMRGLIQG   120
FPKRLGAVHQ TRTFSAPSRA AAQVEPGARF AATASTAGQR IARGEVQLQH KIDDVSKLGF   180
GARPLINLRH FPPRLATGQHN DPAVHELVVS VMDNPNIVDA WAGEGNLVFP QAEGEEVSDL   240
APTRVGAGFR ASMSYTVTDL KALPNATIER                                    270

SEQ ID NO: 22            moltype = AA  length = 267
FEATURE                  Location/Qualifiers
source                   1..267
                         mol_type = protein
                         organism = Afipia sp.
SEQUENCE: 22
MLRGFTVPKS PFGQAALTPP PPWHYAGDVV GVEFWTDPEA TAATLPNGLS PDPNSNGHAV    60
MMFLDWQFTA QDDEYLEPAR YQYREAFILV DAMYRDEPVM WCPYIYVDND AALARGWTQG   120
FPKKMGSIFQ TRSFAASGPA AAPVASGSRF GASLSAHGQR LAEACVTLHR PVENGLSLLS   180
RPTVLLRYFP RLAAGYQDKP AVNELAMSIT DNLTVAGAWI GKGELNFPEA SGEELNALAP   240
KRIESGFRYS LSYSVSDLKI LEDHGSQ                                       267

SEQ ID NO: 23            moltype = AA  length = 331
FEATURE                  Location/Qualifiers
source                   1..331
                         mol_type = protein
                         organism = Pseudomonas kilonensis
SEQUENCE: 23
MSTKRTLMTA NDVQGAWAIM PTSAKDGSES WRMTDSLDLD ATVAAINGLI DSGVDGILTM    60
GTYGEAATLT VDEKKRFMAC LVETVAGRVP CFVGTTTLNT RDTIELTRYA ADLGADGTML   120
GLPMWCAPTL PAAVRFYRDV AEACPDMAQC IYANPEAFRY DFPPPFWAQV ADIPQVVSAK   180
FTSVGHLIQN LEITRGKVRA LPIELDYYAA TRVDDDVCAF WSSGAVCGPT PTIALRDEIT   240
RAKTSGDWTK AKELTDKMWA AVTPMFPAGG FREFSMYNIA IDKMRMQTAG WMRVGPTRPP   300
YDMMPDHIRG GAVEAGKLWA ELAKATVLAG A                                  331

SEQ ID NO: 24            moltype = AA  length = 270
FEATURE                  Location/Qualifiers
source                   1..270
                         mol_type = protein
                         organism = Paraburkholderia hospita
SEQUENCE: 24
MSKQYAVPLS PRGLSSIAPP PPWHYSGDFL IVEFWADPAA VAATLPAGLS VDPSSPGHAT    60
ALFVDWQFTG QNDELLDPAR YQYREFFLLV DALYEGQPVA YCPYIFVDND SAMMRGLIQG   120
FPKRLGAVHQ TRTFAAPSLA AAQVAPGARF AATASTAGQR IARAEVKLTG KVDDPSTVSL   180
AGRPIVNLRH FPPRLAAGQHE TPAVHELVMS IMDDPRMADV WAGEGQLSLP VAEGEEISDL   240
APVRVGAGYR LSMSYTVTDL KTLSDGTQAA                                    270

SEQ ID NO: 25            moltype = AA  length = 331
FEATURE                  Location/Qualifiers
source                   1..331
                         mol_type = protein
                         organism = Celeribacter persicus
SEQUENCE: 25
MKKPLLTVDD VTGCWAIMPT PSKPNGSDIN ATDTVDLDET ARAAEALVAS GVNGILSQGT    60
FGEAATTTWE EKQAFLRTLV ETVDGRVPVF GGTTSLNTRD TIRMTKAVRE IGVDGVMLGP   120
PMWCQPDVPT AVQFFRDVAE ACPDTAICAY ANPEAFKFDF PRAFWAQIAE IPQVVSAKYM   180
NIAALYMDLN LTGRKIRLMP LDMDYYAAAR MDPEACTAFW TSGAICGPEP VIQLRDLVAE   240
AHKTGDWGKA KALTDRIAAT YRTLFPNGSF KEFSVYNIGI EKARIDAAGW MTAGPCRPPY   300
HVIPEPILDG AREAGLQWAK LVSALESEKT A                                  331

SEQ ID NO: 26            moltype = AA  length = 334
FEATURE                  Location/Qualifiers
source                   1..334
```

```
                        mol_type = protein
                        organism = Pseudomonas stutzeri
SEQUENCE: 26
MSNKTMKPAR  LTAEDIHGVW  AIMPTPATPD  ASNWRSTNTV  DLNETARIVE  ELIAAGVNGI   60
LSMGTFGECA  TLTWEEKRDY  VSTIVETIRG  RVPYFCGTTA  LNTREVIRQT  REFMDMGASG  120
TMLGVPMWVK  MDLPTAVQFY  RDVAEAVPEA  AIAIYANPEA  FKFDFPRPFW  AEMSKIPQVV  180
TAKYLGIGML  DLDLKLAPNI  RFLPHEDDYY  AAARINPERM  TAFWSSGSMC  GPATAIMLRD  240
AVDQAKSSGD  WIKAKAISDD  MRAADSTLFP  RGDFSEFSKY  NIGLEKARMD  AAGWLTAGPC  300
RPPYNIVPED  YIAGALKSGK  AWAALHAKYS  KELK                                334

SEQ ID NO: 27           moltype = AA  length = 272
FEATURE                 Location/Qualifiers
REGION                  1..272
                        note = Description of Unknown:Candidatus Rokubacteria
                         bacterium sequence
source                  1..272
                        mol_type = protein
                        organism = unidentified
SEQUENCE: 27
MLKGFNYPLT  PKGKSTLNPS  PPWHYSADFL  DIEFWSEPSA  VTAVLPAGLD  PDPAANGHGH   60
ALFYDWQFAG  ENEEYLDPAR  YQYREFFLLV  DALYEGQPIS  YCPYIFVDND  AAIARGWTQG  120
YPKRLGVFQ   TRYYAATGKA  GPALAPGSKF  AGSLTAGGQR  LAEALVTLKE  PVTDPALLKQ  180
RPIVNLLHYP  QLAADKQDEP  AIHQLVENVP  HDLKIEQAWI  GDGSLTLPVC  RSEELSDLAP  240
VRCGKGIRAS  MAYIVDDLKT  LKDLTKGFSL  LA                                  272

SEQ ID NO: 28           moltype = AA  length = 262
FEATURE                 Location/Qualifiers
source                  1..262
                        mol_type = protein
                        organism = Streptomyces sp.
SEQUENCE: 28
MLKGYTVPLS  PKGEANIAPT  PPWHYAGDIV  GVEFFTEPSA  AEATLPEGLD  PDPDTSGRVV   60
AFFVDWQFNG  EQDEYLDPVR  SQYREFFVLV  DARHQGRPVS  WCPYIYVDNH  HALARGWIQG  120
FPKKAGNVHQ  TRVFASPGKA  SPTLSPGARF  GATVSSDERT  LAEARVTLEA  PMEDPSALLA  180
RDTINLRHFP  TLEVGKYDKP  AVHELVRMDY  ADQQVADVWT  GTSEITLFPA  VGEELADLAP  240
VRPGMGFRAS  MSYNVTQVEP  LG                                              262

SEQ ID NO: 29           moltype = AA  length = 268
FEATURE                 Location/Qualifiers
source                  1..268
                        mol_type = protein
                        organism = Paraburkholderia oxyphila
SEQUENCE: 29
MNKPYAVPLS  PRGLSSIAPP  PPWHYAGDFI  LVEFWADPAA  AAAVLPKGLS  LDPASPGHAT   60
ALFIDWQFTG  SNDEMLDPAR  YQYREFFVLV  DALHEGKPVS  FCPYIFVDND  SAMMRGLIQG  120
FPKRYGQIHQ  TRTFAALSPA  AAPVTAGTRF  AATASAAGQR  LAHAEVKLEA  AVQDVSKLGI  180
AGRPVVNQRY  FPRLAAGQHD  TPAVNELVLS  IMDNAQIADV  WAGEGKLTFP  FAQGEEIADL  240
QPVRVGAGFR  GSMAYSVTDL  KTLVDHTK                                        268

SEQ ID NO: 30           moltype = AA  length = 266
FEATURE                 Location/Qualifiers
source                  1..266
                        mol_type = protein
                        organism = Agrobacterium rhizogenes
SEQUENCE: 30
MLKGFTLPKS  PFGQAALTPP  PPWHYSGDVI  GVEFRTDPSA  TAATLPNGLS  PDPKSNGHAV   60
MMFVDWQFTA  QNDEYLDPAR  YRYREAFVLL  DAVYRNAPVM  WCPYVFVDND  AALARGWTQG  120
FPKKIGSIFQ  TRTYAAASPA  AAPVAPGGRF  GASLSAHGQR  LAEARITLQE  PVEDGLSLLS  180
RPTVLLRYFP  RLAAGYQDKP  AVNELTMAIT  DNLTVADAWI  GDGELNLPEV  HGEELHGLAP  240
IAIESGFRYS  LSYSVTDLKI  LEDHAS                                          266

SEQ ID NO: 31           moltype = AA  length = 262
FEATURE                 Location/Qualifiers
source                  1..262
                        mol_type = protein
                        organism = Escherichia coli
SEQUENCE: 31
MENSFKAALK  AGRPQIGLWL  GLSSSYSAEL  LAGAGFDWLL  IDGEHAPNNV  QTVLTQLQAI   60
APYPSQPVVR  PSWNDPVQIK  QLLDVGTQTL  LVPMVQNADE  AREAVRATRY  PPAGIRGVGS  120
ALARASRWNR  IPDYLQKAND  QMCVLVQIET  REAMKNLPQI  LDVEGVDGVF  IGPADLSADM  180
GYAGNPQHPE  VQAAIEQAIV  QIRESGKAPG  ILIANEQLAK  RYLELGALFV  AVGVDTTLLA  240
RAAEALAARF  GAQATAVKPG  VY                                              262

SEQ ID NO: 32           moltype = AA  length = 302
FEATURE                 Location/Qualifiers
source                  1..302
                        mol_type = protein
                        organism = Escherichia coli
SEQUENCE: 32
```

```
MPQSALFTGI IPPVSTIFTA DGQLDKPGTA ALIDDLIKAG VDGLFFLGSG GEFSQLGAEE    60
RKAIARFAID HVDRRVPVLI GTGGTNARET IELSQHAQQA GADGIVVINP YYWKVSEANL   120
IRYFEQVADS VTLPVMLYNF PALTGQDLTP ALVKTLADSR SNIIGIKDTI DSVAHLRSMI   180
HTVKGAHPHF TVLCGYDDHL FNTLLLGGDG AISASGNFAP QVSVNLLKAW RDGDVAKAAG   240
YHQTLLQIPQ MYQLDTPFVN VIKEAIVLCG RPVSTHVLPP ASPLDEPRKA QLKTLLQQLK   300
LC                                                                 302

SEQ ID NO: 33           moltype = AA  length = 297
FEATURE                 Location/Qualifiers
source                  1..297
                        mol_type = protein
                        organism = Escherichia coli
SEQUENCE: 33
MATNLRGVMA ALLTPFDQQQ ALDKASLRRL VQFNIQQGID GLYVGGSTGE AFVQSLSERE    60
QVLEIVAEEA KGKIKLIAHV GCVSTAESQQ LAASAKRYGF DAVSAVTPFY YPFSFEEHCD   120
HYRAIIDSAD GLPMVVYNIP ALSGVKLTLD QINTLVTLPG VGALKQTSGD LYQMEQIRRE   180
HPDLVLYNGY DEIFASGLLA GADGGIGSTY NIMGWRYQGI VKALKEGDIQ TAQKLQTECN   240
KVIDLLIKTG VFRGLKTVLH YMDVVSVPLC RKPFGPVDEK YLPELKALAQ QLMQERG      297

SEQ ID NO: 34           moltype = AA  length = 256
FEATURE                 Location/Qualifiers
source                  1..256
                        mol_type = protein
                        organism = Escherichia coli
SEQUENCE: 34
MNNDVFPNKF KAALAAKQVQ IGCWSALSNP ISTEVLGLAG FDWLVLDGEH APNDISTFIP    60
QLMALKGSAS APVVRVPTNE PVIIKRLLDI GFYNFLIPFV ETKEEAELAV ASTRYPPEGI   120
RGVSVSHRAN MFGTVADYFA QSNKNITILV QIESQQGVDN VDAIAATEGV DGIFVGPSDL   180
AAALGHLGNA SHPDVQKAIQ HIFNRASAHG KPSGILAPVE ADARRYLEWG ATFVAVGSDL   240
GVFRSATQKL ADTFKK                                                  256

SEQ ID NO: 35           moltype = AA  length = 213
FEATURE                 Location/Qualifiers
source                  1..213
                        mol_type = protein
                        organism = Escherichia coli
SEQUENCE: 35
MKNWKTSAES ILTTGPVVPV IVVKKLEHAV PMAKALVAGG VRVLEVTLRT ECAVDAIRAI    60
AKEVPEAIVG AGTVLNPQQL AEVTEAGAQF AISPGLTEPL LKAATEGTIP LIPGISTVSE   120
LMLGMDYGLK EFKFFPAEAN GGVKALQAIA GPFSQVRFCP TGGISPANYR DYLALKSVLC   180
IGGSWLVPAD ALEAGDYDRI TKLAREAVEG AKL                               213

SEQ ID NO: 36           moltype = AA  length = 205
FEATURE                 Location/Qualifiers
source                  1..205
                        mol_type = protein
                        organism = Escherichia coli
SEQUENCE: 36
MQWQTKLPLI AILRGITPDE ALAHVGAVID AGFDAVEIPL NSPQWEQSIP AIVDAYGDKA    60
LIGAGTVLKP EQVDALARMG CQLIVTPNIH SEVIRRAVGY GMTVCPGCAT ATEAFTALEA   120
GAQALKIFPS SAFGPQYIKA LKAVLPSDIA VFAVGGVTPE NLAQWIDAGC AGAGLGSDLY   180
RAGQSVERTA QQAAAFVKAY REAVQ                                        205

SEQ ID NO: 37           moltype = AA  length = 301
FEATURE                 Location/Qualifiers
source                  1..301
                        mol_type = protein
                        organism = Azotobacter vinelandii
SEQUENCE: 37
MPAPVLAATS PGAGRAIHLI NPAMPAFRAA FEETLMKMPH NAFKAALQRP ETQYGIWAGF    60
ASGYAAEIVA GTGYDWMLID GEHAPNSVPT ILAQLQSVAP YPTQPVVRPV CGDPVLIKQL   120
LDIGAQTLMV PMVESAEQAR ALVRAMRYPP HGIRGVGGGL ARATRWDGVP DYLNTAHEEL   180
CLIVQVESRA GVENVEAIAA VEGVDAVFIG PADLSIGLGH PGDPGHPVQV ELIHHAIEAT   240
RAAGKACGIL APHEEDARRY REWGCRFIAV AIDISLLRQG ALAGLARFRD TPASDAPSRT   300
Y                                                                  301

SEQ ID NO: 38           moltype = AA  length = 312
FEATURE                 Location/Qualifiers
source                  1..312
                        mol_type = protein
                        organism = Corynebacterium glutamicum
SEQUENCE: 38
MASATFTGVI PPVMTPLHAD GSVDVESLRK LVDHLINGGV DGLFALGSSG EAAFLTRAQR    60
KLALTTIIEH TAGRVPVTAG VIETTTARVI ELVEDALEAG AEGLVATAPF YTRTHDVEIE   120
EHFRKIHAAA PELPLFAYNI PVSVHSNLNP VMLLTLAKDG VLAGTKDSSG NDGAIRSLIE   180
ARDDAGLTEQ FKILTGSETT VDFAYLAGAD GVVPGLGNVD PAAYAALAKL CLDGKWAEAA   240
ALQKRINHLF HIVFVGDTSH MSGSSAGLGG FKTALAHLGI IESNMAVPH  QSLSDEETAR   300
IHAIVDEFLY TA                                                      312
```

```
SEQ ID NO: 39            moltype = AA   length = 298
FEATURE                  Location/Qualifiers
source                   1..298
                         mol_type = protein
                         organism = Campylobacter jejuni
SEQUENCE: 39
MDKNIIIGAM TALITPFKNG KVDEQSYARL IKRQIENGID AVVPVGTTGE SATLTHEEHR    60
TCIEIAVETC KETKVKVLAG AGSNATHEAV GLAKFAKEHG ADGILSVAPY YNKPTQQGLY   120
EHYKAIAQSV DIPVLLYNVP GRTGCEISTD TIIKLFRDCE NIYGVKEASG NIDKCVDLLA   180
HEPRMMLISG EDAINYPILS NGGKGVISVT SNLLPDMIST LTHFALDENY KEAKKINDEL   240
YNINKILFCE SNPIPIKTAM YIAGLIESLE FRLPLCPPSK ENFAKIEEVM KKYKIKGF     298

SEQ ID NO: 40            moltype = AA   length = 297
FEATURE                  Location/Qualifiers
source                   1..297
                         mol_type = protein
                         organism = Caldanaerobacter subterraneus
SEQUENCE: 40
MPVFKGSCVA IVTPFTENGV NFDKLGELIE WHIKEGTDAI LICGTTGEAS TMTDEEQKEA    60
IKFTVEKVAK RIPVIAGTGS NNTAHAIELS EYAQSVGADA LLVITPYYNK TTQKGLVAHF   120
TEIARHVDIP IIIYNVPSRT SLNMLPETYL EVKKKAENVV GVKEASGDIS QIAEIARIMG   180
KSFEIYSGND DQVIPIMSLG GLGVISVTAN IIPAKIHEMT TAYLNGDIEK ARDMQLELNP   240
LNKALFIETN PIPVKTAMNL MGFGVGPLRL PLVEMSEKNL EYLKSVLRQY GLLKEEN      297

SEQ ID NO: 41            moltype = AA   length = 310
FEATURE                  Location/Qualifiers
source                   1..310
                         mol_type = protein
                         organism = Scheffersomyces stipitis
SEQUENCE: 41
MTISAALPKR GVYTPVPTFF KKDLHTIDYD SQIEHAKFLQ QNGITGLVLL GSTGENSHLT    60
RKERIELVST IHEELPDFPL MAGVAQNSVE DAIEEILQLK NAGAQHALVL PSSYFGASIK   120
QQGIIDWYTE VADNASLPVL IYYPGVSNN ISIDPRTIKK LSAHPNIVGA KISHGDVSHH    180
AIIGLDQEIA ANQFITLTGL GQILLPVLVV GIQGTVDALC GAFPKIYVKL LENYDKGDLR   240
AAAELQLVIS RAEELVVKFG VVGIKKAIHF ATGIGETYLG RAPLTQDVND ADWKSYNDYL   300
LGIVSVESTL                                                          310

SEQ ID NO: 42            moltype = AA   length = 288
FEATURE                  Location/Qualifiers
source                   1..288
                         mol_type = protein
                         organism = Sulfolobus acidocaldarius
SEQUENCE: 42
MEIISPIITP FDKQGKVNVD ALKTHAKNLL EKGIDAIFVN GTTGLGPALS KDEKRQNLNA    60
LYDVTHKLIF QVGSLNLNDV MELVKFSNEM DILGVSSHSP YYFPRLPEKF LAKYYEEIAR   120
ISSHSLYIYN YPAATGYDIP PSILKSLPVK GIKDTNQDLA HSLEYKLNLP GVKVYNGSNT   180
LIYYSLLSLD GVVASFTNFI PEVIVKQRDL IKQGKLDDAL RLQELINRLA DILRKYGSIS   240
AIYVLVNEFQ GYDVGYPRPP IFPLTDEEAL SLKREIEPLK RKIQELVH               288

SEQ ID NO: 43            moltype = AA   length = 294
FEATURE                  Location/Qualifiers
source                   1..294
                         mol_type = protein
                         organism = Saccharolobus solfataricus
SEQUENCE: 43
MPEIITPIIT PFTKDNRIDK EKLKIHAENL IRKGIDKLFV NGTTGLGPSL SPEEKLENLK    60
AVYDVTNKII FQVGGLNLDD AIRLAKLSKD FDIVGIASYA PYYYPRMSEK HLVKYFKTLC   120
EVSPHPVYLY NYPTATGKDI DAKVAKEIGC FTGVKDTIEN IIHTLDYKRL NPNMLVYSGS   180
DMLIATVAST GLDGNVAAGS NYLPEVTVTI KKLAMERKID EAKLQFLHD EVIEASRIFG    240
SLSSNYVLTK YFQGYDLGYP RPPIFPLDDE EERQLIKKVE GIRAKLVELK ILKE         294

SEQ ID NO: 44            moltype = AA   length = 290
FEATURE                  Location/Qualifiers
source                   1..290
                         mol_type = protein
                         organism = Sulfurisphaera tokodaii
SEQUENCE: 44
MDIVTPILTP FTKEGKIDVE KLKAHAKFLI DNGIDLLFVN GTTGLGPALS KEEKLTTLKT    60
IYDVTNKVIF QVGSLNINDV IDLVKASKDF DIVGIASYPP FYFPRLPEKF LLKYFTTIAN   120
YSPHSLYIYN YPLATGYDIS AKIVYQMKDL ITGLKDTNQD LSHSLEYKIL MPNLKVYNGS   180
DSLVFYSLTS LDGSVTAASN YLPHVMKKMK EHITSGQVSK AIELQKLINK ALDISRKYGQ   240
LSAIYYLVKE FLGYDVGYPR GPIFPLEEDE VKALLSEIQP VKKEIERAVS             290

SEQ ID NO: 45            moltype = AA   length = 327
FEATURE                  Location/Qualifiers
source                   1..327
                         mol_type = protein
                         organism = Escherichia coli
SEQUENCE: 45
```

```
MATRIEFHKH GGPEVLQAVE FTPADPAENE IQVENKAIGI NFIDTYIRSG LYPPPSLPSG    60
LGTEAAGIVS KVGSGVKHIK AGDRVVYAQS ALGAYSSVHN IIADKAAILP AAISFEQAAA   120
SFLKGLTVYY LLRKTYEIKP DEQFLFHAAA GGVGLIACQW AKALGAKLIG TVGTAQKAQS   180
ALKAGAWQVI NYREEDLVER LKEITGGKKV RVVYDSVGRD TWERSLDCLQ RRGLMVSFGN   240
SSGAVTGVNL GILNQKGSLY VTRPSLQGYI TTREELTEAS NELFSLIASG VIKVDVAEQQ   300
KYPLKDAQRA HEILESRATQ GSSLLIP                                      327

SEQ ID NO: 46           moltype = AA  length = 327
FEATURE                 Location/Qualifiers
source                  1..327
                        mol_type = protein
                        organism = Salmonella enterica
SEQUENCE: 46
MATRIEFHKH GGPEVLQTVE FTPAEPAEHE IQVENKAIGI NFIDTYIRSG LYPPPSLPAG    60
LGTEAAGVVS KVGNGVEHIR VGDRVVYAQS TLGAYSSVHN VTADKAAILP DAISFEQAAA   120
SFLKGLTVFY LLRKTYEVKP DEPFLFHAAA GGVGLIACQW AKALGAKLIG TVGSAQKAQR   180
ALDAGAWQVI NYREESIVER VKEITGGKKV RVVYDSVGKD TWEASLDCLQ RRGLMVSFGN   240
ASGPVTGVNL GILNQKGSLY ATRPSLQGYI TTREELTEAS NELFSLIASG VIKVDVAENQ   300
RYALKDARRA HEVLESRATQ GSSLLIP                                      327

SEQ ID NO: 47           moltype = AA  length = 354
FEATURE                 Location/Qualifiers
source                  1..354
                        mol_type = protein
                        organism = Cupriavidus necator
SEQUENCE: 47
MPRHGCLTIV TVAPMIAARA GHDNQETALA KAIRMYETGG PEVLRYEDAE VGDPGPGEVR    60
IRHAAVGLNY ADTYFRNGTY PVPLPGGMGV EAAGVVQAVG PGVTHVAEGD RVTYTGFINT   120
LGAYSTERLV PAAPLIRLPE AISFETAAAM TMRGLTSAYL MRRIYPFQGG EAILLHAAAG   180
GVGLIVSQWA RLLGLTVIGT VSTEAKAEVA RAHGCDHIIN YSHEDVAKRV RELTDGAGVS   240
VVFDSVGKST FMASLDSLKR RGLMVCVGTA SGTIPPFDPQ LLARKGSVYL TRPALADYIA   300
DPAEKAELAA EVFGHVAAGR IRIEINQRYA LQDAVQAHRD LESRKTTGSS IFVL         354

SEQ ID NO: 48           moltype = AA  length = 327
FEATURE                 Location/Qualifiers
source                  1..327
                        mol_type = protein
                        organism = Proteus mirabilis
SEQUENCE: 48
MAKRIQFAAH GNADVLELTS FTPAPLGDNE VQVANKAIGI NYIDTYVRSG LYPVEHFPSG    60
LGTEAAGVVI KTGAHVTSLK EGDRVVYAQS PLGAYSDTHN VPENKVARLP DNISFEQAAA   120
SFLKGLTVYY LFNETYKLRA GETFLFHAAA GGVGLIASQW AKAIGAKMIG TAGSDEKVAK   180
AKAAGAWKVI NYQTESIVER VLALTNNQKV PVVYDSVGKA TWLDSLHCLQ RRGLMVSFGN   240
ASGAVTGVDL GILNKLGSLY VTRPSISGYI TTREELDAAS EALFTLIGRG KIDVSVPDNQ   300
KFALADAKAA HRYLESRQSQ GSSLLIP                                      327

SEQ ID NO: 49           moltype = AA  length = 325
FEATURE                 Location/Qualifiers
source                  1..325
                        mol_type = protein
                        organism = Pseudomonas aeruginosa
SEQUENCE: 49
MAKRIQFAAY GGPEVLEYRD YQPAEPGPRE VRVRNRAIGL NFIDTYYRSG LYPAPGLPSG    60
LGSEGAGEVE AVGSEVTRFK VGDRVAYATG PLGAYSELHV LAEEKLVHLP DGIDFEQAAA   120
VMLKGLTTQY LLRQTYELRG GETILFHAAA GGVGLFACQW AKALGVQLIG TVSSPEKARL   180
ARQHGAWETI DYSHENVARR VLELTDGKKC PVVYDSVGKD TWETSLDCVA PRGLLVSFGN   240
ASGPVTGVNL GILSQKGSLY VTRPTLGSYA DTPEKLQAMA DELFGLIERG DIRIEINQRF   300
ALAEAARAHT ELAARRTTGS TVLLP                                        325

SEQ ID NO: 50           moltype = AA  length = 326
FEATURE                 Location/Qualifiers
source                  1..326
                        mol_type = protein
                        organism = Mycolicibacterium smegmatis
SEQUENCE: 50
MHAIEVAETG GPEVLNYIER PEPSPGPGEV LIKADAIGVN FIDTYFRSGL YPRELPFVVG    60
TEVCGTVAAI GNDVAALKVG DRVVTANAVG AYADYCVAPA DFVAYVPDGV APEAVASALL   120
KGMTAHYLLK STYPVQPSDT VLVHAGAGGV GLILTGWATS LGTRVITTAS TPEKAELSRQ   180
AGAVEVLDYP DPDDQPPFAS RVRELTGGAG VAAVYDGVGA TTFDASLASL AVRGTLALFG   240
ASSGPVPPFD PQRLNAAGSV FLTRPTLAHH TRTADEFSWR AGELINAIAD GSIKITVGGT   300
YPLAEASRAH TDLQGRKTVG SIVLIP                                       326

SEQ ID NO: 51           moltype = AA  length = 324
FEATURE                 Location/Qualifiers
source                  1..324
                        mol_type = protein
                        organism = Paraburkholderia xenovorans
SEQUENCE: 51
MVKAIRFDKT GGPEVMKWVD VEVGEPGAGE IRVRQTAVGL NYIDVYFRTG LYPLPLPGGL    60
```

```
GMEAAGEVTA LGSGVSGLKV GDRIAYVARP PGAYAQERVL QAAQVVKVPD ALTDEQAASV   120
MLQGLTAQYL LRRTYPVKAG DTILIQAAAG GVGLLVCQWA KALGATVIGT VGSDEKAEIA   180
TAHGCDHAIV YTRENFTRRV REITNGAGVP VVYDSIGKDT FTGSLDCLAP LGMFVSFGNA   240
SGPLPPIDSS EFAGRGSLFF TRPTLFTYIA KRSDYEAMST ELFDVLVSGK VKTSINQRYA   300
LADVGRAHAD LEGRRTTGST VLLP                                         324

SEQ ID NO: 52          moltype = AA  length = 324
FEATURE                Location/Qualifiers
source                 1..324
                       mol_type = protein
                       organism = Burkholderia cepacia
SEQUENCE: 52
MPKAIRYDQP GGPDVMKWVD VEVGEPKAGE VRIRQHAVGL NYIDVYFRTG LYSQPLPGGL    60
GMEAAGEVTA VGEGVTALKA GDRVAYVGQP PGAYAQERVM PAERLVKLPD GISYDDAASV   120
MLQGLTAHYL LRRTYPVKAG DTILIHAAAG GVGLLVCQWA KALGATVIGT VGSDEKAALA   180
KAHGCDHPIV YTRENFTQRV KEITNGAGVP VVYDSIGKDT YIGSLDCLAP LGYFVSFGNA   240
SGPLPAIDSK EFSSRGSLFF TRPTLFSYIA KRADLESAAA ELFDVILSGK VKTSINQRYP   300
LAEVGRAHAD LESRNTTGST ILVP                                         324

SEQ ID NO: 53          moltype = AA  length = 310
FEATURE                Location/Qualifiers
source                 1..310
                       mol_type = protein
                       organism = Gluconobacter oxydans
SEQUENCE: 53
MSSKPDILTI DPLVPVMKER LEKSFTLHPY TSLENLKNIA PAIRGITTGG GSGVPSEIMD    60
ALPNLEVISV NGVGTDRINL DEARRRNIGV AITQNTLTDD VADMAVALMM AVMRSIVTND   120
AFVRAGKWPS ATAPLGRSLT RKKVGIAGFG HIGQAIAKRV SAFGMEVAYF NSHARPESTC   180
HFEPDLKALA TWCDVLILAV SGGPRSANMI DRDTLDALGK DGFLVNIARG TVVDEAALLS   240
ALQEKRIAGA GLDVFQNEPN INPAFLSLPN TVLQAHQASA TVETRTTMAN LVVDNLIAYF   300
TDKTLLTPVI                                                         310

SEQ ID NO: 54          moltype = AA  length = 331
FEATURE                Location/Qualifiers
source                 1..331
                       mol_type = protein
                       organism = Clostridium sporogenes
SEQUENCE: 54
MKILAYCVRP DEIDSFKNFS EKYGHTVDLI PDSFGPSVAH LAKGYDGISI LGNDTCNREA    60
LEKIKDCGIK YLATRTAGVN NIDFDAAKEF GINVANVPAY SPNSVSEFTV GLALSLTRKI   120
PFALKRVELN NFALGGLIGV ELRNLTLGVI GTGRIGLKVI EGFSGFGMKK MIGYDIFENE   180
KAKEYIEYKS LDEVYKEADI ITLHAPLTDD NYHMIGKESI AKMKDGVFII NAARGALIDS   240
EALIEGLKSG KIAGAALDSY EYEQGVFHNN KMNEIMKDDT LARLKSFPNV VITPHLGFYT   300
DEAVSNMVEI TLMNLQEFEL KGTCKNQRVC K                                 331

SEQ ID NO: 55          moltype = AA  length = 410
FEATURE                Location/Qualifiers
source                 1..410
                       mol_type = protein
                       organism = Paraclostridium bifermentans
SEQUENCE: 55
MDNKALLKGV RVVELSSFVA APCCAKLLGD WGAEVIKIEP LGGDGIRVMG GTFKSPCTDE    60
ENPMFELENG NKKGISVNVK TKEGVEIIHK LLAKADIFIT NVREQALSKI GLTYDQLKDE   120
FPALIHAHIL GYGENGPLKD KPGFDYTAYF ARGGVSQSLM EKGTSPCNTA AAFGDHYAGV   180
SLTAGILAAL YKKQMTGEGD RVTVSLYHTA LYGMGMMITT AQYGNKMPIS RANPNSPLMT   240
TYKCKDGKWI QLALIQYNKW LPKFCNVINR PEIMEDERFN DIKVMPLHVD EMVEIVGEAM   300
LEKTLDEWSA LLEEADLPFE KVQSCEDILE DEQAWANDFL FKTKYANGNE GVLVNGPVKF   360
KTMGIKEYTP APRVGEHTEE VLKELGYTEE EILNMVNSQA VKLDDSKELV              410

SEQ ID NO: 56          moltype = AA  length = 410
FEATURE                Location/Qualifiers
source                 1..410
                       mol_type = protein
                       organism = Paeniclostridium sordellii
SEQUENCE: 56
MDNRALLKGV RVVELSSFVA APCCAKLLAD WGAEVIKIEP LGGDGIRVMG GTFKSPCTDD    60
ENPMFELENG NKKGISVNVK TKEGVEILHK LLSKSDIFVT NVREKALAKM GLTYDQLKDD   120
FPGLIHAHIL GYGEEGPLKD KPGFDYTAYF ARGGVSQSLM EKGTSPCNTA AGFGDHYAGI   180
SLTAGILAAL YKKQITGEGD RVTVSLFHTA LYGMGMMITT SQYGNEMPIS RTEPNSPLMT   240
TYKCKDGKWI QLALIQYNKW LPKFCEVINR PEIMKDDRFN DIKVMPLHVD EMVKIVEKAM   300
LEKTLDEWSD LLEEADLPFE KVQSCEDIIN DDQAWANDFL FKTTYENGNE GVLVNGPVKF   360
KTMGIKEYEP APRLGQHTEE VLKSIGYTEE EILDMVNSQA IKLDDAKELV              410

SEQ ID NO: 57          moltype = AA  length = 404
FEATURE                Location/Qualifiers
source                 1..404
                       mol_type = protein
                       organism = Clostridium botulinum
SEQUENCE: 57
```

-continued

```
MTKEGLALEG VKVVELSSFV AAPSCSKLLA DWGADVIKIE PIQGDNIRVV GGVYNSPARD  60
DENPMFELEN GNKRGIAINT RSEKGKEVLG KLLKDADVFV TNVREKALQR SGLSYDQLKD  120
KYPSLIHAHI LGYGEKGPLK DKPGFDYTAY FARGAVSTSL MEKGTSPANT NAGFGDHYAG  180
MSLAAGILAA LHRKTLTGKG DRVTVSLYHT AIFGMGLMIT TAQYGNKMPL SRRTPNNPLA  240
TTYRCKDDRW IQLALLKYDA WFPKFCKEVI NRPDLIEDLR FNKQSEVVKH VETFVGILEE  300
EFIKKDLKEW ADLLDKADLP YEKLQYCEDI LEDEQAWAND YLFKTTYDSG NTGVLVNSPV  360
KFSEAGMRTY KAAPKIGEDT EVVLTSLGYS KEEIEEMRKE ESIK                  404

SEQ ID NO: 58          moltype = AA  length = 404
FEATURE                Location/Qualifiers
source                 1..404
                       mol_type = protein
                       organism = Clostridium sporogenes
SEQUENCE: 58
MTKEGLALEG VKVVELSSFV AAPSCSKLLA DWGADVIKIE PIQGDNIRVV GGVYNSPARD  60
DENPMFELEN GNKRGVAINT RSEKGKEVLG KLLKDADVFV TNVREKALQR SGLSYDQLKD  120
KYPSLIHAHI LGYGEKGPLK DKPGFDYTAY FARGAVSTSL MEKGTSPANT NAGFGDHYAG  180
MSLAAGILAA LHRKTLTGKG DRVTVSLYHT AIFGMGLMIT TAQYGNKMPL SRRTPNNPLA  240
TTYRCKDDRW IQLALLKYDA WFPKFCKEVI NRPDLIEDSR FNKQSEVVKH VETFVGVLEG  300
EFIKKDLKEW ADLLDKADLP YEKLQYCEDI LEDEQAWAND YLFKTTYDSG NTGVLVNSPV  360
KFSEAGMRPY KAAPKIGEDT EAILTSLGYS KEEIEEMRKE NAIK                  404

SEQ ID NO: 59          moltype = AA  length = 408
FEATURE                Location/Qualifiers
source                 1..408
                       mol_type = protein
                       organism = Clostridioides difficile
SEQUENCE: 59
MSEKKEARVV INDLLAEQYA NAFKAKEEGR PVGWSTSVFP QELAEVFDLN VLYPENQAAG  60
VAAKKGSLEL CEIAESKGYS IDLCAYARTN FGLLENGGCE ALDMPAPDFL LCCNNICNQV  120
IKWYENISRE LDIPLIMIDT TFNNEDEVTQ SRIDYIKAQF EEAIKQLEII SGKKFDPKKF  180
EEVMKISAEN GRLWKYSMSL PADSSPSPMN GFDLFTYMAV IVCARGKKET TEAFKLLIEE  240
LEDNMKTGKS SFRGEEKYRI MMEGIPCWPY IGYKMKTLAK FGVNMTGSVY PHAWALQYEV  300
NDLDGMAVAY STMFNNVNLD RMTKYRVDSL VEGKCDGAFY HMNRSCKLMS LIQYEMQRRA  360
AEETGLPYAG FDGDQADPRA FTNAQFETRI QGLVEVMEER KKLNRGEI              408

SEQ ID NO: 60          moltype = AA  length = 410
FEATURE                Location/Qualifiers
source                 1..410
                       mol_type = protein
                       organism = Clostridium sporogenes
SEQUENCE: 60
MADKKEVKKN AAKMINGILA KSYADAWKAK EEGKPVGWST SVFPQELVET FGLDVLYPEN  60
QAAGVAAKKE SLSLCEAAES AGYSIDLCAY ARTNFGLLEK GGSENLNMPK PDFICCCNNI  120
CNQVIKWYEN IAKELDIPLI MIDTTFNNED EVTENRIKYL RAQFEEAIKQ LEKISGKKFD  180
PKKFEEVMKI SAENGKLWKY SMSLPSGSFP SPMNGFDLFT YMAVIVCYRG KKETTEAFKL  240
LISELEDNIK NKATSFRGEE KYRIMMEGIP CWPYIGYKMR TLAGYGVNMT GSVYPHAWAL  300
QYEVNDLDGM AKAYSTMFNN VNLETMCKYR IDSLIDGNCD GAFYHMNRSC KLMSFIQYEM  360
ERKVFEETGI PYAGFDGDQA DPRNFSKAQF ETRLQGLVEV MEERKKGGNK            410

SEQ ID NO: 61          moltype = AA  length = 266
FEATURE                Location/Qualifiers
source                 1..266
                       mol_type = protein
                       organism = Clostridioides difficile
SEQUENCE: 61
MYTMGLDIGS TASKGVILKN GEDIVASETI SSGTGTTGPS RVLEKLYGKT GLAREDIKKV  60
VVTGYGRMNY SDADKQISEL SCHARGVNFI IPETRTIIDI GGQDAKVLKL DNNGRLLNFL  120
MNDKCAAGTG RFLDVMAKII EVDVSELGSI SMNSQNEVSI SSTCTVFAES EVISHLSENA  180
KIEDIVAGIH TSVAKRVSSL VKRIGVQRNV VMVGGVARNS GIVRAMAREI NTEIIVPDIP  240
QLTGALGAAL YAFDEAKESQ KEVKNI                                      266

SEQ ID NO: 62          moltype = AA  length = 375
FEATURE                Location/Qualifiers
source                 1..375
                       mol_type = protein
                       organism = Clostridium sporogenes
SEQUENCE: 62
MDNIKNILSK LEGIVKNPKK VVSDYKERTG NKVIGCFPVY TPEEIVYAAD MLPIGIWGGD  60
VEANLAKQYY PAFCCSIMQS CMEFGLKGIY EGLSAVIIPG MCDTLNCMGQ NWKFAIKDIP  120
YIALVHPQNR KLEAGVEYLV EEYKHVKAKI EEIRGKEITE EEMQNSIDIY NEHRKVMRSF  180
VDEAAKHPNT INNYQRNLVI KSGFFMRKDE HTKIVKELNE LLAVLPEEKY DGKKVLVTGI  240
LLDSKEMLDV FEENKLRIVA DDLAQESRQF RTDVPEGKNA LDRLARQWSN IEGCSLAYDP  300
KKIRGSMIAK EAKAKGIDGV VFAMMKFCDP EEYDYPIVKK DIEKEDIPTT MIEVDQQNKS  360
VEQIRTRIQT FSEIL                                                  375

SEQ ID NO: 63          moltype = AA  length = 375
FEATURE                Location/Qualifiers
source                 1..375
```

```
                        mol_type = protein
                        organism = Clostridioides difficile
SEQUENCE: 63
MEAILSKMKE VVENPNAAVK KYKSETGKKA IGCFPVYCPE EIIHAAGMLP VGIWGGQTEL    60
DLAKQYFPAF ACSIMQSCLE YGLKGAYDEL SGVIIPGMCD TLICLGQNWK SAVPHIKYIS   120
LVHPQNRKLE AGVKYLISEY KGVKRELEEI CGYEIEEAKI HESIEVYNEH RKTMRDFVEV   180
AYKHSNTIKP SIRSLVIKSG FFMRKEEHTE LVKDLIAKLN AMPEEVCSGK KVLLTGILAD   240
SKDILDILED NNISVVADDL AQETRQFRTD VPAGDDALER LARQWSNIEG CSLAYDPKKK   300
RGSLIVDEVK KKDIDGVIFC MMKFCDPEEY DYPLVRKDIE DSGIPTLYVE IDQQTQNNEQ   360
ARTRIQTFAE MMSLA                                                   375

SEQ ID NO: 64           moltype = AA  length = 257
FEATURE                 Location/Qualifiers
source                  1..257
                        mol_type = protein
                        organism = Clostridium sporogenes
SEQUENCE: 64
MYTMGLDIGS TTSKGVIIKD GEEIVASVLV PVGTGTSGPL KLIKELKEKS NLTEKDIEKT    60
VVTGYGRIQY KDADKQISEL SCHAKGVAFL IPGARTIIDI GGQDAKAMKL NDKGKLINFI   120
MNDKCAAGTG RFLDVMAGVL ETDVSKLGEI SEKSTKEVSI SSTCTVFAES EVISHLSANA   180
KKEDIVAGIH TSVVRRVSTL AMRVGIEDQV VMVGGVARNK GIVKAMEKEL GHDIKVPELA   240
QLTGALGAAI YAFEETK                                                 257

SEQ ID NO: 65           moltype = AA  length = 397
FEATURE                 Location/Qualifiers
source                  1..397
                        mol_type = protein
                        organism = Treponema denticola
SEQUENCE: 65
MIVKPMVRNN ICLNAHPQGC KKGVEDQIEY TKKRITAEVK AGAKAPKNVL VLGCSNGYGL    60
ASRITAAFGY GAATIGVSFE KAGSETKYGT PGWYNNLAFD EAAKREGLYS VTIDGDAFSD   120
EIKAQVIEEA KKKGIKFDLI VYSLASPVRT DPDTGIMHKS VLKPFGKTFT GKTVDPFTGE   180
LKEISAEPAN DEEAAATVKV MGGEDWERWI KQLSKEGLLE EGCITLAYSY IGPEATQALY   240
RKGTIGKAKE HLEATAHRLN KENPSIRAFV SVNKGLVTRA SAVIPVIPLY LASLFKVMKE   300
KGNHEGCIEQ ITRLYAERLY RKDGTIPVDE ENRIRIDDWE LEEDVQKAVS ALMEKVTGEN   360
AESLTDLAGY RHDFLASNGF DVEGINYEAE VERFDRI                           397

SEQ ID NO: 66           moltype = AA  length = 1173
FEATURE                 Location/Qualifiers
source                  1..1173
                        mol_type = protein
                        organism = Mycolicibacterium smegmatis
SEQUENCE: 66
MTSDVHDATD GVTETALDDE QSTRRIAELY ATDPEFAAAA PLPAVVDAAH KPGLRLAEIL    60
QTLFTGYGDR PALGYRAREL ATDEGGRTVT RLLPRFDTLT YAQVWSRVQA VAAALRHNFA   120
QPIYPGDAVA TIGFASPDYL TLDLVCAYLG LVSVPLQHNA PVSRLAPILA EVEPRILTVS   180
AEYLDLAVES VRDVNSVSQL VVFDHHPEVD DHRDALARAR EQLAGKGIAV TTLDAIADEG   240
AGLPAEPIYT ADHDQRLAMI LYTSGSTGAP KGAMYTEAMV ARLWTMSFIT GDPTPVINVN   300
FMPLNHLGGR IPISTAVQNG GTSYFVPESD MSTLFEDLAL VRPTELGVP RVADMLYQHH   360
LATVDRLVTQ GADELTAEKQ AGAELREQVL GGRVITGFVS TAPLAAEMRA FLDITLGAHI   420
VDGVGLTETG AVTRDGVIVR PPVIDYKLID VPELGYFSTD KPYPRGELLV RSQTLTPGYY   480
KRPEVTASVF DRDGYYHTGD VMAETAPDHL VYVDRRNNVL KLAQGEFVAV ANLEAVFSGA   540
ALVRQIFVYG NSERSFLLAV VVPTPEALEQ YDPAALKAAL ADSLQRTARD AELQSYEVPA   600
DFIVETEPFS AANGLLSGVG KLLRPNLKDR YGQRLEQMYA DIAATQANQL RELRRAAATQ   660
PVIDTLTQAA ATILGTGSEV ASDAHFTDLG GDSLSALTLS NLLSDFFGFE VPVGTIVNPA   720
TNLAQLAQHI EAQRTAGDRR PSFTTVHGAD ATEIRASELT LDKFIDAETL RAAPGLPKVT   780
TEPRTVLLSG ANGWLGRFLT LQWLERLAPV GGTLITIVRG RDDAAARARL TQAYDTDPEL   840
SRRFAELADR HLRVVAGDIG DPNLGLTPEI WHRLAAEVDL VVHPAALVNH VLPYRQLFGP   900
NVVGTAEVIK LALTERIKPV TYLSTVSVAM GIPDFEEDGD IRTVSPVRPL DGGYANGYGN   960
SKWAGEVLLR EAHDLCGLPV ATFRSDMILA HPRYRGQVNV PDMFTRLLLS LLITGVAPRS  1020
FYIGDGERPR AHYPGLTVDF VAEAVTTLGA QQREGYVSYD VMNPHDDGIS LDVFVDWLIR  1080
AGHPIDRVDD YDDWVRRFET ALTALPEKRR AQTVLPLLHA FRAPQAPLRG APEPTEVFHA  1140
AVRTAKVGPG DIPHLDEALI DKYIRDLREF GLI                              1173

SEQ ID NO: 67           moltype = AA  length = 1168
FEATURE                 Location/Qualifiers
source                  1..1168
                        mol_type = protein
                        organism = Mycolicibacterium smegmatis
SEQUENCE: 67
MTIETREDRF NRRIDHLFET DPQFAAARPD EAISAAAADP ELRRLPAAVKQ ILAGYADRPA    60
LGKRAVEFVT DEEGRTTAKL LPRFDTITYR QLAGRIQAVT NAWHNHPVNA GDRVAILGFT   120
SVDYTTIDIA LLELGAVSVP LQTSAPVAQL QPIVAETEPK VIASSVDFLA DAVALVESGP   180
APSRLVVFDY SHEVDDQREA FEAAKGKLAG TGVVVETITD ALDRGRSLAD APLYVPDEAD   240
PLTLLIYTSG STGTPKGAMY PESKTATMWQ AGSKARWDET LGVMPSITLN FMPMSHVMGR   300
GILCSTLASG GTAYFAARSD LSTFLEDLAL VRPTQLNFVP RIWDMLFQEY QSRLDNRRAE   360
GSEDRAEAAV LEEVRTQLLG GRFVSALTGS APISAEMKSW VEDLLDMHLL EGYGSTEAGA   420
VFIDGQIQRP PVIDYKLVDV PDLGYFATDR PYPRGELLVK SEQMFPGYYK RPEITAEMFD   480
EDGYYRTGDI VAELGPDHLE YLDRRNNVLK LSQGEFVTVS KLEAVFGDSP LVRQIYVYGN   540
```

```
SARSYLLAVV VPTEEALSRW DGDELKSRIS DSLQDAARAA GLQSYEIPRD FLVETTPFTL    600
ENGLLTGIRK LARPKLKAHY GERLEQLYTD LAEGQANELR ELRRNGADRP VVETVSRAAV    660
ALLGASVTDL RSDAHFTDLG GDSLSALSFS NLLHEIFDVD VPVGVIVSPA TDLAGVAAYI    720
EGELRGSKRP TYASVHGRDA TEVRARDLAL GKFIDAKTLS AAPGLPRSGT EIRTVLLTGA    780
TGFLGRYLAL EWLERMDLVD GKVICLVRAR SDDEARARLD ATFDTGDATL LEHYRALAAD    840
HLEVIAGDKG EADLGLDHDT WQRLADTVDL IVDPAALVNH VLPYSQMFGP NALGTAELIR    900
IALTTTIKPY VYVSTIGVGQ GISPEAFVED ADIREISATR RVDDSYANGY GNSKWAGEVL    960
LREAHDWCGL PVSVFRCDMI LADTTYSGQL NLPDMFTRLM LSLVATGIAP GSFYELDADG   1020
NRQRAHYDGL PVEFIAEAIS TIGSQVTDGF ETPHVMNPYD DGIGLDEYVD WLIEAGYPVH   1080
RVDDYATWLS RFETALRALP ERQRQASLLP LLHNYQQPSP PVCGAMAPTD RFRAAVQDAK   1140
IGPDKDIPHV TADVIVKYIS NLQMLGLL                                     1168

SEQ ID NO: 68             moltype = AA  length = 1186
FEATURE                   Location/Qualifiers
source                    1..1186
                          mol_type = protein
                          organism = Segniliparus rotundus
SEQUENCE: 68
MTQSHTQGPQ ASAAHSRLAR RAAELLATDP QAAATLPDPE VVRQATRPGL RLAERVDAIL     60
SGYADRPALG QRSFQTVKDP ITGRSSVELL PTFDTITYRE LRERATAIAS DLAHHPQAPA    120
KPGDFLASIG FISVDYVAID IAGVFAGLTA VPLQTGATLA TLTAITAETA PTLFAASIEH    180
LPTAVDAVLA TPSVRRLLVF DYRAGSDEDR EAVEAAKRKI ADAGSSVLVD VLDEVIARGK    240
SAPKAPLPPA TDAGDDSLSL LIYTSGSTGT PKGAMYPERN VAHFWGGVWA AAFDEDAAPP    300
VPAINITFLP LSHVASRLSL MPTLARGGLM HFVAKSDLST LFEDLKLARP TNLFLVPRVV    360
EMLYQHYQSE LDRRGVQDGT REAEAVKDDL RTGLLGGRIL TAGFGSAPLS AELAGFIESL    420
LQIHLVDGYG STEAGPVWRD GYLVKPPVTD YKLIDVPELG YFSTDSPHPR GELAIKTQTI    480
LPGYYKRPET TAEVFDEDGF YLTGDVVAQI GPEQFAYVDR RKNVLKLSQG EFVTLAKLEA    540
AYSSSPLVRQ LFVYGSSERS YLLAVIVPTP DALKKFGVGE AAKAALGESL QKIARDEGLQ    600
SYEVPRDFII ETDPFTVENG LLSDARKSLR PKLKEHYGER LEAMYKELAD GQANELRDIR    660
RGVQQRPTLE TVRRAAAAML GASAAEIKPD AHFTDLGGDS LSALTFSNFL HDLFEVGVPV    720
GVIVSAANTL GSVAEHIDAQ LAGGRARPTF ATVHGKGSTT IKASDLTLDK FIDEQTLEAA    780
KHLPKPADPP RTVLLTGANG WLGRFLALEW LERLAPAGGK LITIVRGKDA AQAKARLDAA    840
YESGDPKLAG HYQDLAATTL EVLAGDFSEP RLGLDEATWN RLADEVDFIS HPGALVNHVL    900
PYNQLFGPNV AGVAEIIKLA ITTRIKPVTY LSTVAVAAGV EPSALDEDGD IRTVSAERSV    960
DEGYANGYGN SKWGGEVLLR EAHDRTGLPV RVFRSDMILA HQKYTGQVNA TDQFTRLVQS   1020
LLATGLAPKS FYELDAQGNR QRAHYDGIPV DFTAESITTL GGDGLEGYRS YNVFNPHRDG   1080
VGLDEFVDWL IEAGHPITRI DDYDQWLSRF ETSLRGLPES KRQASVLPLL HAFARPGPAV   1140
DGSPFRNTVF RTDVQKAKIG AEHDIPHLGK ALVLKYADDI KQLGLL                  1186

SEQ ID NO: 69             moltype = AA  length = 224
FEATURE                   Location/Qualifiers
source                    1..224
                          mol_type = protein
                          organism = Bacillus subtilis
SEQUENCE: 69
MKIYGIYMDR PLSQEENERF MSFISPEKRE KCRRFYHKED AHRTLLGDVL VRSVISRQYQ     60
LDKSDIRFST QEYGKPCIPD LPDAHFNISH SGRWVICAFD SQPIGIDIEK TKPISLEIAK    120
RFFSKTEYSD LLAKDKDEQT DYFYHLWSMK ESFIKQEGKG LSLPLDSFSV RLHQDGQVSI    180
ELPDSHSPCY IKTYEVDPGY KMAVCAAHPD FPEDITMVSY EELL                     224

SEQ ID NO: 70             moltype = AA  length = 251
FEATURE                   Location/Qualifiers
source                    1..251
                          mol_type = protein
                          organism = Leifsonia sp.
SEQUENCE: 70
MAQYDVADRS AIVTGGGSGI GRAVALTLAA SGAAVLVTDL NEEHAQAVVA EIEAAGGKAA     60
ALAGDVTDPA FGEASVAGAN ALAPLKIAVN NAGIGGEAAT VGDYSLDSWR TVIEVNLNAV    120
FYGMQPQLKA MAANGGGAIV NMASILGSVG FANSSAYVTA KHALLGLTQN AALEYAADKV    180
RVVAVGPGFI RTPLVEANLS ADALAFLEGK HALGRLGEPE EVASLVAFLA SDAASFITGS    240
YHLVDGGYTA Q                                                         251

SEQ ID NO: 71             moltype = AA  length = 352
FEATURE                   Location/Qualifiers
source                    1..352
                          mol_type = protein
                          organism = Rhodococcus sp.
SEQUENCE: 71
MRVFAVQPED TTIHDLQVPT PSPEGREVLL RVVRAGVCHT DTHLRAGGYD LGSRGMMSMK     60
ERGIEYPMVL GHEVVGVVEK VGDGVESVQV GDRLIYPWI GCGECRQCRA GHDNRCAAGK    120
NLGVARHGGY AENILVPDEK YLVDIDGLDP SWAATLACSG LTAYSAVDKA LPLEPDEPVV    180
VFGAGGLGLT AIAILRSRGH RNICAVDVAE RNLALARDMG ASSTVLSGTG SGADDIRGAA    240
GGPAGAVIDF VNNGATATTA FEVLAKAGIM IQVGLFGGEV TLPTALLALR MIRIEGSFVG    300
TLVQMQDLVR LAQRGELPHI PVVERSLSAA AVSQALDDLT AGGVAGRIVL TA            352

SEQ ID NO: 72             moltype = AA  length = 352
FEATURE                   Location/Qualifiers
source                    1..352
                          mol_type = protein
```

```
                          organism = Acinetobacter sp.
SEQUENCE: 72
MHCYCVTHHG QPLEDVEKEI PQPKGTEVLL HVKAAGLCHT DLHLWEGYYD LGGGKRLSLA  60
DRGLKPPLTL SHEITGQVVA VGPDAESVKV GMVSLVHPWI GCGECNYCKR GEENLCAKPQ  120
QLGIAKPGGF AEYIIVPHPR YLVDIAGLDL AEAAPLACAG VTTYSALKKF GDLIQSEPVV  180
IIGAGGLGLM ALELLKAMQA KGAIVVDIDD SKLEAARAAG ALSVINSRSE DAAQQLIQAT  240
DGGARLILDL VGSNPTLSLA LASAARGGHI VICGLMGGEI KLSIPVIPMR PLTIQGSYVG  300
TVEELRELVE LVKETHMSAI PVKKLPISQI NSAFGDLKDG NVIGRIVLMH EN          352

SEQ ID NO: 73             moltype = AA  length = 391
FEATURE                   Location/Qualifiers
source                    1..391
                          mol_type = protein
                          organism = Clostridium ljungdahlii
SEQUENCE: 73
MENFIFKNAT EIIFGKDTEN LVGSKVKEYS KSDKILFCYG GGSIKRSGLY DRVIKSLKEN  60
GIEFIELPGI KPNPRLGPVK EGIRLCRENN IKFVLSVGGG SSADTAKAIA VGVPYKGDVW  120
DFYTGKAEVK EALPVGVVIT LPATGTESSN SSVIMNEDGW FKKGLNTVLI RPAFSIMNPE  180
LTFTLPEYQT ACGACDIMAH IMERYFTNVK HVDITDRLCE AALRNVINNA PIVLKDPKNY  240
DARAEIMWTG TIAHNDVLSA GRIGDWASHK IEHELSGETD IAHGAGLAIV FPAWMKYVYK  300
HDINRFVQFA VRVWDVDLSY SSCEDIVLEG IRRMTAFFKS MGLPVTLKEG SIGEDKIEEM  360
ANKCTDNGTK TVGQFVKLNK DDIVKILNLA K                                391

SEQ ID NO: 74             moltype = AA  length = 389
FEATURE                   Location/Qualifiers
source                    1..389
                          mol_type = protein
                          organism = Clostridium acetobutylicum
SEQUENCE: 74
MLSFDYSIPT KVFFGKGKID VIGEEIKKYG SRVLIVYGGG SIKRNGIYDR ATAILKENNI  60
AFYELSGVEP NPRITTVKKG IEICRENNVD LVLAIGGGSA IDCSKVIAAG VYYDGDTWDM  120
VKDPSKITKV LPIASILTLS ATGSEMDQIA VISNMETNEK LGVGHDDMRP KFSVLDPTYT  180
FTVPKNQTAA GTADIMSHTF ESYFSGVEGA YVQDGIAEAI LRTCIKYGKI AMEKTDDYEA  240
RANLMWASSL AINGLLSLGK DRKWSCHPME HELSAYYDIT HGVGLAILTP NWMEYILNDD  300
TLHKFVSYGI NVWGIDKNKD NYEIAREAIK NTREYFNSLG IPSKLREVGI GKDKLELMAK  360
QAVRNSGGTI GSLRPINAED VLEIFKKSY                                  389

SEQ ID NO: 75             moltype = AA  length = 477
FEATURE                   Location/Qualifiers
source                    1..477
                          mol_type = protein
                          organism = Acinetobacter sp.
SEQUENCE: 75
MNYPNIPLYI NGEFLDHTNR DVKEVFNPVN HECIGLMACA SQADLDYALE SSQQAFLRWK  60
KTSPITRSEI LRTFAKLARE KAAEIGRNIT LDQGKPLKEA IAEVTVCAEH AEWHAEECRR  120
IYGRVIPPRN PNVQQLVVRE PLGVCLAFSP WNFPFNQAIR KISAAIAAGC TIIVKGSGDT  180
PSAVYAIAQL FHEAGLPNGV LNVIWGDSNF ISDYMIKSPI IQKISFTGST PVGKKLASQA  240
SLYMKPCTME LGGHAPVIVC DDADIDAAVE HLVGYKFRNA GQVCVSPTRF YVQEGIYKEF  300
SEKVVLRAKQ IKVGCGLDAS SDMGPLAQAR RMHAMQQIVE DAVHKGSKLL LGGNKISDKG  360
NFFEPTVLGD LCNDTQFMND EPFGPIIGLI PFDTIDHVLE EANRLPFGLA SYAFTTSSKN  420
AHQISYGLEA GMVSINHMGL ALAETPFGGI KDSGFGSEGG IETFDGYLRT KFITQLN     477

SEQ ID NO: 76             moltype = AA  length = 787
FEATURE                   Location/Qualifiers
source                    1..787
                          mol_type = protein
                          organism = Clostridium butyricum
SEQUENCE: 76
MISKGFSTQT ERINILKAQI LNAKPCVESE RAILITESFK QTEGQPAILR RALALKHILE  60
NIPITIRDQE LIVGSLTKEP RSSQVFPEFS NKWLQDELDR LNKRTGDAFQ ISEESKEKLK  120
DVFEYWNGKT TSELATSYMT EETREAVNCD VFTVGNYYYN GVGHVSVDYG KVLRVGFNGI  180
INEAKEQLEK NRSIDPDFIK KEKFLNSVII SCEAAITYVN RYAKKAKEIA DNTSDAKRKA  240
ELNEIAKICS KVSGEGAKSF YEACQLFWFI HAIINIESNG HSISPARFDQ YMYPYYENDK  300
NITDKFAQEL IDCIWIKLND INKVRDEIST KHFGGYPMYQ NLIVGGQNSE GKDATNKVSY  360
MALEAAVHVK LPQPSLSVRI WNKTPDEFLL RAAELTREGL GLPAYYNDEV IIPALVSRGL  420
TLEDARDYGI IGCVEPQKPG KTEGWHDSAF FNLARIVELT INSGFDKNKQ IGPKTQNFEE  480
MKSFDEFMKA YKAQMEYFVK HMCCADNCID IAHAERAPLP FLSSMVDNCI GKGKSLQDGG  540
AEYNFSGPQG VGVANIGDSL VAVKKIVFDE NKITPSELKK TLNNDFKNSE EIQALLKNAP  600
KFGNDIDEVD NLAREGALVY CREVNKYTNP RGGNFQPGLY PSSINVYFGS LTGATPDGRK  660
SGQPLADGVS PSRGCDVSGP TAACNSVSKL DHFIASNGTL FNQKFHPSAL KGDNGLMNLS  720
SLIRSYFDQK GFHVQFNVID KKILLAAQKN PEKYQDLIVR VAGYSAQFIS LDKSIQNDII  780
ARTEHVM                                                          787

SEQ ID NO: 77             moltype = AA  length = 304
FEATURE                   Location/Qualifiers
source                    1..304
                          mol_type = protein
                          organism = Clostridium butyricum
SEQUENCE: 77
```

```
MSKEIKGVLF NIQKFSLHDG PGIRTIVFFK GCSMSCLWCS NPESQDIKPQ VMFNKNLCTK    60
CGRCKSQCKS AAIDMNSEYR IDKSKCTECT KCVDNCLSGA LVIEGRNYSV EDVIKELKKD   120
SVQYRRSNGG ITLSGGEVLL QPDFAVELLK ECKSYGWHTA IETAMYVNSE SVKKVIPYID   180
LAMIDIKSMN DEIHRKFTGV SNEIILQNIK LSDELAKEII IRIPVIEGFN ADLQSIGAIA   240
QFSKSLTNLK RIDLLPYHNY GENKYQAIGR EYSLKELKSP SKDKMERLKA LVEIMGIPCT   300
IGAE                                                                304

SEQ ID NO: 78           moltype = AA  length = 558
FEATURE                 Location/Qualifiers
source                  1..558
                        mol_type = protein
                        organism = Lactobacillus reuteri
SEQUENCE: 78
MKRQKRFEEL EKRPIHQDTF VKEWPEEGFV AMMGPNDPKP SVKVENGKIV EMDGKKLEDF    60
DLIDLYIAKY GINIDNVEKV MNMDSTKIAR MLVDPNVSRD EIIEITSALT PAKAEEIISK   120
LDFGEMIMAV KKMRPRRKPD NQCHVTNTVD NPVQIAADAA DAALRGFPEQ ETTTAVARYA   180
PFNAISILIG AQTGRPGVLT QCSVEEATEL QLGMRGFTAY AETISVYGTD RVFTDGDDTP   240
WSKGFLASCY ASRGLKMRFT SGAGSEVLMG YPEGKSMLYL EARCILLTKA SGVQGLQNGA   300
VSCIEIPGAV PNGIREVLGE NLLCMMCDIE CASGCDQAYS HSDMRRTERF IGQFIAGTDY   360
INSGYSSTPN YDNTFAGSNT DAMDYDDMYV MERDLGQYYG IHPVKEETII KARNKAAKAL   420
QAVFEDLGLP KITDEEVEAA TYANTHDDMP KRDMVADMKA AQDMMDRGIT AIDIIKALYN   480
HGFKDVAEAI LNLQKQKVVG DYLQTSSIFD KDWNVTSAVN DGNDYQGPGT GYRLYEDKEE   540
WDRIKDLPFA LDPEHLEL                                                 558

SEQ ID NO: 79           moltype = AA  length = 236
FEATURE                 Location/Qualifiers
source                  1..236
                        mol_type = protein
                        organism = Lactobacillus reuteri
SEQUENCE: 79
MADIDENLLR KIVKEVLSET NQIDTKIDFD KSNDSTATAT QEVQQPNSKA VPEKKLDWFQ    60
PVGEAKPGYS KDEVVIAVGP AFATVLDKTE TGIPHKEVLR QVIAGIEEEG LKARVVKVYR   120
SSDVAFCAVQ GDHLSGSGIA IGIQSKGTTV IHQKDQDPLG NLELFPQAPV LTPETYRAIG   180
KNAAMYAKGE SPEPVPAKND QLARIHYQAI SAIMHIRETH QVVVGKPEEE IKVTFD       236

SEQ ID NO: 80           moltype = AA  length = 172
FEATURE                 Location/Qualifiers
source                  1..172
                        mol_type = protein
                        organism = Lactobacillus reuteri
SEQUENCE: 80
MMSEVDDLVA KIMAQMGNSS SANSSTGTST ASTSKEMTAD DYPLYQKHRD LVKTPKGHNL    60
DDINLQKVVN NQVDPKELRI TPEALKLQGE IAANAGRPAI QKNLQRAAEL TRVPDERVLE   120
MYDALRPFRS TKQELLNIAK ELRDKYDANV CAAWFEEAAD YYESRKKLKG DN           172

SEQ ID NO: 81           moltype = AA  length = 616
FEATURE                 Location/Qualifiers
source                  1..616
                        mol_type = protein
                        organism = Lactobacillus reuteri
SEQUENCE: 81
MATEKVIGVD IGNSSTEVAL ADVSDSGQVH FINSGIAPTT GIKGTKQNLV GIRDSITQVL    60
NKSNLTIDDI DLIRINEATP VIGDVAMETI TETVVTESTM IGHNPNTPGG IGTGAGITVR   120
LLDLLKKTDK SKNYIVVVPK DIDFEDVAKL INAYVASGYK ITAAILRNDD GVLVDNRLNH   180
KIPIVDEVAM IDKVPLNMLA AVEVAGPGQV ISQLSNPYGI ATLFGLTPEE TKNIVPVSRA   240
LIGNRSAVVI KTPAGDVKAR VIPAGKIIIN GDTGKEEVGV SEGADAIMKK VSSFRHINNI   300
TGESGTNVGG MLENVRQTMA DLTGKKNDEI AIQDLLAVDT QVPVEVRGGL AGEFSNESAV   360
GIAAMVKSDH LQMEVIAKLI EKEFNTKVEI GGAEVESAIR GALTTPGTDK PIAILDLGAG   420
STDASIINKE NNTVAIHLAG AGDMVTMIIN SELGLNDIHL AEDIKRYPLA KVENLFQIRH   480
EDGSVQFFKD PLPSSLFAKV VVIKPDGYEP VTGNPSIEKI KLVRQSAKKR VFVTNALRAL   540
KYVSPTGNIR DIPFVVIVGG SALDFEIPQL VTDELAHFNL VAGRGNVRGV EGPRNAVATG   600
LILRYGEERR KRYEQR                                                   616

SEQ ID NO: 82           moltype = AA  length = 119
FEATURE                 Location/Qualifiers
source                  1..119
                        mol_type = protein
                        organism = Lactobacillus reuteri
SEQUENCE: 82
MNNDDSQRPS IVVGLENGIT IPDSVKPLFY GIEEEQIPVS VRKININDTV ERAYQSALAS    60
RLSVGIAFEG DHFIVHYKNL KENQPLFDMT INDKKQLRIL GANAARLVKG IPFKEMANR    119

SEQ ID NO: 83           moltype = AA  length = 547
FEATURE                 Location/Qualifiers
source                  1..547
                        mol_type = protein
                        organism = Lactococcus lactis
SEQUENCE: 83
MYTVGDYLLD RLHELGIEEI FGVPGDYNLQ FLDQIISRED MKWIGNANEL NASYMADGYA    60
```

```
RTKKAAAFLT TFGVGELSAI NGLAGSYAEN LPVVEIVGSP TSKVQNDGKF VHHTLADGDF  120
KHFMKMHEPV TAARTLLTAE NATYEIDRVL SQLLKERKPV YINLPVDVAA AKAEKPALSL  180
EKESSTTNTT EQVILSKIEE SLKNAQKPVV IAGHEVISFG LEKTVTQFVS ETKLPITTLN  240
FGKSAVDESL PSFLGIYNGK LSEISLKNFV ESADFILMLG VKLTDSSTGA FTHHLDENKM  300
ISLNIDEGII FNKVVEDFDF RAVVSSLSEL KGIEYEGQYI DKQYEEFIPS SAPLSQDRLW  360
QAVESLTQSN ETIVAEQGTS FFGASTIFLK SNSRFIGQPL WGSIGYTFPA ALGSQIADKE  420
SRHLLFIGDG SLQLTVQELG LSIREKLNPI CFIINNDGYT VEREIHGPTQ SYNDIPMWNY  480
SKLPETFGAT EDRVVSKIVR TENEFVSVMK EAQADVNRMY WIELVLEKED APKLLKKMGK  540
LFAEQNK                                                           547

SEQ ID NO: 84           moltype = AA  length = 331
FEATURE                 Location/Qualifiers
source                  1..331
                        mol_type = protein
                        organism = Puniceibacterium sp.
SEQUENCE: 84
MSAKRTLLTV DDVTGCWAIM PTPAKDDASD WRTEFSVDLD ETARVANALV ESGVDGILAL   60
GTFGEGATLT WEEKEAYVRT VVDAVAGRVP FFAGTTSLNT RETIRQMRIV RDIGVDGVML  120
GIPMWVEADT ATAVQFYRDV TEACPDVAIC AYANPEAFKY EFGRAFWAQV SDLPQIVSAK  180
YLNMGGLYPD LNLSKRRIRL MPLDVDYYAA ARIDPDHCTA FWTSGAVCGP EPAILLRDLM  240
EKARKSGDWA EAKALTDRIG MTYKTLFPNG SFKEFSRYNI SIEKIRMDAA GWMKAGPCRP  300
PYHVTPEPIL EGGRIAGQKW AELAESLRAG N                                331

SEQ ID NO: 85           moltype = AA  length = 327
FEATURE                 Location/Qualifiers
source                  1..327
                        mol_type = protein
                        organism = Streptomyces sp.
SEQUENCE: 85
MITAAEINGM YGIIPTPALP GAERLDARDT VDVDETARVV DRLIRDGVSG IIALGTTGEC   60
PALSEDDFDV VTDTVVEAVA GRVPVFVGAT GAGGHGTARR LRKVAASGAT GALLGLPMWQ  120
PLTTAMAVEY YAQASAAFPD LALMVYANAR AFRYTFPVEF WQGVSSQAPT VTSAKVSRAP  180
QLERMLEVTG KKVNFIPSDM VVHDFAARAP QTTTACWATA AGMGPEPSIA LMDALRRGDS  240
EAAGRAVAGI AWANEPLAHL FADQEIFASY NTQIEKSRIA AAGYCRPGPV RSPYHHLPEE  300
YAAASAVCGQ RWRELRERIA AGTNDQK                                     327

SEQ ID NO: 86           moltype = AA  length = 261
FEATURE                 Location/Qualifiers
source                  1..261
                        mol_type = protein
                        organism = Clostridium magnum
SEQUENCE: 86
MIKGYSLPLT PKGTSNIVPA PPWHYVGNVL AIEYEAYAEN IAAFLPEGLE FSSNQCAIYF   60
IEWQYCSEFG EEHLDPVNSQ YKETIVLVSA NYKGTPVSYC PFIWVDQDLS LMRGLIQGWP  120
KQLGETYITR PYNLPSKAAS NLEKGGKLGA TLSVKGRRLV DARITVNKKT ETLPNPTFAQ  180
AINLRHPEL VLGRHNQPLI HELVQLKSRD LHISPIWKGD AILNFFDHPF IELSDLKPTK  240
VKNSYYFSAA LTVDDLSQLE V                                           261

SEQ ID NO: 87           moltype = AA  length = 323
FEATURE                 Location/Qualifiers
source                  1..323
                        mol_type = protein
                        organism = Allokutzneria albata
SEQUENCE: 87
MRAVVVRSHG GPEVLVAEEL DRPEPGPGAV LVDVAAAGVN YIDTYHREGV YPIPTPFTLG   60
LEGAGTVAAL GEGVTEFAVG DRVAWASAIG SYAQQVAAPA AQLVPVPSTV DLEIAAGAML  120
QGMTAHYLTA STHPIAEGDV ALVHAAAGGM GLLLTQMIKA RGGRVIGTVS TAEKEKLARE  180
AGADEVIRYT EQDVAQRVRE LTDGVGVHVV YDGVGKDTFD ASLASLRPRG LLALYGAASG  240
AVPPFDAQRL NAGGSLFLTR PSLGHHTATR EELLWRAGEV FDAIQAGELD IAIGGRYALD  300
SARQAHEDLQ GRRTTGKLLL TTS                                         323

SEQ ID NO: 88           moltype = AA  length = 326
FEATURE                 Location/Qualifiers
source                  1..326
                        mol_type = protein
                        organism = Acidaminococcus intestini
SEQUENCE: 88
MKAIVMKEFG GPEVLKYVDV PDPVPEANEV LIKLAFCGVN PNETYVRTGT YNFYKPELPY   60
TPGYDGAGVI EKVGAGVTHV KVGDRVFVAA LLAKRNTGTY AQKVVCDADS VHKLPDFISF  120
EEGASFGIPA MAAYRALFHR AHIKAGEIVM IHGAEGGVGS LAVQMAKAVG AIVIGTGTTP  180
EGLDIVRSFG ADYAIYHLKA DNQDELMELT KGKGPDVIIE FLANVNLQTD LKVIAKYGRI  240
VVVGNRGTIE INPRLAMANE STILGMALWN APANEYRESL FALRAFMQSG AVRAKVGKQL  300
LLKDAAQAHN EIINGLAKGK MILKIE                                      326

SEQ ID NO: 89           moltype = AA  length = 325
FEATURE                 Location/Qualifiers
source                  1..325
                        mol_type = protein
                        organism = Mycobacteroides chelonae
```

```
SEQUENCE: 89
MRAIEVPVTG GPEVLTLVEK TAPTPGPGEV LIDVDAVGVN FRDIYLRNGS YAAPLPHIPG    60
SEVTGVVSAV GEGVENLAPG DRVASPVAAW GYAESTTAPA DYTAKVPAGL SSEVAASALL   120
QGITAHYLLT SVYPVAAGDT VLVHAGAGGM GLLLTQWASH RGVRVITTVS SAAKEKLSRE   180
AGAAEVLPYP DPTDPAEFAE KILELTSGEG VAVAYDGVGK STFEASLAAV RVRGLIALYG   240
AASGQVPPFD PQRLTAKSAV LTRPTMGHFI RTPAEFWARA DDVLDLVSRG TLKITVGASY   300
PLEQAAQAHI DLEARKTTGS VVLVP                                        325

SEQ ID NO: 90            moltype = AA  length = 321
FEATURE                  Location/Qualifiers
source                   1..321
                         mol_type = protein
                         organism = Nocardia brasiliensis
SEQUENCE: 90
MRAIQVSEHG GPEVLHHVEL PDPTIDADQL LVDVQATGIN FIDTYIRTGR YPQDVPYVPG    60
SEATGVVAEV GANVTEFAVG DRVAWASAPG SYAERVAVRA DVAVEVPDGV EPPVAASALL   120
QGMTAHYLLE SIYTPEPGET VLVHAGAGGV GLILTQLAVA RGARVITTVS SDVKEKLSRE   180
AGATEVLRYG DDLADEVRTL TDGVGVAAVY DGVGASTFEA SLRSLRVRGM LALFGASGP    240
VPPFDLQRLN GAGSLFVTRP SLAFYTRDRA ELLWRATDIF TAIAEGTLQI RIGATYPLAE   300
AEQAHRDLES RKTTGSIVLL P                                            321

SEQ ID NO: 91            moltype = AA  length = 325
FEATURE                  Location/Qualifiers
source                   1..325
                         mol_type = protein
                         organism = Pseudomonas oleovorans
SEQUENCE: 91
MAKRIQFSQH GGSEVLEYRD YQPAAPGPRE VRVANKAIGL NFIDTYFRSG LYQPPALPSS    60
LGTEGAGVVE AIGSEVEGLK VGDRVAYATG PLGAYSELHV LPADNLVHLP DSISFEQAAA   120
VMLKGLTVQY LLRQTYELKG GETILFHAAA GGVGSFACQW AKALGVNLIG TVSSAKKAAL   180
AKELGAWETI DYSHENVVQR VLELTDGAKC PVVYDGVGKD TWETSLDCVA PRGLLVSFGN   240
ASGAVTGVNL GILAQKGSLY VTRPTLASYA NTPQNLQAMA DELFAMISSG KLQVDISNRY   300
ALKDAAAAQD ALSSRQTTGS TILLP                                        325

SEQ ID NO: 92            moltype = AA  length = 321
FEATURE                  Location/Qualifiers
source                   1..321
                         mol_type = protein
                         organism = Caulobacter vibrioides
SEQUENCE: 92
MLAVQAVRTG GPEVLEVVDL PLPSPGPGQI LVRHQAVGLN YIDTYHRSGL YPVKTPLVIG    60
LEAAGVVESV GEAVTRFKVG DRVAYNGTMG AYAQAAVVPA ERAVLPDGV SLEVAAAALL   120
KGMTAEFLVR RCFHVKQGDW VLVHAAAGGV GQILVQWCKA LGATVVATVG STAKATIARD   180
LGADHVIDYS HEDVAARVAE LTGGRGVAVV YDGVGKDTWE ASLASLARRG MLVTFGNASG   240
PAPAPFPPLAL APKSAFVTRP KLFDYIVTTE ELDESAQALF AVIASGAIKI DIGQTFPLAE   300
ARAAHEALEG RRTTGATLLL P                                            321

SEQ ID NO: 93            moltype = AA  length = 322
FEATURE                  Location/Qualifiers
source                   1..322
                         mol_type = protein
                         organism = Saccharopolyspora flava
SEQUENCE: 93
MRAIRVTSHG GPEALEVSEV EVPEPGPGQL LVDVAASGVN FIDTYQRSGV YSVPLPFTPG    60
SEGAGEIVAV GPDVDGFAVG ERVAWAMTPG SYAEKALVPA RAAVKIPDGV DTRTAAAATL   120
QGMTAHFLVT STHEIKTGET ALVHAAAGGM GLLLTQLIKS KGGNVIGTVS TDEKERLARE   180
AGADEIIRYT EADVAAEVKD LTDGRGVDVV YDGVGKSTFE ASLASLRPRG TLALFGGASG   240
QVPPFDPQRL NGAGSLFLTR PSLAHHVLTR EELEWRAGEV FGWISSGALH IRVSGTYSLE   300
DAARAHEDLE GRRTTGKLLI LP                                           322

SEQ ID NO: 94            moltype = AA  length = 320
FEATURE                  Location/Qualifiers
source                   1..320
                         mol_type = protein
                         organism = Sciscionella marina
SEQUENCE: 94
MTNAIRVHET GGPEVLRLDE VTREAGAGQL LVRVEAAGVN FIDTYQRSGV YSVELPHALG    60
LEGAGTVEAV GDEASDFTPG DRVAWVWAAG SYAEHTVVPV ERAVRIPDDV DTKTAGALML   120
QGLTAHYLLR STYRVDETDT VLVHAAAGGV GLLLVQLAKS LGARVIATAS TAEKRALATG   180
AGADEVLGYE GFDTKLRELT GGIGVSVVYD GVGKDTFDAS LASIRPRGYL VLFGGSSGQV   240
PPFDLQRLNA AGSLFVTRPS LGPYIADRTE YEWRVGELFE AVGNGSLNVR IGGSYPLAEA   300
ANAHRDLEGR KTTGKLLLVP                                              320

SEQ ID NO: 95            moltype = AA  length = 332
FEATURE                  Location/Qualifiers
source                   1..332
                         mol_type = protein
                         organism = Zymomonas mobilis
SEQUENCE: 95
```

```
MSEAYAIIAE KAGGPEVLVK KPLDLGKMKP EAGQVLLRHQ AIGLNFIDIY HRSGLYKQDF    60
PANLGCEAAG VIEVVGDKVK GFKAGDRVAV FTSKPGAYAT HRIVDASELV ALPDDISAET   120
AAAVLLKGMT SWMLAEKCLA HAAIEGEAPK VMVLAAAGGV GSLLIPWLKY LGVTVFAHTS   180
TEEKAAKVKA NGADYVTTLP YSDLPDWVRK QNHGEGVHAV LDSVGADSWK SSIASLRKKG   240
LWVVYGNASG PVPALSPLEL SKAGSIYTSR PRLIDYVDNS VDLTTASQKL FALLRKNILK   300
VEINQRFPLT EVAKAHQLLE SRKTTGSTVL IP                                332

SEQ ID NO: 96           moltype = AA  length = 324
FEATURE                 Location/Qualifiers
source                  1..324
                        mol_type = protein
                        organism = Methylobacterium sp.
SEQUENCE: 96
MPKAIRVHEY GGPEVMRYEE VDLPAPGPGQ IRVRQRAVGV NFIDIYFRSG LYKAPQLPFT    60
PGNEGTGEVV AVGEGVAGLA VGDRVAYGSA AQTYAQEAVI EARMAVKVPD GIDDATAAAM   120
MLKGLTAQYL LRKTYRVQPG DTILFHAAAG GVGLIATQWA KHLGATVIGT VGSRDKAELA   180
KQHGCDHVIL YRDEDFAARV KEITGGKGCA VVYDGVGQAT YPASLDCLRP FGMFVSFGNA   240
SGVIENFNIG LLGPKGSLYA TRPTLFTHVA ERASLEAMAD DLFGVVGSGA VRIPVHSRVP   300
LAEAAQVHRD LAGRQTTGAT VLIP                                         324

SEQ ID NO: 97           moltype = AA  length = 324
FEATURE                 Location/Qualifiers
source                  1..324
                        mol_type = protein
                        organism = Trinickia sp.
SEQUENCE: 97
MAKAIRFEKT GGPEVMQWVD VEVGDPGSGE VRIKQHAVGL NYIDVYFRTG LYPMPLPGGL    60
GMEAAGEVTA VGPDVEGLRV GDRVAYVARP PGAYAQERVL PAAALVKLPG ALGYDDAASA   120
MLQGLTAQYL LRRTYRVKAG DTILIQAAAG GVGLFVCQWA KALGATVIGT VSSDEKAELA   180
KAHGCDYPIV YTRESFTKRV KEITGGAGVP VVYDSIGKDT FTGSLDCLAP LGLFVSFGNA   240
SGPLPPIDSS EFAGRGSLFF TRPTLFTHIA KRSDYDAMAA ELFDVIVSGK VKTMIRQRFP   300
LAEVGQAHAD LEARRTTGST ILIP                                         324

SEQ ID NO: 98           moltype = AA  length = 332
FEATURE                 Location/Qualifiers
source                  1..332
                        mol_type = protein
                        organism = Clostridioides difficile
SEQUENCE: 98
MKILVFGARD YEEPVIKKWS EEHKDVQVDI YPENMTEENV VKAKGYDGIS IQQTNYIDNP    60
YIYETLKDAG VKVIASRTAG VDMIHFDLVN ENGLIVTNVP SYSPNAIAEL AVTQAMNLLR   120
KTPLVKKKVC EGDYRWIAEL LGTEVRSITV GVIGTGKIGA TSAKLFKGLG ANVIAFDQYP   180
NSDLNDILTY KDSLEDLLKE ADLITLHTPL LEGTKHMINK DTLAIMKDGA YIVNTGRGGL   240
INTGDLIEAL ESGKIRAAAL DTFETEGLFL NKKMNPGELT DPEINKLLSM EQVIFTHHLG   300
FFTSTAIENI VYSSLSSAVE VIKTGTATNR VN                                332

SEQ ID NO: 99           moltype = AA  length = 312
FEATURE                 Location/Qualifiers
source                  1..312
                        mol_type = protein
                        organism = Lactococcus lactis
SEQUENCE: 99
MRITIAGAGA MGSRFGLMLH KGGNEVTLID GWPEHVKAIK DHGLRANYNG EELTAHLSVE    60
LQSEISSKEK TDLIILFTKA MQLDKMLQDI KPLIDEHTKV LCLLNGIGHE DTIEKYVSKN   120
NIFIGNTMWT AGLEGPGKAK LFGDGSVELQ NLISGEEETA KKLAEILSES GLNAKYSNNI   180
HYSIYRKACV NGTMNGLCTI LDTNMAGLGE TKPAHDMVVT IVNEFAAVAK FENVNLDIAE   240
VVQHVETCFD PATIGLHYPS MYQDLIKNNR LTEIDYINGA VSRKGKKYNV ATPYCDFLTQ   300
LVHSKEELLK AK                                                      312

SEQ ID NO: 100          moltype = AA  length = 334
FEATURE                 Location/Qualifiers
source                  1..334
                        mol_type = protein
                        organism = Clostridium sporogenes
SEQUENCE: 100
MKILMYSVRE HEKPAIKKWL EANPGVQIDL SDEALSEDTV CKVKDYDGIA IQQTNSIGGE    60
TVYSTLKKYG IRQIASRTAG VDMIDLKMAS ENNIIVTNVP AYSPNAIAEL AVTHTMNLLR   120
NIKTVNKRIA FGDYRWSADL IAREVRSITV GVVGTGKIGR TSAKLFKGLG ANVIGYDAYP   180
DKKLEENNLL TYKDSLEDLL KEADVVTLHT PLLESTKHMI NKNNLKYMKP NAFIVNTGRG   240
GIINTEDLIE ALEENKIAGA ALDTFENEGL FLNKVIDPTK IPDPQLDKLL KMDQVLITHH   300
VGFFTTTAVQ NMVDTSLDSV MEVLKTNDSV NKAN                              334

SEQ ID NO: 101          moltype = AA  length = 333
FEATURE                 Location/Qualifiers
source                  1..333
                        mol_type = protein
                        organism = Lactobacillus delbrueckii
SEQUENCE: 101
MTKIAMYNVS PIEVPYIEDW AKKNDVEIKT TDQALTSATV DLAEGCSSVS LKPLGPVDEE    60
```

```
VVYQKLSEYG VKCIGLRIVG FNTINFDWTK KYNLLVTNVP VYSPRAIAEM TVTQAMYLLR    120
KIGEFRYRMD HDHDFTWPSN LISNEIYNLT VGLIGVGHIG SAVAEIFSAM GAKVIAYDVA    180
YNPEFEPFLT YTDFDTVLKE ADIVSLHTPL LPSTENMIGE KQLKEMKKSA YLINCARGEL    240
VDTGALIKAL QDGEIAGAGL DTLAGESSYF GHTGLTDSEI PEDYKTLAKM PNVVITPHSA    300
FYTETSIRNM VQICLTDQLT IAKGGRPRSI VNL                                333

SEQ ID NO: 102           moltype = AA   length = 330
FEATURE                  Location/Qualifiers
source                   1..330
                         mol_type = protein
                         organism = Lacticaseibacillus paracasei
SEQUENCE: 102
MTKILMYTVR PDERAAIDAW VAANDIQVDT NTVEFGPDTV DLAKGYDGVV IQQHGAIPEE    60
MVYQKLKAFG IKQLTLRITG YDIVNLDAAT ANGLVVTNVP AYSPRSVSEL VLAQVMRLIR    120
HLGEASAREA KDDYSWTGLE APEIHNLTVG IIGAGKIGSA VARIFRALGA TVIVSDPVKR    180
PELADTVSYV DLNTLLTTSD VVTVHTPLDG LTTHLIDADA LRKMKSTAYL INAARGPIVD    240
TEALIKALND HTIAGAALDT IEGEAGIFGE DRSQTLVDNQ TLETLKAMPN VEISPHIGFY    300
TDAAVKNMID ISLDDVKTIL EGGKSAHQVN                                    330

SEQ ID NO: 103           moltype = AA   length = 332
FEATURE                  Location/Qualifiers
REGION                   1..332
                         note = Description of Unknown:Lactobacillaceae family
                          sequence
source                   1..332
                         mol_type = protein
                         organism = unidentified
SEQUENCE: 103
MKIIAYAVRD DERPFFDTWM KENPDVEVKL VPELLTEDNV DLAKGFDGAD VYQQKDYTAE    60
VLNKLADEGV KNISLRNVGV DNLDVPTVKA RGLNISNVPA YSPNAIAELS VTQLMQLLRQ    120
TPLFNKKLAK QDFRWAPDIA KELNTMTVGV IGTGRIGRAA IDIFKGFGAK VIGYDVYRNA    180
ELEKEGMYVD TLDELYAQAD VITLHVPALK DNYHMLNADA FSKMKDGAYI LNFARGTLID    240
SEDLIKALDS GKVAGAALDT YEYETKIFNK DLEGQTIDDK VFMNLFNRDN VLITPHTAFY    300
TETAVHNMVH VSMNSNKQFI ETGKADTQVK FD                                 332

SEQ ID NO: 104           moltype = AA   length = 331
FEATURE                  Location/Qualifiers
source                   1..331
                         mol_type = protein
                         organism = Clostridium sporogenes
SEQUENCE: 104
MKILAYCVRP DEIDSFKNFS EKYGHTVDLI PDSFGPSVAH LAKGYDGISI LGNDTCNREA    60
LEKIKDCGIK YLATRTAGVN NIDFDAAKEF GINVANVPAY SPNSVSEFTV GLALSLTRKI    120
PPFALKRVELN NFALGGLIGV ELRNLTLGVI GTGRIGLKVI EGFSGFGMKK MIGYDIFENE    180
KAKEYIEYKS LDEVYKEADI ITLHAPLTDD NYHMIGKESI AKMKDGVFII NAARGALIDS    240
EALIEGLKSG KIAGAALDSY EYEQGVFHNN KMNEIMKDDT LARLKSFPNV VITPHLGFYT    300
DEAVSNMVEI TLMNLQEFEL KGTCKNQRVC K                                  331

SEQ ID NO: 105           moltype = AA   length = 334
FEATURE                  Location/Qualifiers
source                   1..334
                         mol_type = protein
                         organism = Clostridium sporogenes
SEQUENCE: 105
MKILMYSVRE HEKPAIKKWL EANPGVQIDL SDEALSEDTV CKVKDYDGIA IQQTNSIGGE    60
TVYSTLKKYG IRQIASRTAG VDMIDLKMAS ENNIIVTNVP AYSPNAIAEL AVTHTMNLLR    120
NIKTVNKRIA FGDYRWSADL IAREVRSITV GVVGTGKIGR TSAKLFKGLG ANVIGYDAYP    180
DKKLEENNLL TYKDSLEDLL KEADVVTLHT PLLESTKHMI NKNNLKYMKP NAFIVNTGRG    240
GIINTEDLIE ALEENKIAGA ALDTFENEGL FLNKVIDPTK IPDPQLDKLL KMDQVLITHH    300
VGFFTTTAVQ NMVDTSLDSV MEVLKTNDSV NKAN                               334

SEQ ID NO: 106           moltype = AA   length = 6
FEATURE                  Location/Qualifiers
REGION                   1..6
                         note = Description of Artificial Sequence: Synthetic 6xHis
                          tag
source                   1..6
                         mol_type = protein
                         organism = synthetic construct
SEQUENCE: 106
HHHHHH                                                              6
```

The invention claimed is:

1. A method, comprising:
   contacting pyruvate and HO—$CH_2$—$CH_2$—CHO (3-hydroxy propanal) with a polypeptide having the sequence of SEQ ID NO: 27 so that HO—$CH_2$—$CH_2$—CH=CH—C(O)—COOH (6-hydroxy-2-oxo-3-hexenoic acid) or a salt thereof is produced.

2. The method of claim 1, wherein the polypeptide is in a microbe.

3. The method of claim 2, wherein the microbe is engineered to express the polypeptide.

4. The method of claim 3, wherein the microbe is *E. coli*.

5. The method of claim 2, wherein the contact is performed in a culture comprising the microbe, pyruvate and 3 hydroxy propanal.

6. The method of claim 2, wherein (E)-6-hydroxy-2-oxo-3-hexenoic acid or a salt thereof is produced.

7. The method of claim 3, wherein the contact is performed in a culture comprising the microbe, pyruvate and 3 hydroxy propanal.

8. The method of claim 3, wherein (E)-6-hydroxy-2-oxo-3-hexenoic acid or a salt thereof is produced.

9. The method of claim 4, wherein the contact is performed in a culture comprising the microbe, pyruvate and 3 hydroxy propanal.

10. The method of claim 4, wherein (E)-6-hydroxy-2-oxo-3-hexenoic acid or a salt thereof is produced.

11. The method of claim 5, wherein (E)-6-hydroxy-2-oxo-3-hexenoic acid or a salt thereof is produced.

12. The method of claim 7, wherein (E)-6-hydroxy-2-oxo-3-hexenoic acid or a salt thereof is produced.

13. The method of claim 9, wherein (E)-6-hydroxy-2-oxo-3-hexenoic acid or a salt thereof is produced.

14. The method of claim 1, wherein (E)-6-hydroxy-2-oxo-3-hexenoic acid or a salt thereof is produced.

* * * * *